(12) United States Patent
Huang et al.

(10) Patent No.: US 11,753,408 B2
(45) Date of Patent: *Sep. 12, 2023

(54) COMPOUNDS AND METHOD FOR BLOCKING TRANSMISSION OF MALARIAL PARASITE

(71) Applicants: The United States of America, as represented by the Secretary, Department of Health and Human Services, Bethesda, MD (US); Loyola University of Chicago, Chicago, IL (US)

(72) Inventors: Wenwei Huang, Rockville, MD (US); Hao Li, Rockville, MD (US); Wei Sun, Germantown, MD (US); Xiuli Huang, Potomac, MD (US); Paresma R. Patel, Rockville, MD (US); Hangmao Sun, Germantown, MD (US); Wei Zheng, Potomac, MD (US); Xiao Lu, Rockville, MD (US); Philip E. Sanderson, Bethesda, MD (US); Myunghoon Kim, Olympia, WA (US); Meghan J. Orr, Nashville, IL (US); Gregory J. Tawa, Doylestown, PA (US); Kim C. Williamson, Bethesda, MD (US)

(73) Assignees: The United States of America, as represented by the Secretary, Department of Health and Human Services, Bethesda, MD (US); Loyola University of Chicago, Chicago, IL (US)

( * ) Notice: Subject to any disclaimer, the term of this patent is extended or adjusted under 35 U.S.C. 154(b) by 58 days.

This patent is subject to a terminal disclaimer.

(21) Appl. No.: 17/237,351

(22) Filed: Apr. 22, 2021

(65) Prior Publication Data
US 2021/0246137 A1 Aug. 12, 2021

Related U.S. Application Data

(63) Continuation of application No. 16/341,000, filed as application No. PCT/US2017/056619 on Oct. 13, 2017, now Pat. No. 10,988,472.
(Continued)

(51) Int. Cl.
*C07D 471/14* (2006.01)
*A61K 31/4375* (2006.01)
(Continued)

(52) U.S. Cl.
CPC ............ *C07D 471/04* (2013.01); *A61P 33/06* (2018.01); *C07D 487/04* (2013.01); *C07D 487/08* (2013.01); *C07D 519/00* (2013.01)

(58) Field of Classification Search
CPC ............... C07D 471/14; C07D 471/06; A61K 31/4375; A61P 33/06
(Continued)

(56) References Cited

U.S. PATENT DOCUMENTS 10,988,472 B2 * 4/2021 Huang ................ C07D 487/04

FOREIGN PATENT DOCUMENTS

CN 103373997 A 10/2013
WO WO 03/097641 A2 11/2003
(Continued)

OTHER PUBLICATIONS

World Intellectual Property Organization International Bureau, International Preliminary Report on Patentability in International Patent Application No. PCT/US2017/056619 dated Apr. 25, 2019 (10 pp.).
(Continued)

*Primary Examiner* — Charanjit Aulakh
(74) *Attorney, Agent, or Firm* — Leydig, Voit & Mayer, Ltd.

(57) ABSTRACT

Disclosed are compounds of formula (I) and formula (II):

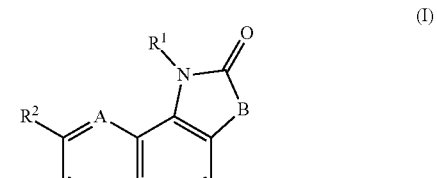

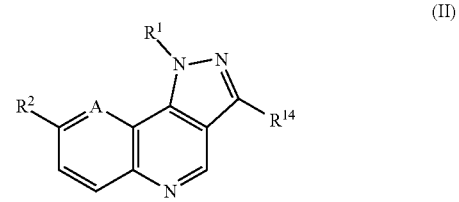

Figure 1A:
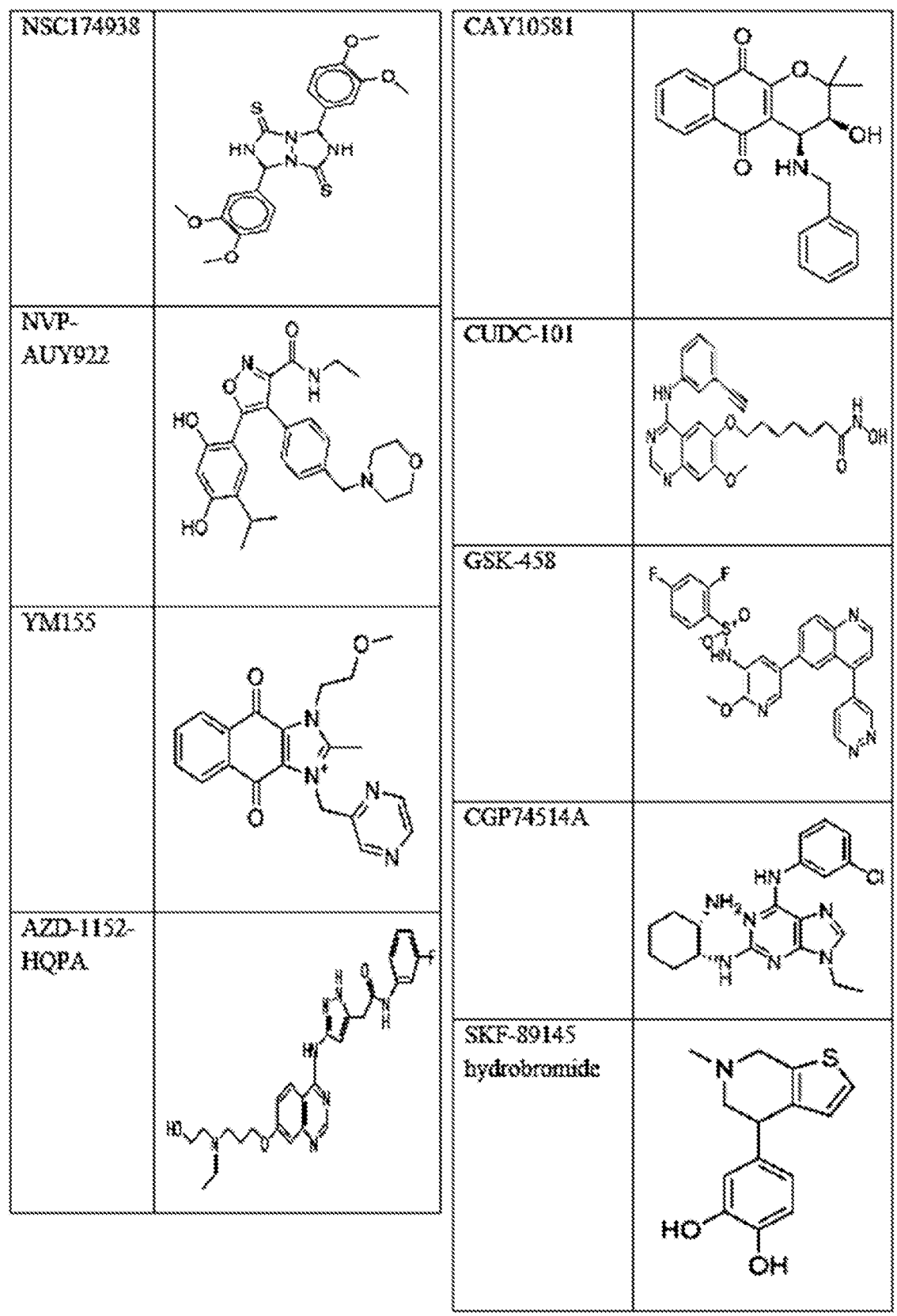

wherein $R^1$, $R^2$, A, and B are as defined herein. Also disclosed is a method of blocking transmission of a *Plasmodium* parasite and a method of treating or preventing malaria comprising administering to an animal an effective amount of a first compound of formula (I) or (II) either alone or in combination with a second compound selected from elesclomol, NSC174938, NVP-AUY922, Maduramicin, Narasin, Alvespimycin, Omacetaxine, Thiram, Zinc pyrithione, Phanquinone, Bortezomib, Salinomycin sodium, Monensin sodium, Dipyrithione, Dicyclopentamethylenethiuram disulfide, YM155, Withaferin A, Adriamycin, Romidepsin, AZD-1152-HQPA, CAY10581, Plicamycin, CUDC-101, Auranofin, Trametinib, GSK-458, Afatinib, and Panobinostat.

8 Claims, 85 Drawing Sheets

Related U.S. Application Data

(60) Provisional application No. 62/407,861, filed on Oct. 13, 2016.

(51) Int. Cl.
*C07D 471/04* (2006.01)
*A61P 33/06* (2006.01)
*C07D 487/04* (2006.01)
*C07D 487/08* (2006.01)
*C07D 519/00* (2006.01)

(58) Field of Classification Search
USPC .............................. 546/82, 81; 514/293, 292
See application file for complete search history.

(56) References Cited

FOREIGN PATENT DOCUMENTS

| WO | WO 2005/054237 A1 | 6/2005 |
|---|---|---|
| WO | WO 2006/122806 A2 | 11/2006 |
| WO | WO 2008/103636 A1 | 8/2008 |
| WO | WO 2010/038165 A1 | 4/2010 |
| WO | WO 2010/044885 A2 | 4/2010 |
| WO | WO 2010/139731 A1 | 12/2010 |
| WO | WO 2010/139747 A1 | 12/2010 |
| WO | WO 2011/054843 A1 | 5/2011 |
| WO | WO 2012/167606 A1 | 12/2012 |
| WO | WO 2013/053273 A1 | 4/2013 |
| WO | WO 2013/154778 A1 | 10/2013 |
| WO | WO 2014/063054 A1 | 4/2014 |
| WO | WO 2015/073804 A2 | 5/2015 |

OTHER PUBLICATIONS

Adjalley et al., "Quantitative assessment of Plasmodium falciparum sexual development reveals potent transmission-blocking activity by methylene blue," PNAS, 108(47):E1214-E1223 (2011).
Alano et al., "Sexual Differentiation in Malaria Parasites," Annu. Rev. Microbiol., 44:429-449 (1990).
Arastu-Kapur et al., "Identification of proteases that regulate erythrocyte rupture by the malaria parasite *Plasmodium falciparum*," Nature Chemical Biology, 4(3):203-213 (2008).
Baird et al., "Consideration of ethics in primaquine therapy against malaria transmission," Trends in Parasitology, 27(1):11-16 (2011).
Baragaña et al., "A novel multiple-stage antimalarial agent that inhibits protein synthesis," Nature, 522(7556):315-320 (2015).
Blagborough et al., "Transmission-blocking interventions eliminate malaria from laboratory populations," Nature Communications, 4:1812 (2013).
Buchholz et al., "A High-Throughput Screen Targeting Malaria Transmission Stages Opens New Avenues for Drug Development," Journal of Infectious Diseases, 203:1445-1453 (2011).
Derbyshire et al., "Chemical interrogation of malarial host and parasite kinomes," Chembiochem., 15(13):1920-1930 (2014).
Eastman et al., "A Class of Tricyclic Compounds Blocking Malaria Parasite Oocyst Development and Transmission," Antimicrobial Agents and Chemotherapy, 57(1):425-435 (2013).
European Patent Office, International Search Report in International Patent Application No. PCT/US2017/056619, dated Mar. 19, 2018 (7 pp.).
European Patent Office, Written Opinion in International Patent Application No. PCT/US2017/056619, dated Mar. 19, 2018 (9 pp.).
Gamo et al., "Thousands of chemical starting points for antimalarial lead identification," Nature, 465:305-310 (2010).
Guiguemde et al., "Chemical genetics of *Plasmodium falciparum*," Nature, 465(7296):311-315 (2010).
Hanson et al., "Torins are potent antimalarials that block replenishment of *Plasmodium* liver stage parasitophorous vacuole membrane proteins," PNAS, 110:E2838-E2847 (2013).
Huang et al., "The NCGC Pharmaceutical Collection: A comprehensive resource of clinically approved drugs enabling repurposing and chemical genomics," Sci. Transl. Med., 3(80):80ps16 (2011).
Kilama et al., "Malaria: a research agenda for the eradication era," The Lancet, 374:1480-1482 (2009).
Kim et al., "In vitro evaluation of imidazo[4,5-c]quinolin-2-ones as gametocytocidal antimalarial agents," $250^{th}$ ACS National Meeting & Exposition, Boston, MA, USA, Aug. 16-20, 2015, MEDI-408.
Kun et al., "Low-Dose Treatment with Sulfadoxine-Pyrimethamine Combinations Selects for Drug-Resistant *Plasmodium falciparum* Strains," Antimicrobial Agents and Chemotherapy, 43(9):2205-2208 (1999).
Liu et al., "Discovery of 1-(4-(4-propionylpiperazin-1-yl)-3-(trifluoromethyl)phenyl)-9-(quinolin-3-yl)benzo[h][1,6]naphthyridin-2(1H)-one as a highly potent, selective Mammalian Target of Rapamycin (mTOR) inhibitor for the treatment of cancer," J. Med. Chem., 53(19):7146-7155 (2010).
Liu et al., "Discovery of 9-(6-aminopyridin-3-yl)-1-(3-(trifluoromethyl)phenyl)benzo[h]1,6]naphthyridin-2(1H)-one (Torin2) as a potent, selective and orally available mTOR inhibitor for treatment of cancer," J. Med. Chem., 54(5):1473-1480 (2011).
Lomenick et al., "Target identification using drug affinity responsive target stability (DARTS)," PNAS, 106(51):21984-21989 (2009).
Mathews et al., "A 1536-Well Quantitative High-Throughput Screen to Identify Compounds Targeting Cancer Stem Cells," Journal of Biomolecular Screening, 17(9):1231-1242 (2012).
Peatey et al., "Effect of Antimalarial Drugs on *Plasmodium falciparaum* Gametocytes," The Journal of Infectious Diseases, 200:1518-1521 (2009).
Seixas et al., "Establishment of a Structure-Activity Relationship of 1H-Imidazo[4,5-c]quinolone-Based Kinase Inhibitor NVP-BEZ235 as a Lead for African Sleeping Sickness," J. Med. Chem., 57:4834-4848 (2014).
Smilkstein et al., "Simple and Inexpensive Fluorescence-Based Technique for High-Throughput Antimalarial Drug Screening," Antimicrobial Agents and Chemotherapy, 48(5):1803-1806 (2004).
Sun et al., "Chemical signatures and new drug targets for gametocytocidal drug development," Scientific Reports, 4:3743 (2014).
Sweeney et al., "Short Report: The Activity of Pamaquine, an 8-Aminoquinoline Drug, Against Sporozoite-Induced Infections of *Plasmodium vivax* (New Guinea Strains)," Am. J. Trop. Med. Hyg., 71(2):187-189 (2004).
Tanaka et al., "A malaria gametocytocidal assay using oxidoreduct ion indicator, alamarBlue," Mol. Biochem. Parasitol., 177(2):160-163 (2011).
Tanaka et al., "A Quantitative High Throughput Assay for Identifying Gametocytocidal Compounds," Mol. Biochem. Parasitol., 188(1):20-25 (2013).
Trager et al., "Human Malaria Parasites in Continuous Culture," J. Parasitol., 91(3):484-486 (2005).
Wang et al., "A Grid Algorithm for High Throughput Fitting of Dose-Response Curve Data," Current Chemical Genomics, 4:57-66 (2010).
Zhang et al., "Small-molecule synergist of the Wnt/β-catenin signaling pathway," PNAS, 104(18):7444-7448 (2007).

\* cited by examiner

COMPOUNDS AND METHOD FOR BLOCKING TRANSMISSION OF MALARIAL PARASITE

CROSS-REFERENCE TO RELATED APPLICATIONS

This patent application is a continuation of copending U.S. patent application Ser. No. 16/341,000, filed Apr. 10, 2019, which is a U.S. National Phase Patent Application of International Patent Application No. PCT/US2017/056619 filed Oct. 13, 2017, which claims the benefit of U.S. Provisional Patent Application No. 62/407,861, filed Oct. 13, 2016, the disclosures of all of which are herein incorporated by reference in their entireties for all purposes.

STATEMENT REGARDING FEDERALLY SPONSORED RESEARCH OR DEVELOPMENT

This invention was made with Government support under project number Z01TR000008-01 by the National Institutes of Health, National Center for Advancing Translational Sciences. The Government has certain rights in the invention.

BACKGROUND OF THE INVENTION

Malaria cases and deaths have dropped 50% in 29 countries since 2000 due to the combined effects of long-lasting insecticidal bed nets, indoor residual spraying, and artemisinin-based combination therapies (ACTs) [Kilama W. et al., Lancet, 2009, 374: 1480-1482], This success has raised hopes for malaria eradication and consequently stimulated interest in developing new reagents that block gametocyte transmission, such as novel and safe gametocytocidal drugs [Buchholz K. et al., The Journal of Infectious Diseases, 2011, 203: 1445-1453], Previous drug development efforts have focused primarily on the asexual parasites that cause symptoms but not malaria transmission. To be transmitted from person to person via mosquitoes, the parasites must switch from asexual to sexual development and produce male and female gametocytes. Once gametocytes are taken up in a blood meal by a mosquito, fertilization is stimulated and the resulting zygote differentiates into a motile ookinete that migrates across the midgut epithelium of the mosquito and forms an oocyst. Over the course of the next 2 weeks, tens of thousands of infectious sporozoites are generated and sequestered in the mosquito salivary glands until released into a vertebrate host for transmission during the next blood meal.

Sexual stage *P. falciparum* gametocytes have a lifespan of over 3 weeks and are not cleared effectively by current antimalarial agents, except primaquine (PQ) [Sweeney A W et al., American Journal of Tropical Medicine and Hygiene, 2004, 71: 187-189; Peatey C L et al., Journal of Infectious Diseases, 2009, 200: 1518-1521] which is not widely used because it causes hemolytic anemia in patients with glucose-6-phosphate dehydrogenase deficiency [Baird J K et al., Trends in Parasitology, 2011, 27: 11-16], Consequently, treatment with current antimalarial drugs often results in asymptomatic carriers who remain infectious for weeks after the clearance of asexual parasites. Despite the risks of PQ, its efficacy with artemisinin combination therapy (ACT) in reducing malaria transmission in the PQ-tolerant patients was recently demonstrated in test regions. Other than PQ, the only other gametocytocidal candidate being tested is methylene blue.

Thus, a new generation of antimalarial agents with potent activities against both sexual and asexual parasites is urgently needed for better therapeutic effect and eradication of malarial infection globally.

BRIEF SUMMARY OF THE INVENTION

The invention provides a compound of formula (I):

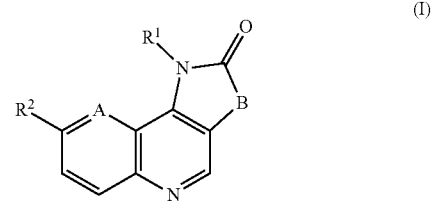

wherein A is $CR^5$ or N,
B is $CR^3\!=\!CR^4$ or $NR^6$,
$R^1$ is $C_{6-10}$ aryl or heteroaryl substituted with at least one substituent selected from —CN, cyanomethyl, —$SO_2R^{13}$, —$SO_2NHR^{15}$, and —$CONR^{11}R^{12}$, optionally further in combination with one or more substituents selected from halo, $C_{1-12}$ alkyl, alkoxy, a heterocyclyl group selected from the group consisting of optionally substituted piperazinyl, morpholinyl, pyrrolinidyl, and diazepinyl, or an aryl bicyclic lactam of the formula:

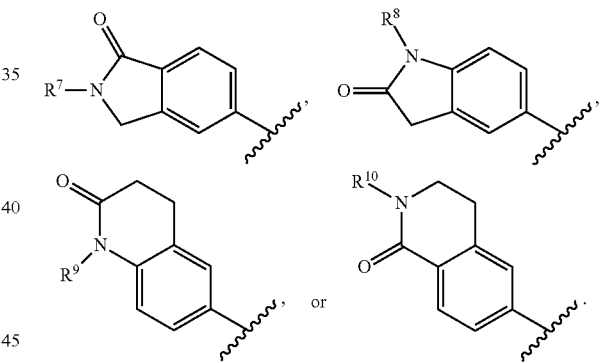

wherein the aryl group of the aryl bicyclic lactam is optionally substituted with at least one substituent selected from —CN, cyanomethyl, —$SO_2R^{13}$, —$SO_2NH_2$, and —$CONR^{11}R^{12}$, optionally further in combination with one or more substituents selected from halo, $C_{1-12}$ alkyl, alkoxy, 2-(dimethylamino)ethyl)amino, dimethylamino, a heterocyclyl group selected from the group consisting of optionally substituted piperazinyl, morpholinyl, pyrrolinidyl, azetidinyl and diazepinyl, $R^2$ is selected from 2-amino-5-pyridinyl, 4-pyridinyl, 2-amino-5-pyrimidinyl, 3-pyridyl, quinolin-3-yl, 5-pyrimidinyl, 2-acetylamino-5-pyridyl, 2-amino-4-methylpyrimidin-5-yl, 1-piperazinyl, indol-5-yl, 1H-imdazol-5-yl, 4-aminophenyl, 1,2,3,6-tetrahydropyridin-4-yl, 1H-pyrazol-4-yl, N-methyl-pyrazol-4-yl, 1H-benzo[d]imidazol-5-yl, 4-sulfonylaminophenyl, 2-dimethylaminopyrimidin-5-yl, 3-trifluoromethylphenyl, bromo, 3-aminophenyl, 4-aminophenyl, vinyl, 4-aminocarbonylphenyl, 3-cyanophenyl, 3-hydroxyphenyl, 3-trifluoromethyl-5-pyridyl, tetrazolyl, 4-chlorophenyl, 4-fluorophenyl, 4-methoxyphenyl, 3-aminocarbonylphenyl, 3-acetylphenyl, 3-cyano-4-chlorophenyl, 3-cyano-5-methylphenyl, 3-hydroxy-4-chlorophenyl, 4-hydroxymethylphenyl, 3-amino-4-chlorophenyl, 2,3-dihydrobenzofuran-6-yl, 1-methyl-1H-indol-5-yl, benzo[d][1,3]dioxo-5-yl, 4-fluorophenyl, 4-hydroxyphenyl, morpholin-1-yl, benzo[b]thiophen-1-yl, 4-methylsulfonylphenyl, benzo[c][1,2,5]oxadiazol-5-yl, 2-(piperidin-1-yl)-3-pyridinyl, 4-carboxyphenyl, 2-methyl-5-pyridyl, 4-methylsulfonylphenyl, 4-dimethylaminocarbonylphenyl, 4-phenylphenyl, 4-methylphenyl, 3-chloro-5-pyridyl, (3-pyrrolidin-1-yl)phenyl, 4-([piperizin-1-yl]carbonyl)phenyl, 4-([morpholin-1-yl]carbonyl)phenyl, 2-hydroxypyrimidin-5-yl, 3-aminosulfonylphenyl, 2-oxo-1,2,3,4,tetrahydroisoquinolin-6-yl, 2-oxo-1,2,3,4,-tetrahydroquinolin-6-yl, 4-(aminomethyl)phenyl, 4-(dimethylaminomethyl)phenyl, 4-(diethylaminomethyl)phenyl, 4-(methylaminocarbonyl)phenyl, 1-oxoindolin-5-yl, 2-oxoindolin-5-yl, 1-oxoisoindolin-5-yl, 2-amino-4-pyridyl, 3-amino-4-chlorophenyl, 4-aminomethylphenyl, 3-methyl-4-chlorophenyl, 3-methoxy-4-chlorophenyl, 4-aminophenyl, 3-methylphenyl, 3-methoxyphenyl, phenyl, 5-indolinone, 5-isoindolinone, 3-aminophenyl, 2-hydroxy-4-chlorophenyl, 4-cyanophenyl, 4-(2-aminoethyl) phenyl, 4-(2-dimethylaminoethyl) phenyl, 4-azetidinylphenyl, 4-ethylphenyl, 3-fluorophenyl, 3-chlorophenyl, 3-dimethylaminomethylphenyl, 3-cyano-4-fluorophenyl, 3-amino-4-fluorophenyl, 4-(1-hydroxy-1-ethylphenyl, 3-methyl-5-pyridyl, 2-acetylamio-5-pyridyl, 2-oxoindolin-5-yl, benzimidazolin-5-yl, 3-dimethylamino-1-propargyl, 2-pyrrolyl, N-methyl-2-pyrrolyl, 2-thiopheneyl, 3-thiopheneyl, 3-furanyl, 3-aminosulfonylphenyl, 4-dimethylaminomethylphenyl, and 4-pyrrolidinomethylphenyl, $R^3$ and $R^4$ are independently selected from hydrogen, hydroxyl, $OR^5$, halogen, optionally substituted $C_{6-10}$ aryl, and optionally substituted $C_{1-6}$ alkyl, $R^5$ is hydrogen, $C_{1-12}$ alkyl, $C_{6-10}$ aryl, halogen, hydroxyl, or $OR^{16}$, $R^6$ is hydrogen, $C_{1-12}$ alkyl, $C_{2-12}$ hydroxyalkyl, $C_{1-6}$ acyl-$C_{1-6}$ alkyl, or $C_{6-10}$ aryl, $R^7$-$R^{10}$ are independently selected from hydrogen, $C_{1-12}$ alkyl, $C_{3-8}$ cycloalkyl, $CH_2COOR^{13}$, and $H_2N(CH_2)_n$— wherein n is an integer of 2-6, $R^{11}$ and $R^{12}$ selected from the group consisting of hydrogen, $C_{1-12}$ alkyl and $C_{3-10}$ cycloalkyl or, taken together with the N to which they are bound, form an optionally substituted 4-7 membered heterocyclyl ring containing O or N atoms, and $R^{13}$ is $C_{1-12}$ alkyl, $R^{15}$ is hydrogen or $C_{1-12}$ alkyl, $R^{16}$ is hydrogen, $C_{1-12}$ alkyl or $C_{6-10}$ aryl, or a pharmaceutically acceptable salt thereof.

The invention also provides a compound of formula (II):

(II)

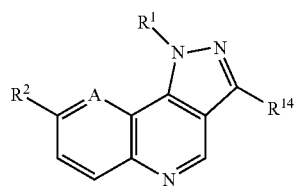

wherein A is $CR^5$ or N, wherein $R^1$ is $C_{6-10}$ aryl or heteroaryl substituted with one or more substituents selected from the group consisting of $C_{1-12}$ alkyl, $C_{3-10}$ cycloalkyl, alkoxy, —$CF_3$, heterocyclyl, —$CONR^{11}R^{12}$, —$SO_2NHR^{16}$, and CN, $R^2$ is selected from 2-amino-5-pyridinyl, 4-pyridinyl, 2-amino-5-pyrimidinyl, 3-pyridyl, quinolin-3-yl, 5-pyrimidinyl, 2-amino-5-trifluoromethylpyrimidin-5-yl, 2-acetylamino-5-pyridyl, 2-amino-4-methylpyrimidin-5-yl, 1-piperazinyl, indol-5-yl, 1H-indazol-5-yl, 4-aminophenyl, 1,2,3,6-tetrahydropyridin-4-yl, 1H-pyrazol-4-yl, 1H-benzo[d]imidazol-5-yl, 4-sulfonylaminophenyl, 2-dimethylaminopyrimidin-5-yl, 3-trifluoromethylphenyl, bromo, 3-aminophenyl, vinyl, 4-aminocarbonylphenyl, 3-cyanophenyl, 3-trifluoromethyl-5-pyridyl, tetrazolyl, 4-chlorophenyl, 4-methoxyphenyl, 3-aminocarbonylphenyl, 3-acetylphenyl, 2,3-dihydrobenzofuran-6-yl, 1-methyl-1H-indol-5-yl, benzo[d][1,3]dioxo-5-yl, 4-fluorophenyl, 4-hydroxyphenyl, morpholin-1-yl, benzo[b]thiophen-1-yl, 4-methylsulfonylphenyl, benzo[c][1,2,5]oxadiazol-5-yl, 2-(piperidin-1-yl)-3-pyridinyl, 4-carboxyphenyl, 2-methyl-5-pyridyl, 4-methylsulfonylphenyl, 4-dimethylaminocarbonylphenyl, 4-phenylphenyl, 4-methylphenyl, 3-chloro-5-pyridyl, (3-pyrrolidin-1-yl)phenyl, 4-([piperizin-1-yl]carbonyl)phenyl, 4-([morpholin-1-yl]carbonyl)phenyl, 2-hydroxypyrimidin-5-yl, 3-aminosulfonylphenyl, 2-oxo-1,2,3,4,tetrahydroisoquinolin-6-yl, 2-oxo-1,2,3,4,-tetrahydroquinolin-6-yl, 4-(aminomethyl)phenyl, 4-(dimethylaminomethyl)phenyl, 4-(methylaminocarbonyl)phenyl, 1-oxoindolin-5-yl, 2-oxoindolin-5-yl, and 1-oxoisoindolin-5-yl, $R^{11}$ and $R^{12}$ selected from the group consisting of hydrogen, $C_{1-12}$ alkyl and $C_{3-10}$ cycloalkyl or, taken together with the N to which they are bound, form an optionally substituted 4-7 membered heterocyclyl ring containing O or N atoms, $R^{14}$ is hydrogen or $C_{1-12}$ alkyl, and $R^{16}$ is hydrogen or $C_{1-12}$ alkyl, or a pharmaceutically acceptable salt thereof.

The invention further provides a pharmaceutical composition comprising a compound or salt of formula (I) or (II) and a pharmaceutically acceptable carrier.

The invention additionally provides a method of blocking transmission of a *Plasmodium* parasite comprising administering to a mammal in need of such treatment, a therapeutically effective amount of a first compound of formula (I) or (II), optionally in combination with an antimalarial compound selected from elesclomol, NSC174938, NVP-AUY922, maduramicin, narasin, alvespimycin, omacetaxine, thiram, zinc pyrithione, phanquinone, bortezomib, salinomycin sodium, monensin sodium, dipyrithione, dicyclopentamethylene-thiuram disulfide, YM155, withaferin A, adriamycin, romidepsin, AZD-1152-HQPA, CAY10581, plicamycin, CUDC-101, auranofin, trametinib, GSK-458, afatinib, and panobinostat.

The invention also provides a method of treating malaria by killing or arresting the growth of *Plasmodium* organisms in a mammal, wherein the *Plasmodium* organisms are in a gametocyte stage, the method comprising administering to a mammal a therapeutically effective amount of a first compound of formula (I) or (II), optionally in combination with an antimalarial compound selected from elesclomol, NSC174938, NVP-AUY922, maduramicin, narasin, alvespimycin, omacetaxine, thiram, zinc pyrithione, phanquinone, bortezomib, salinomycin sodium, monensin sodium, dipyrithione, dicyclopentamethylene-thiuram disulfide, YM155, withaferin A, adriamycin, romidepsin, AZD-1152-HQPA, CAY10581, plicamycin, CUDC-101, auranofin, trametinib, GSK-458, afatinib, and panobinostat.

Advantageously, the compounds and methods of the invention compounds kill all stages of malaria parasites.

BRIEF DESCRIPTION OF THE SEVERAL VIEWS OF THE DRAWING(S)

Figure 1B:
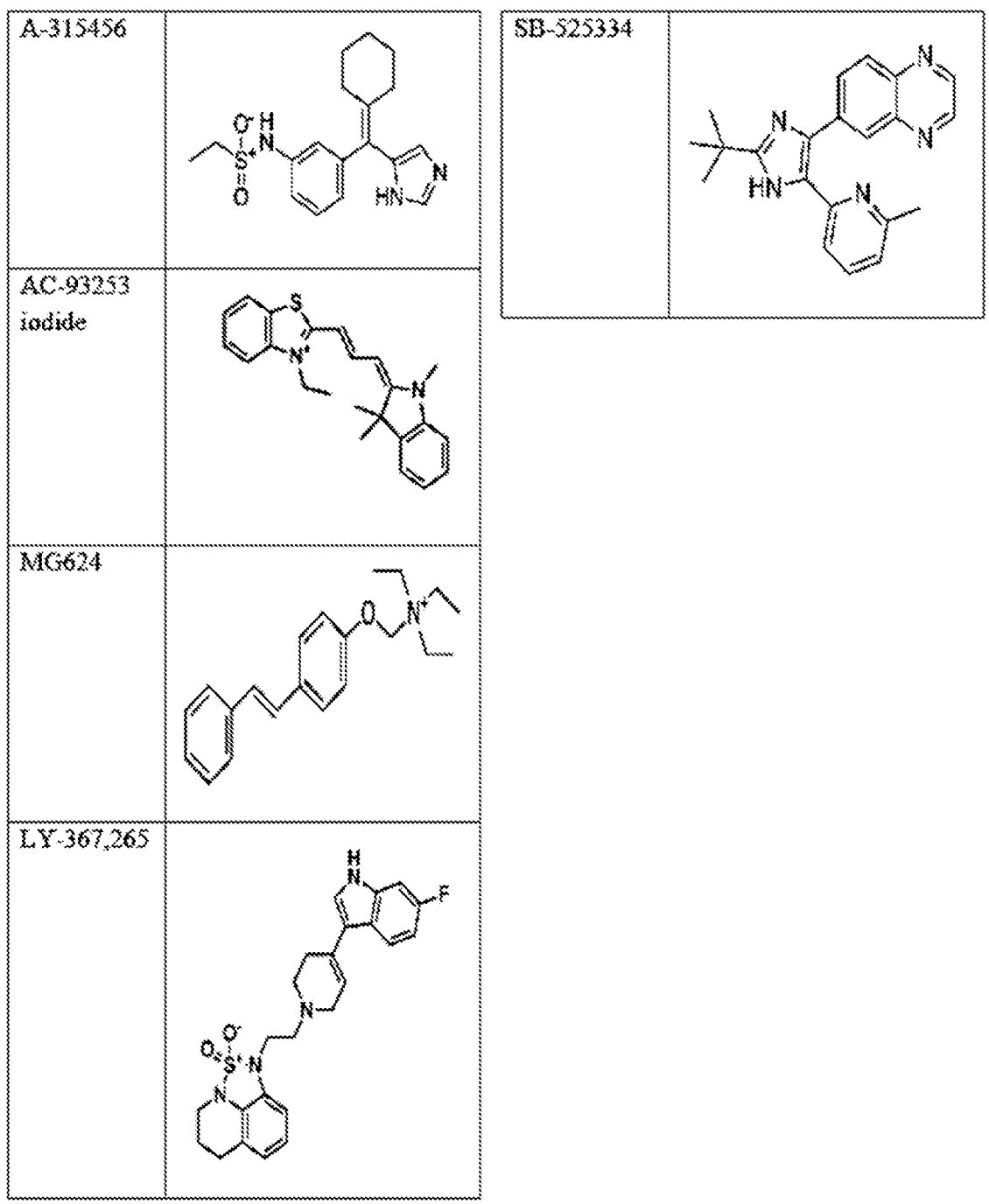

FIG. 1A-1B depict the structures of compounds in accordance with an embodiment of the invention.

Figure 2A:
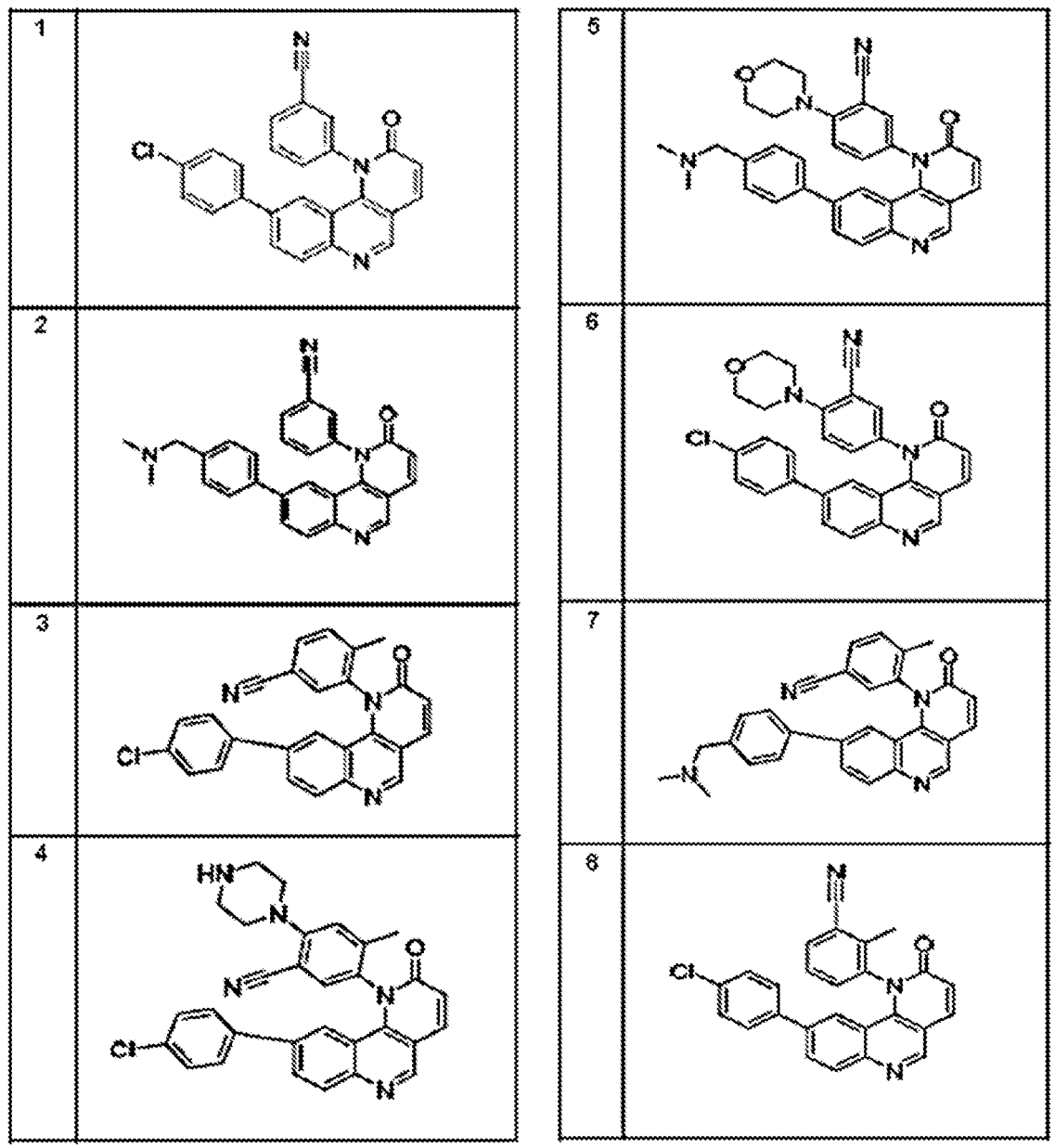
Figure 2A:
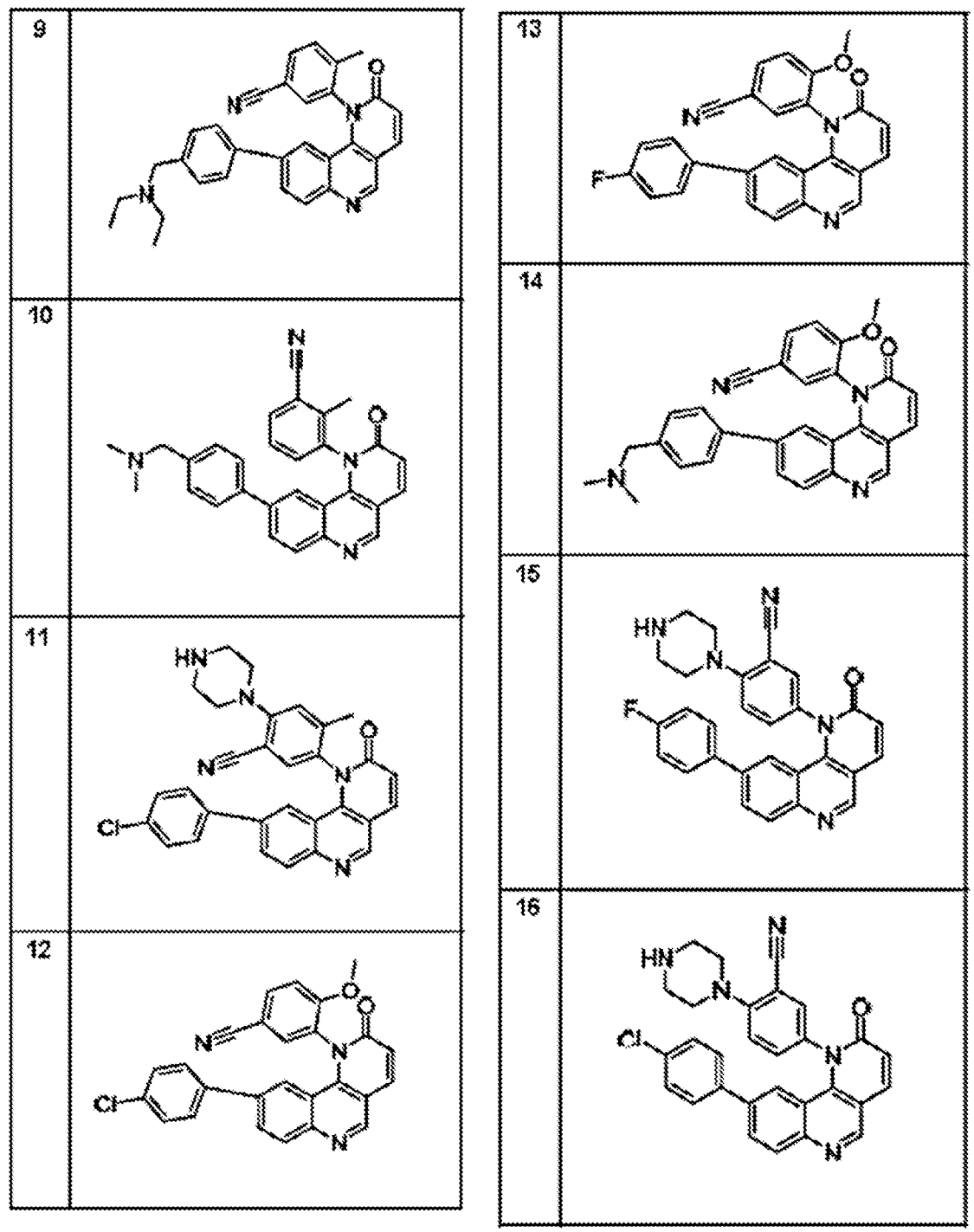
Figure 2A:
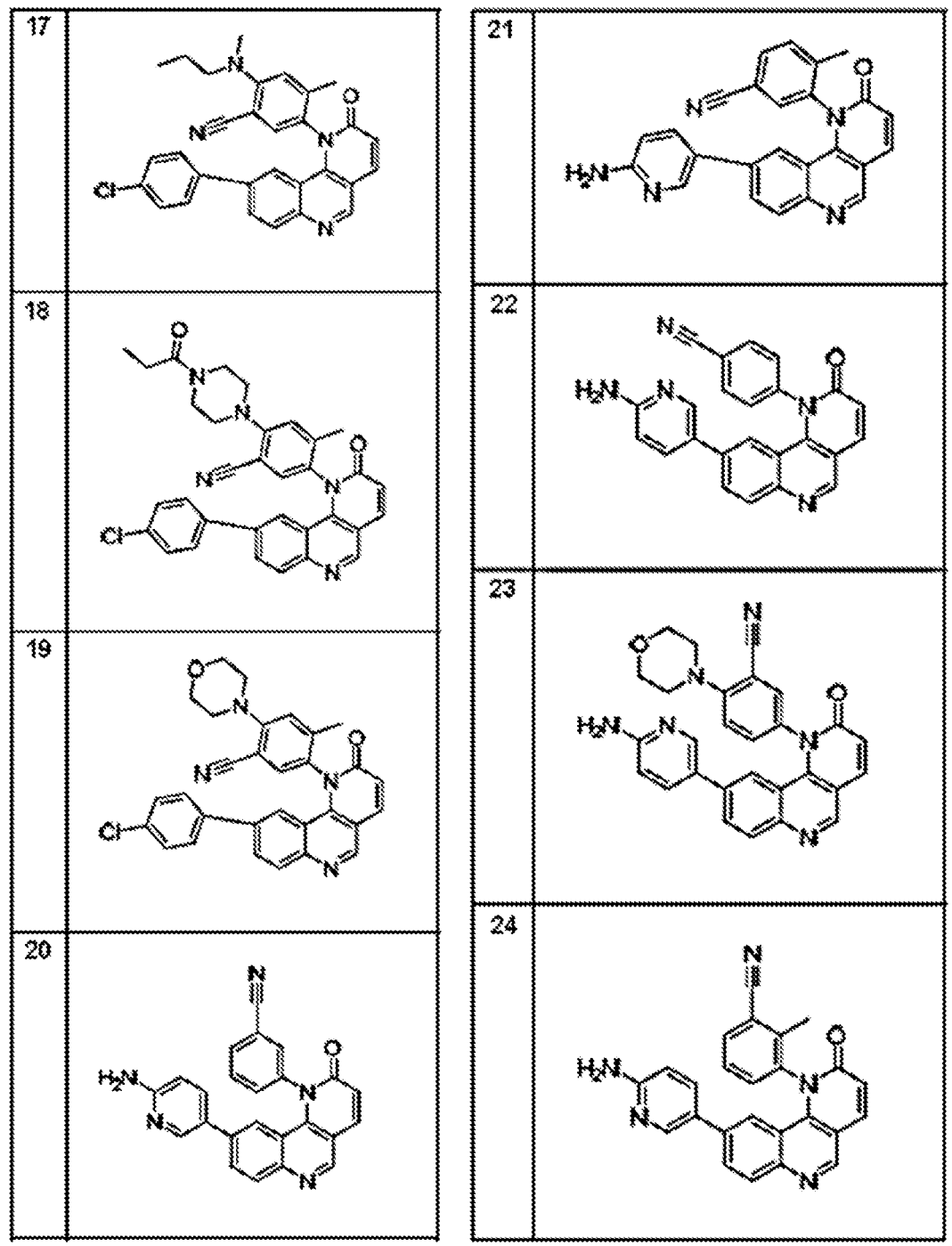
Figure 2A:
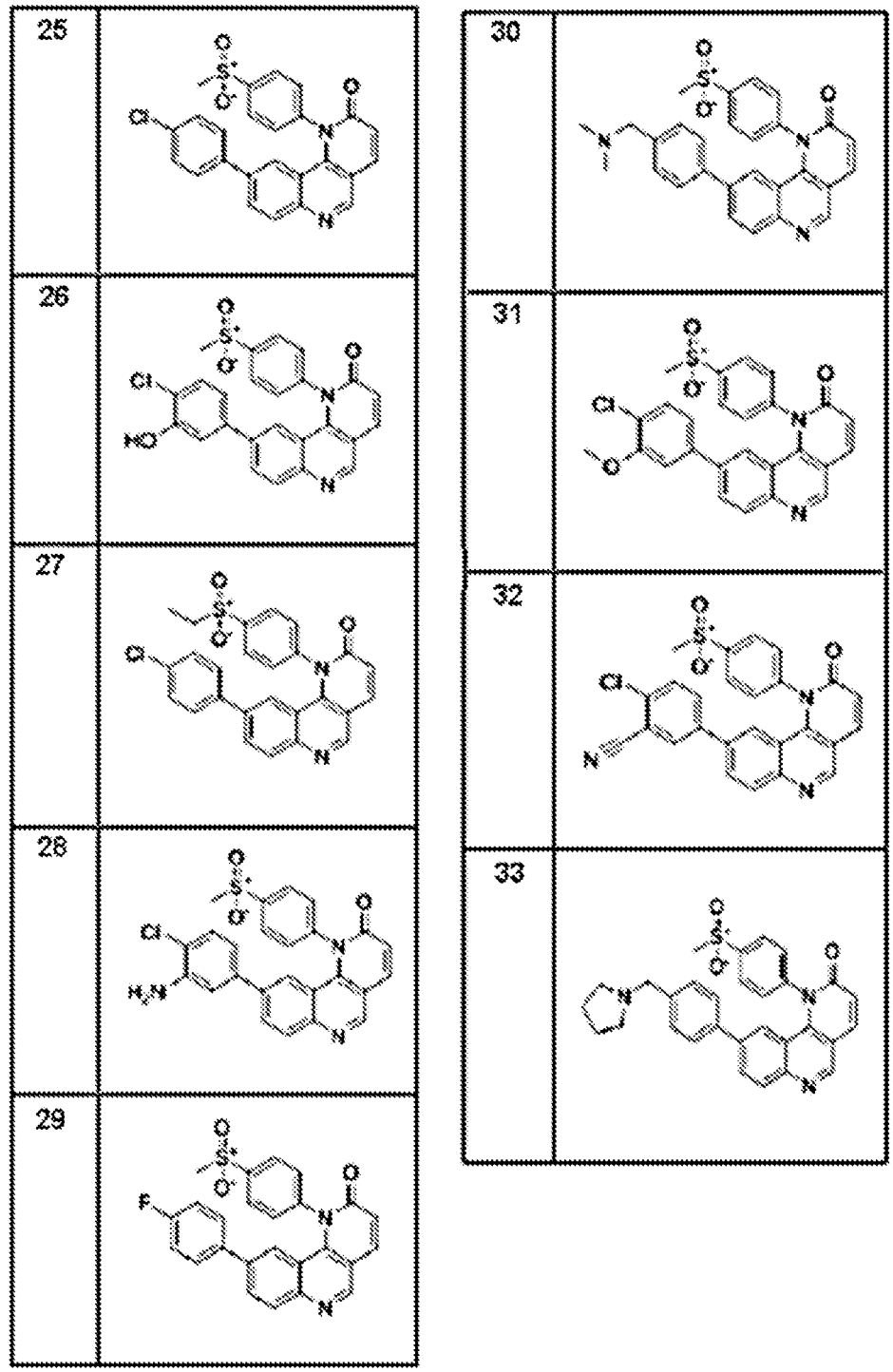
Figure 2A:
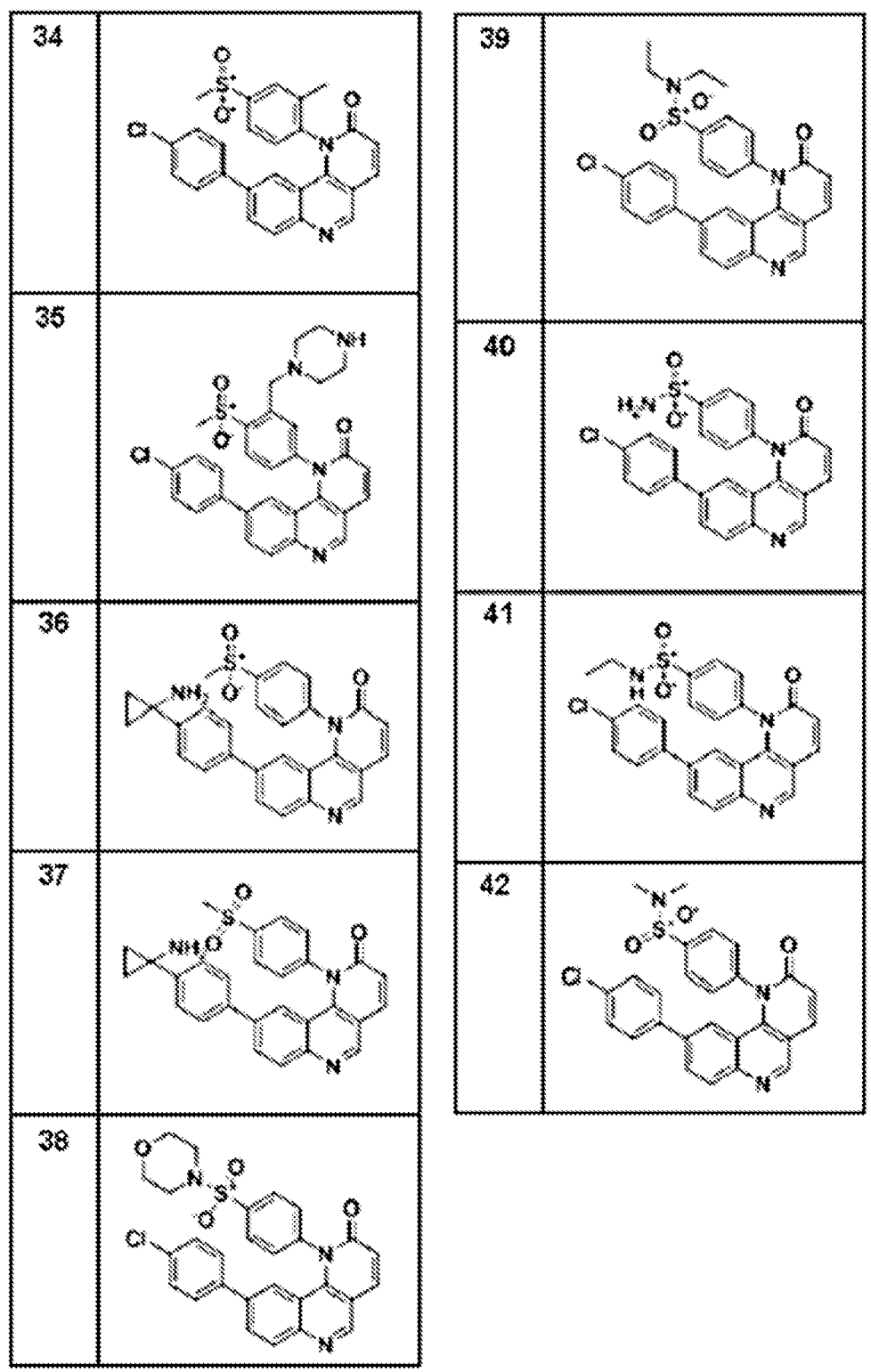
Figure 2A:
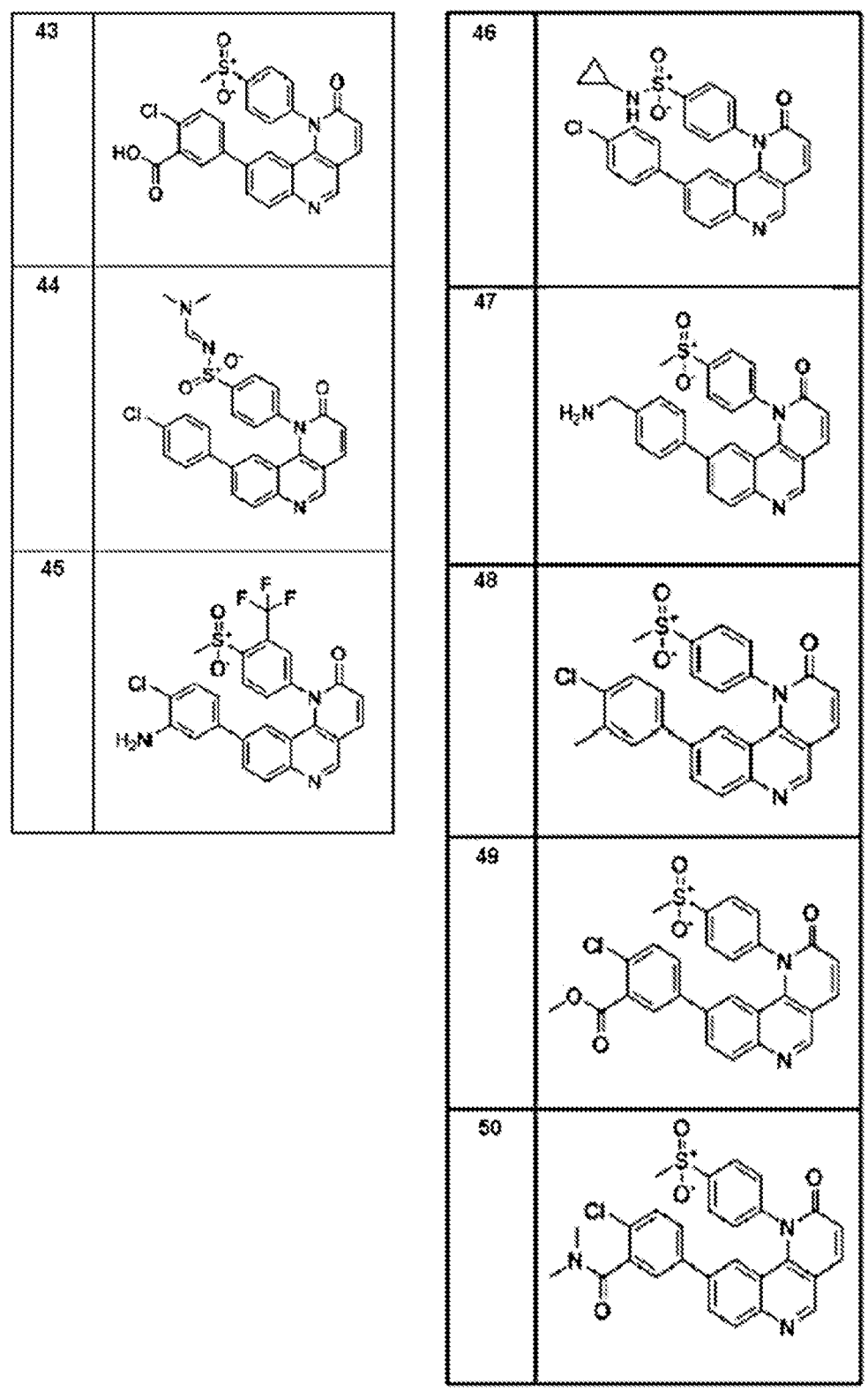
Figure 2A:
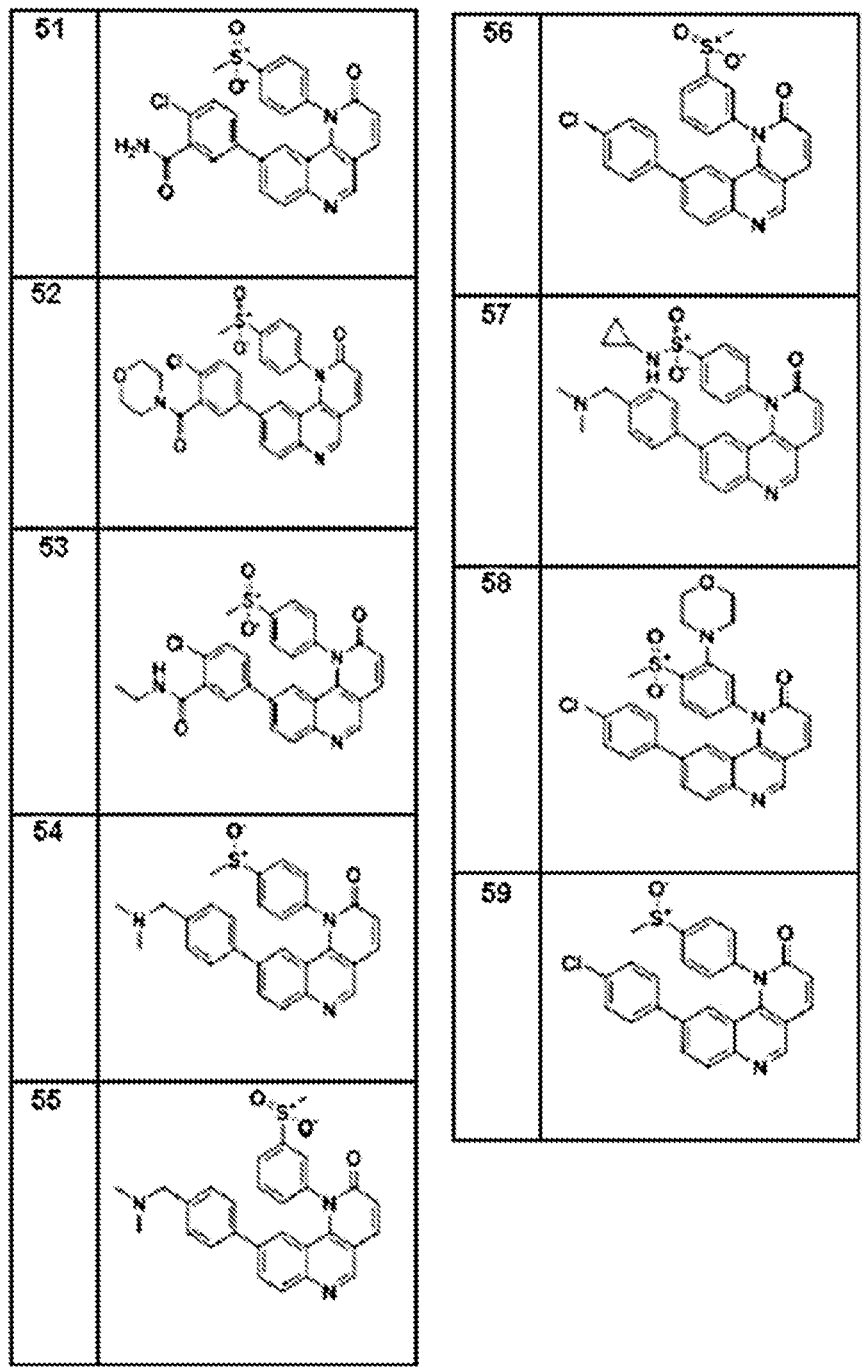
Figure 2A:
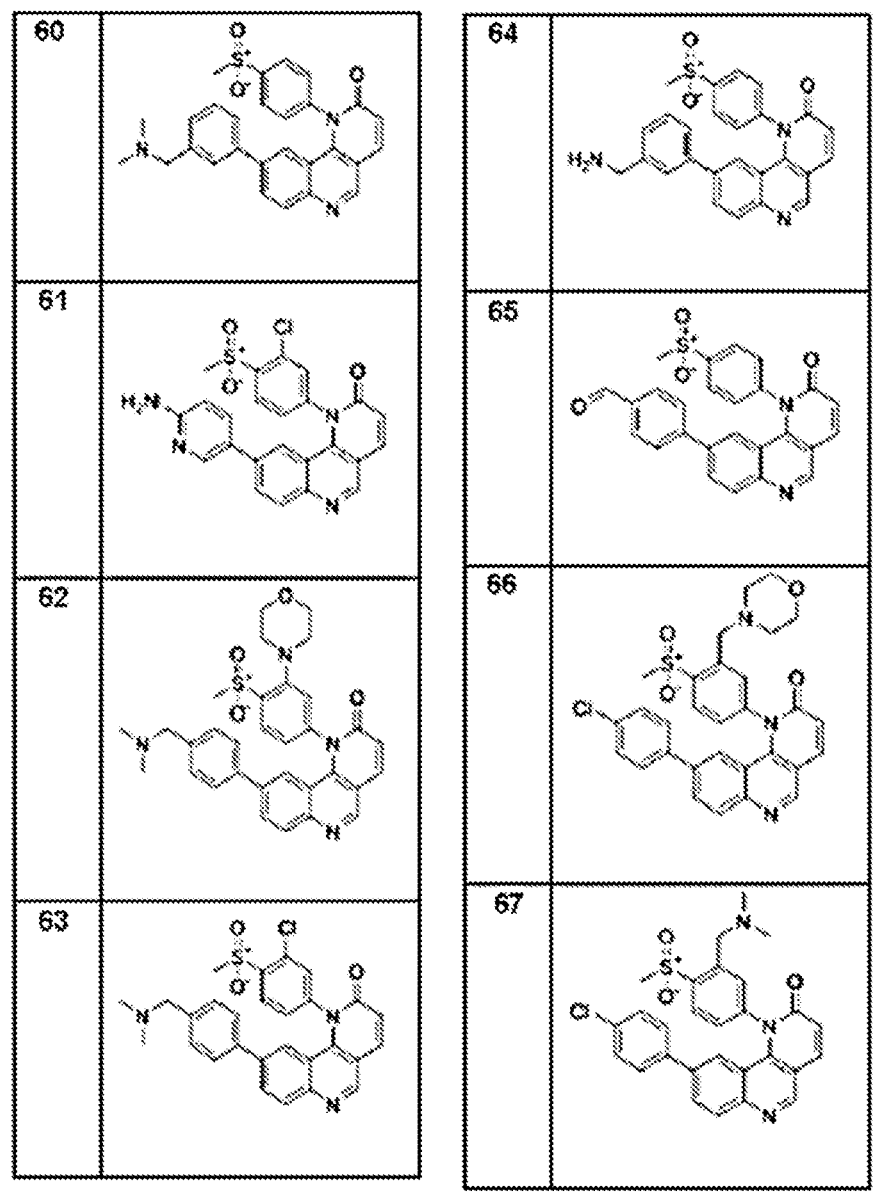
Figure 2A:
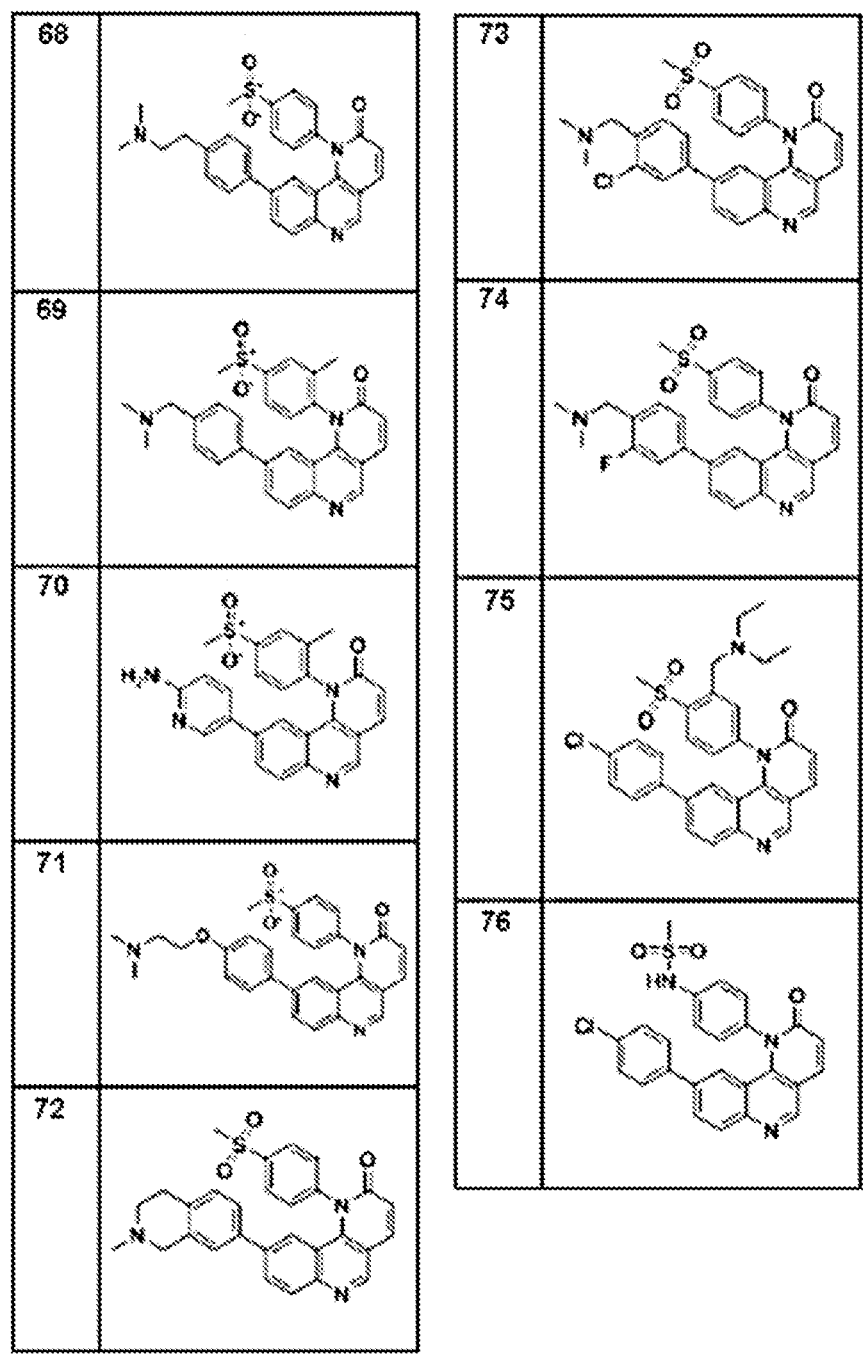
Figure 2A:
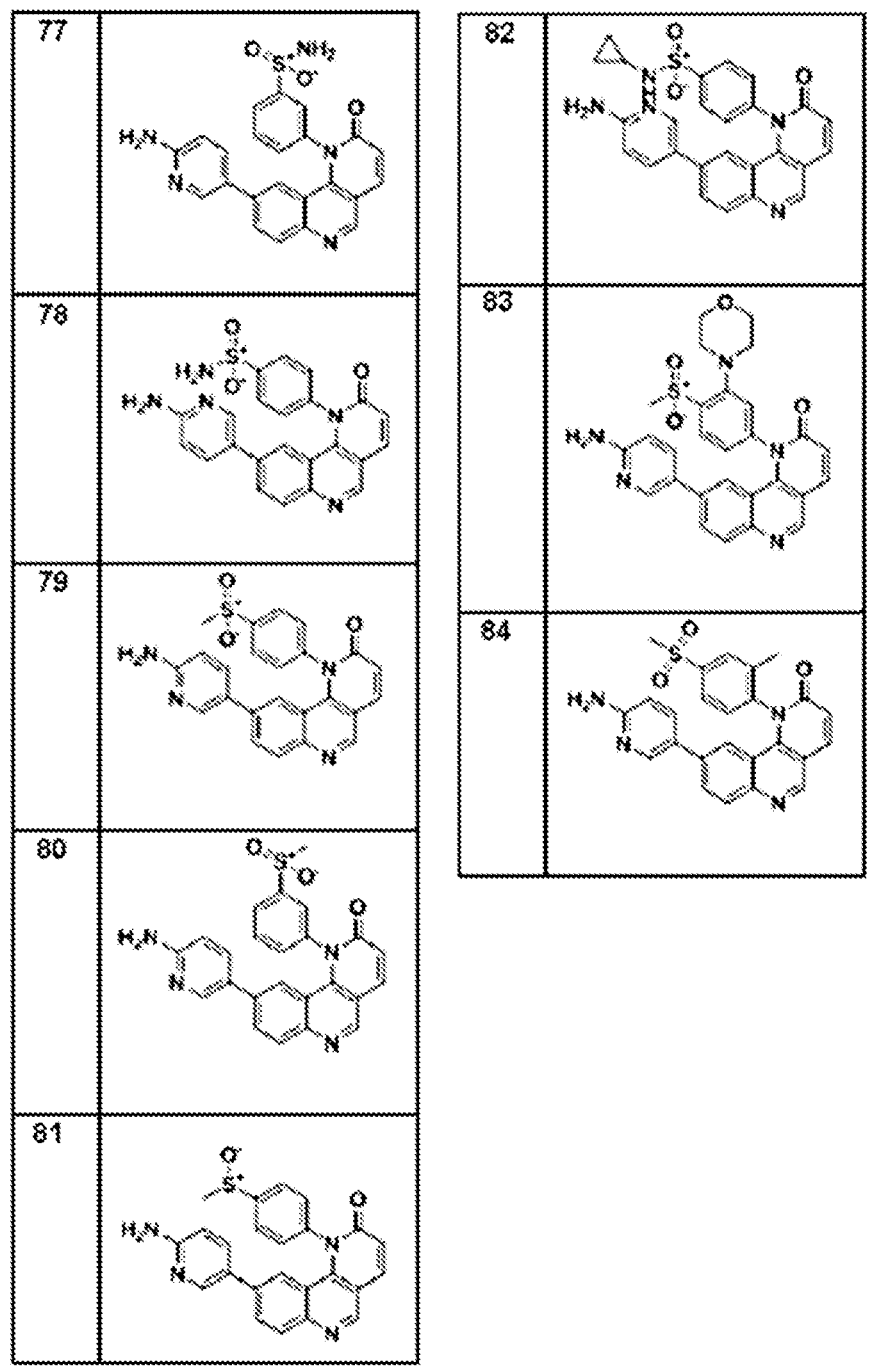
Figure 2A:
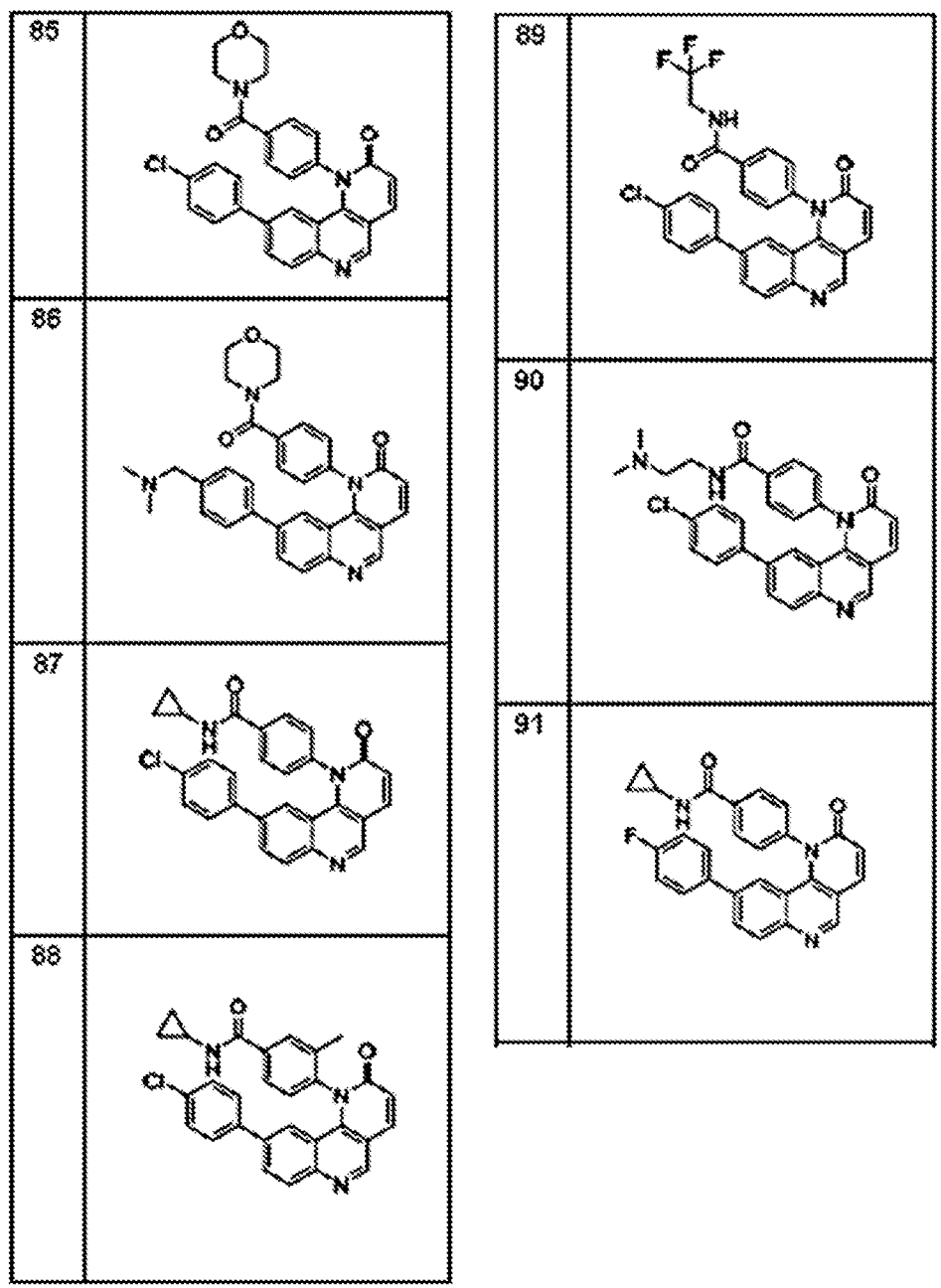
Figure 2A:
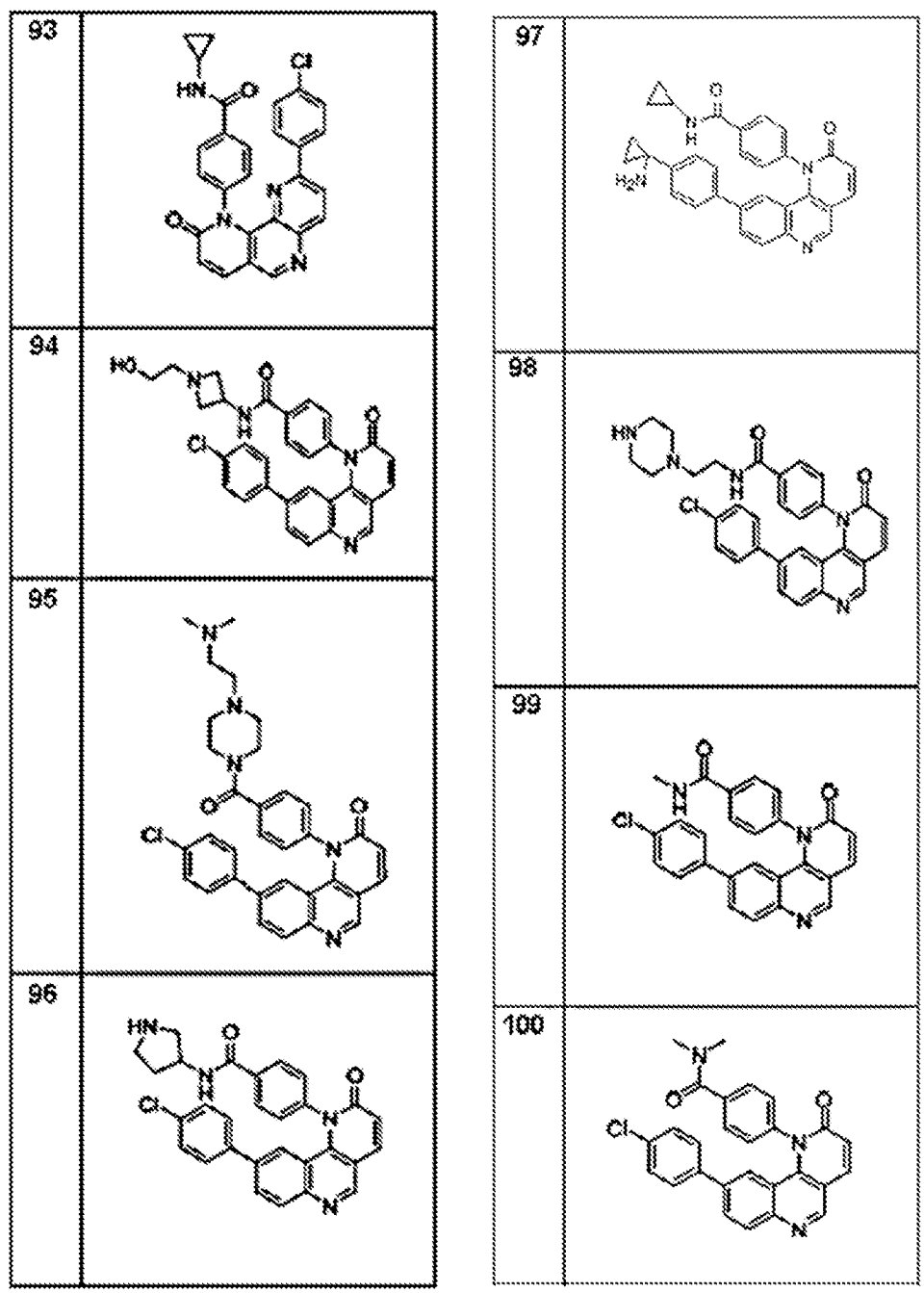
Figure 2A:
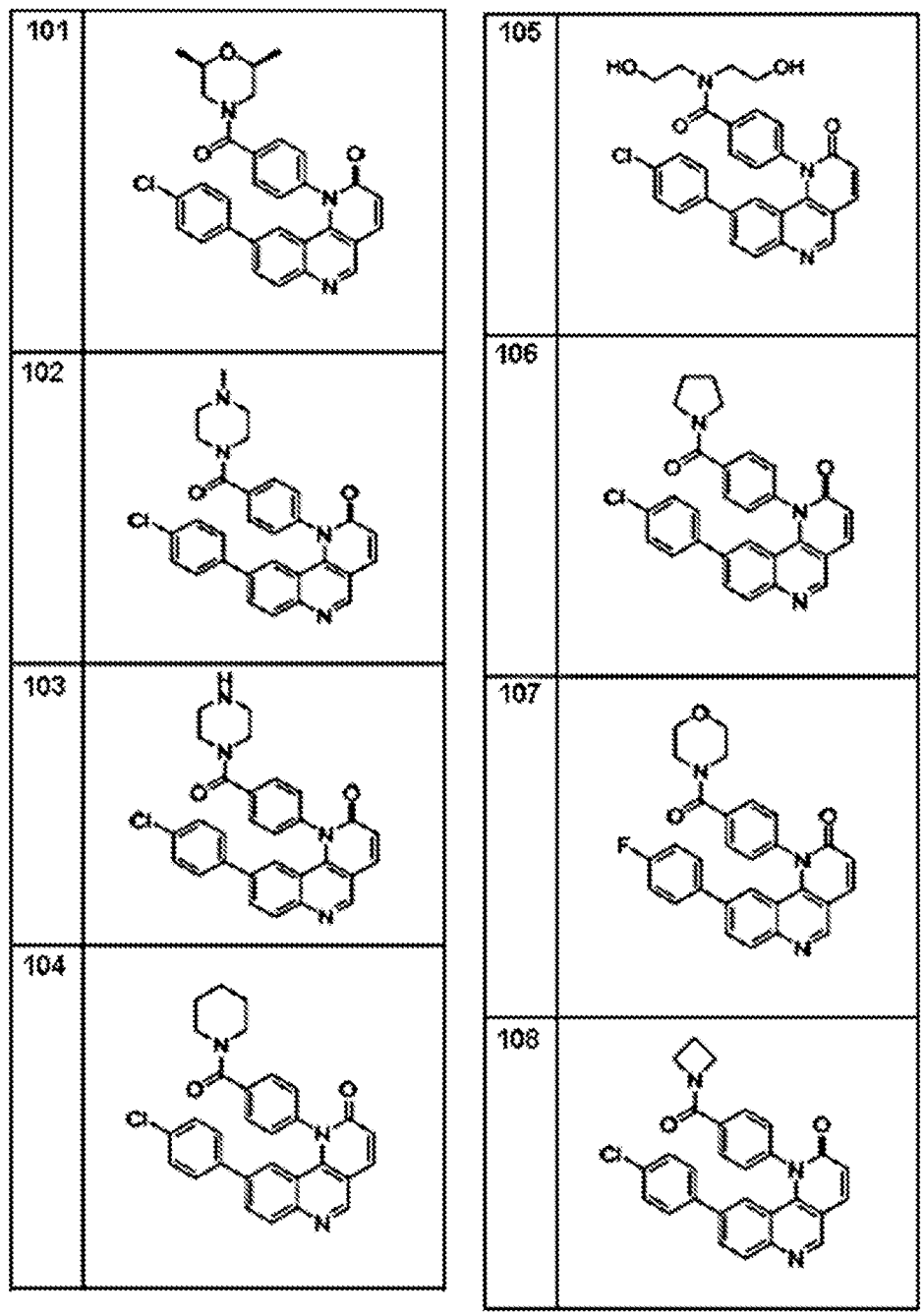
Figure 2A:
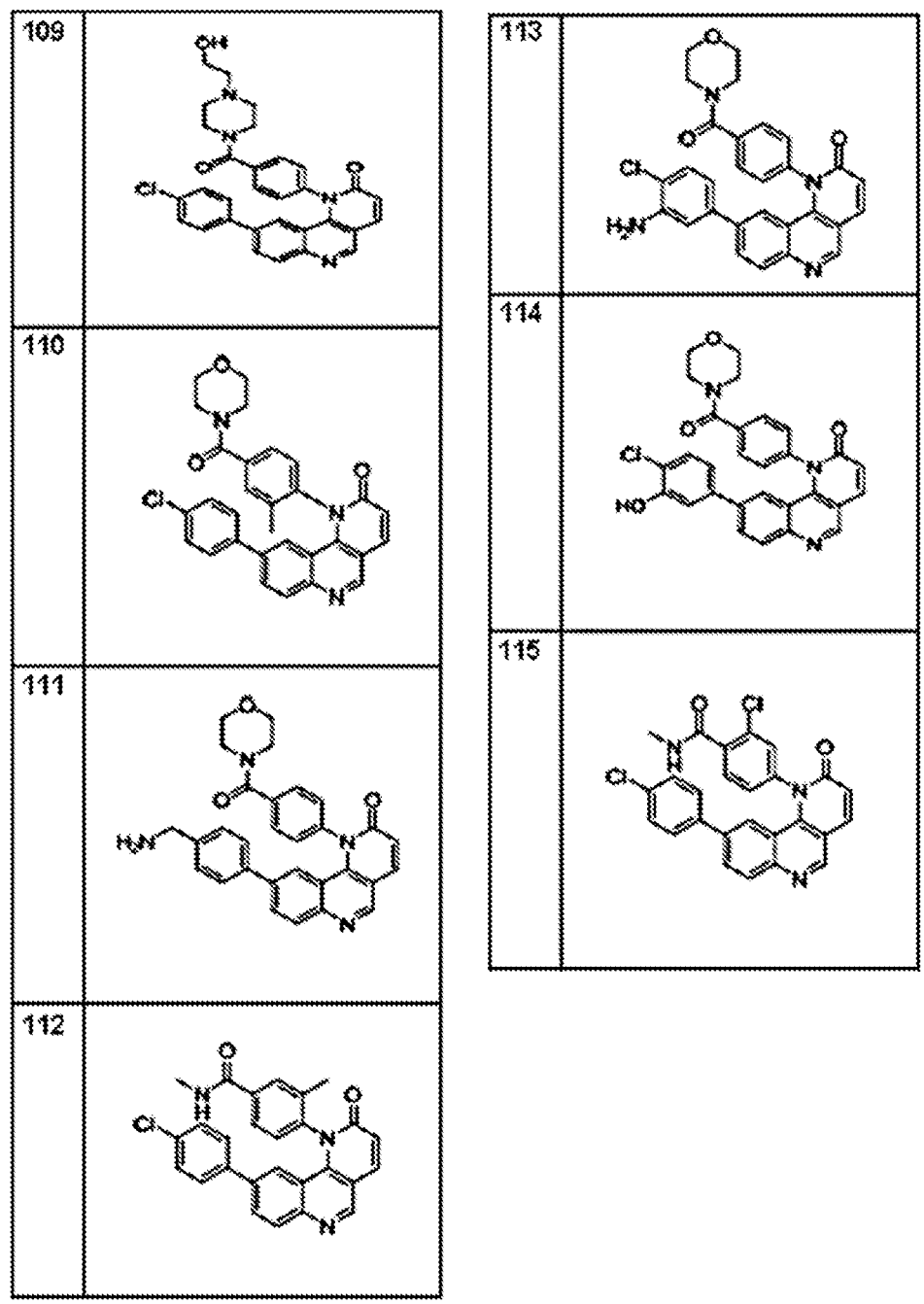
Figure 2A:
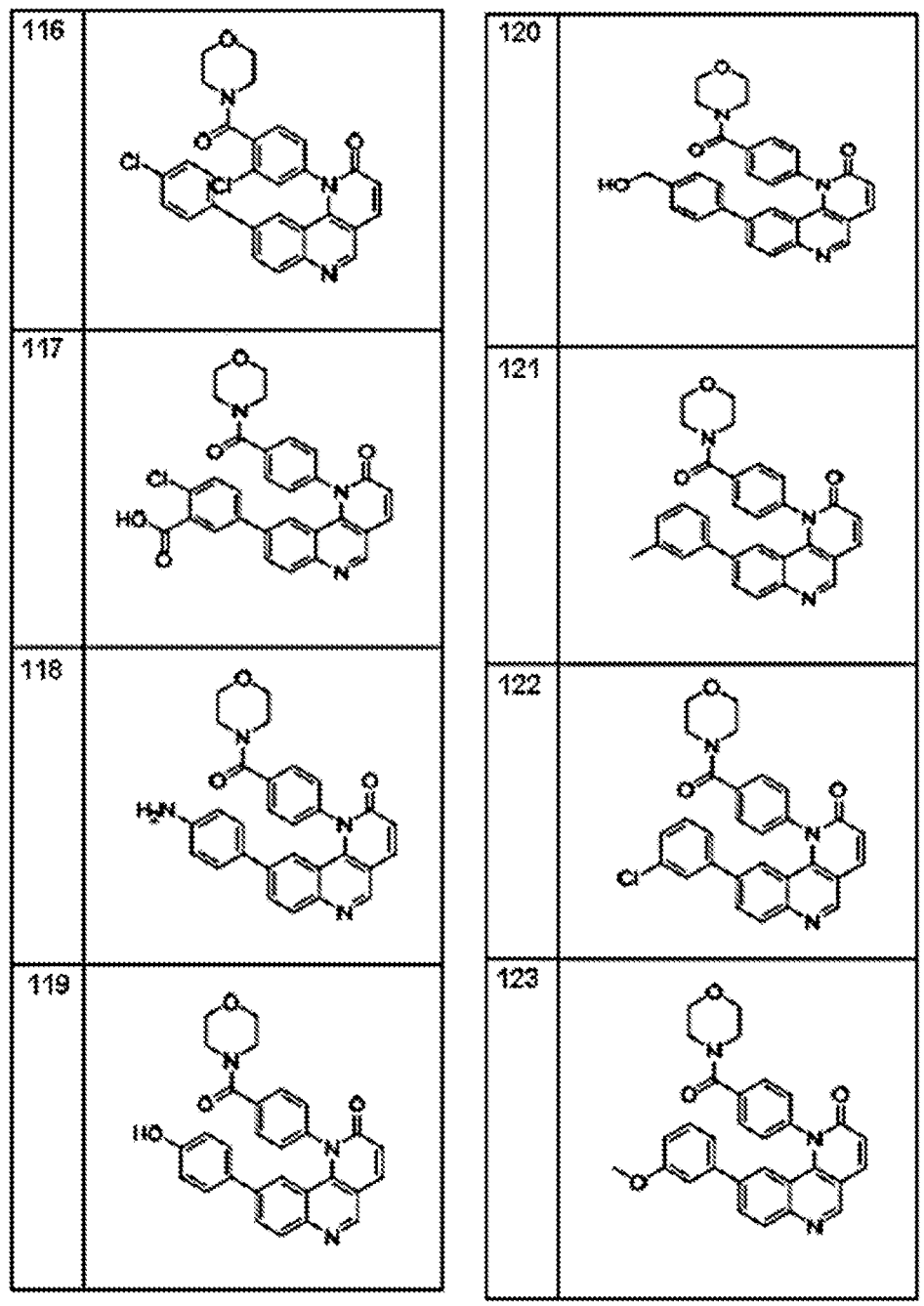
Figure 2A:
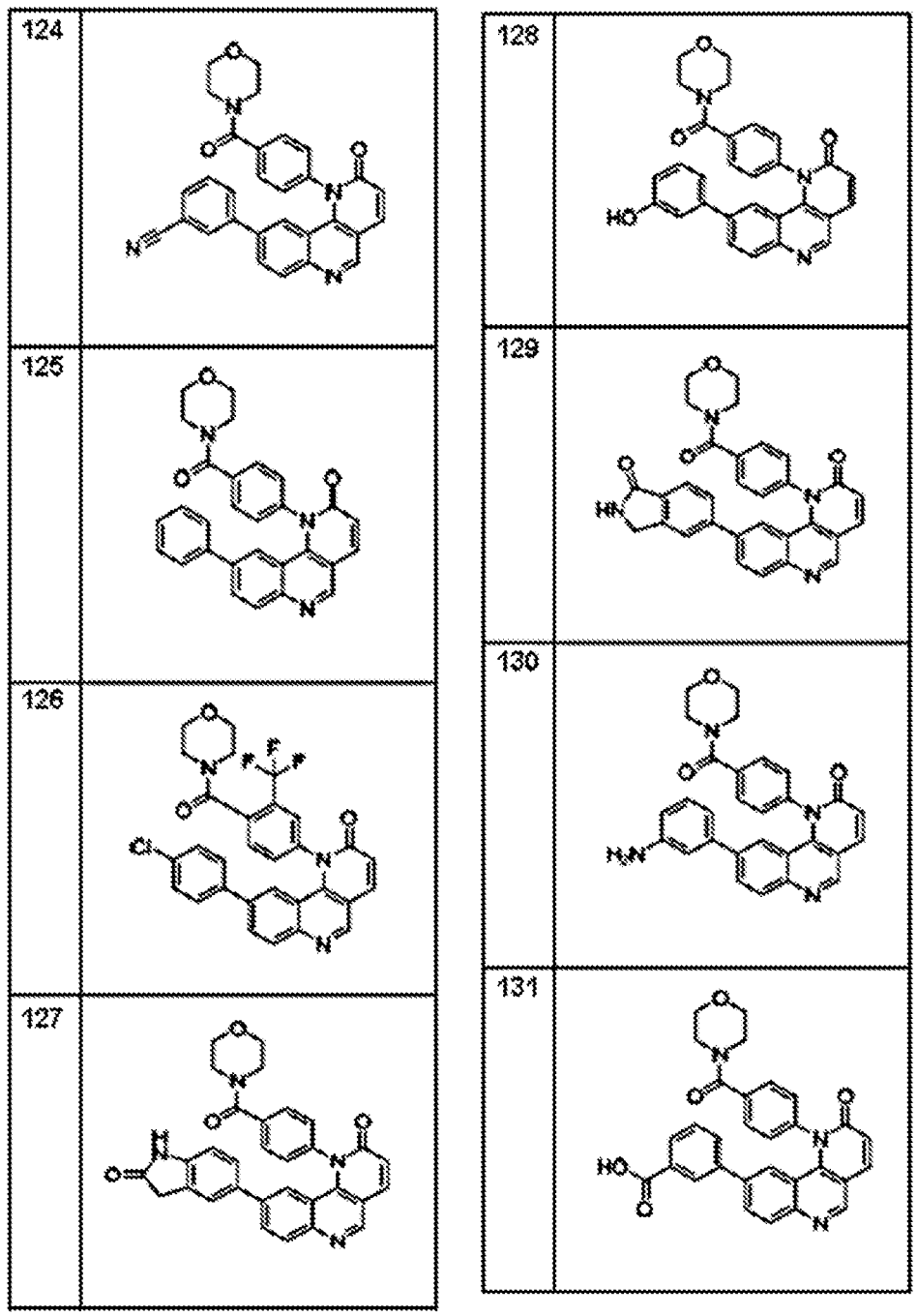
Figure 2A:
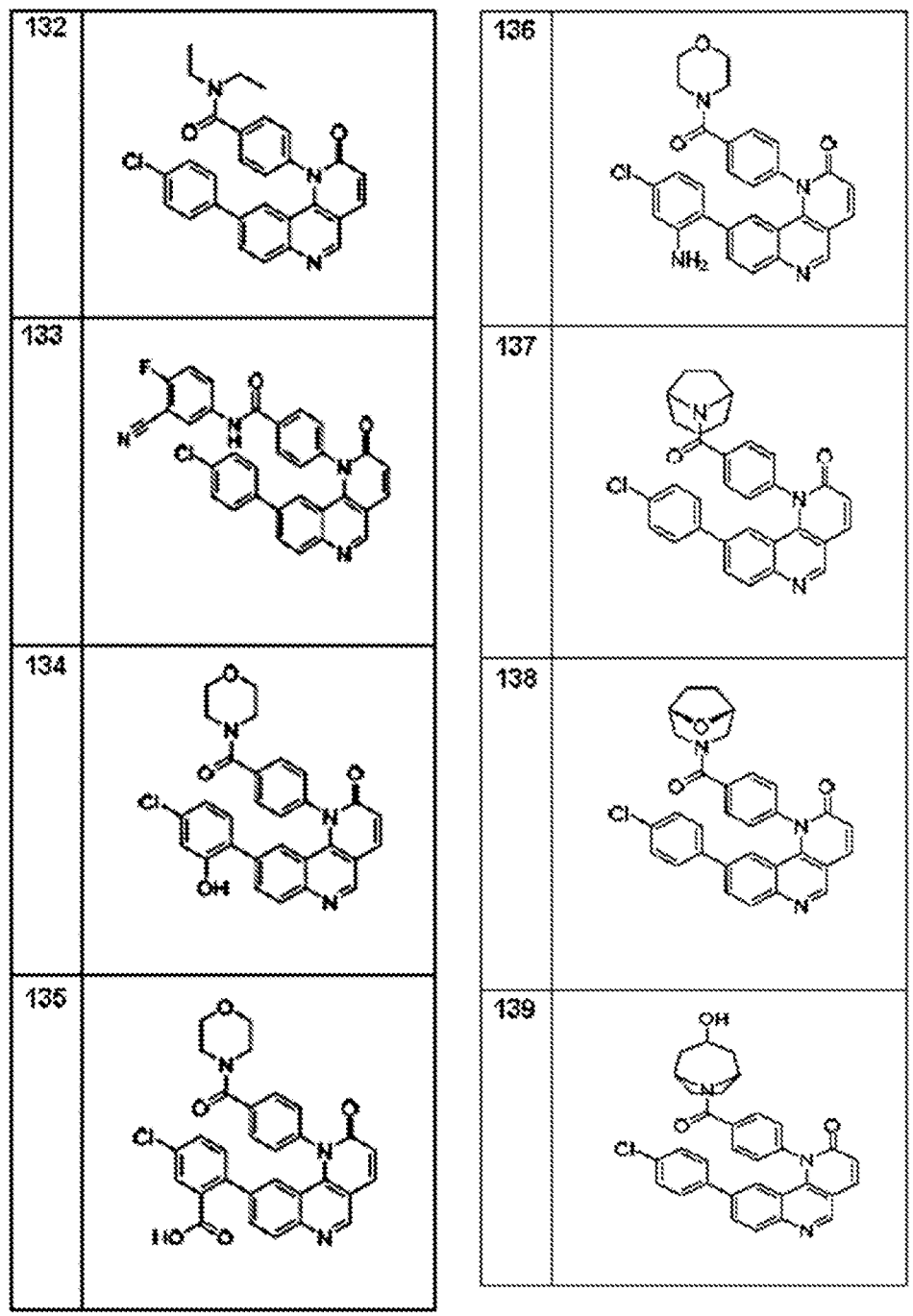
Figure 2A:
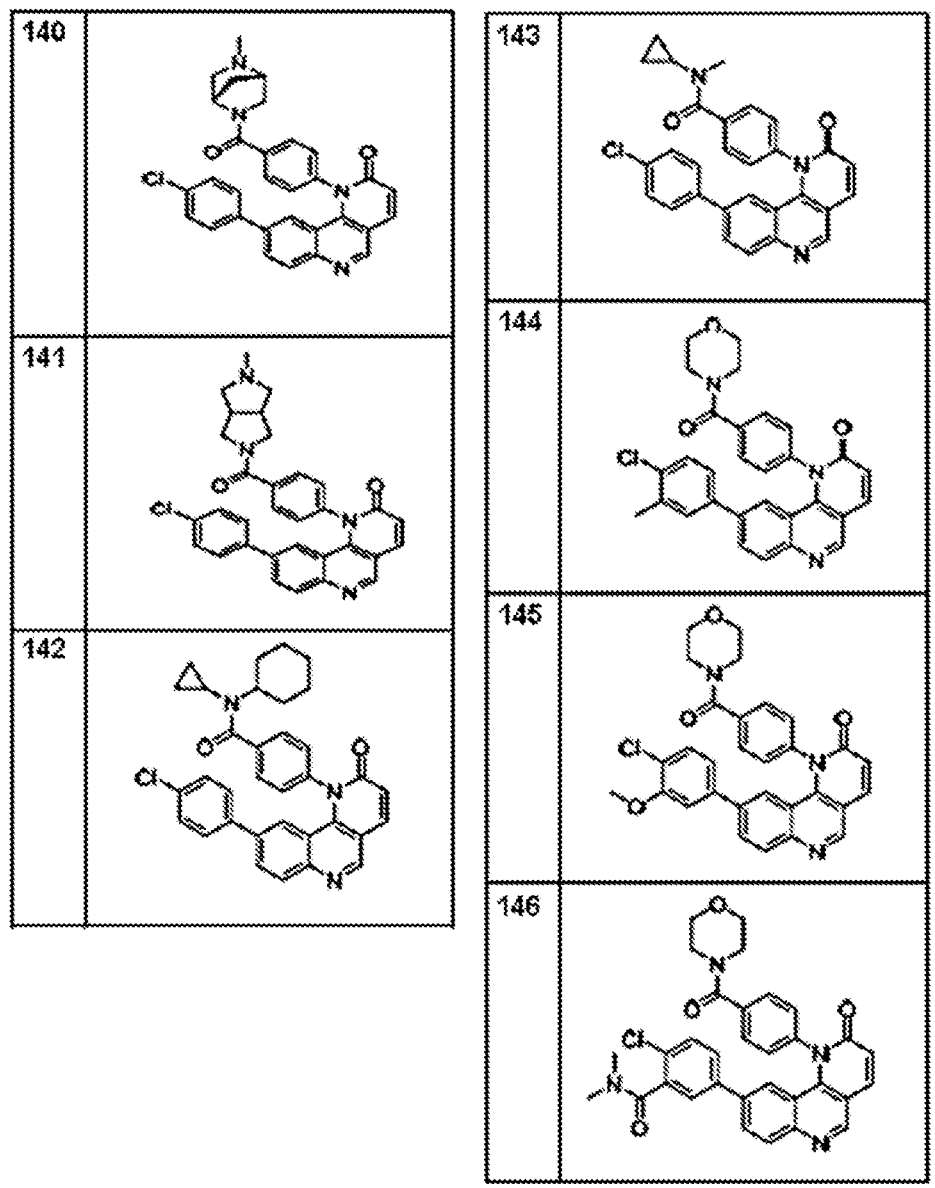
Figure 2A:
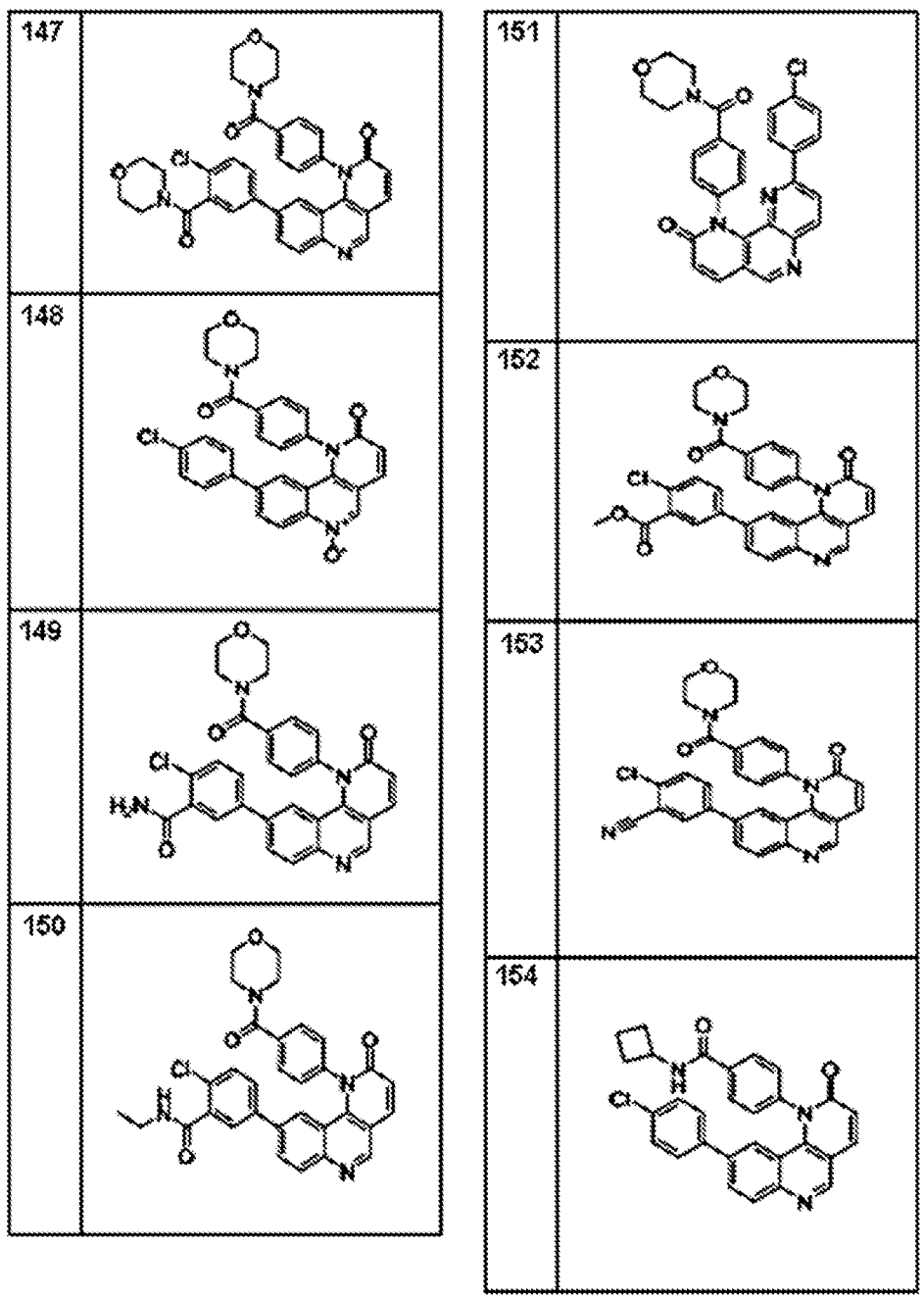
Figure 2A:
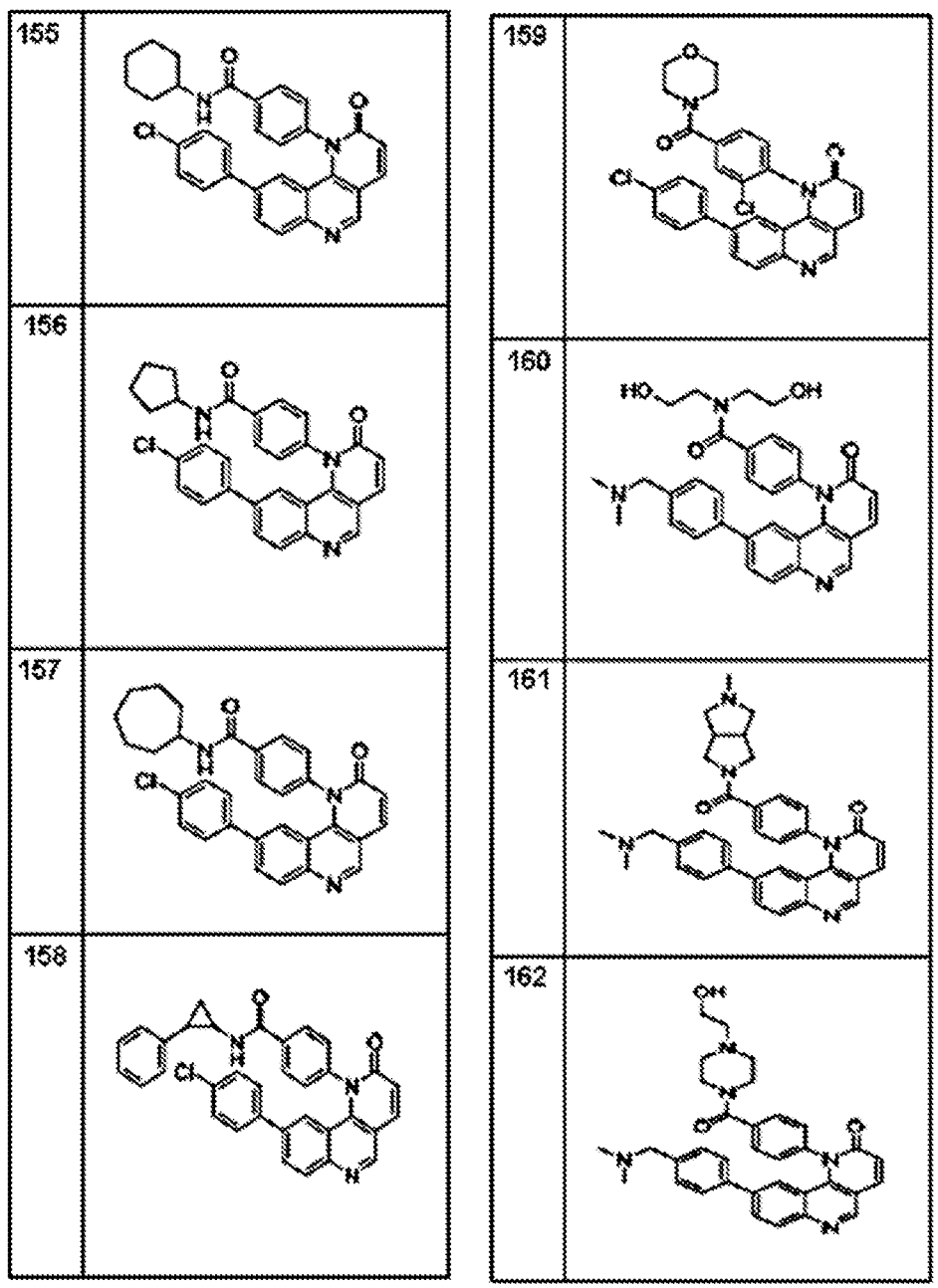
Figure 2A:
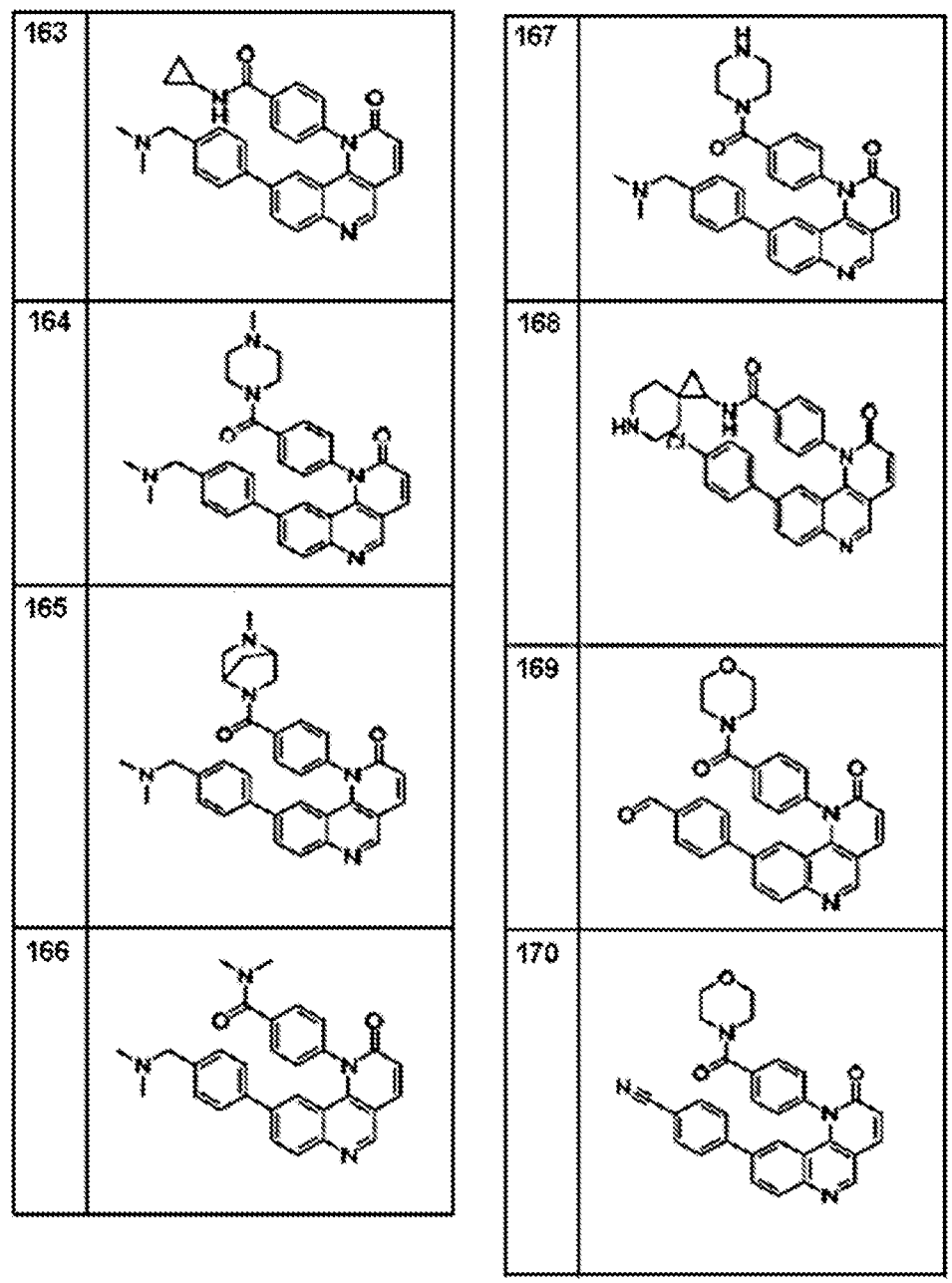
Figure 2A:
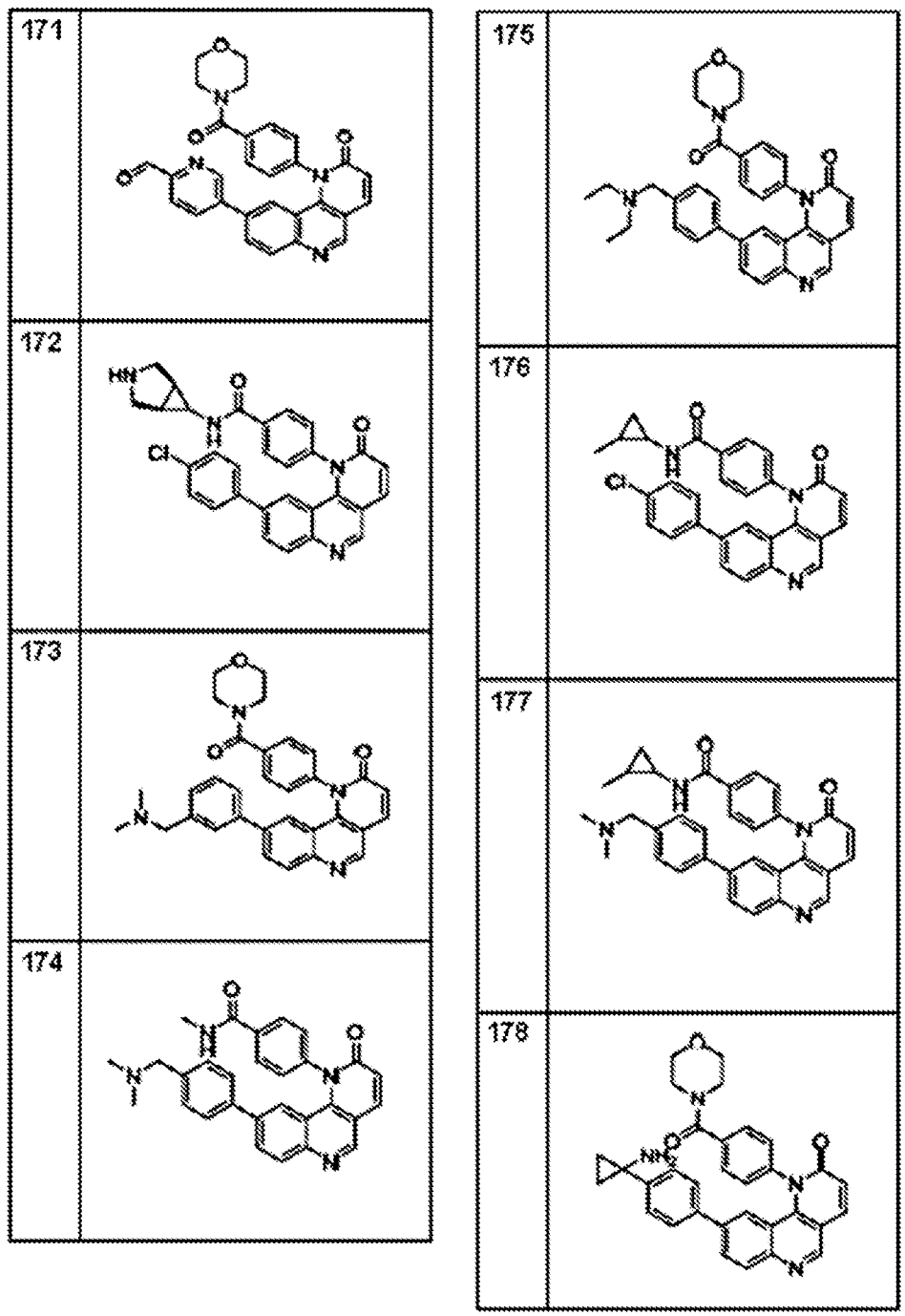
Figure 2A:
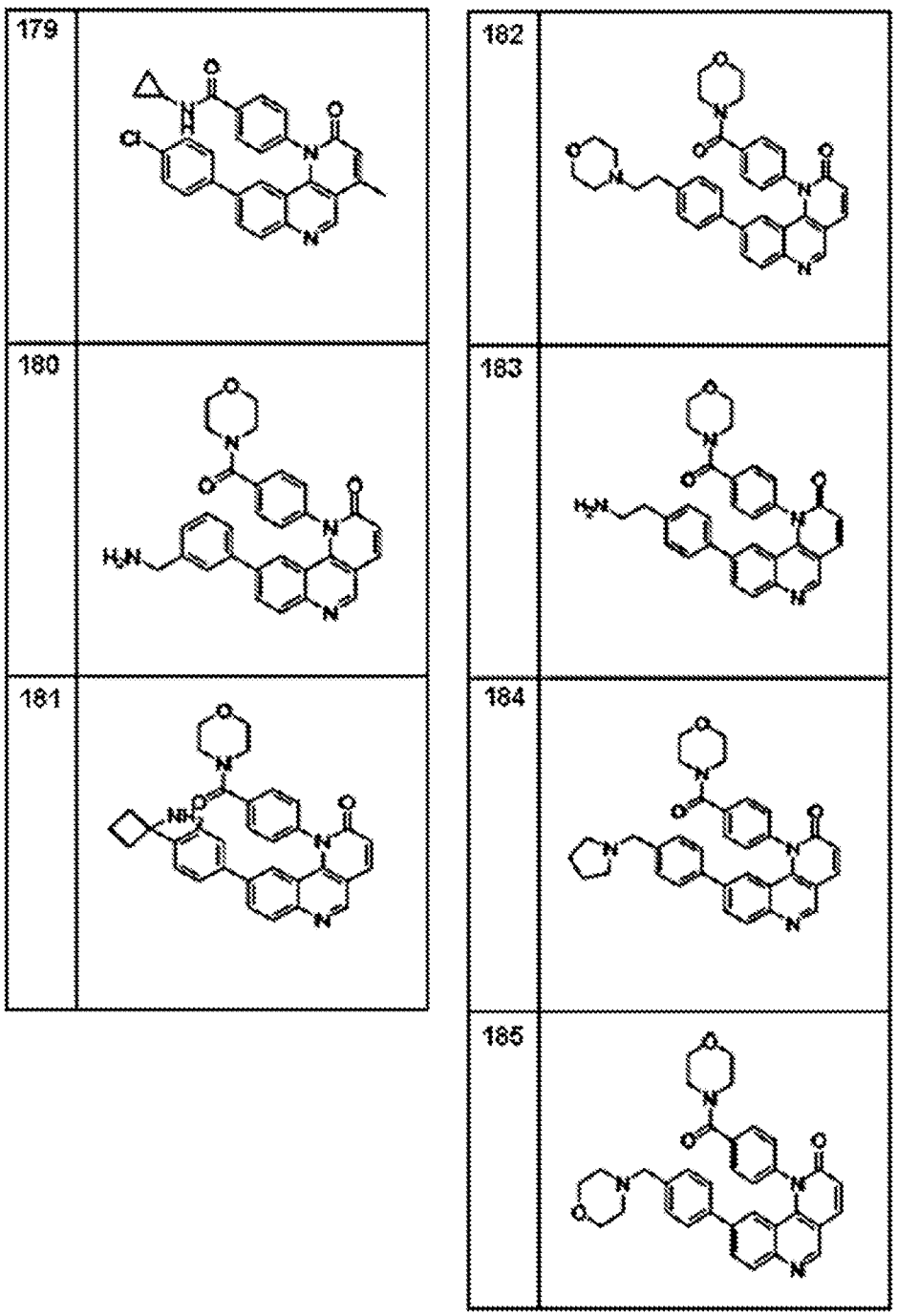
Figure 2A:
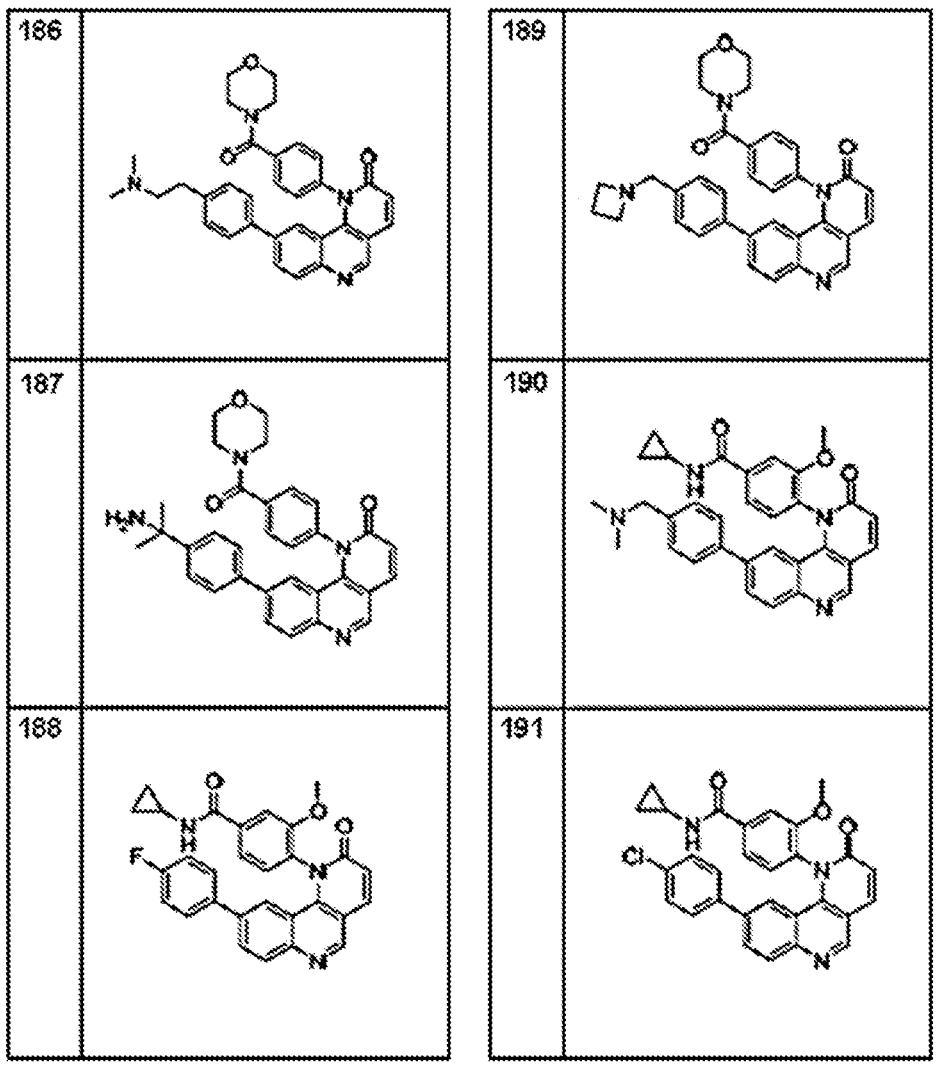
Figure 2A:
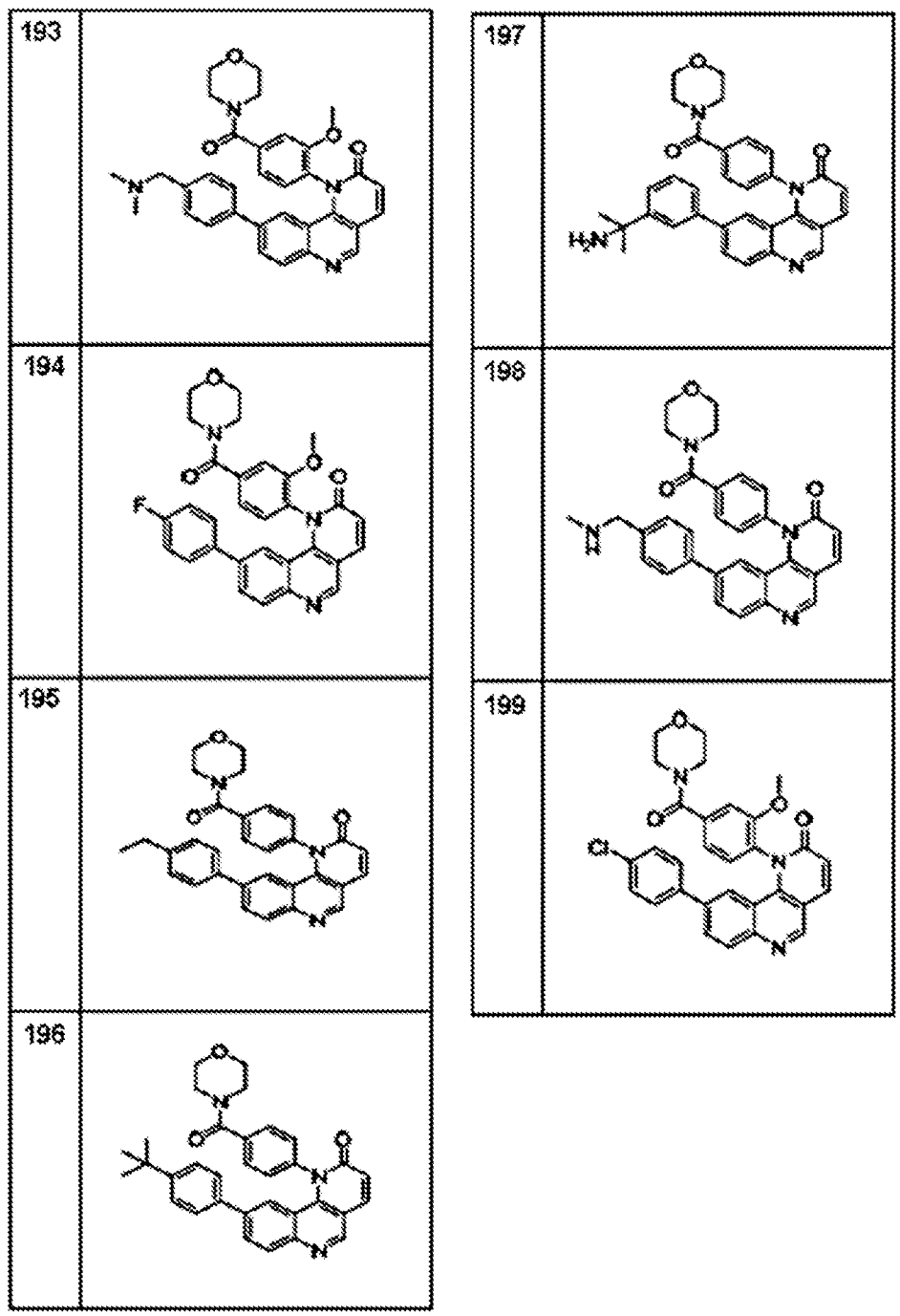
Figure 2A:
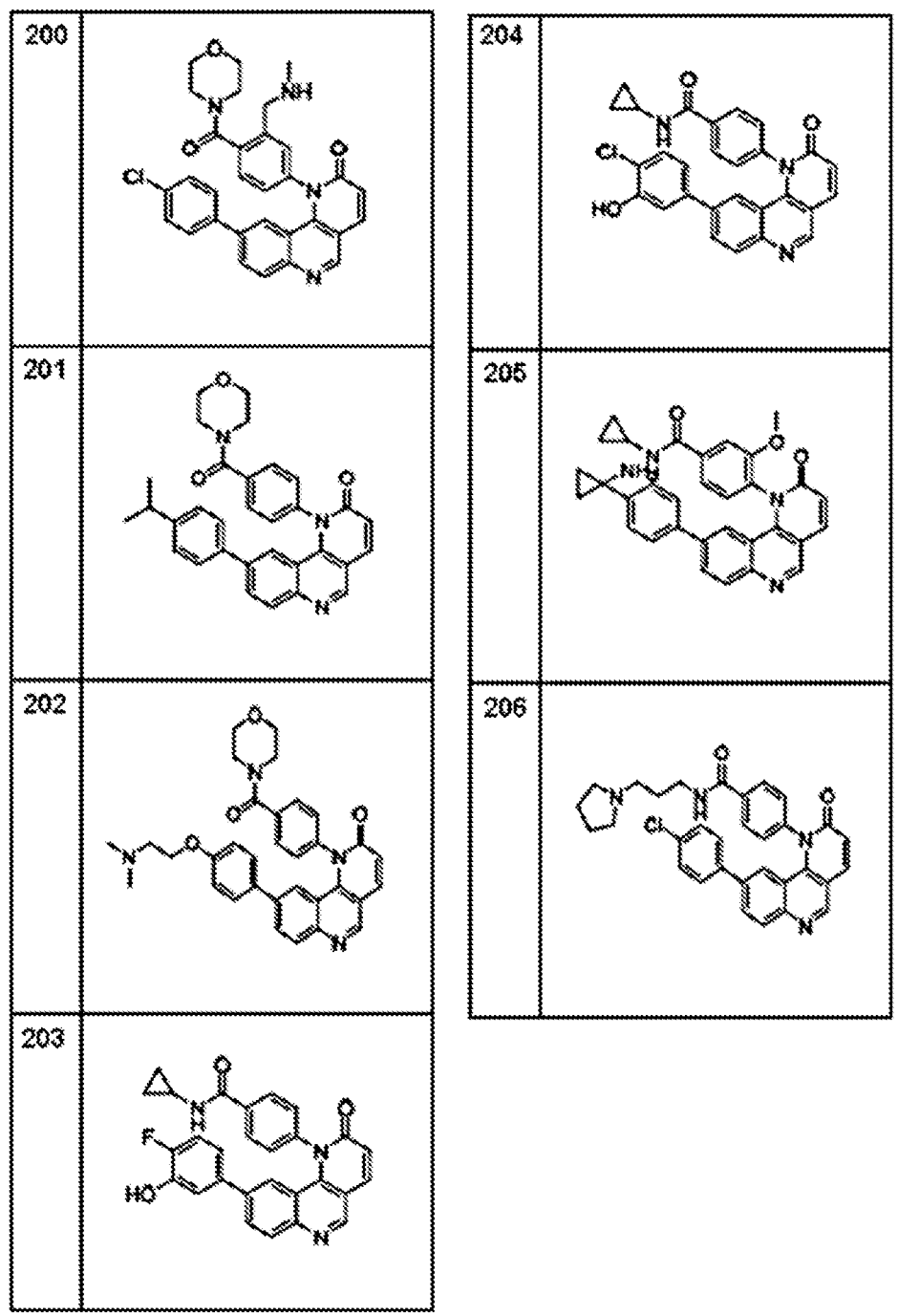
Figure 2B:
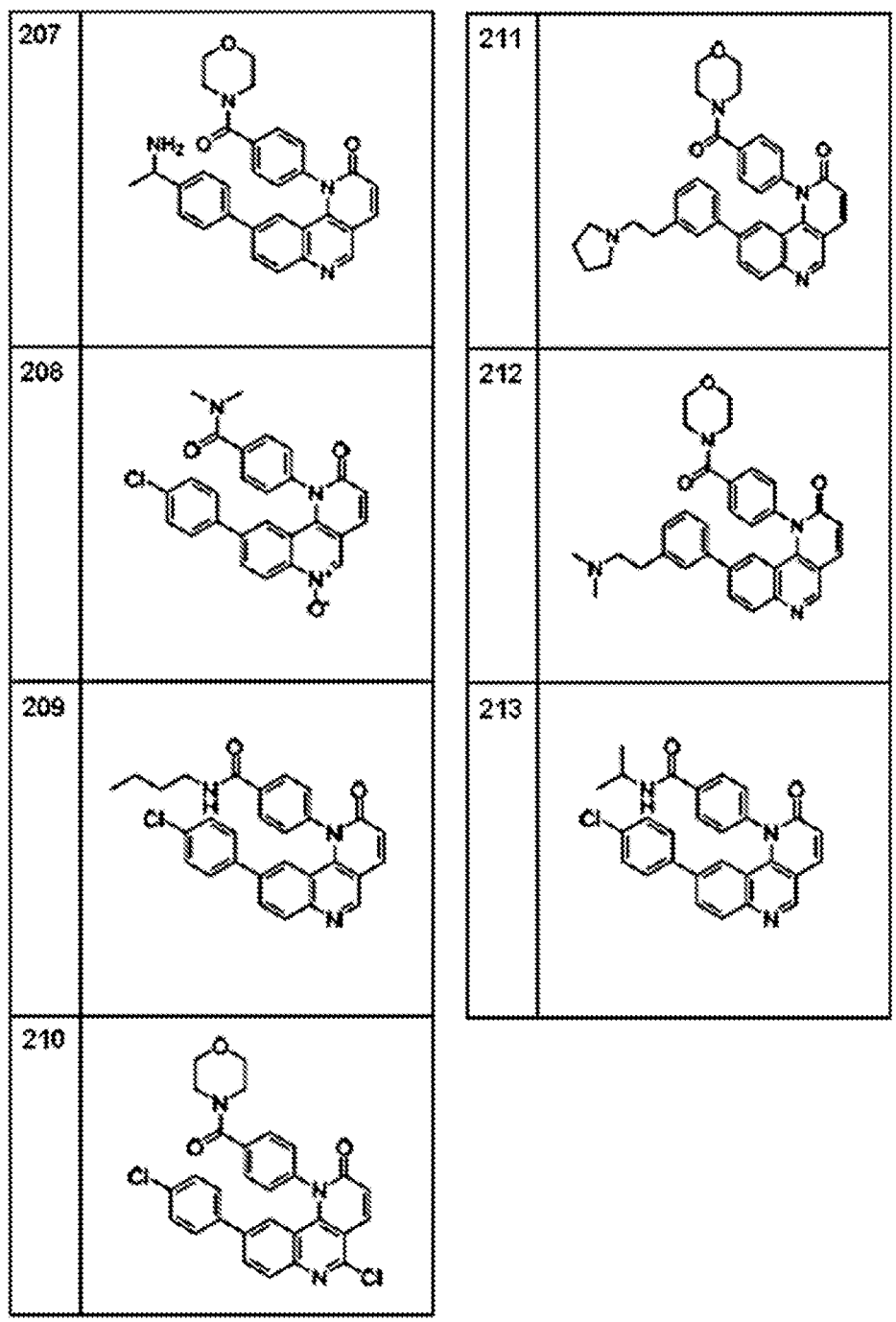
Figure 2B:
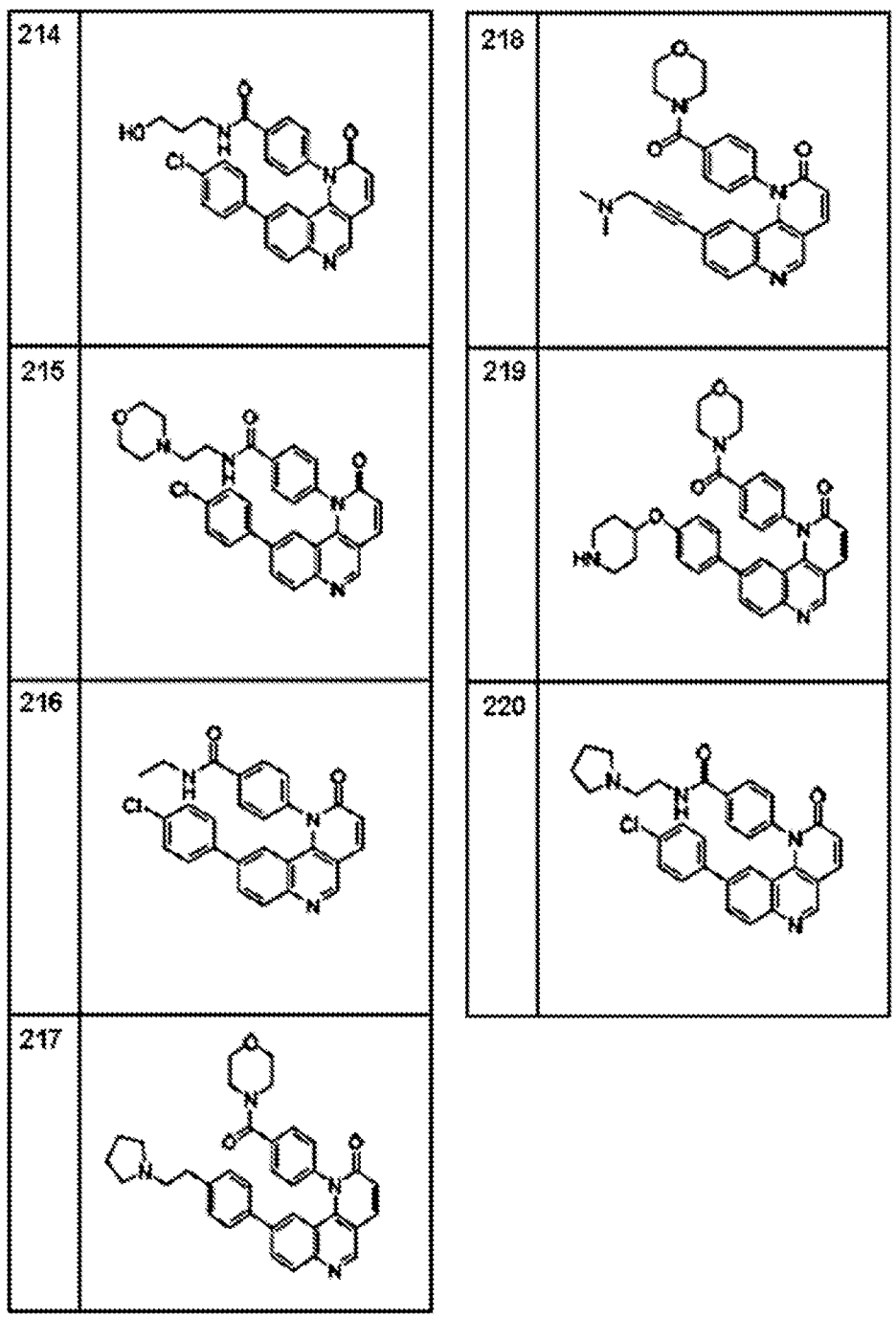
Figure 2B:
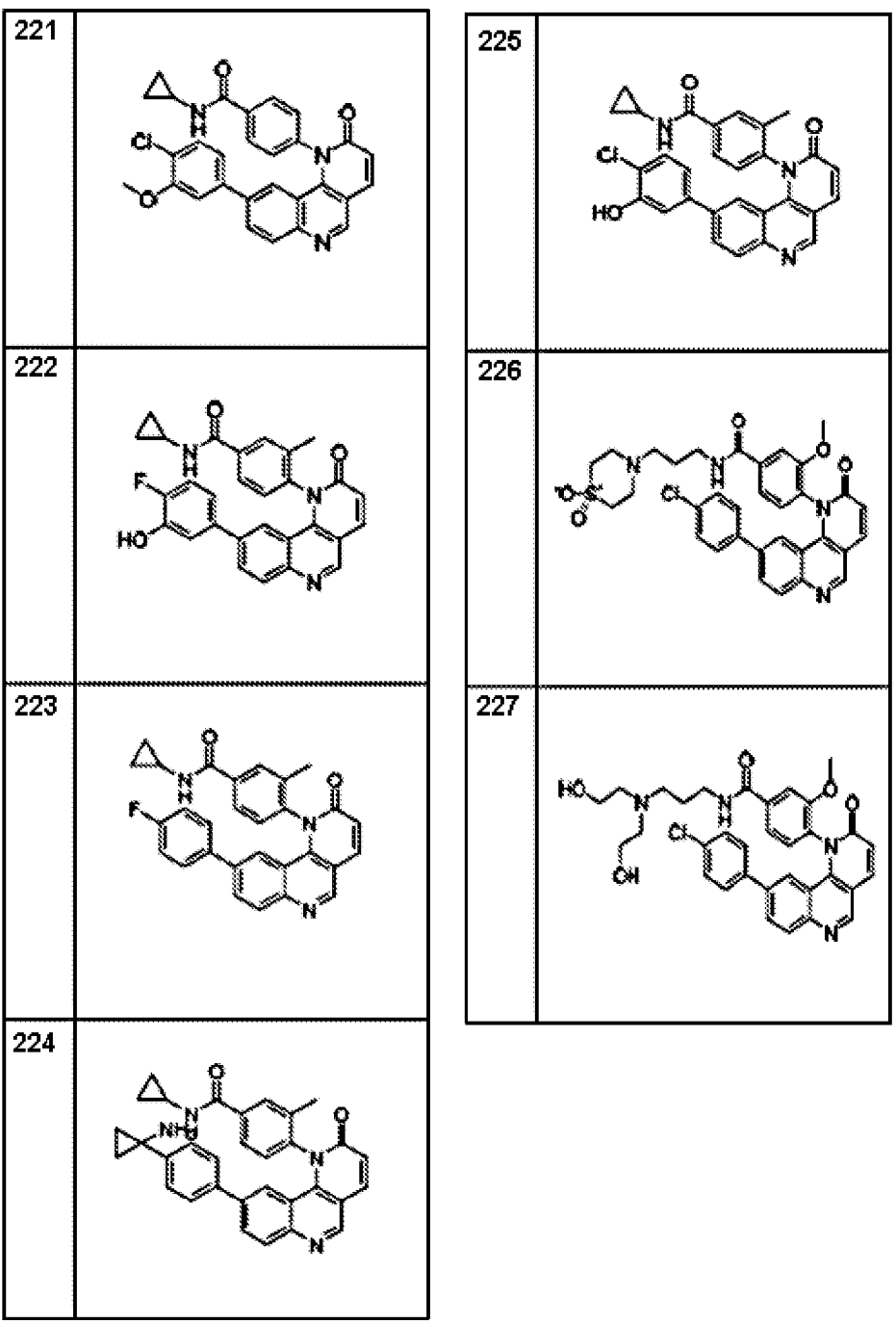
Figure 2B:
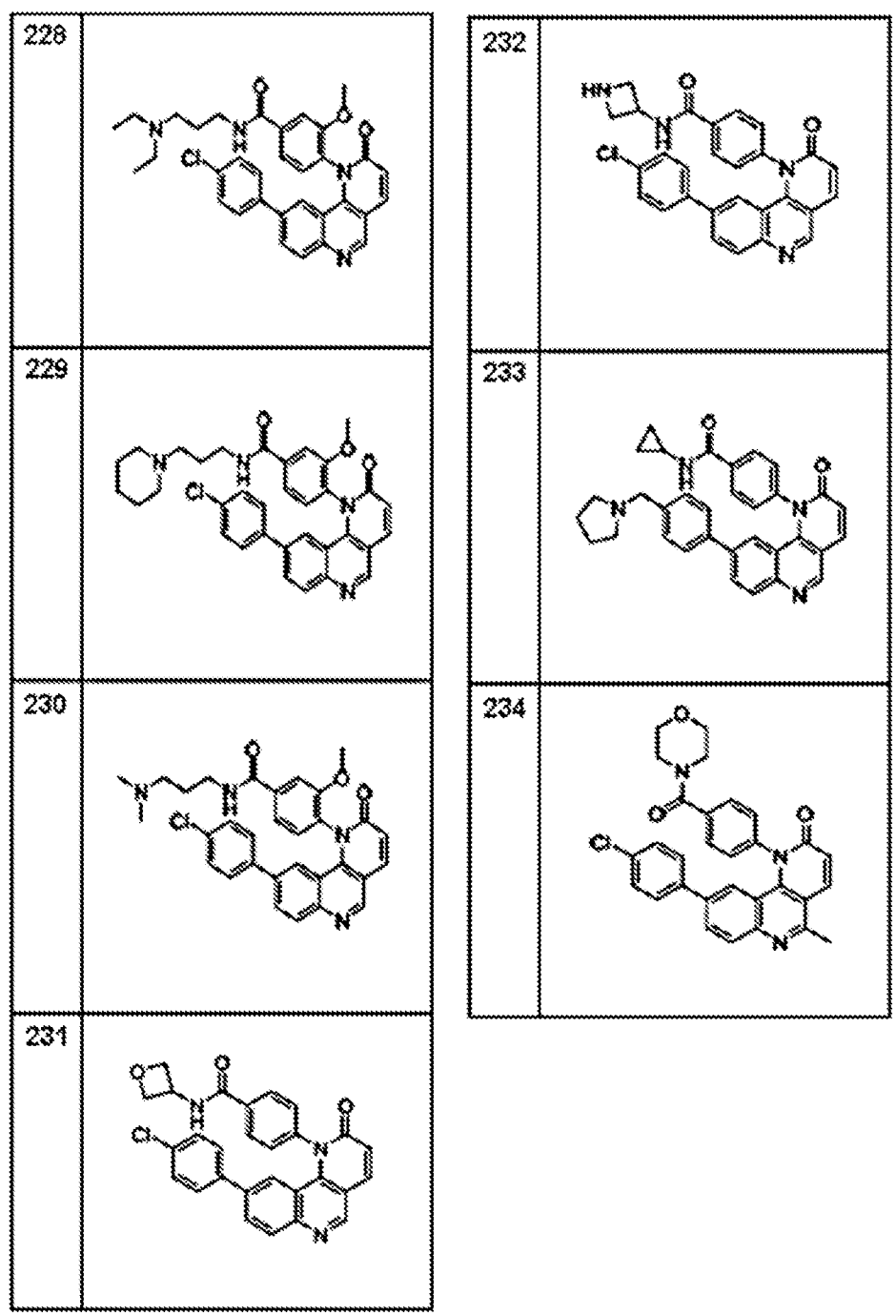
Figure 2B:
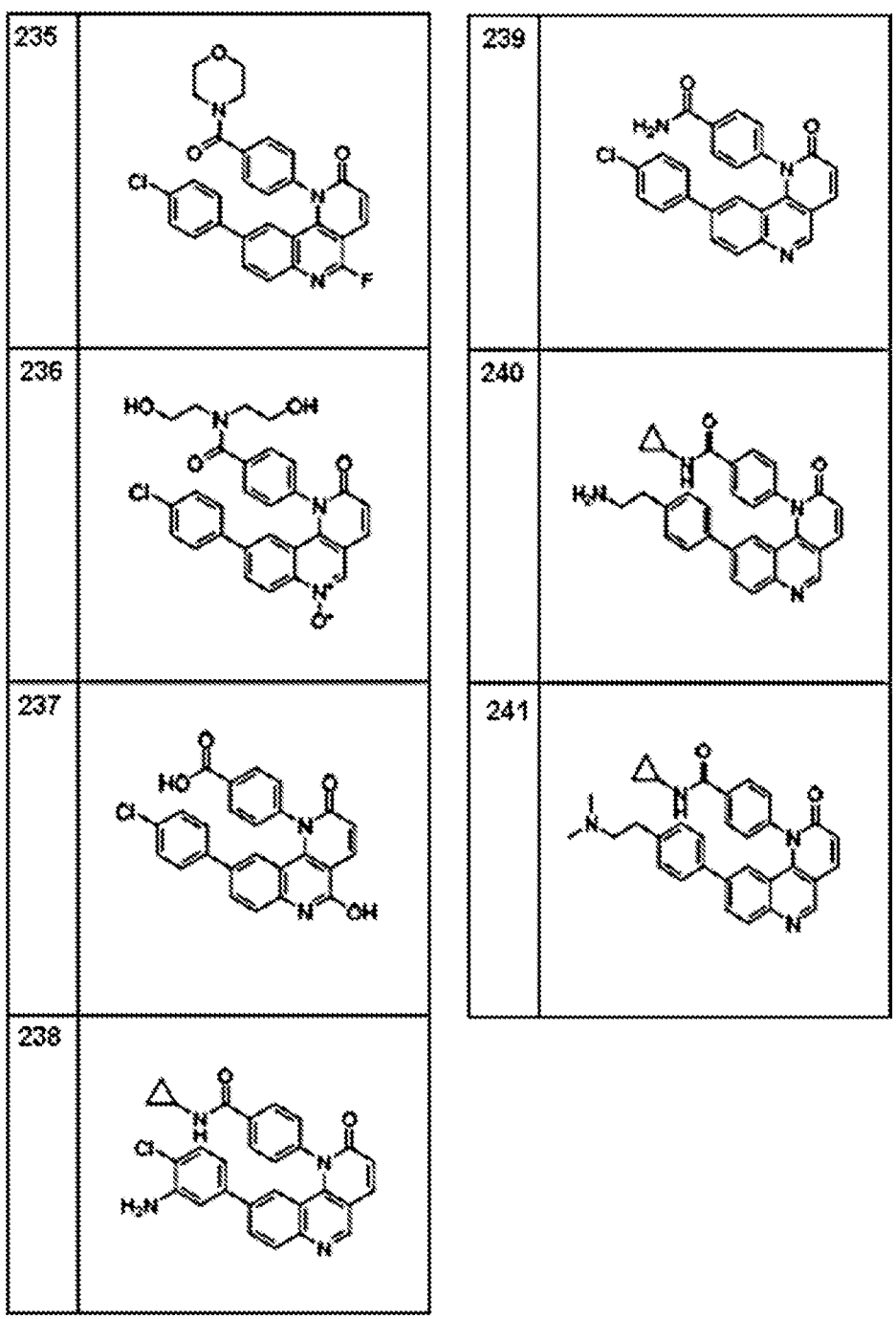
Figure 2B:
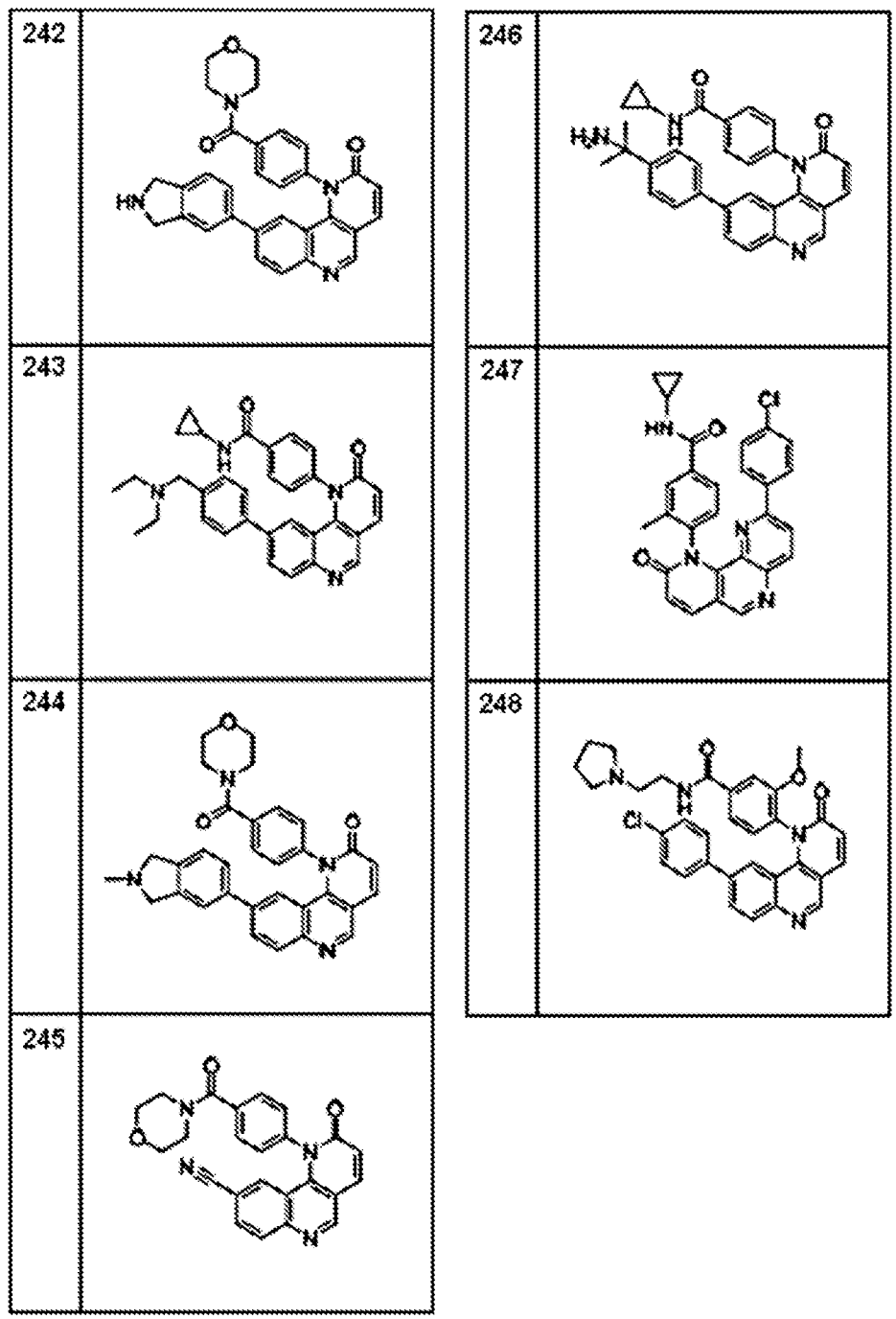
Figure 2B:
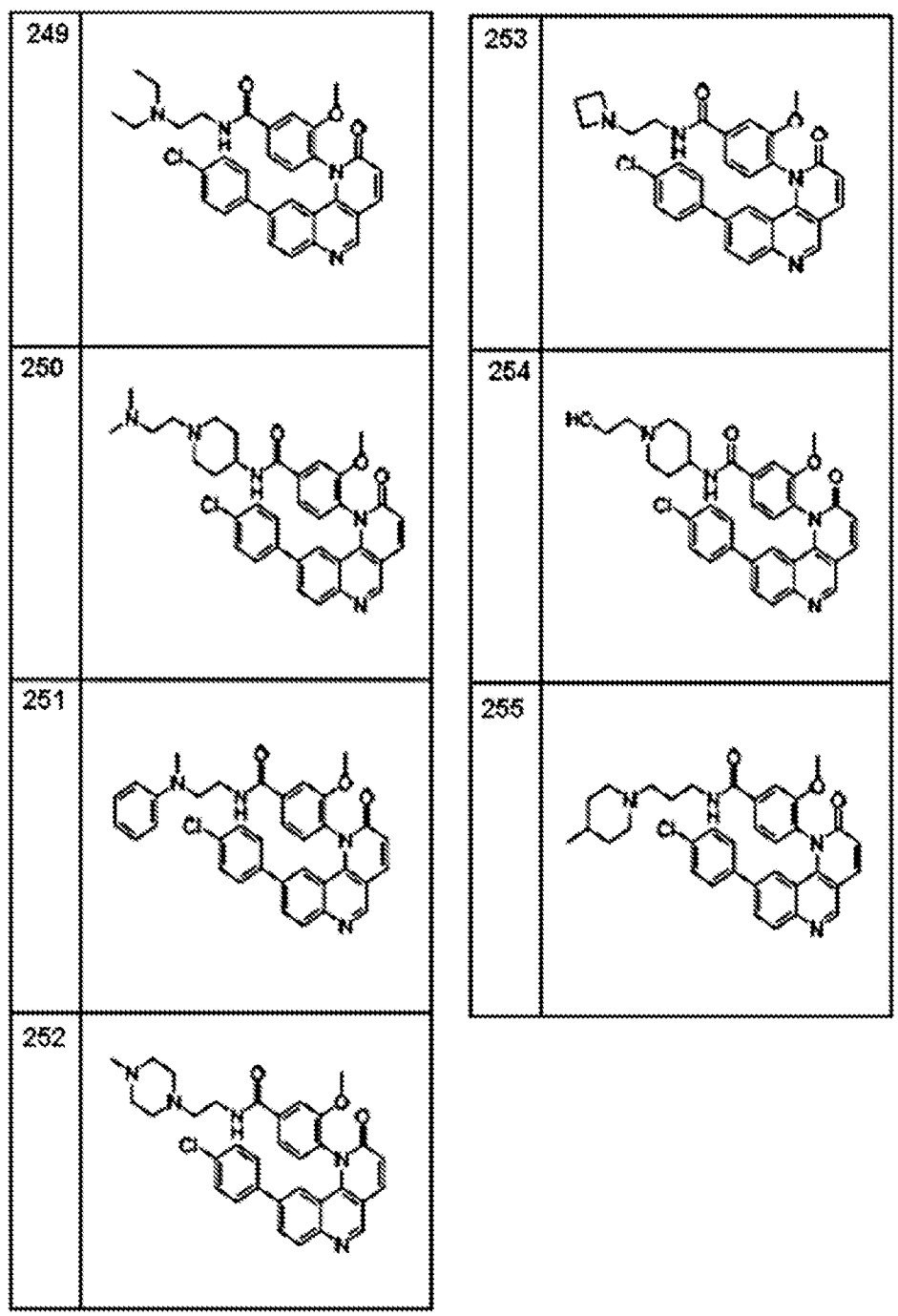
Figure 2B:
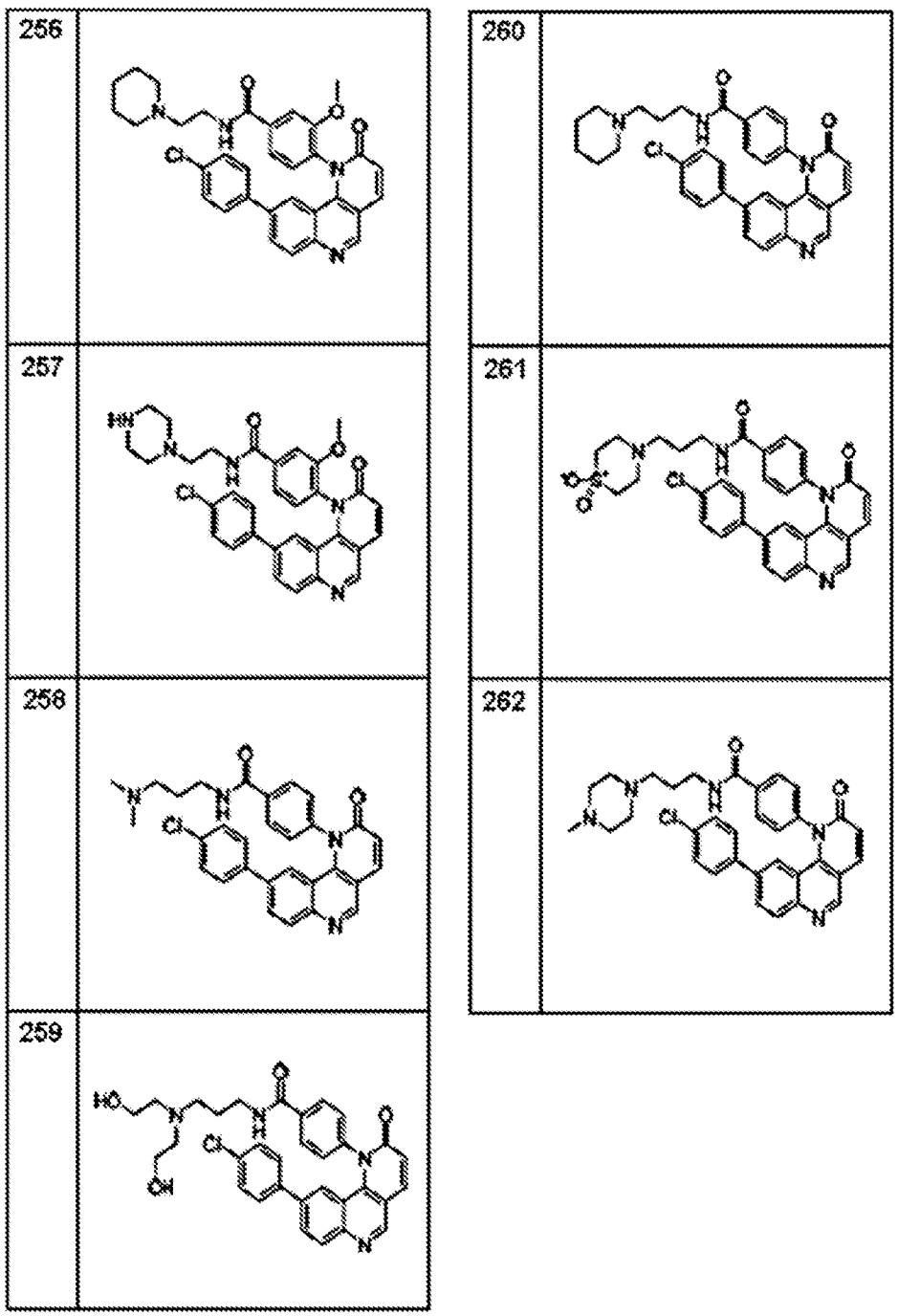
Figure 2B:
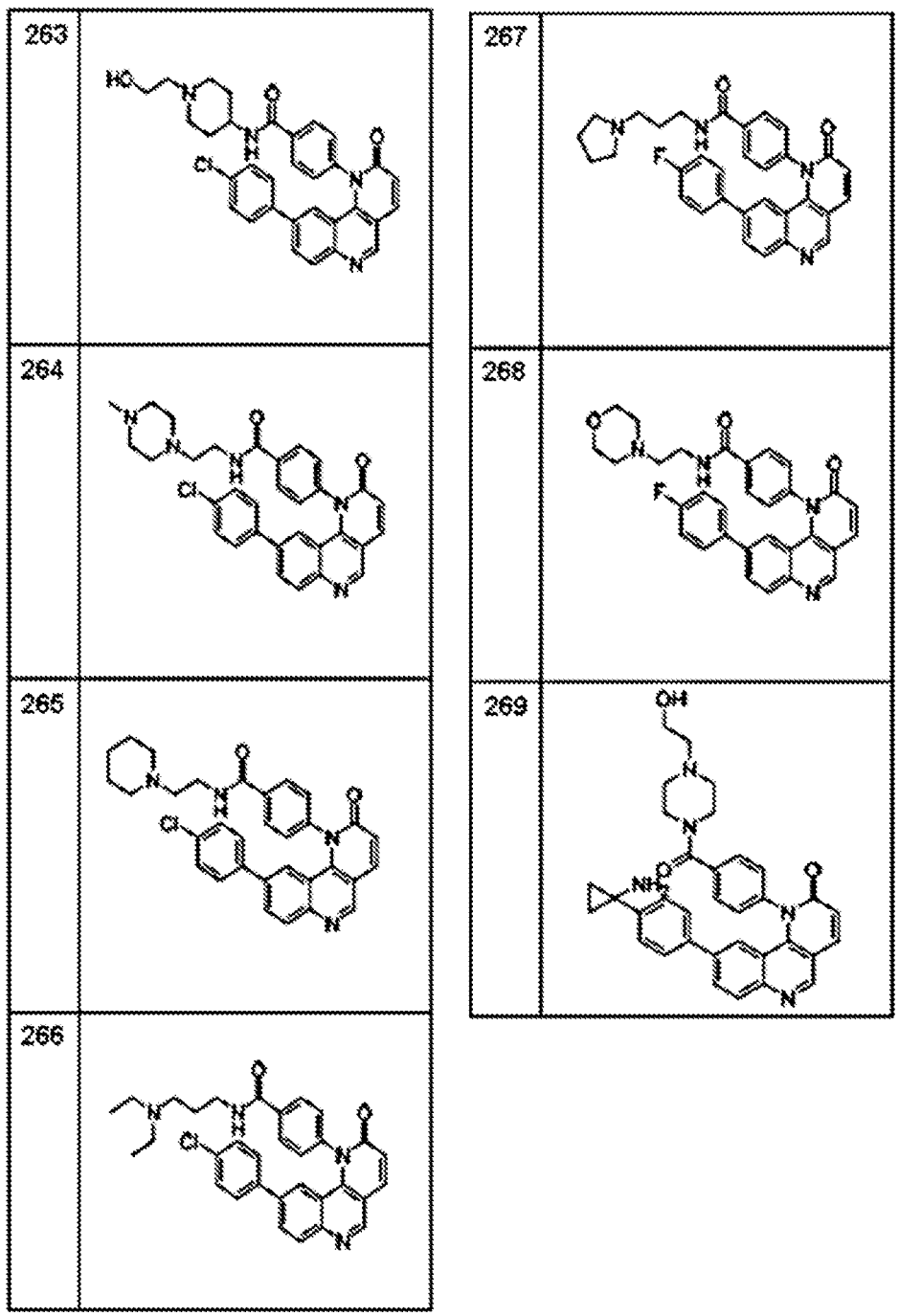
Figure 2B:
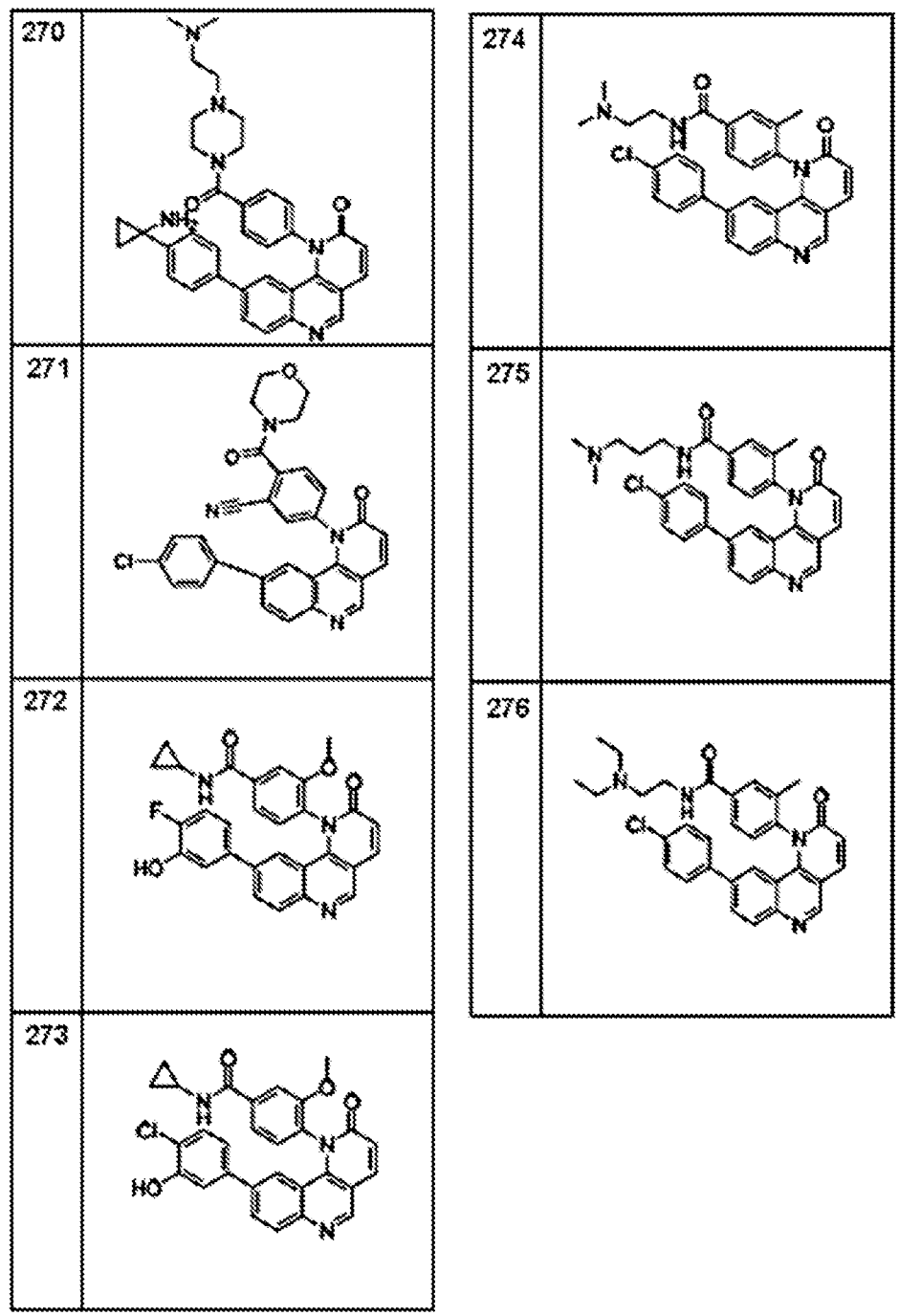
Figure 2B:
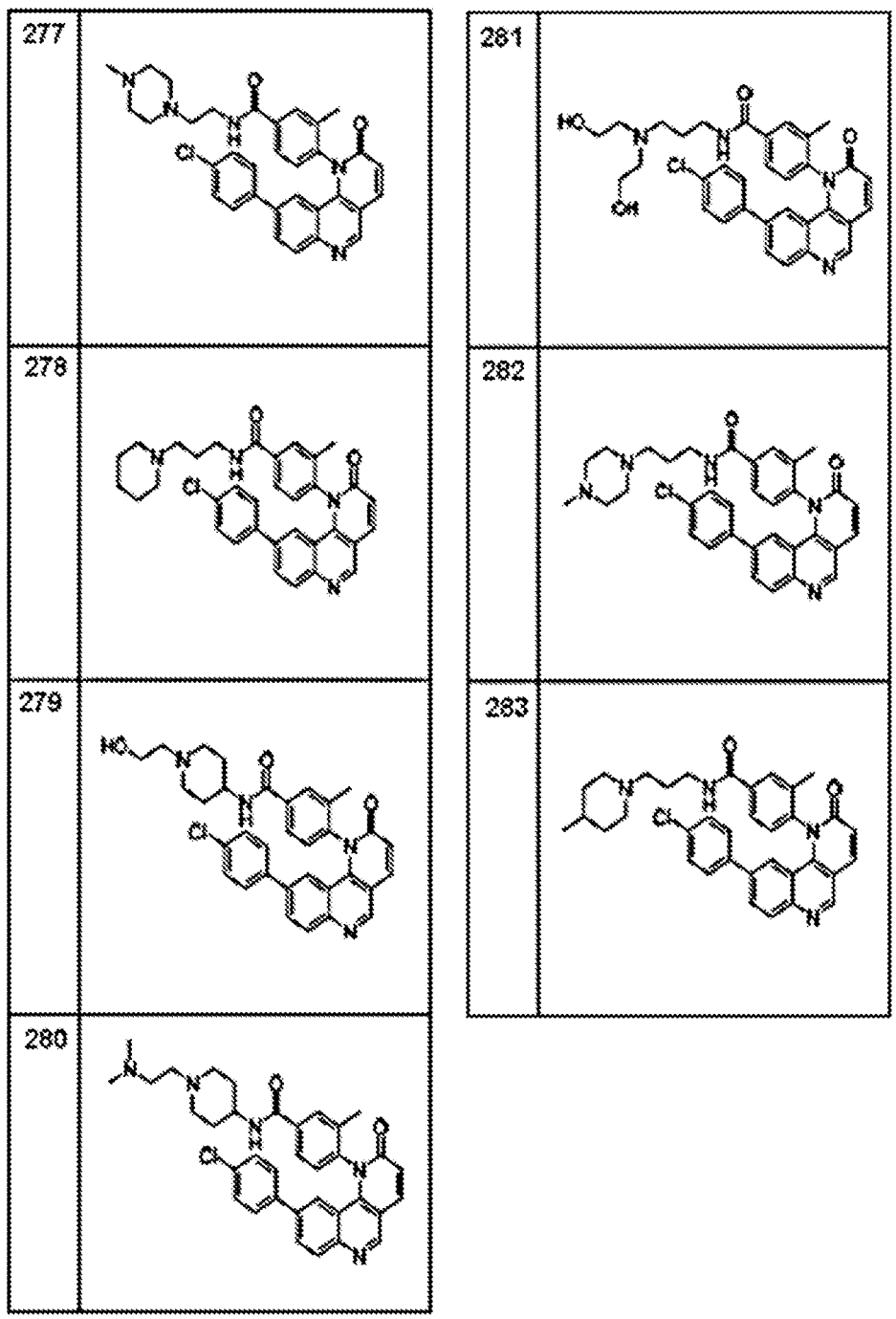
Figure 2B:
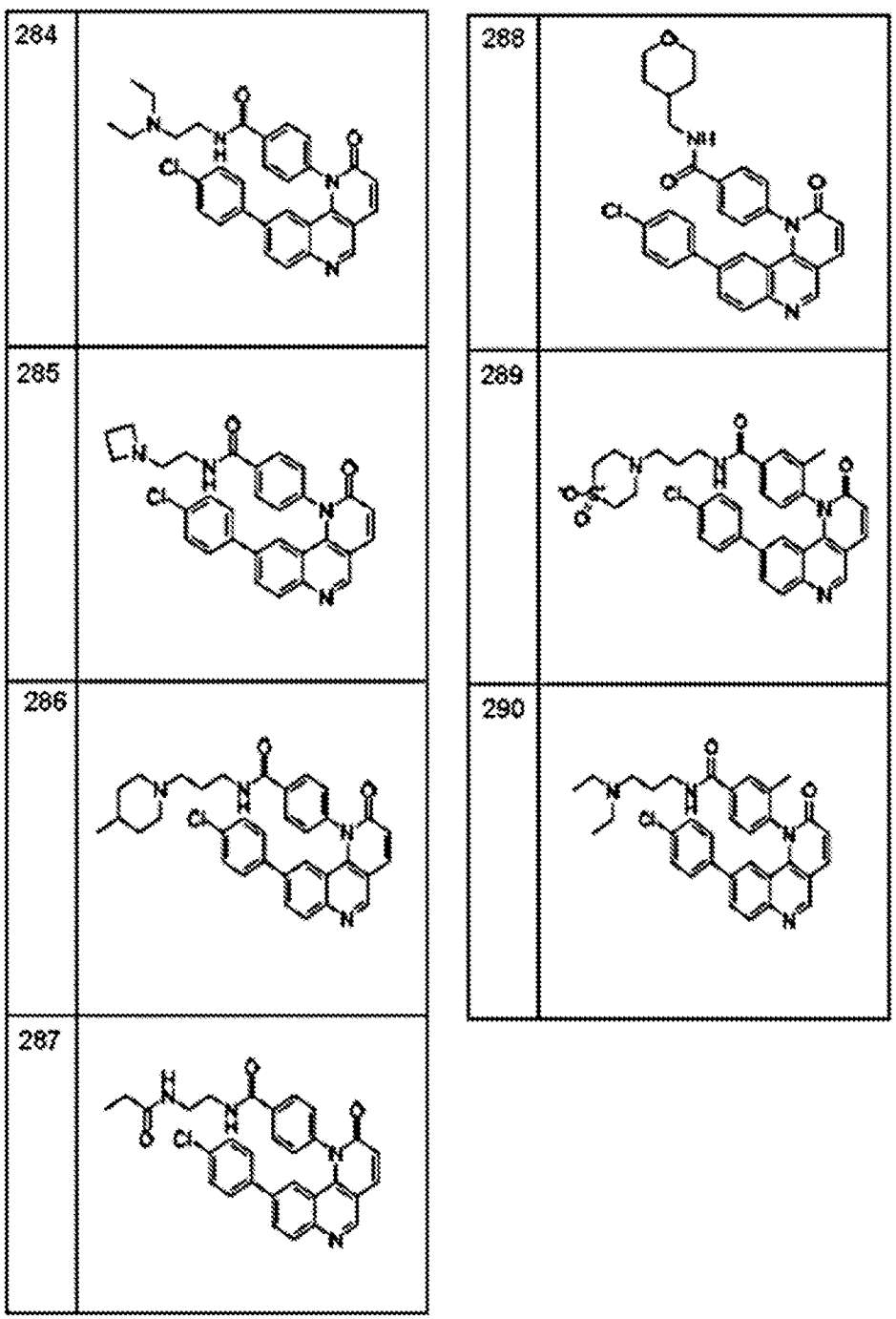
Figure 2B:
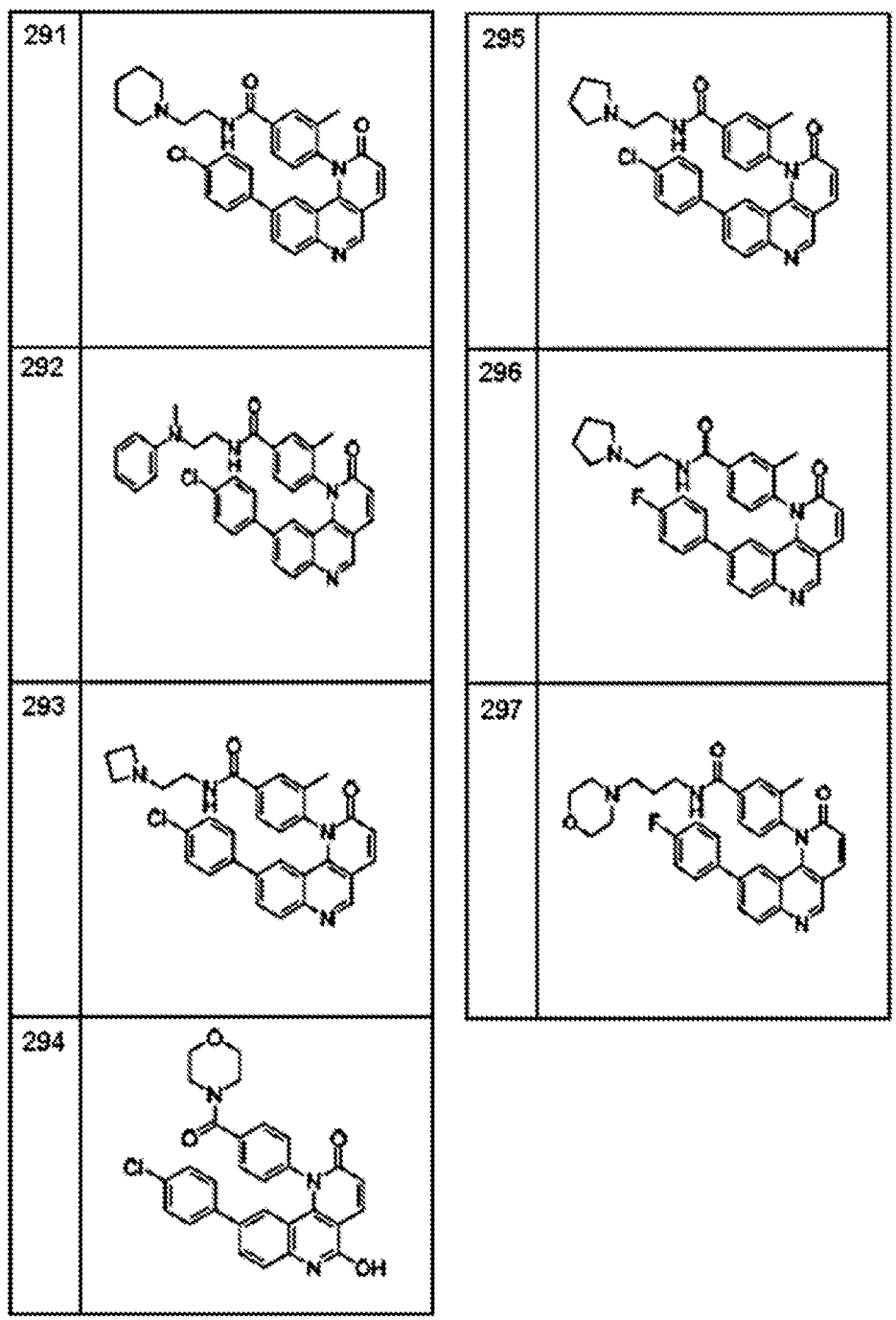
Figure 2B:
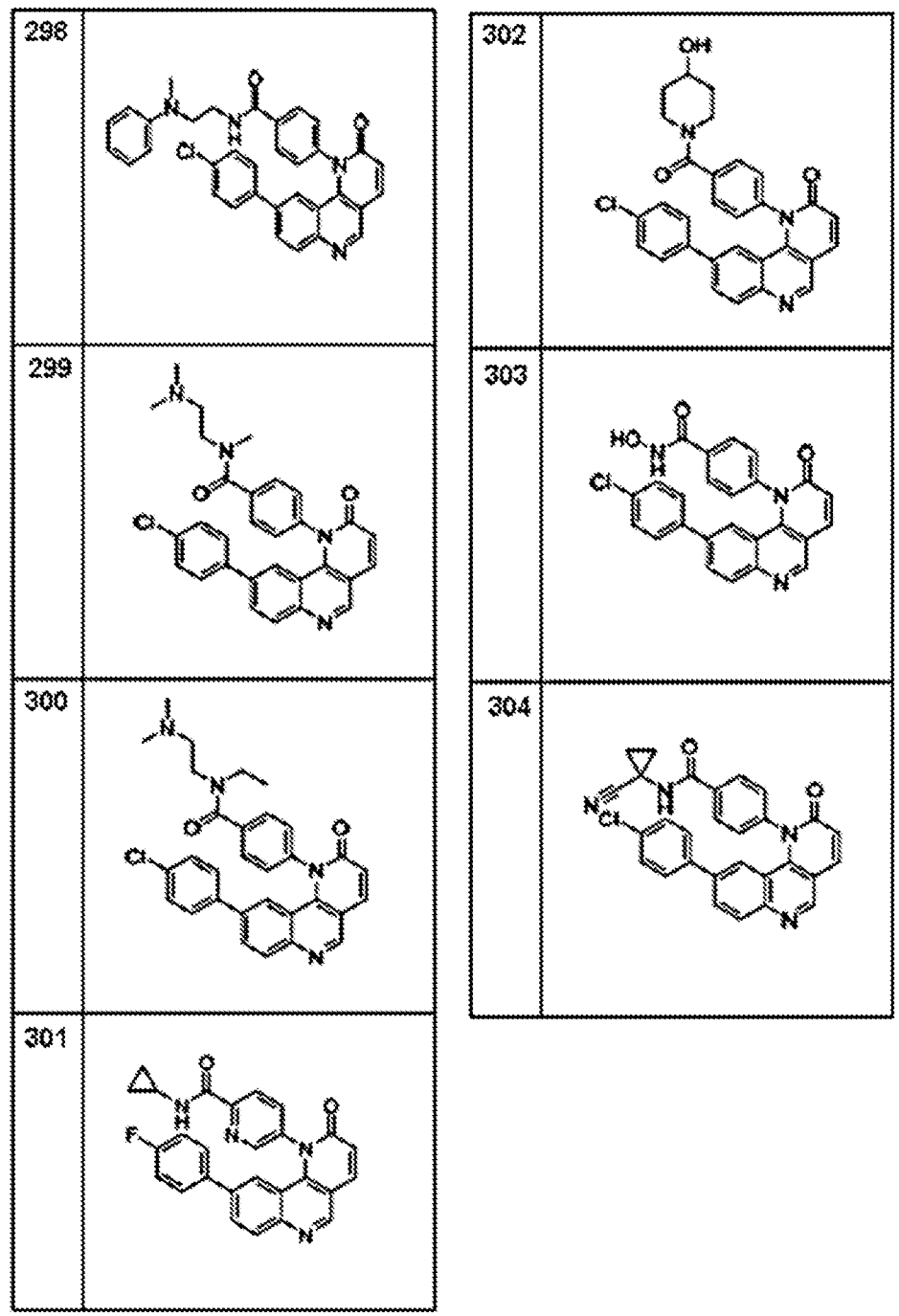
Figure 2B:
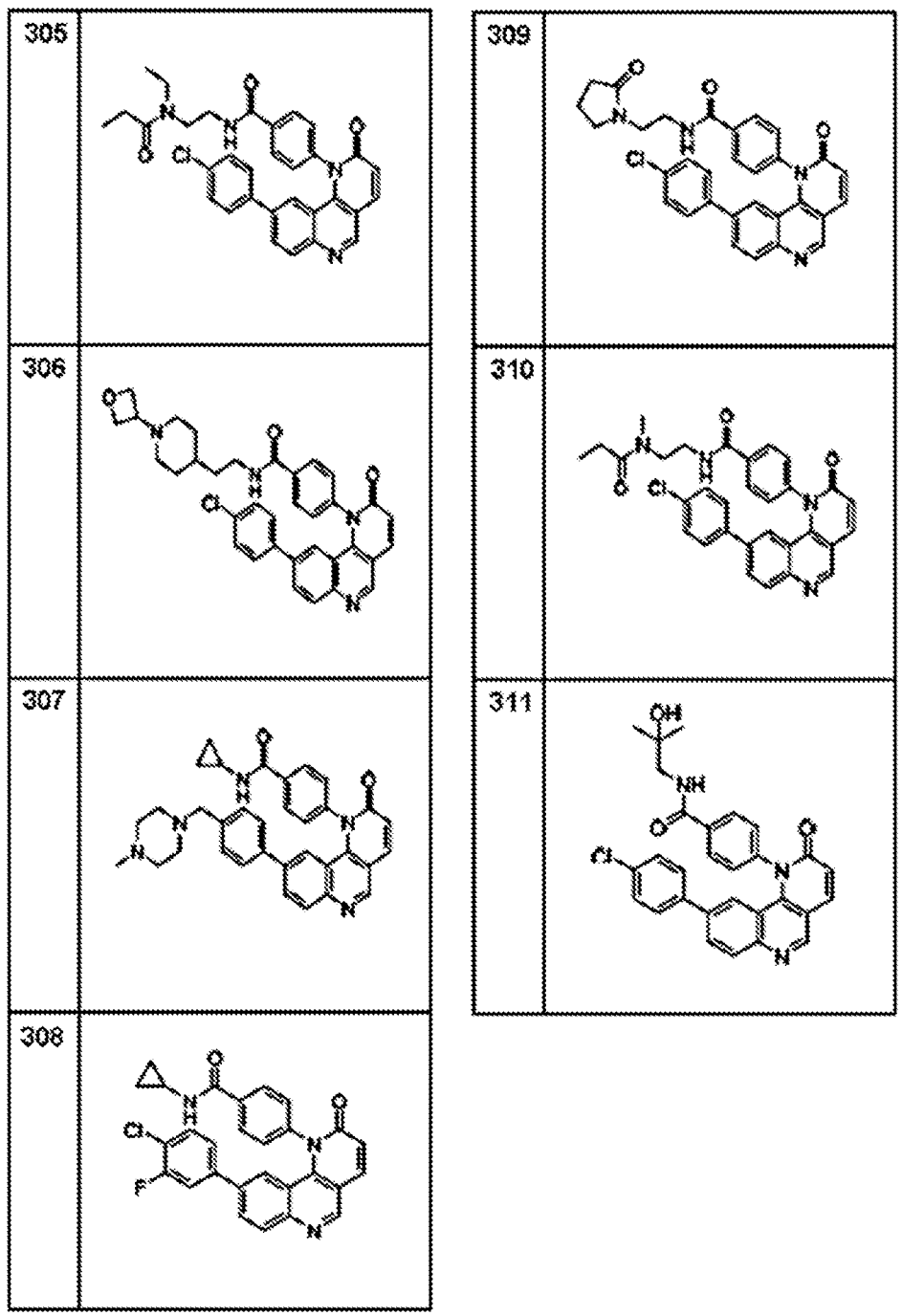
Figure 2B:
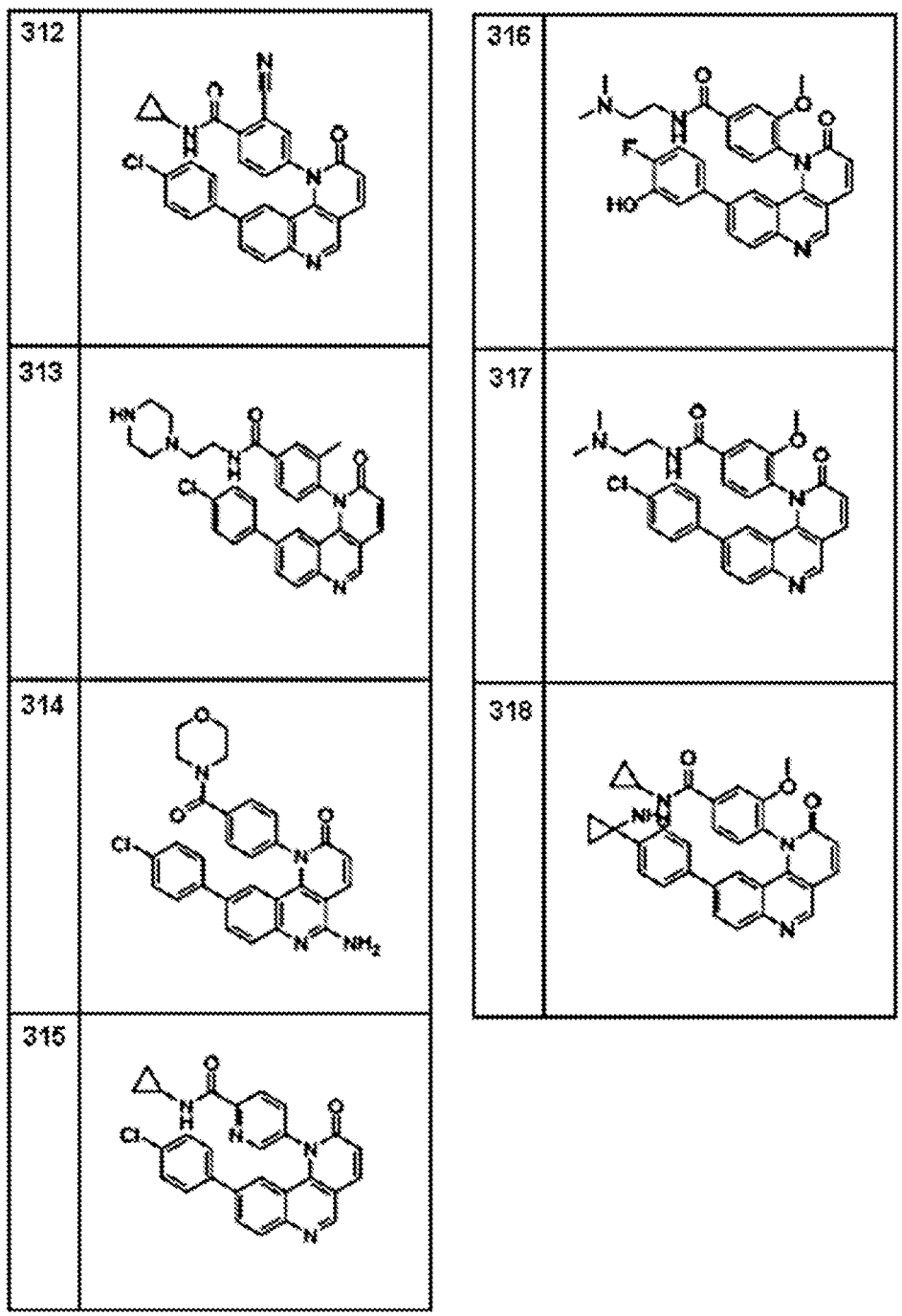
Figure 2B:
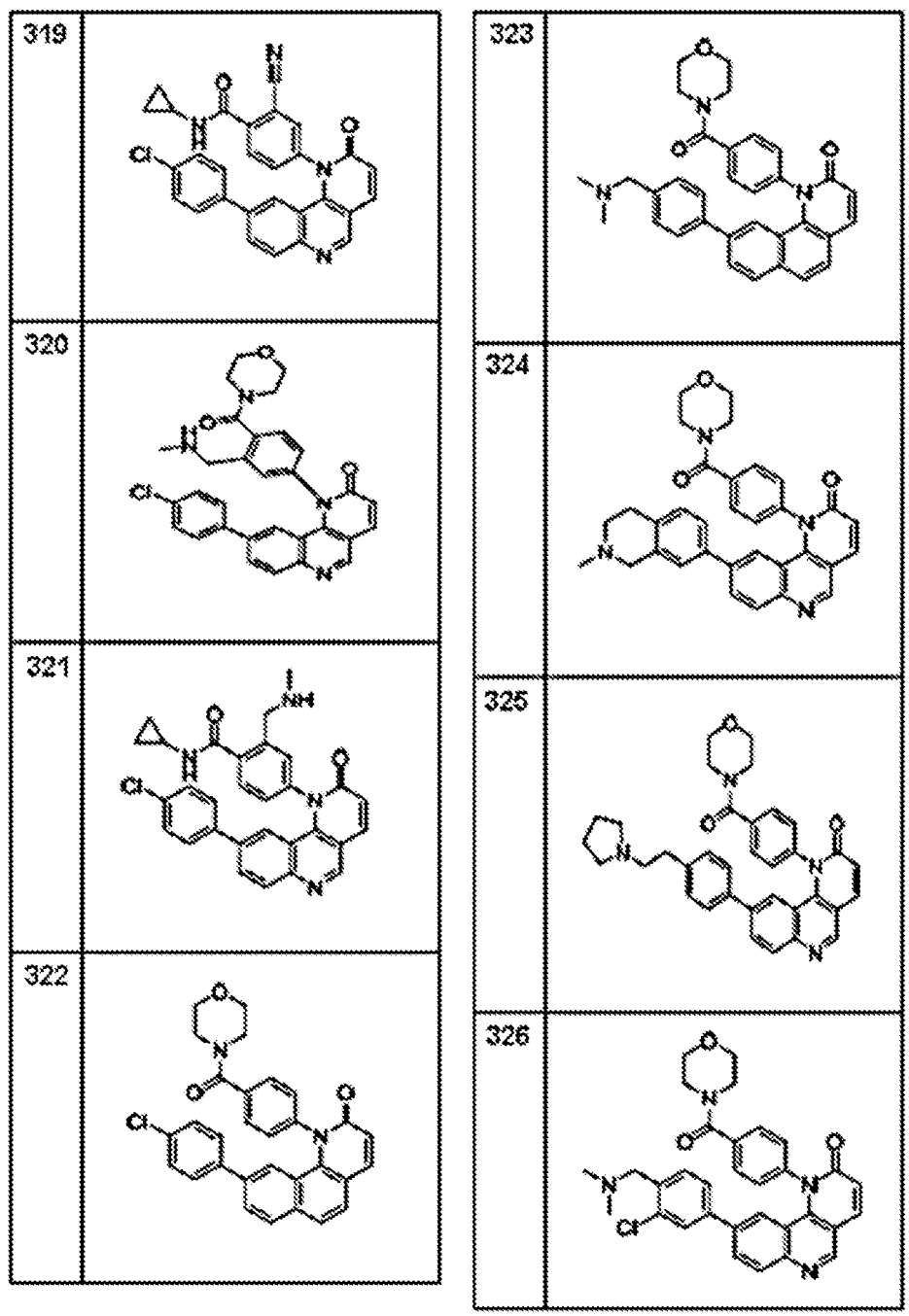
Figure 2B:
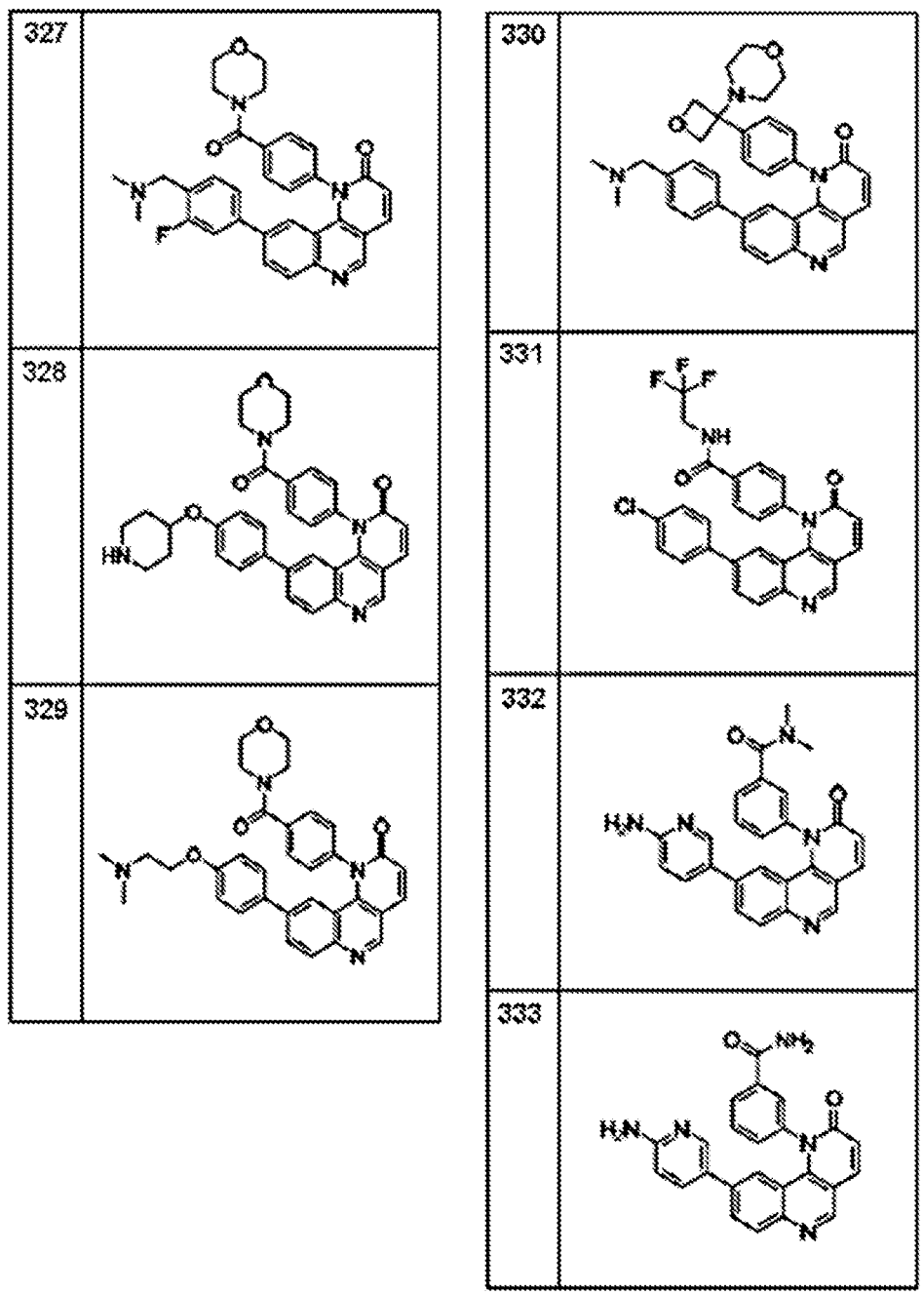
Figure 2B:
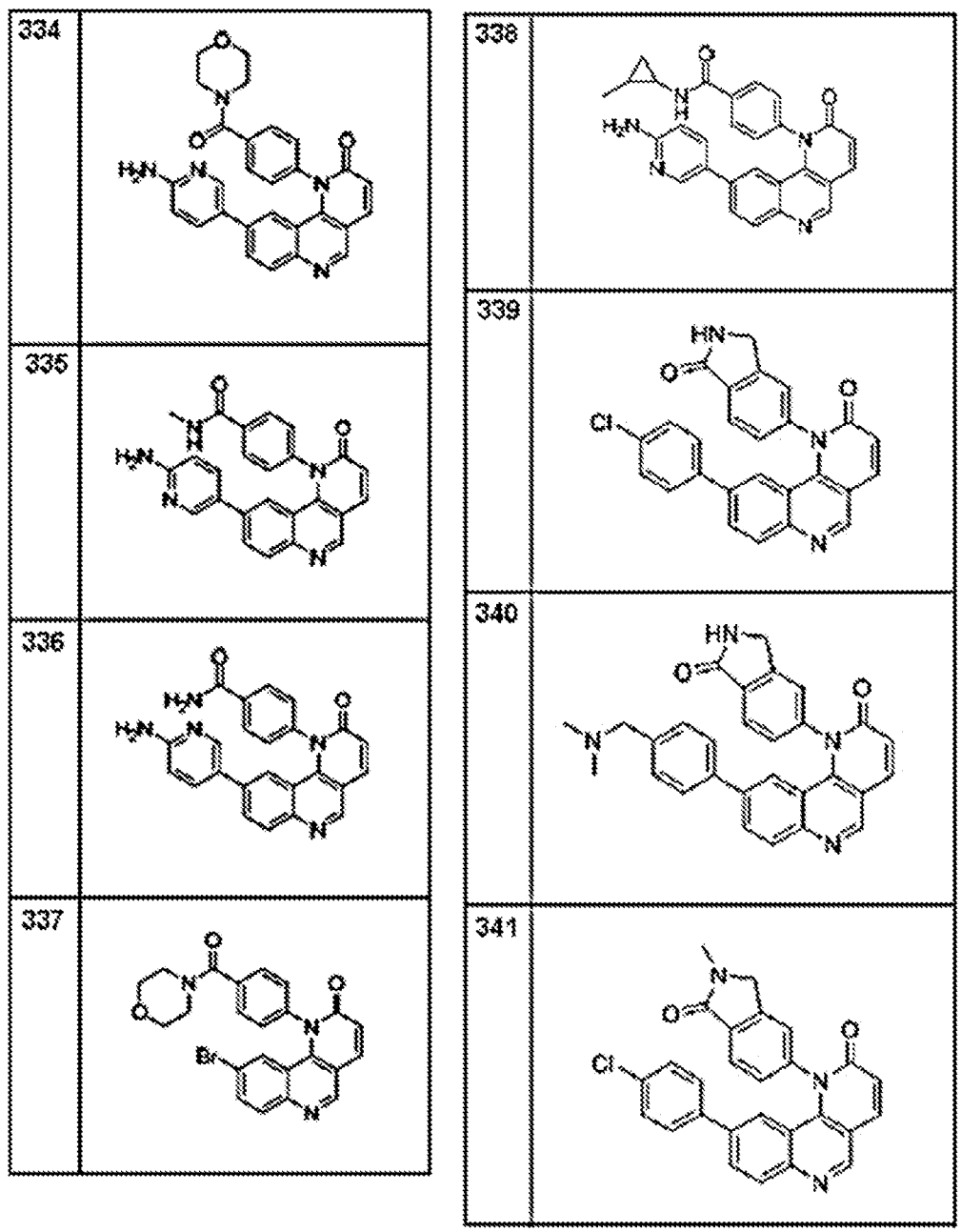
Figure 2B:
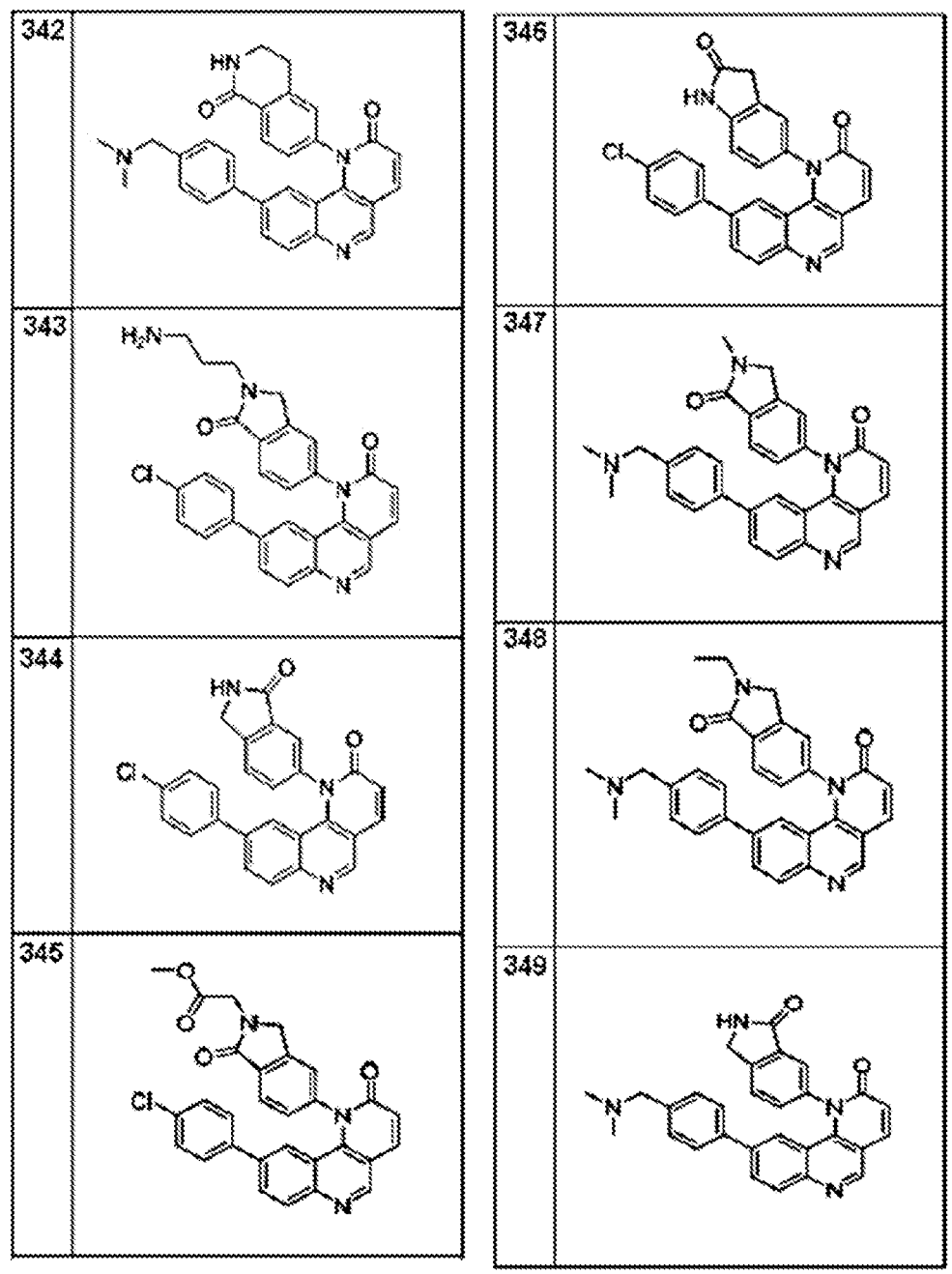
Figure 2B:
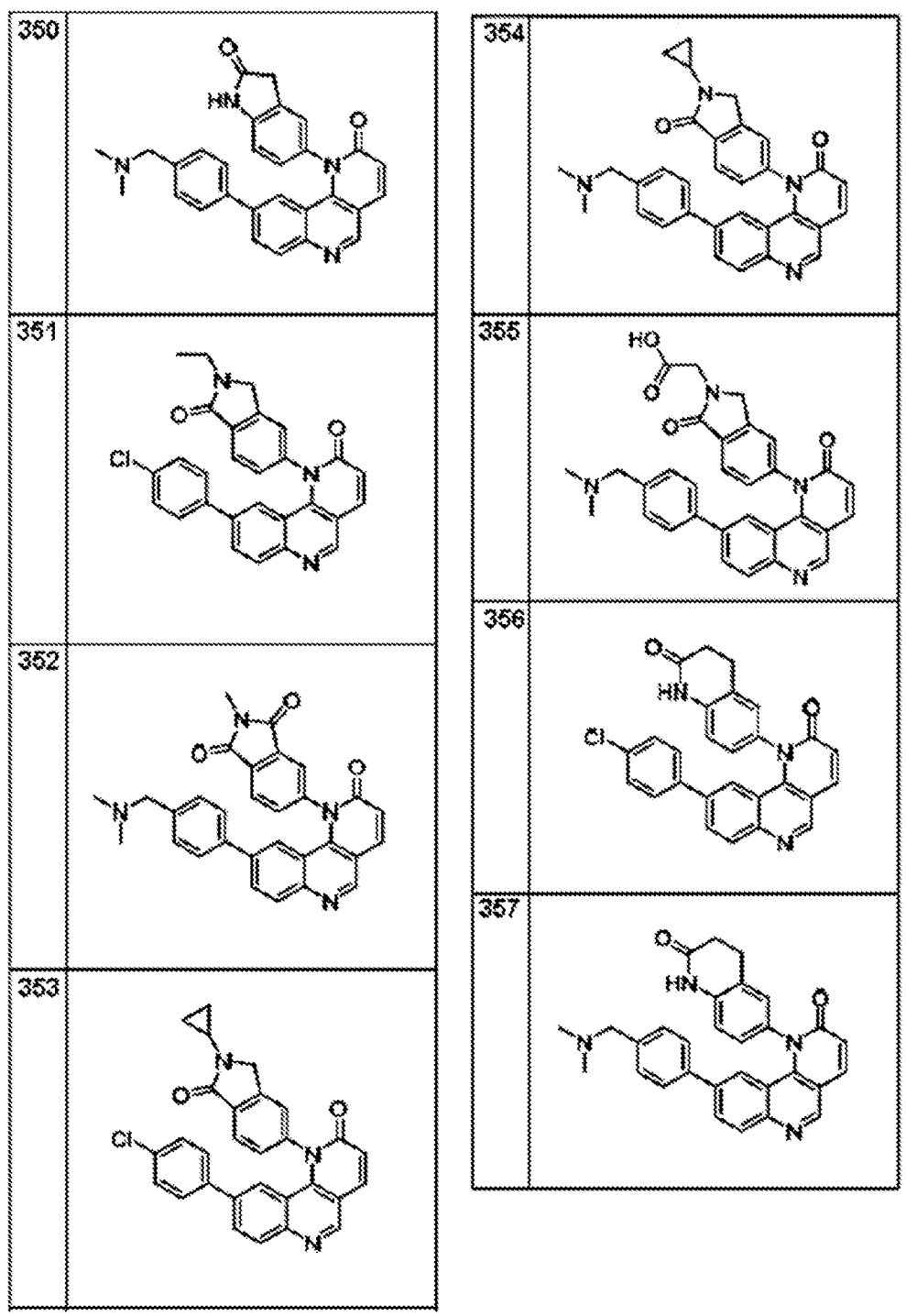
Figure 2B:
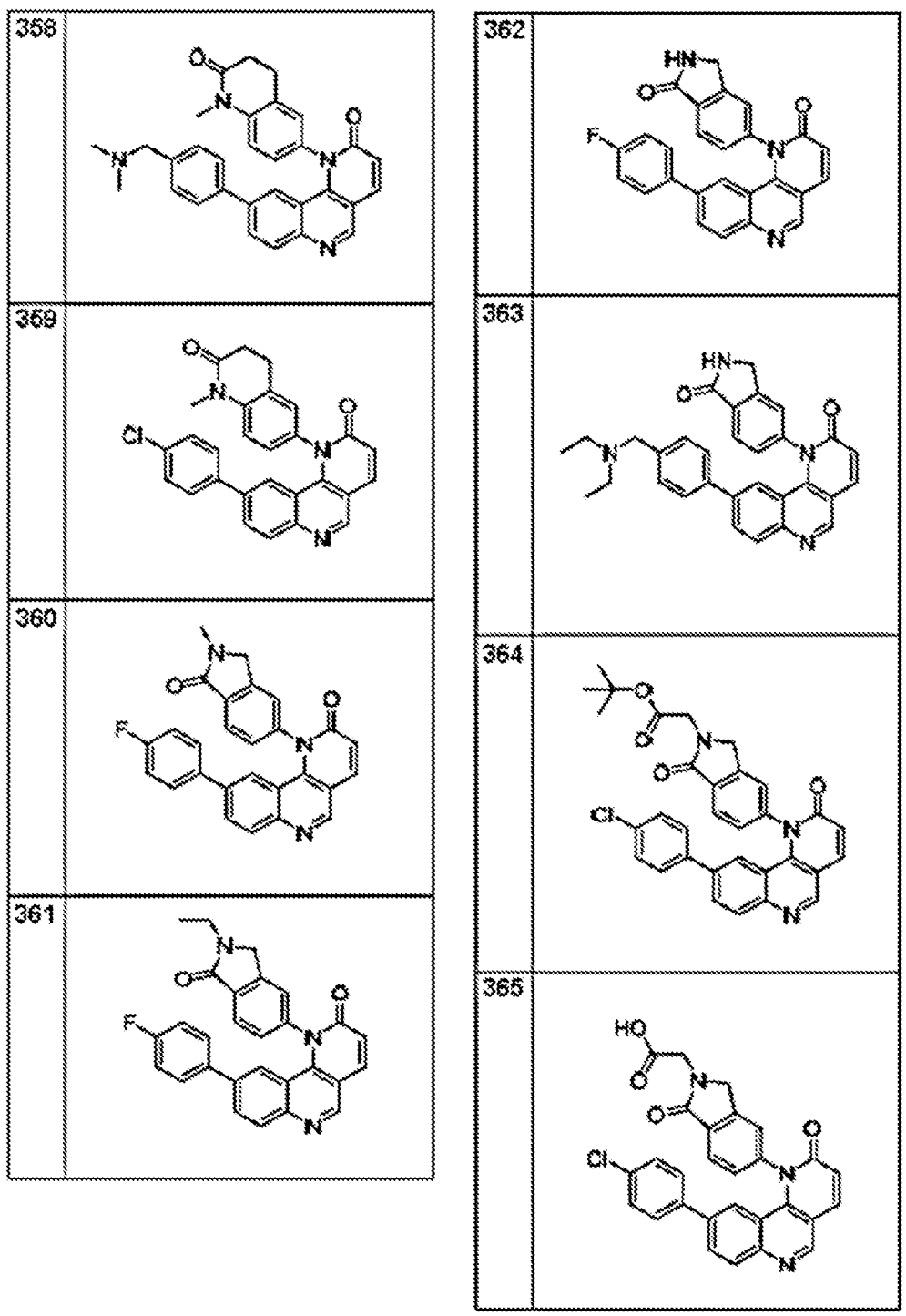
Figure 2B:
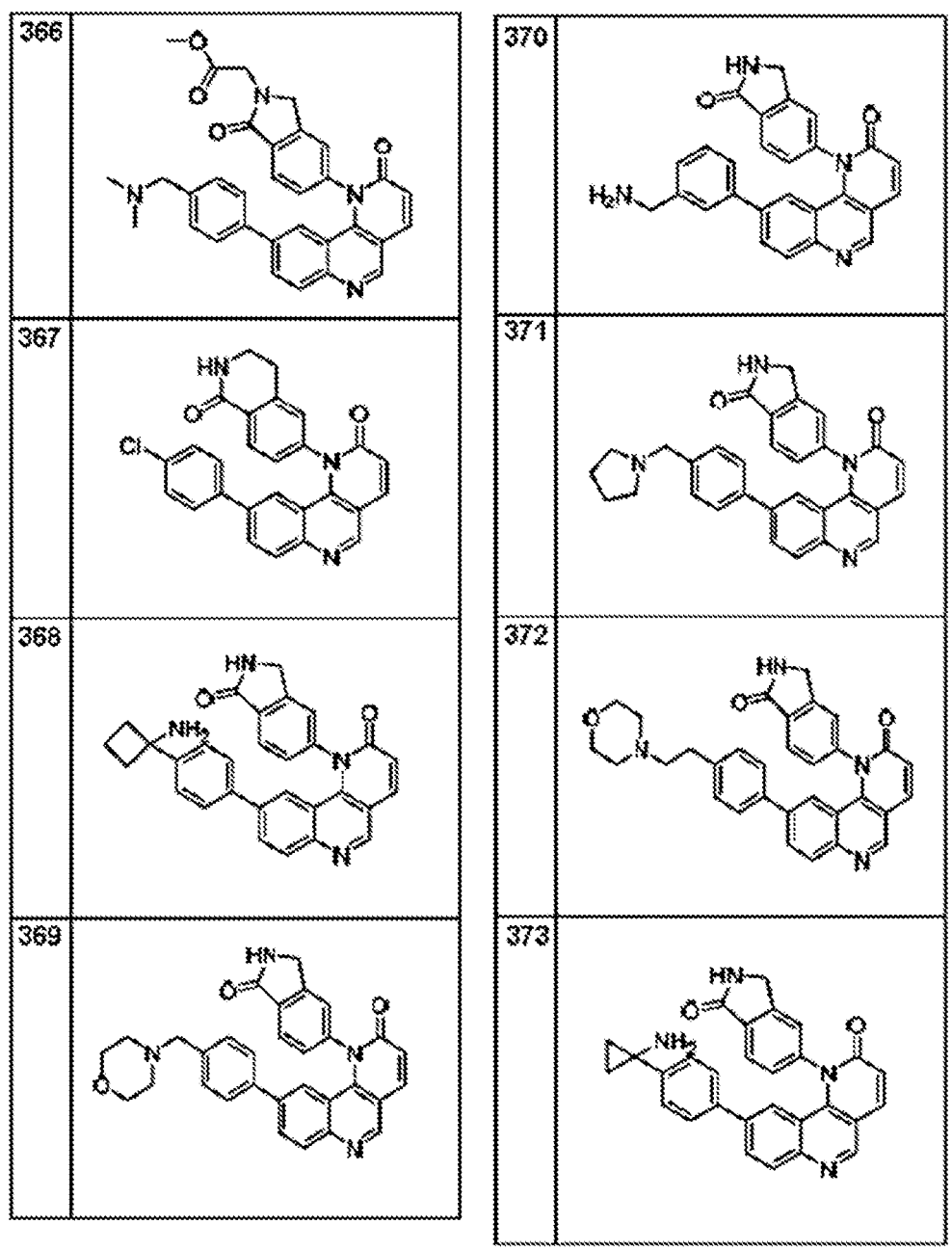
Figure 2B:
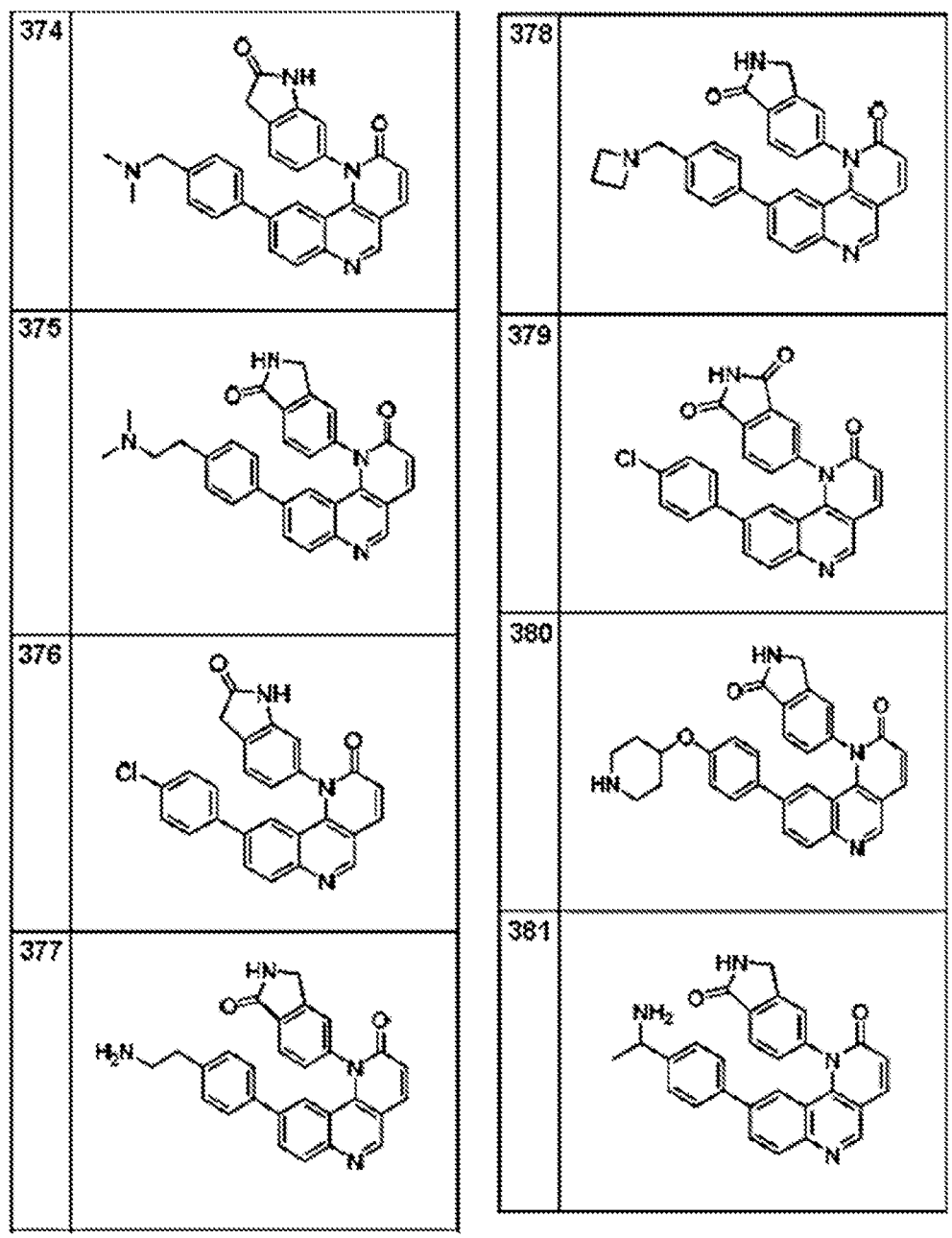
Figure 2B:
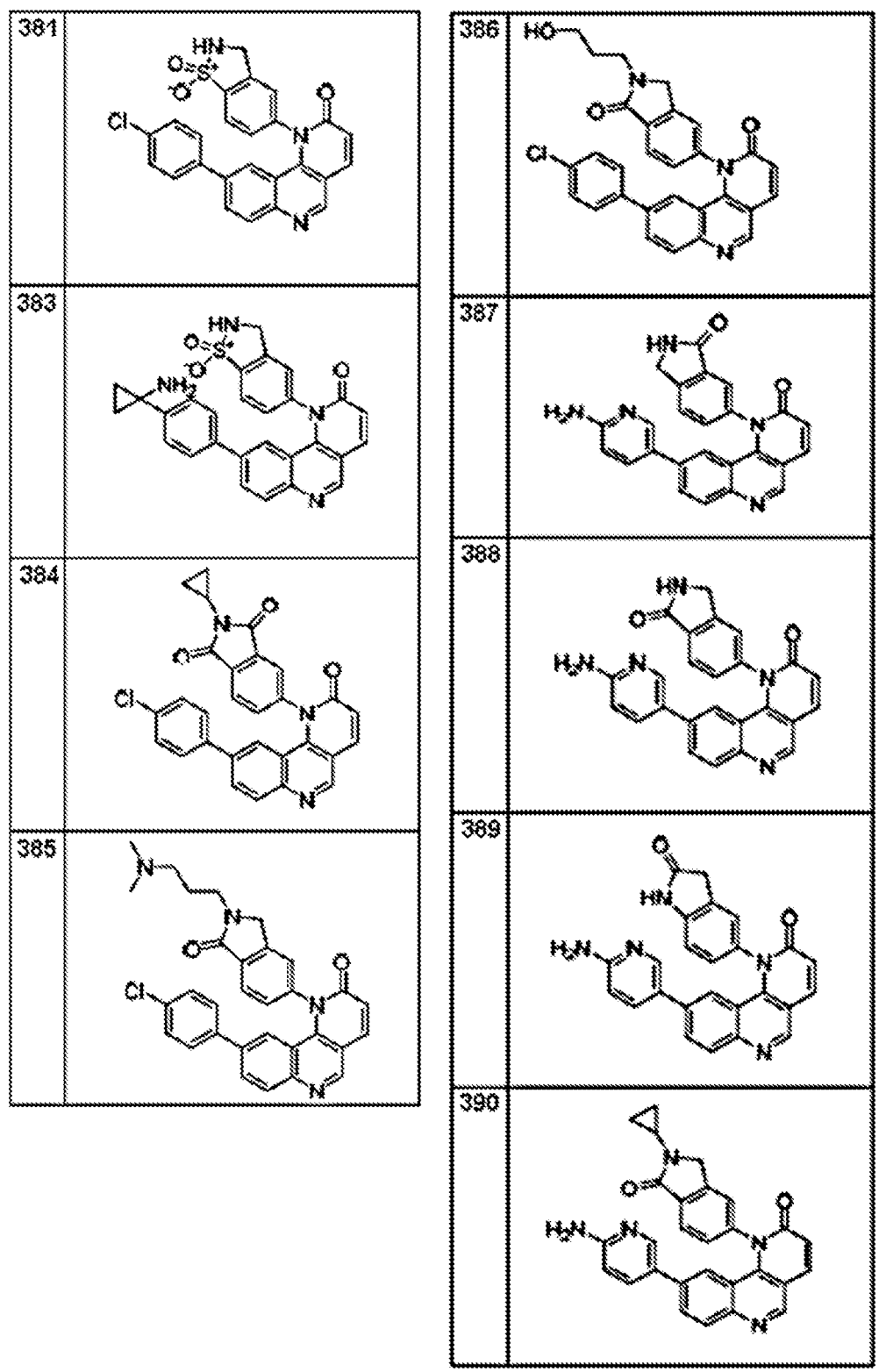
Figure 2B:
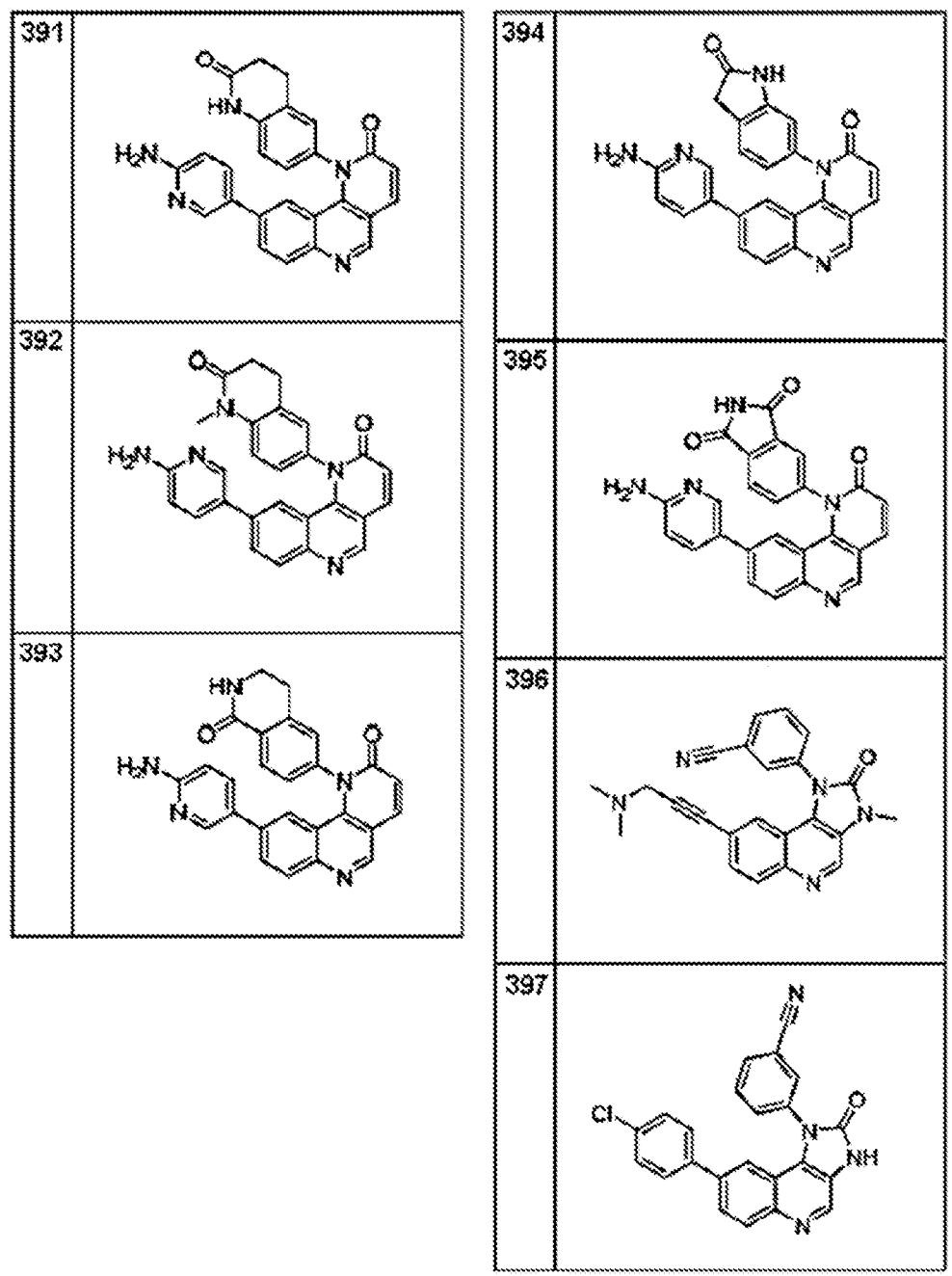
Figure 2C:
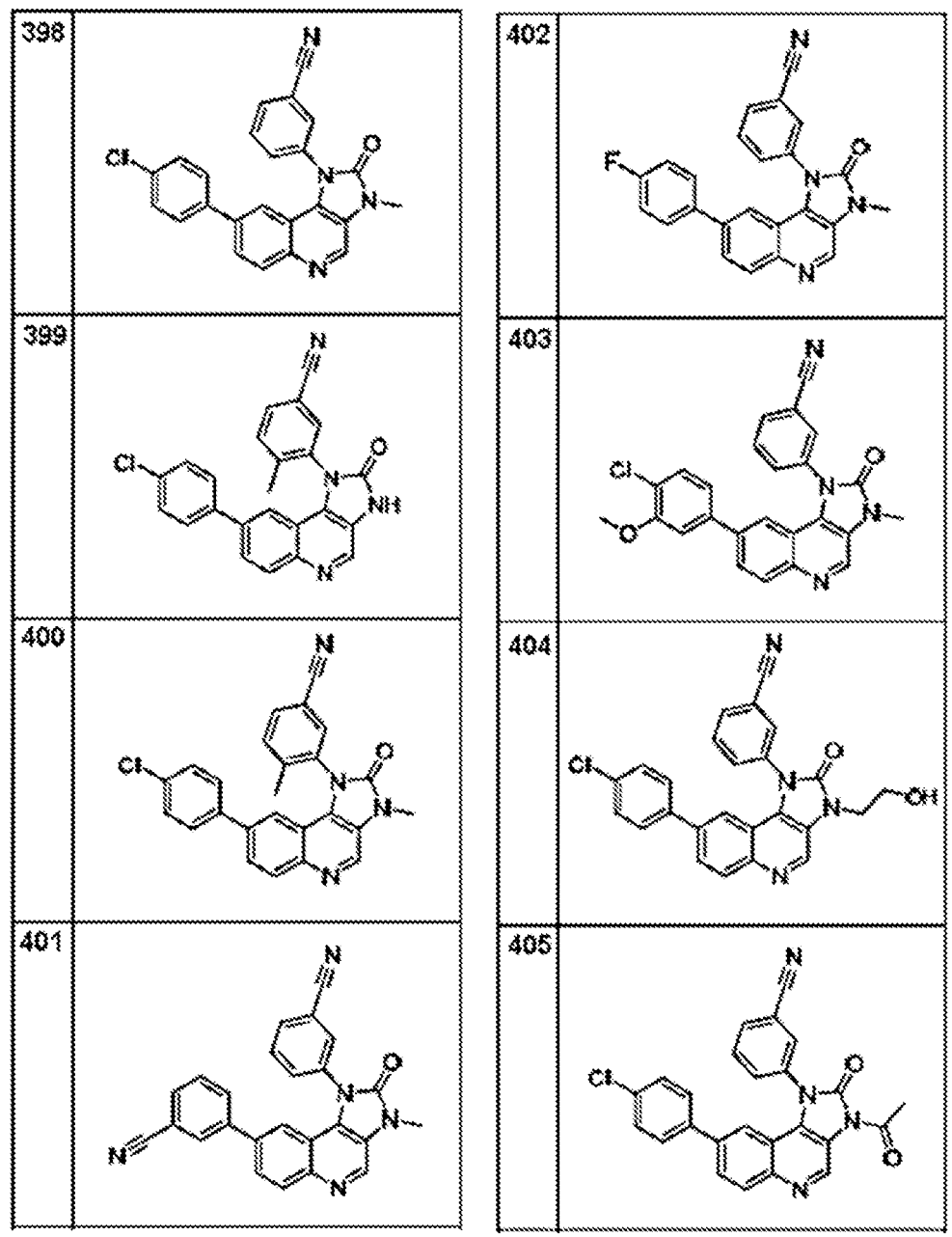
Figure 2C:
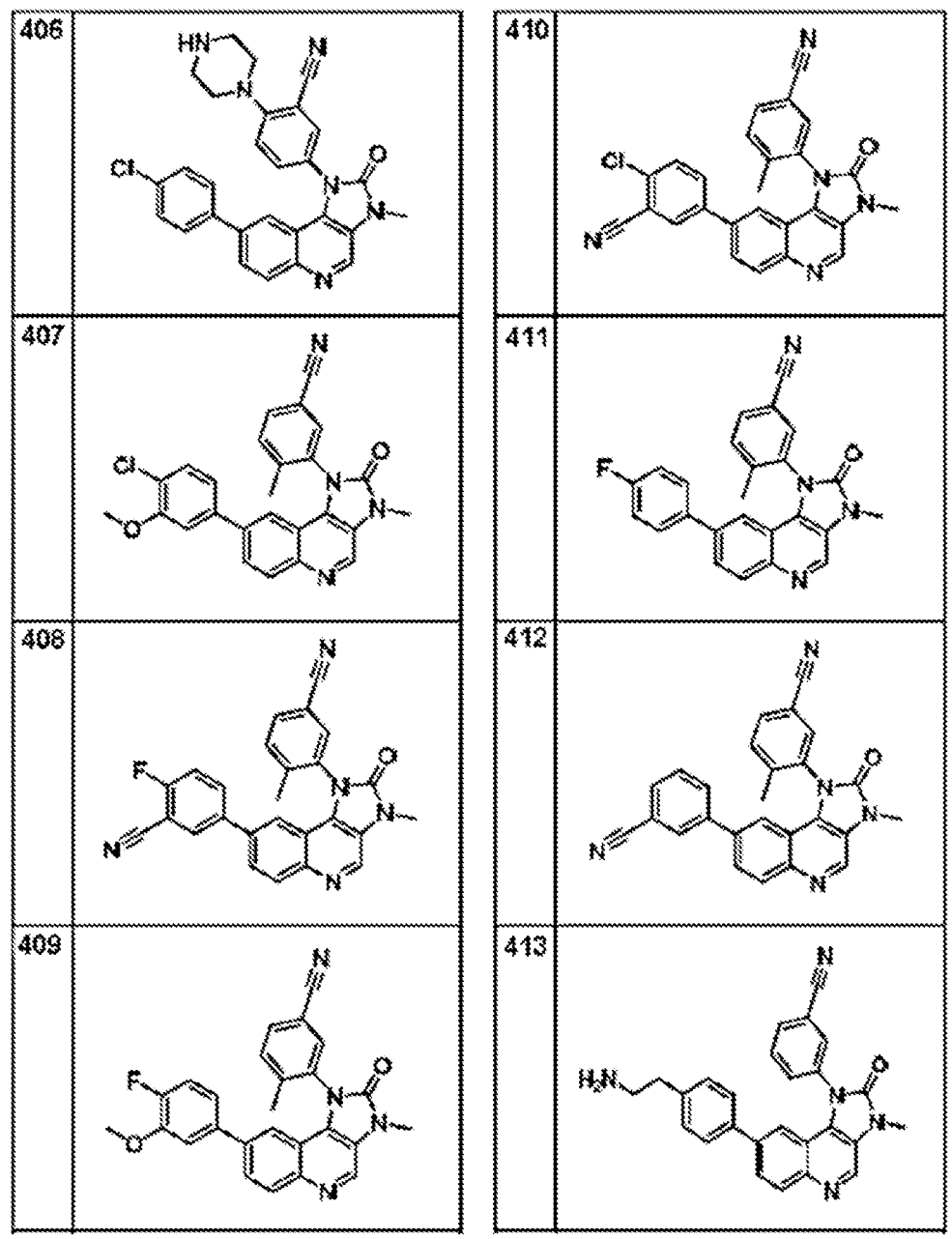
Figure 2C:
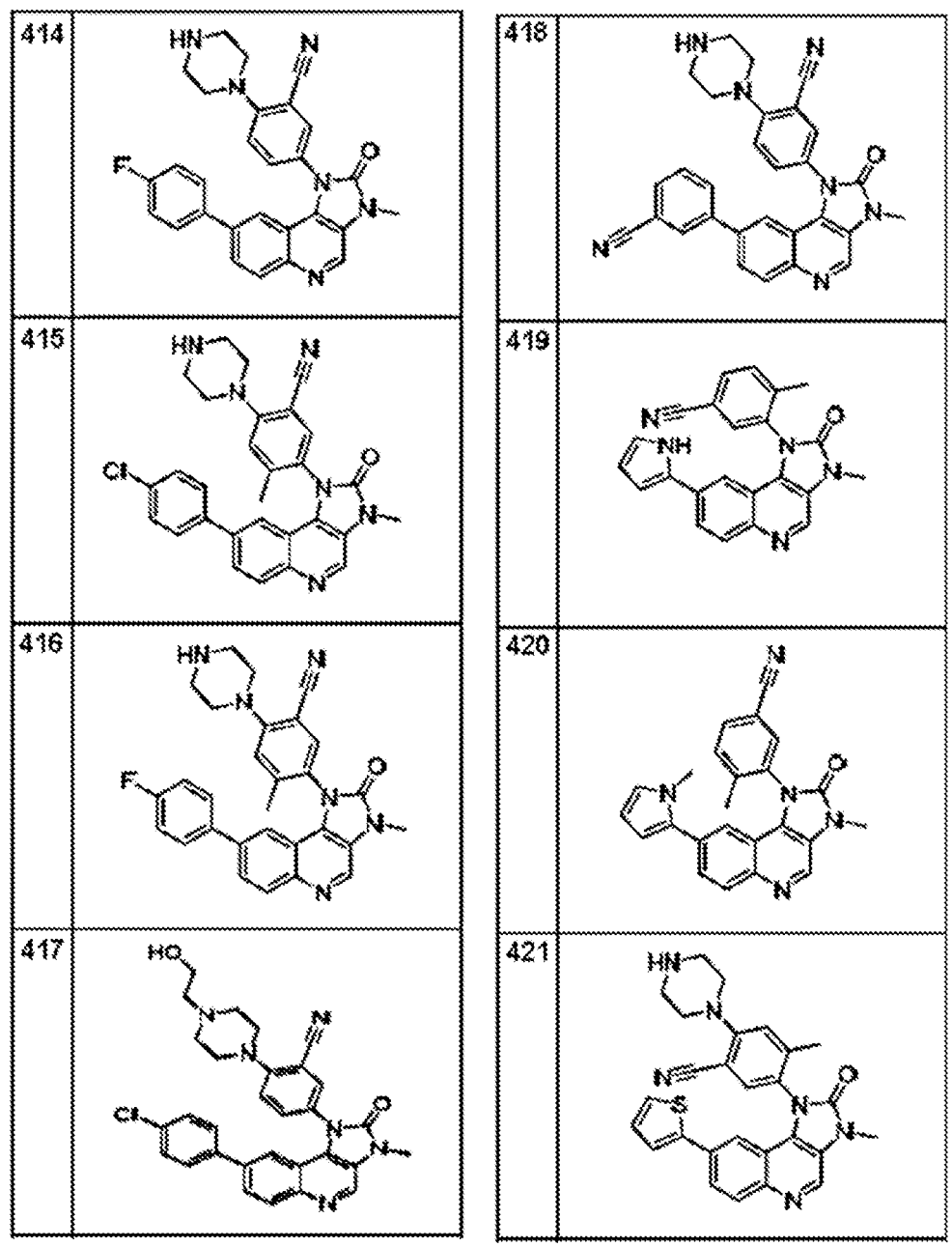
Figure 2C:
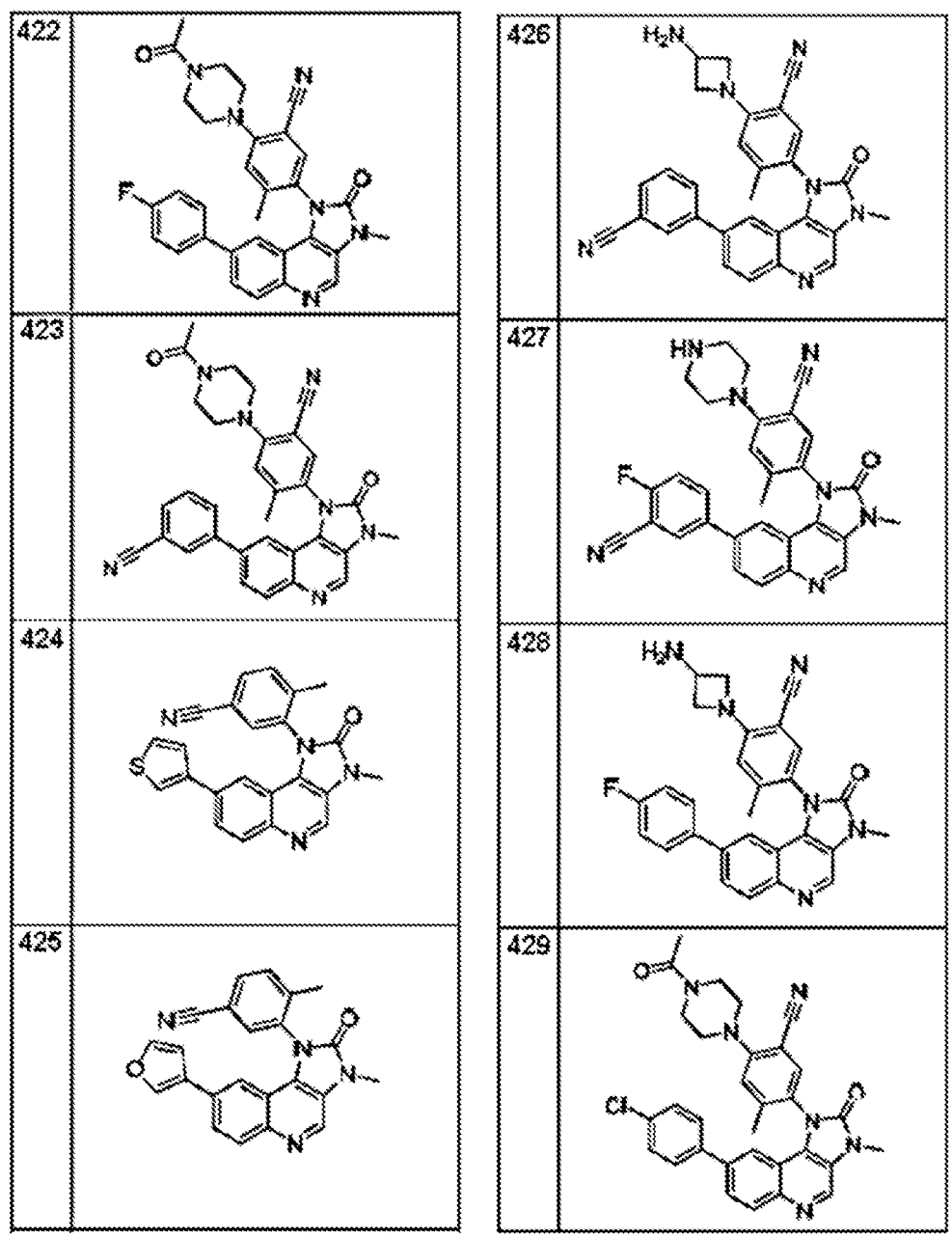
Figure 2C:
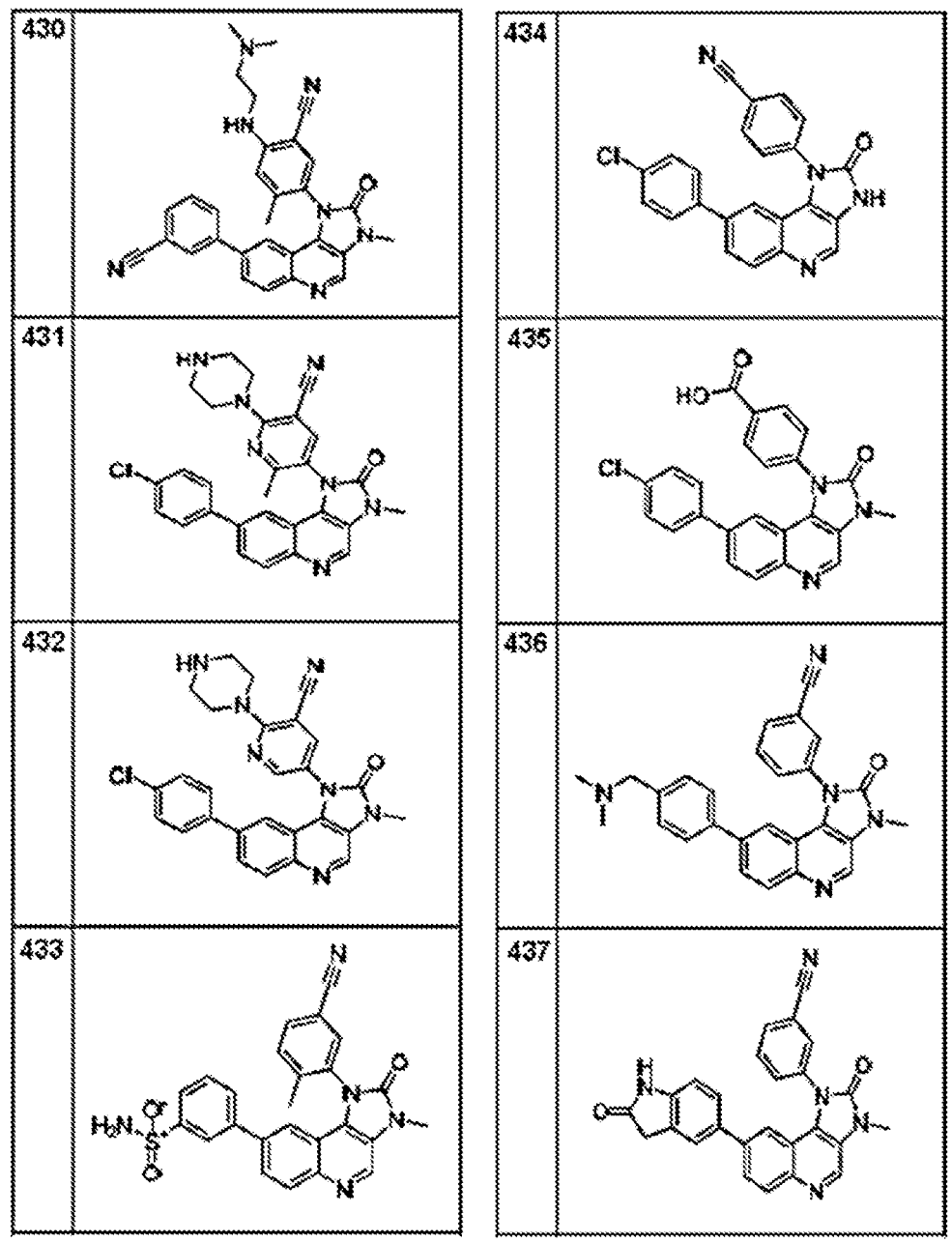
Figure 2C:
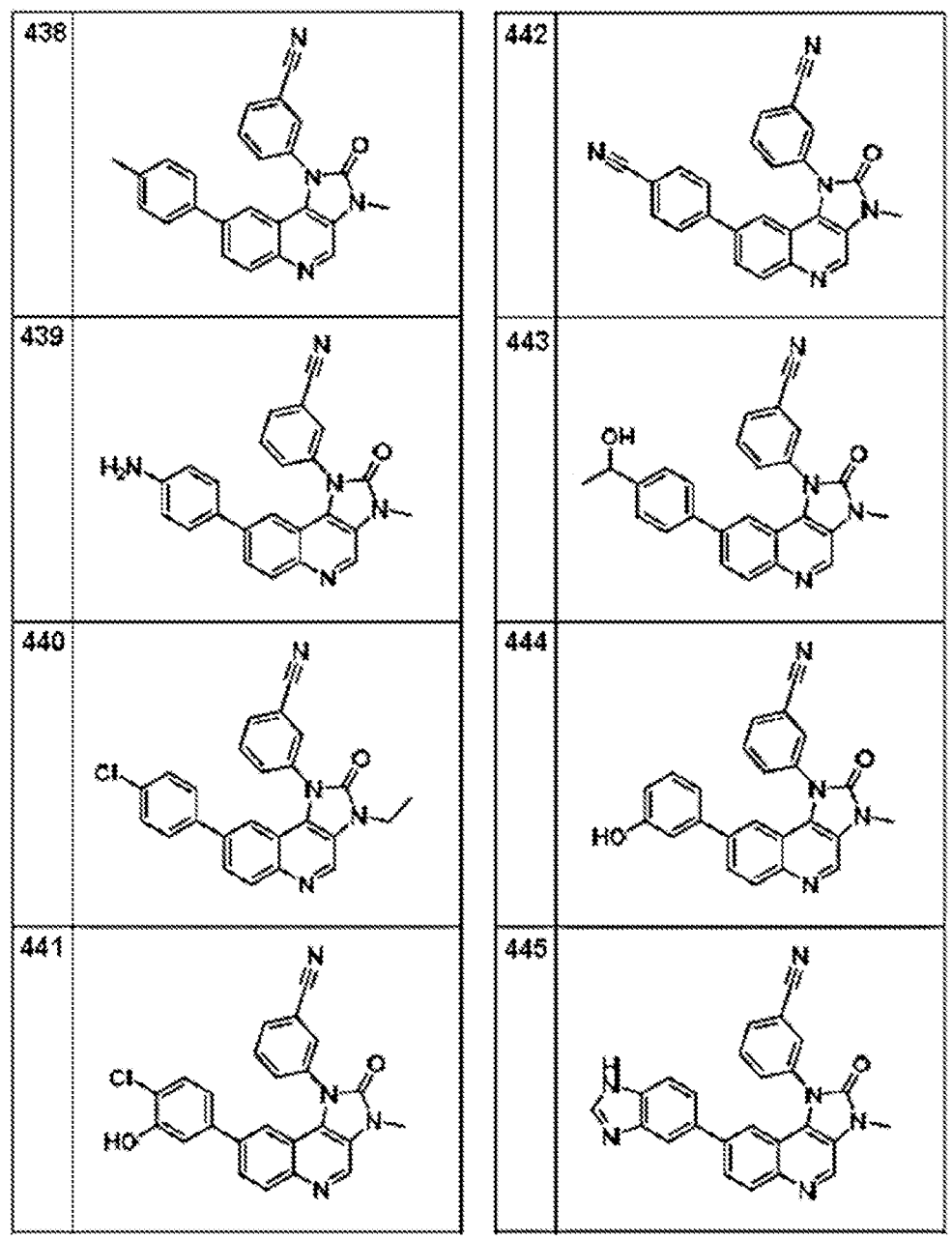
Figure 2C:
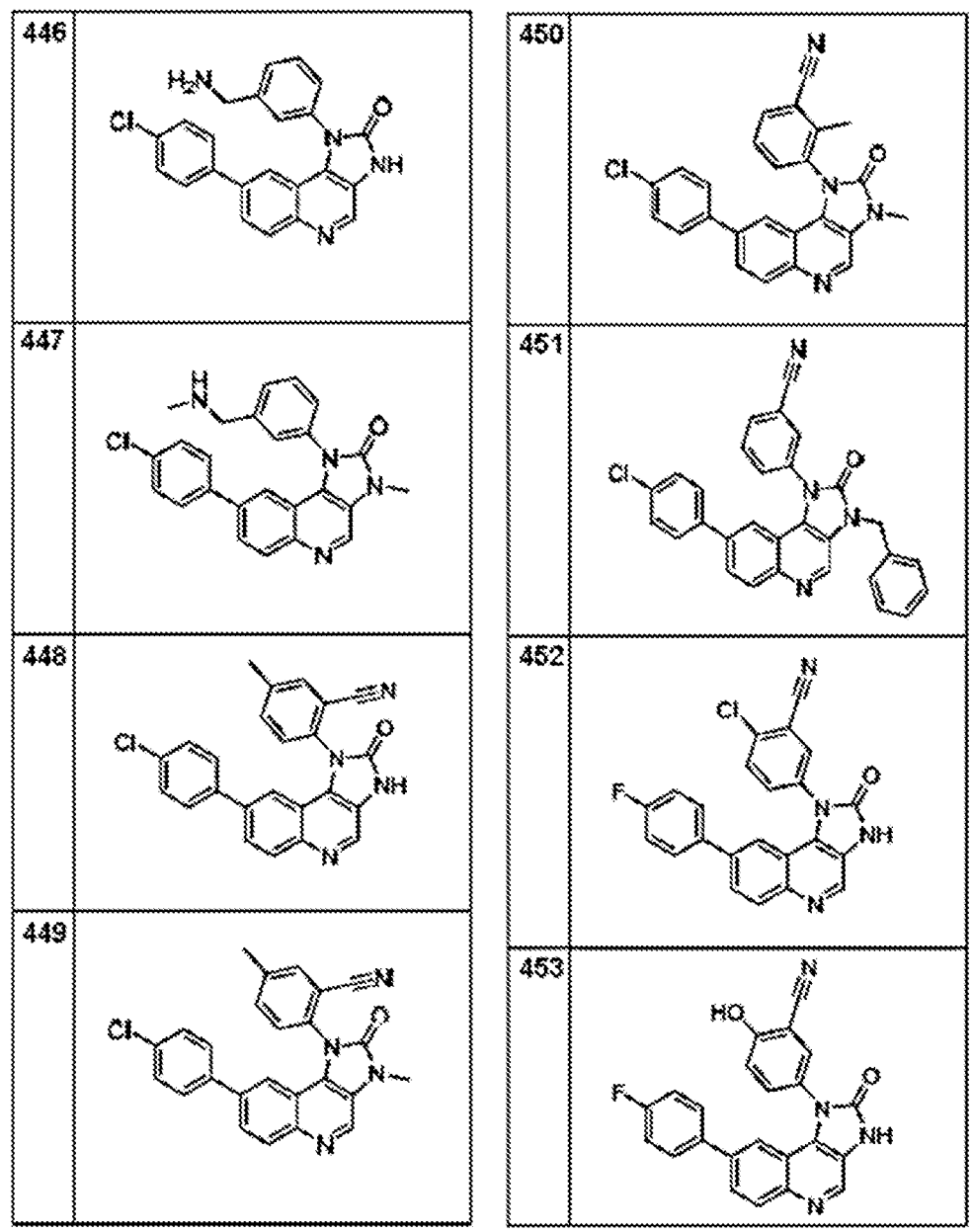
Figure 2C:
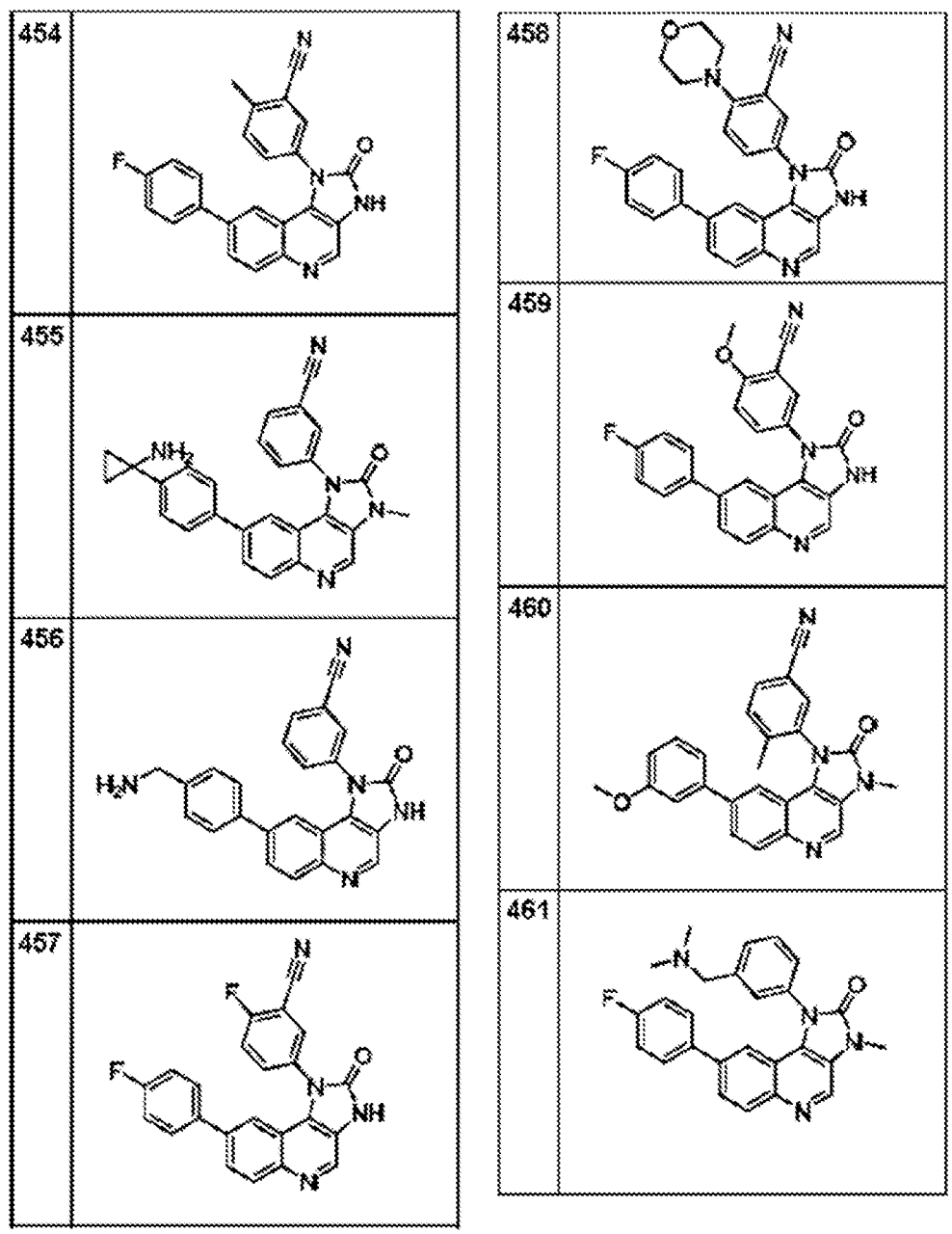
Figure 2C:
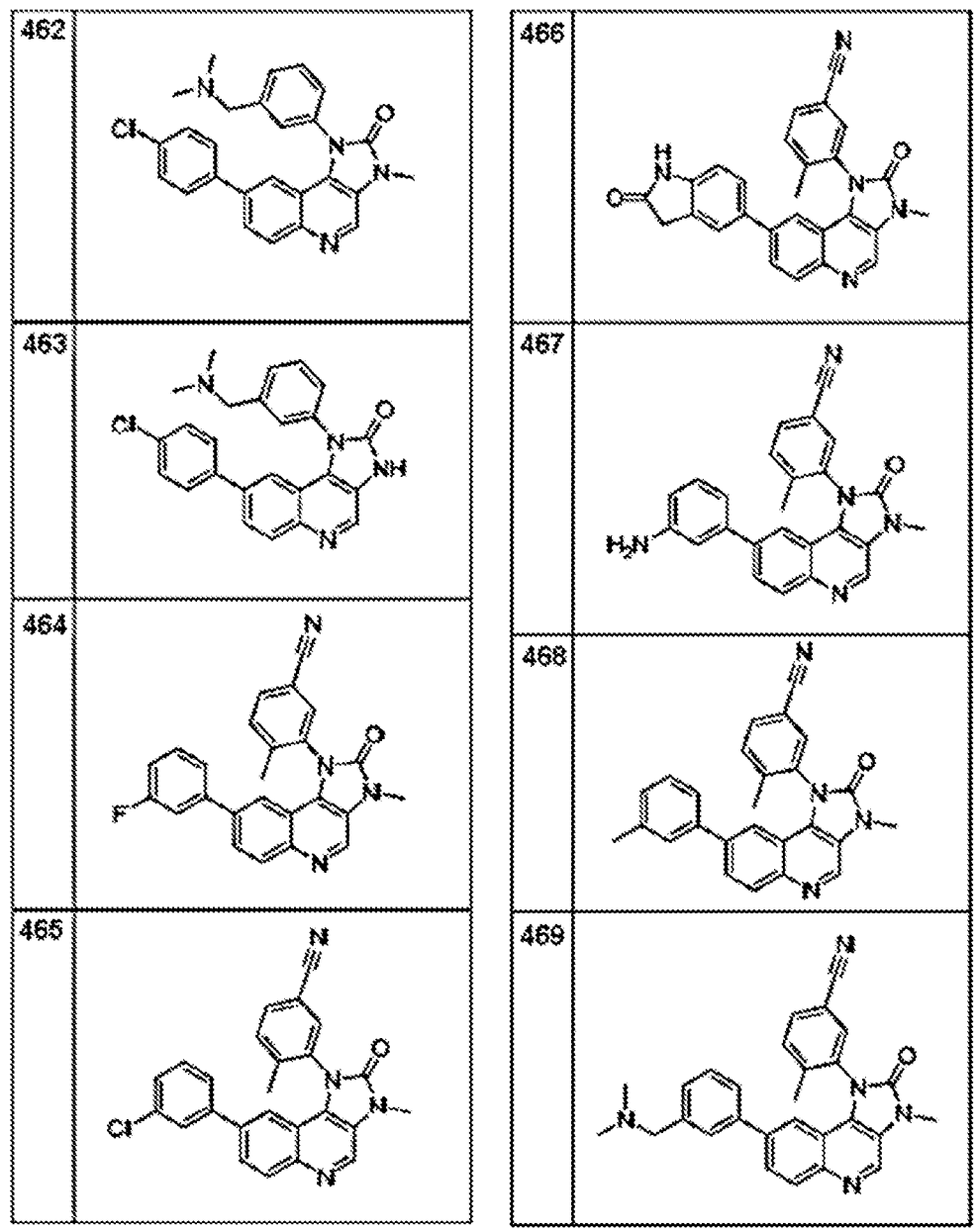
Figure 2C:
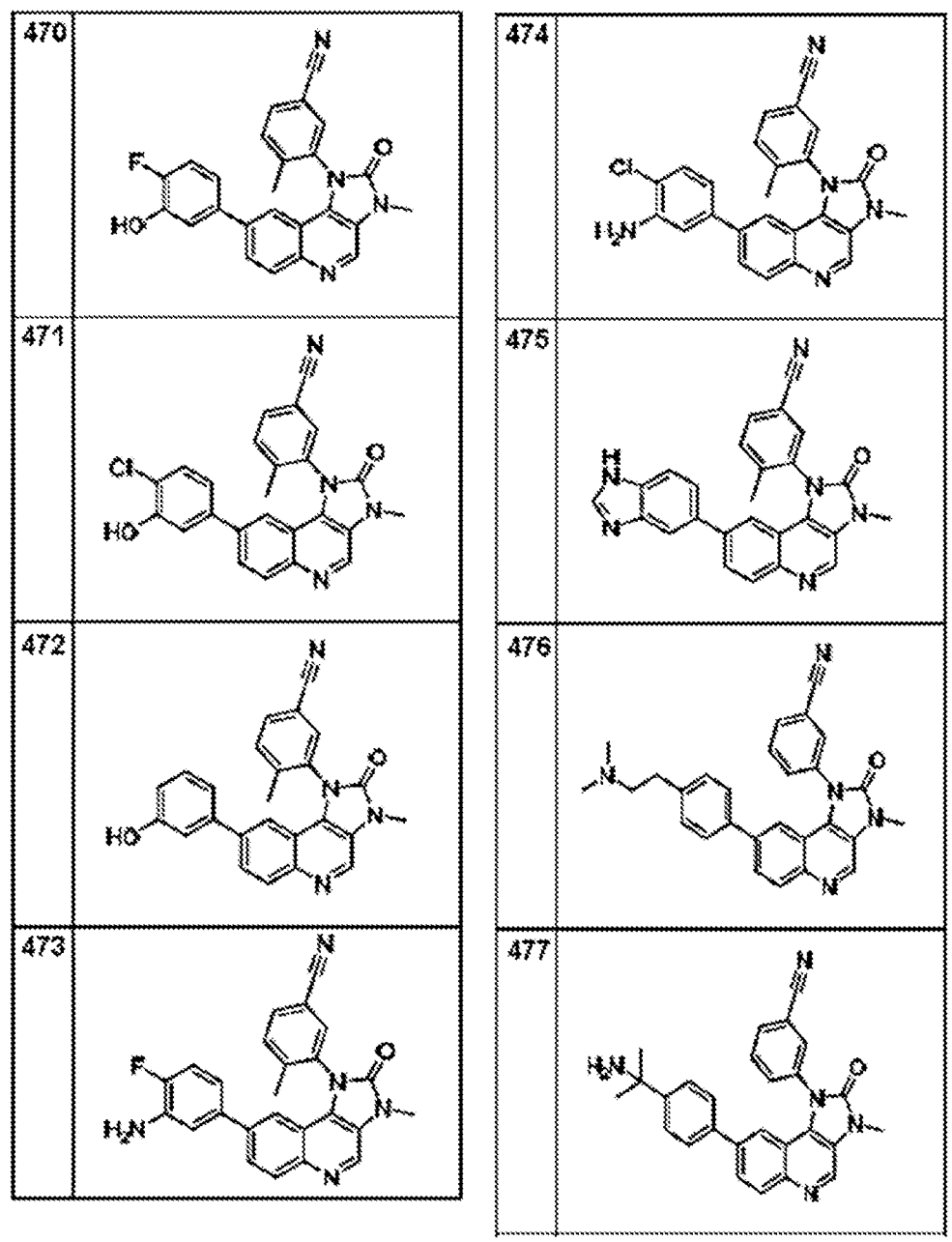
Figure 2C:
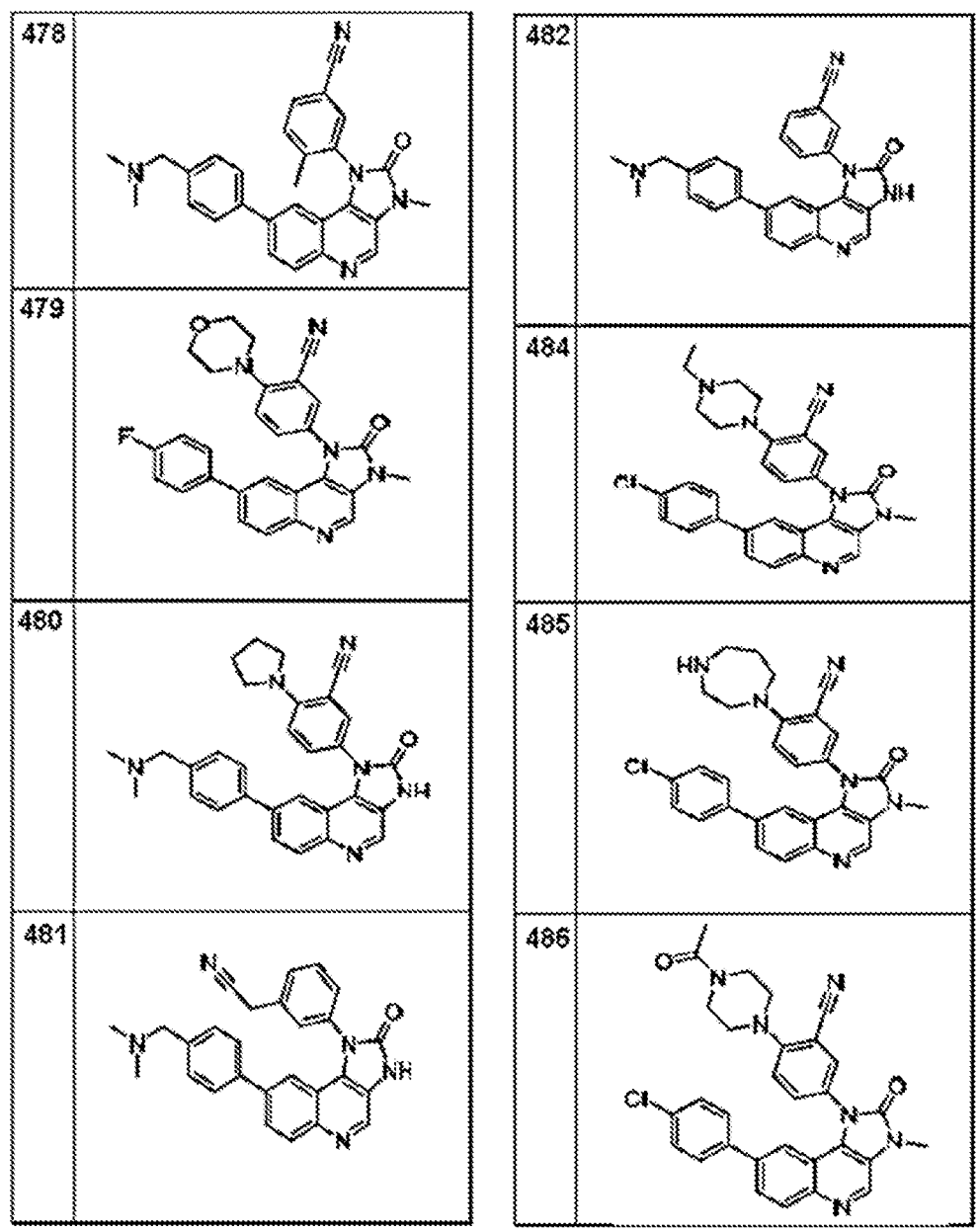
Figure 2C:
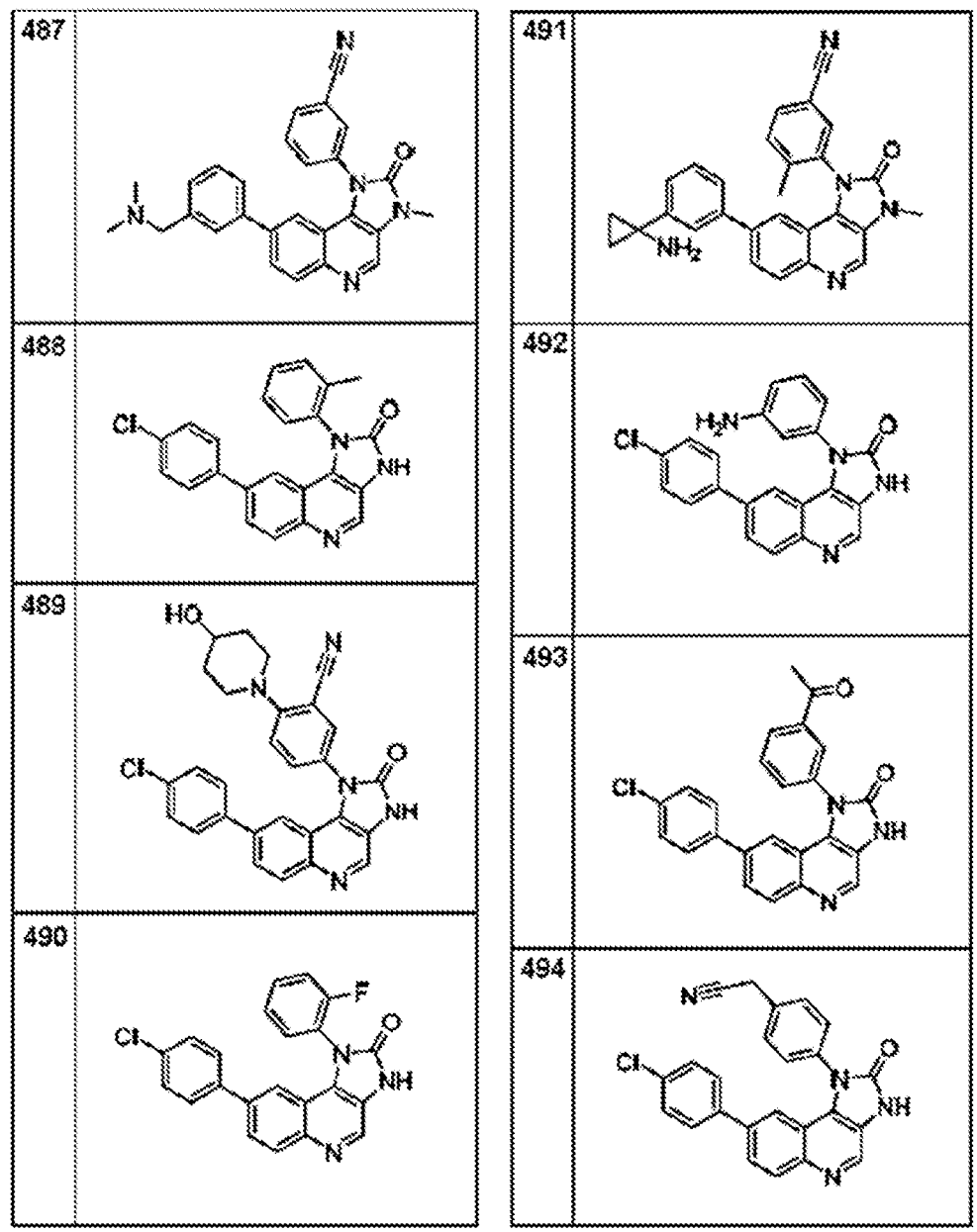
Figure 2C:
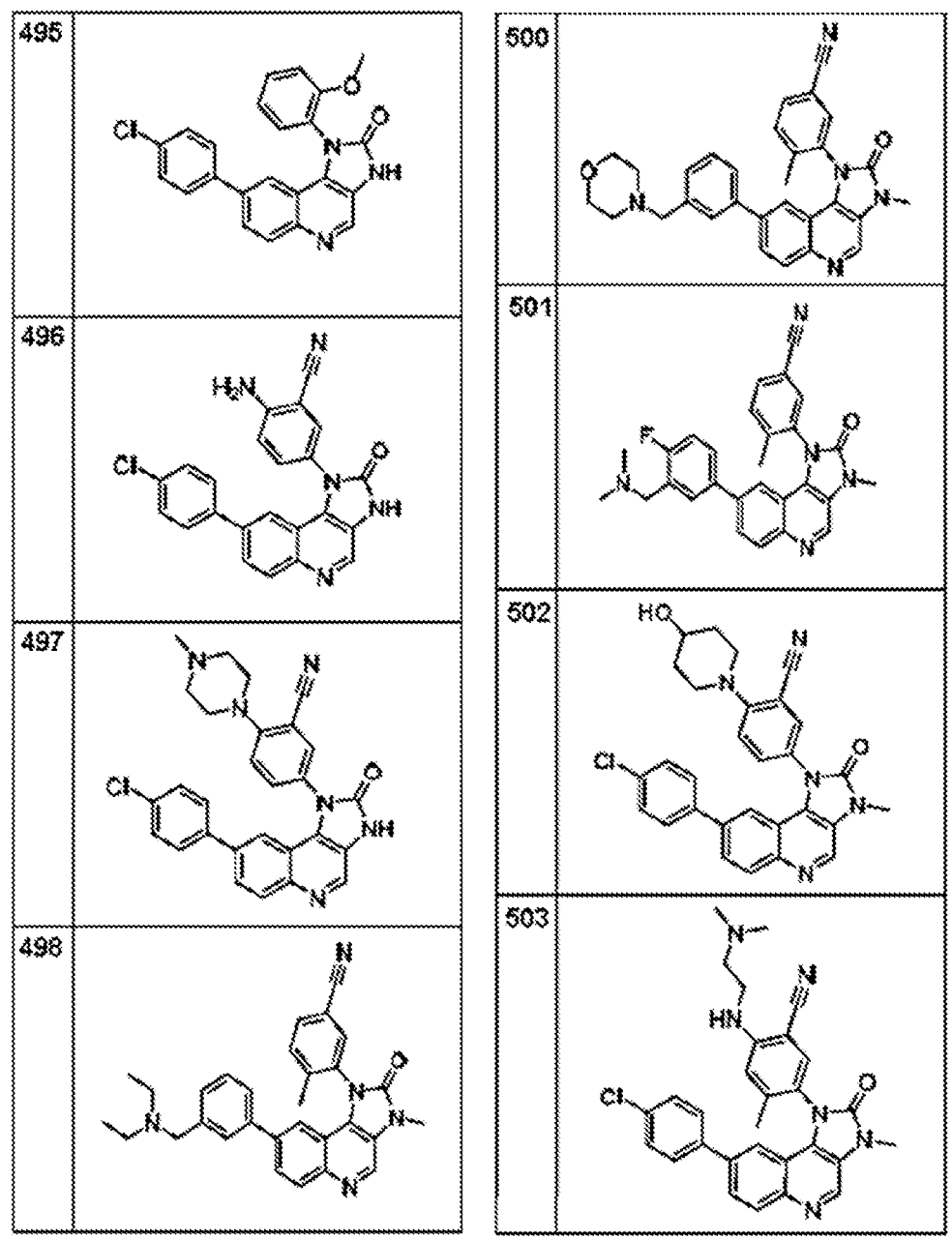
Figure 2C:
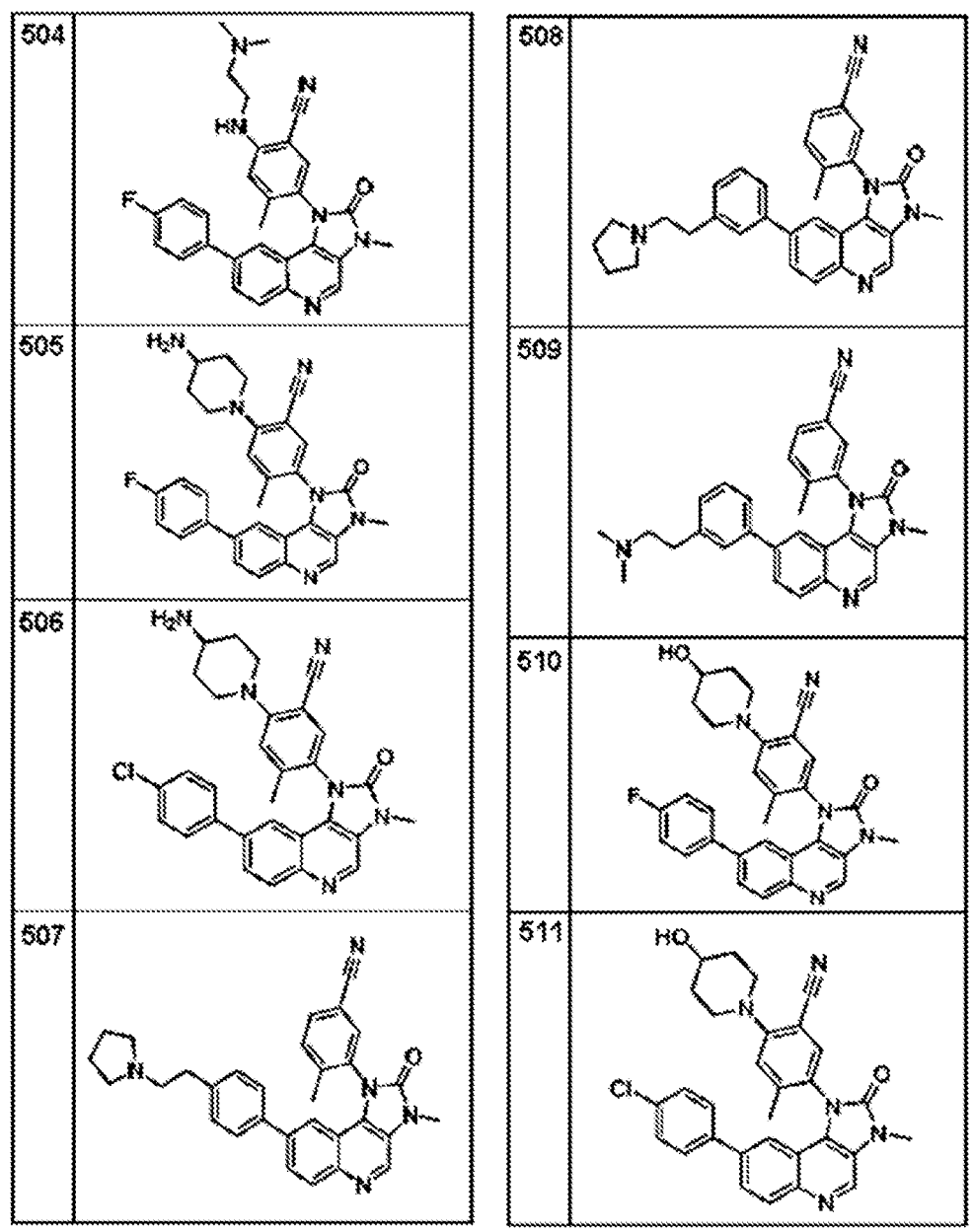
Figure 2C:
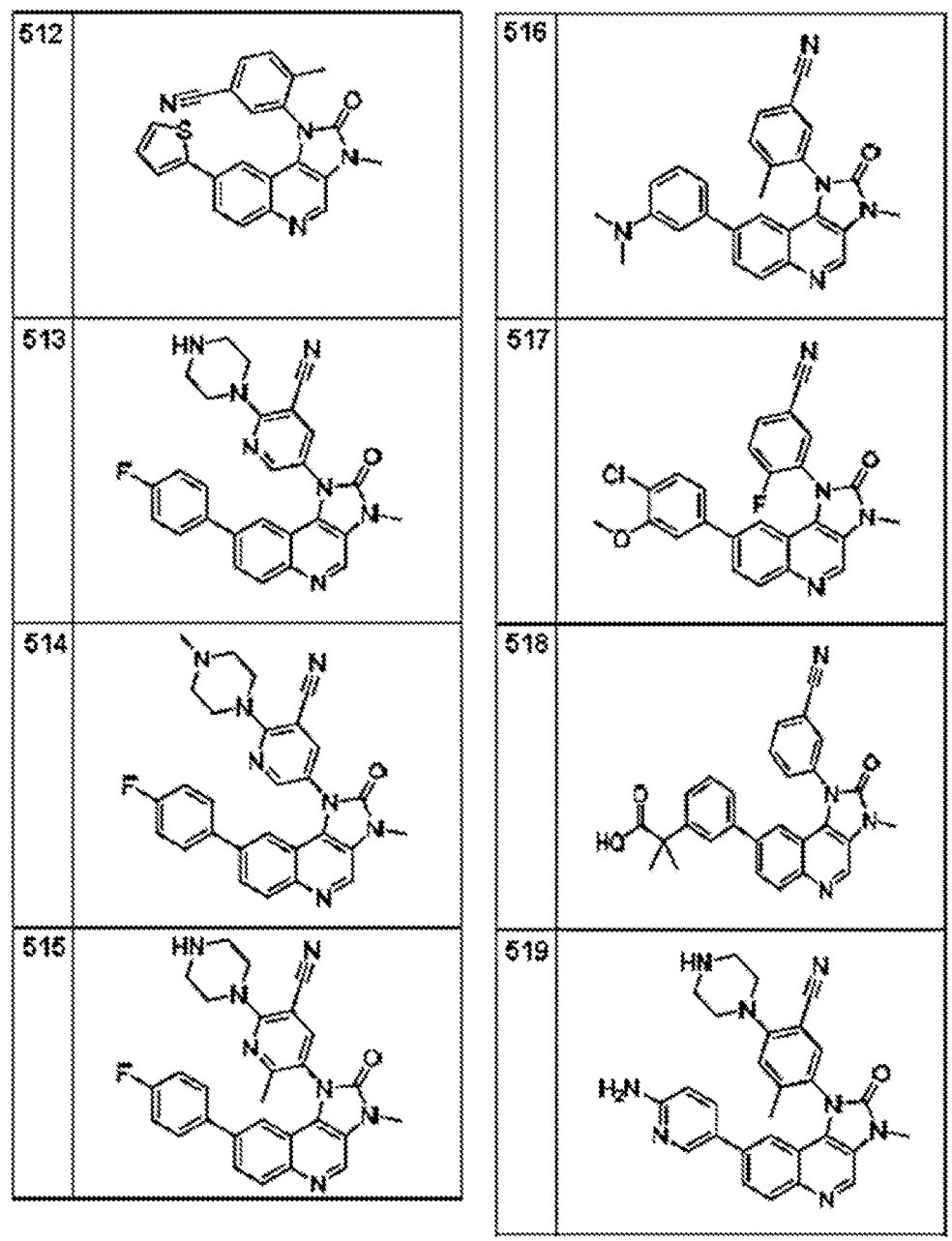
Figure 2C:
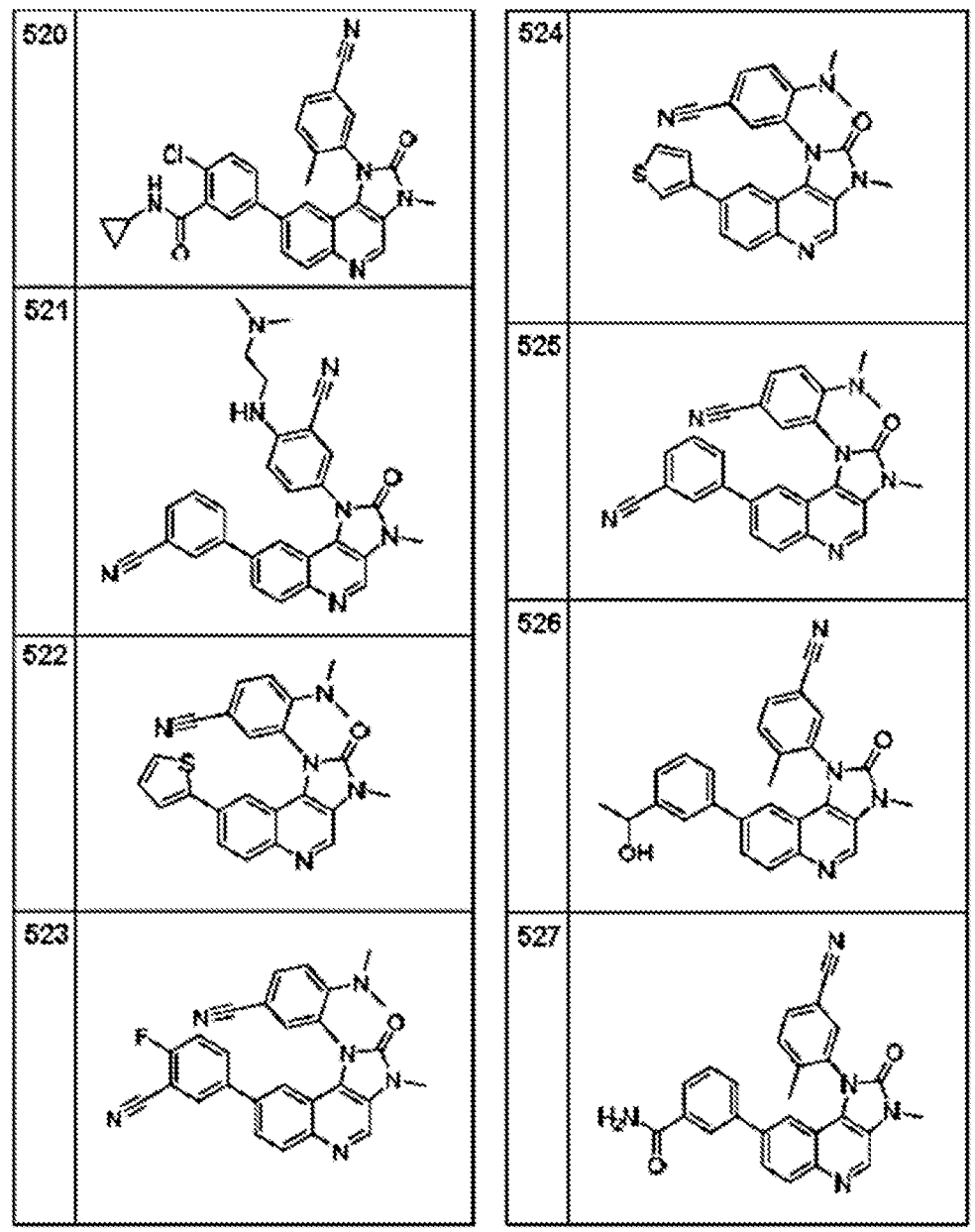
Figure 2C:
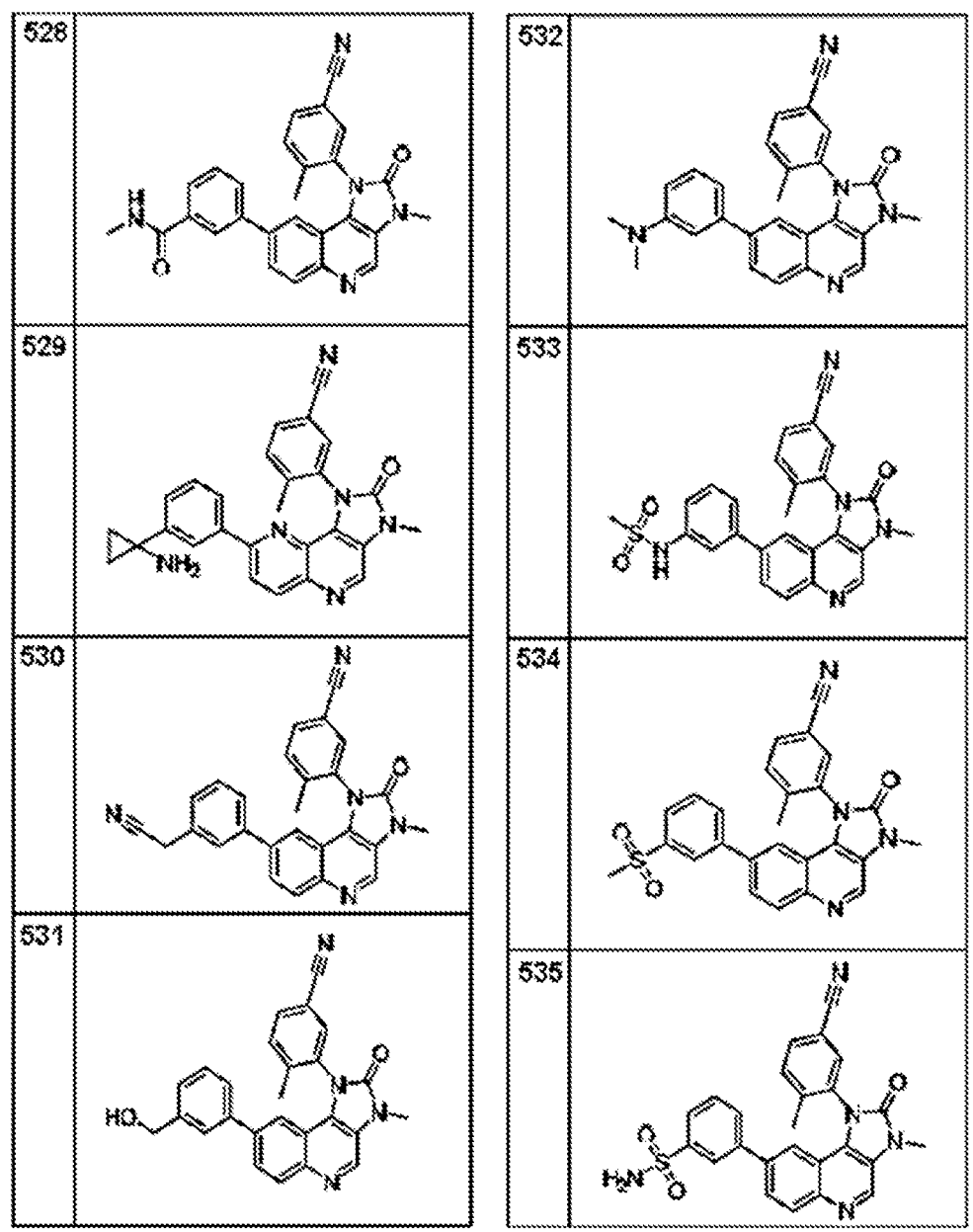
Figure 2C:
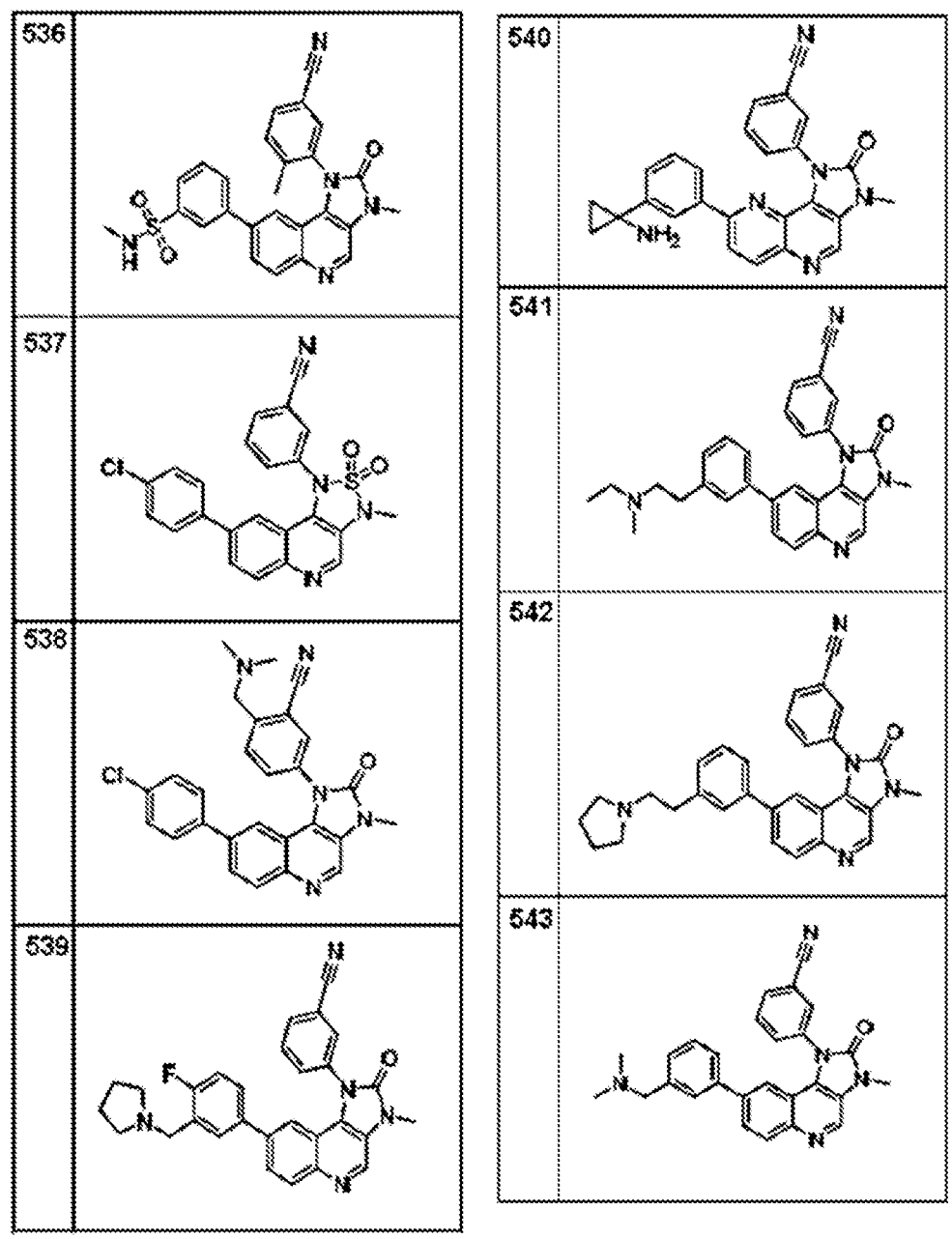
Figure 2C:
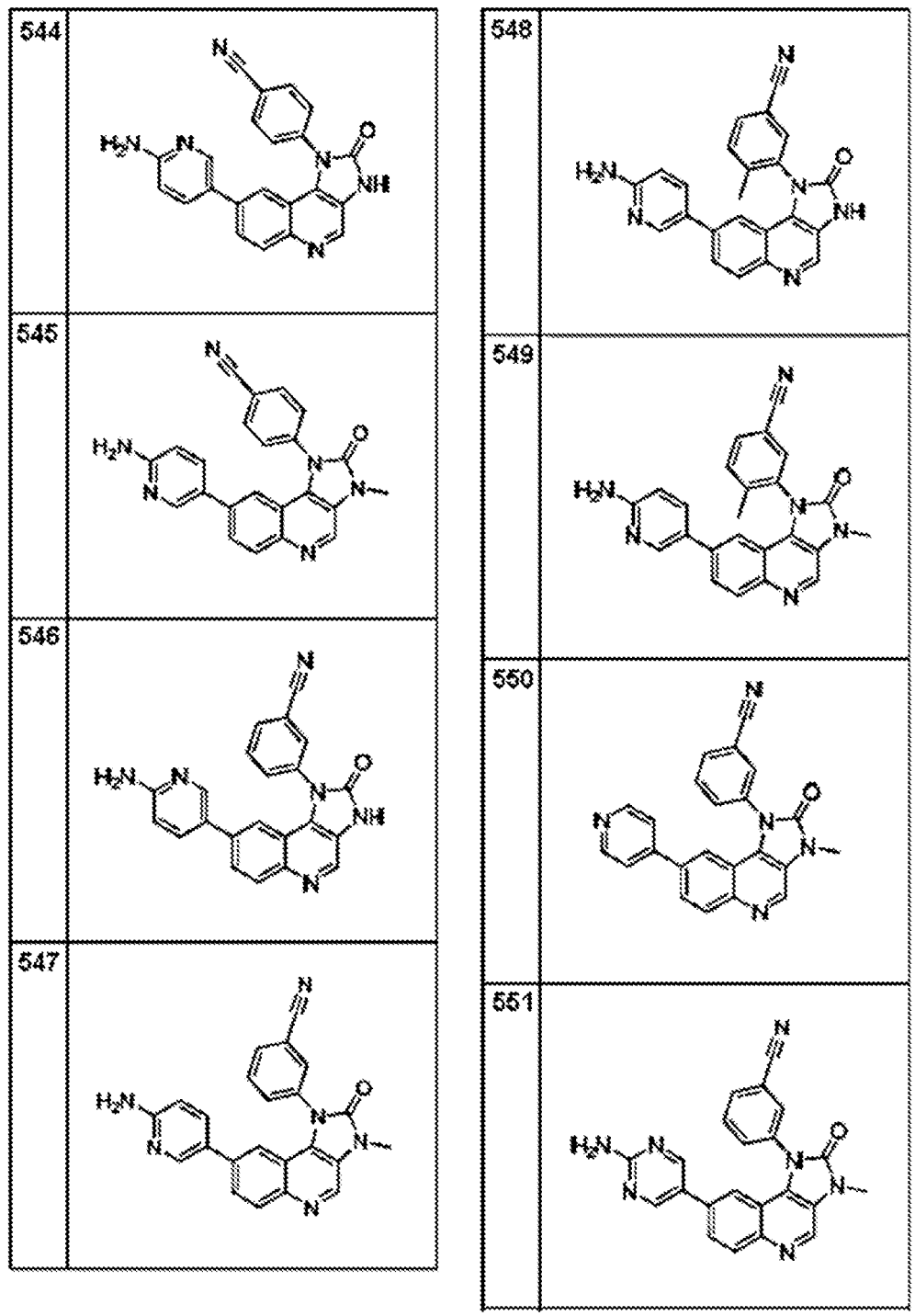
Figure 2C:
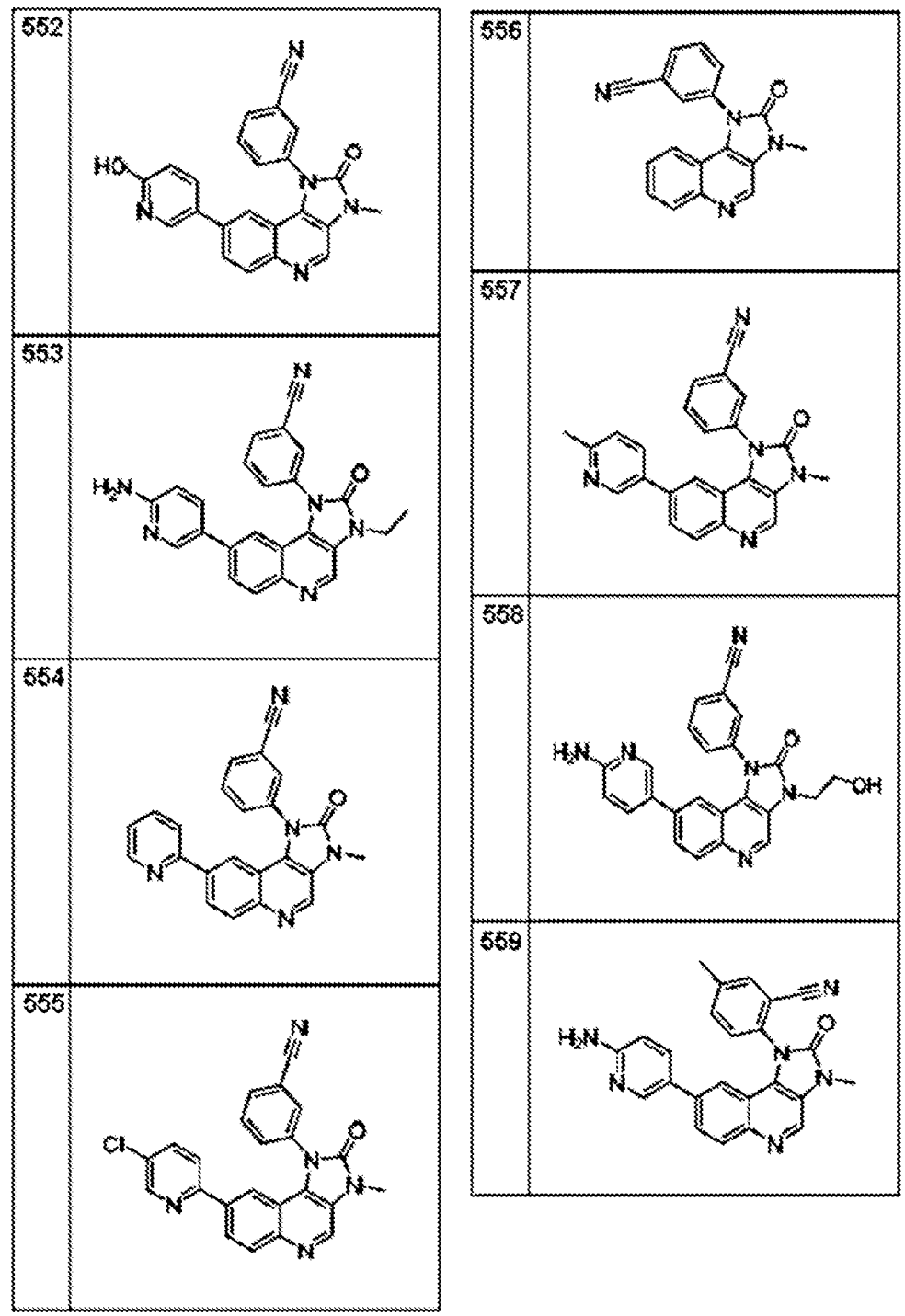
Figure 2C:
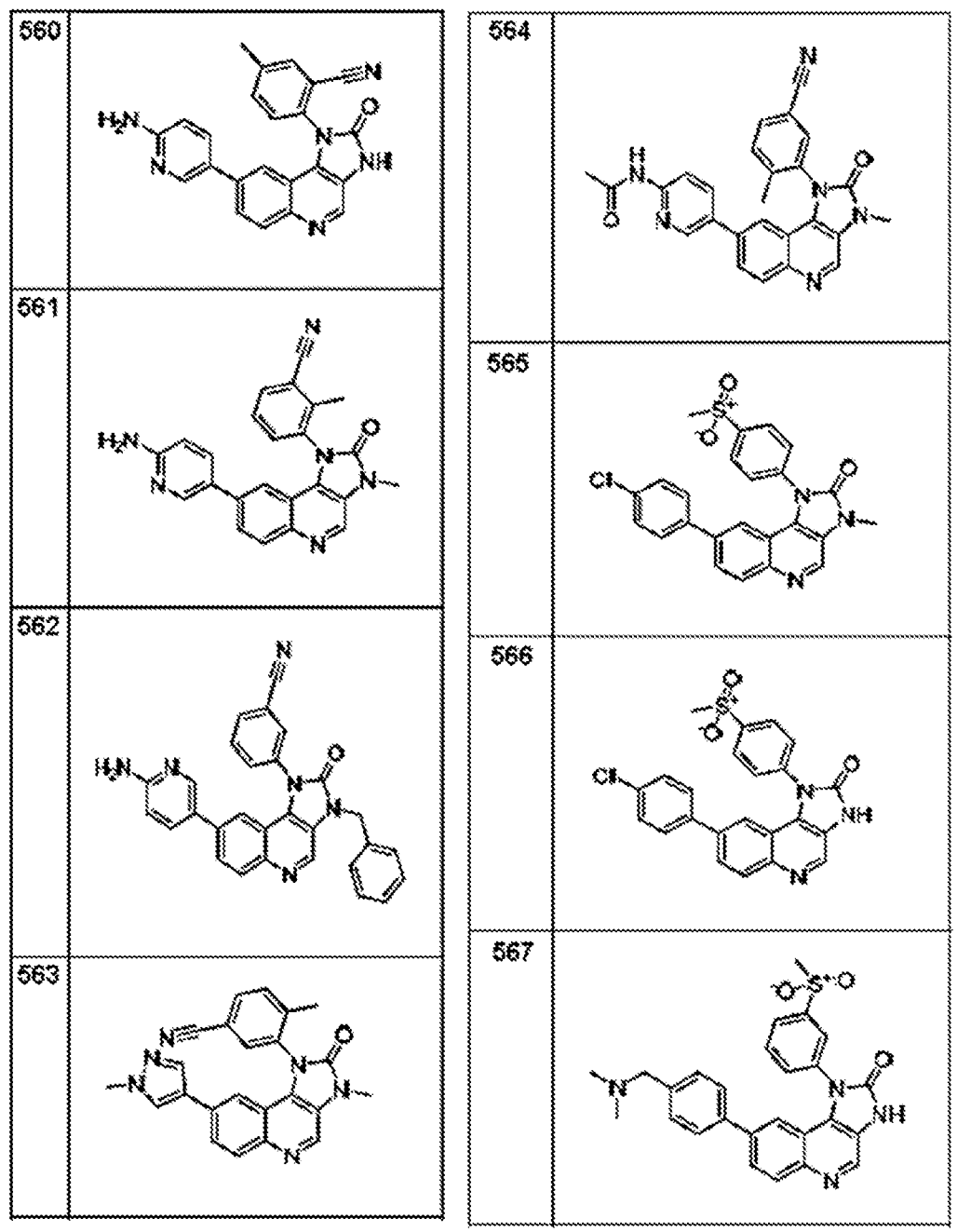
Figure 2C:
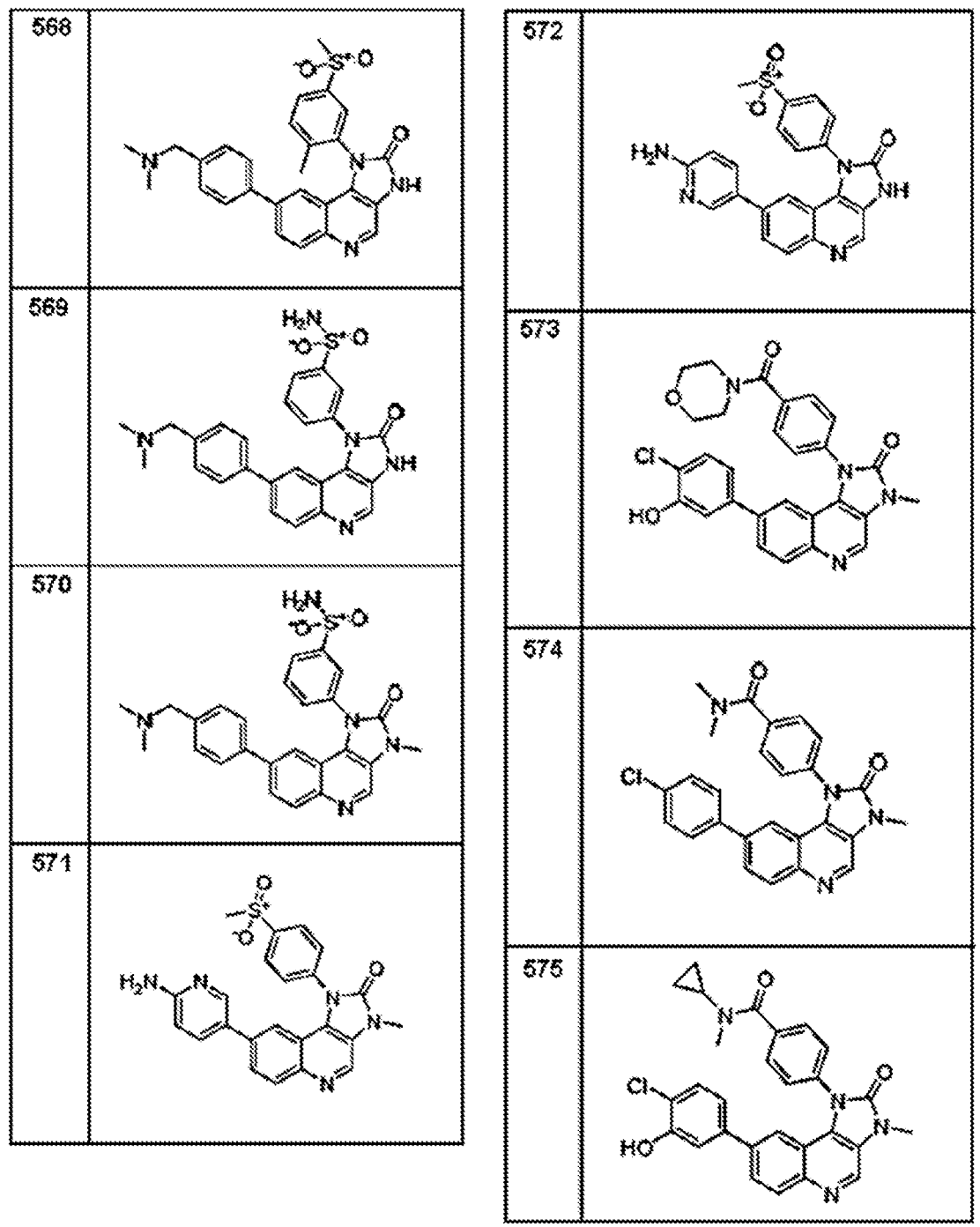
Figure 2C:
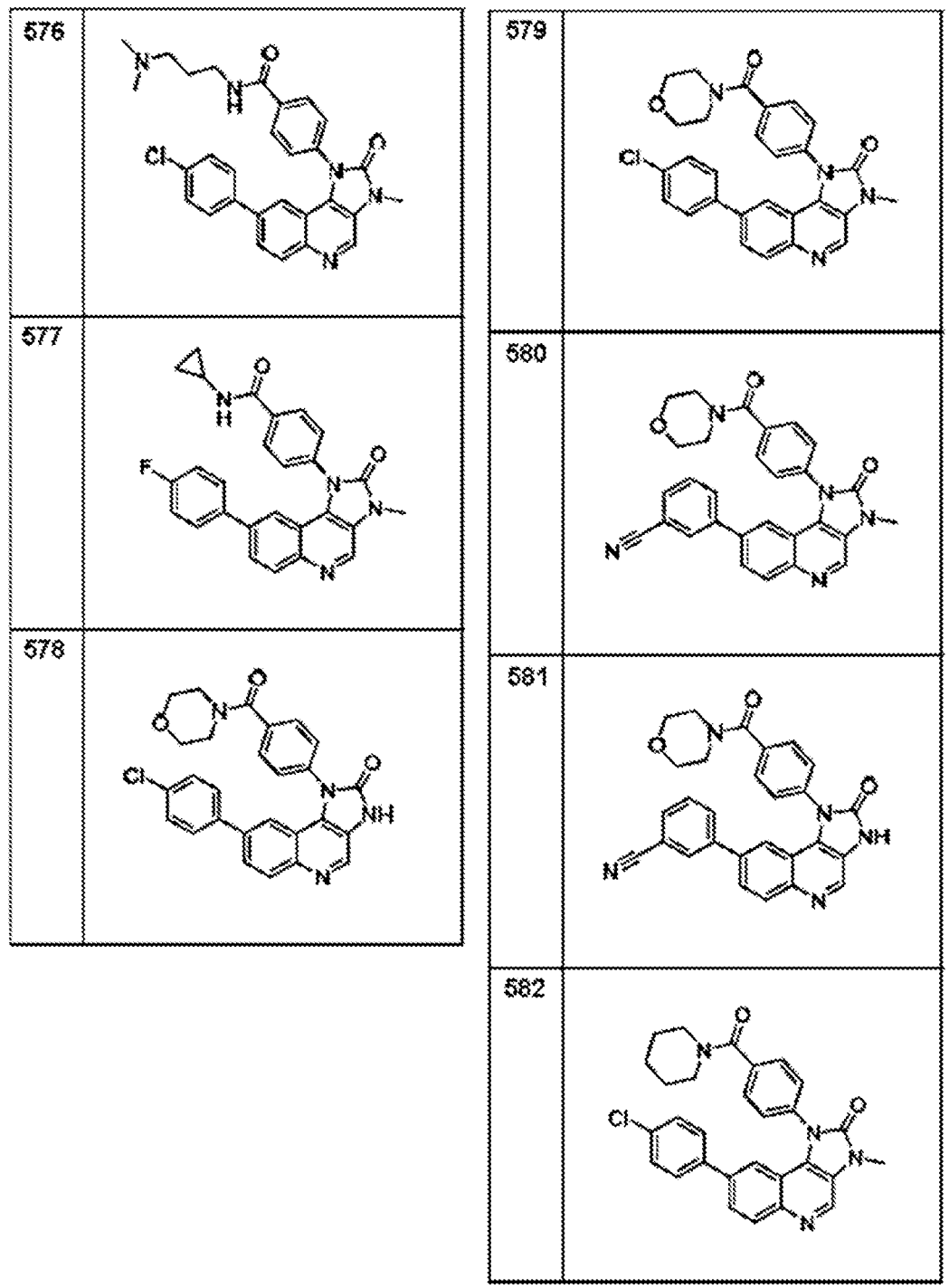
Figure 2C:
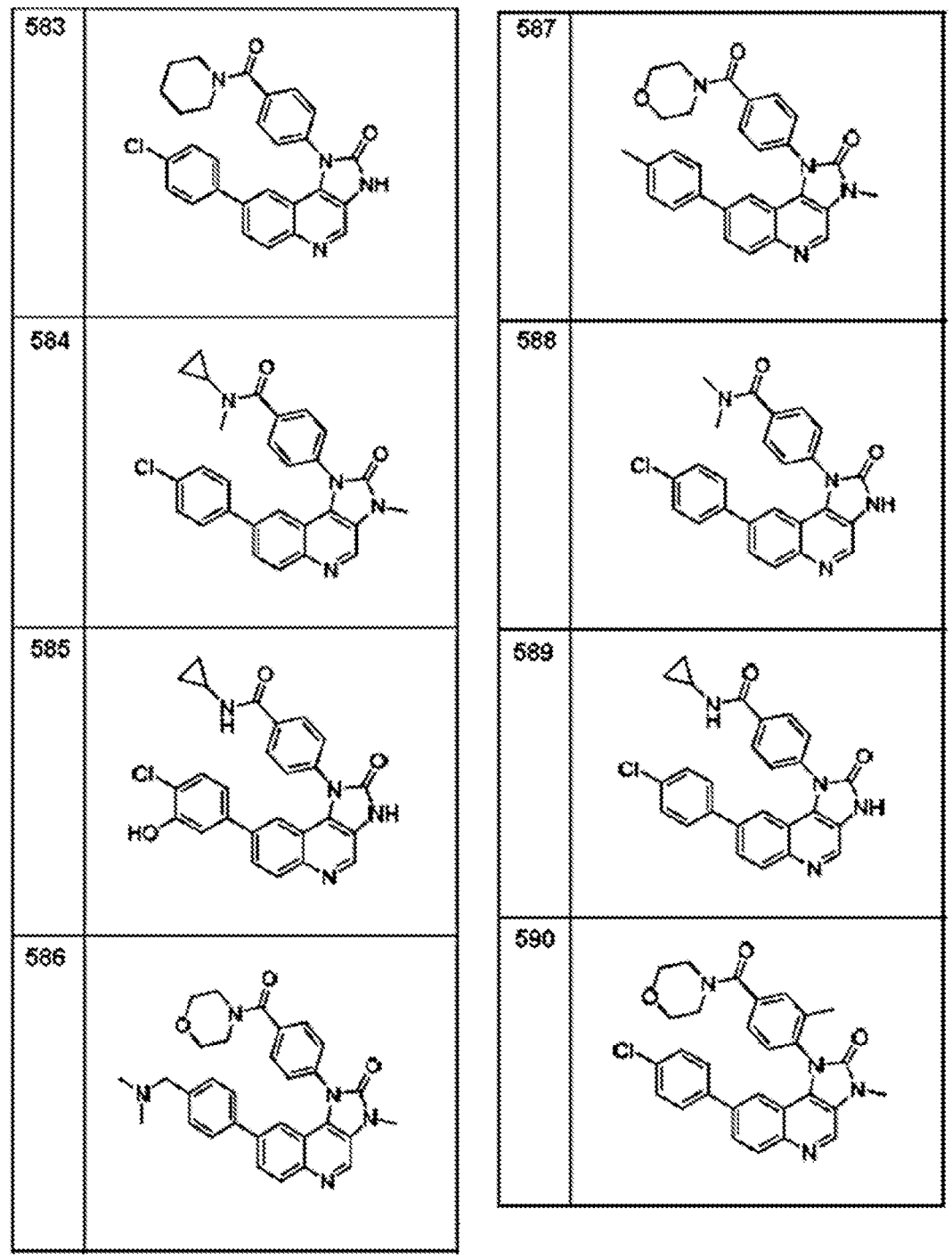
Figure 2C:
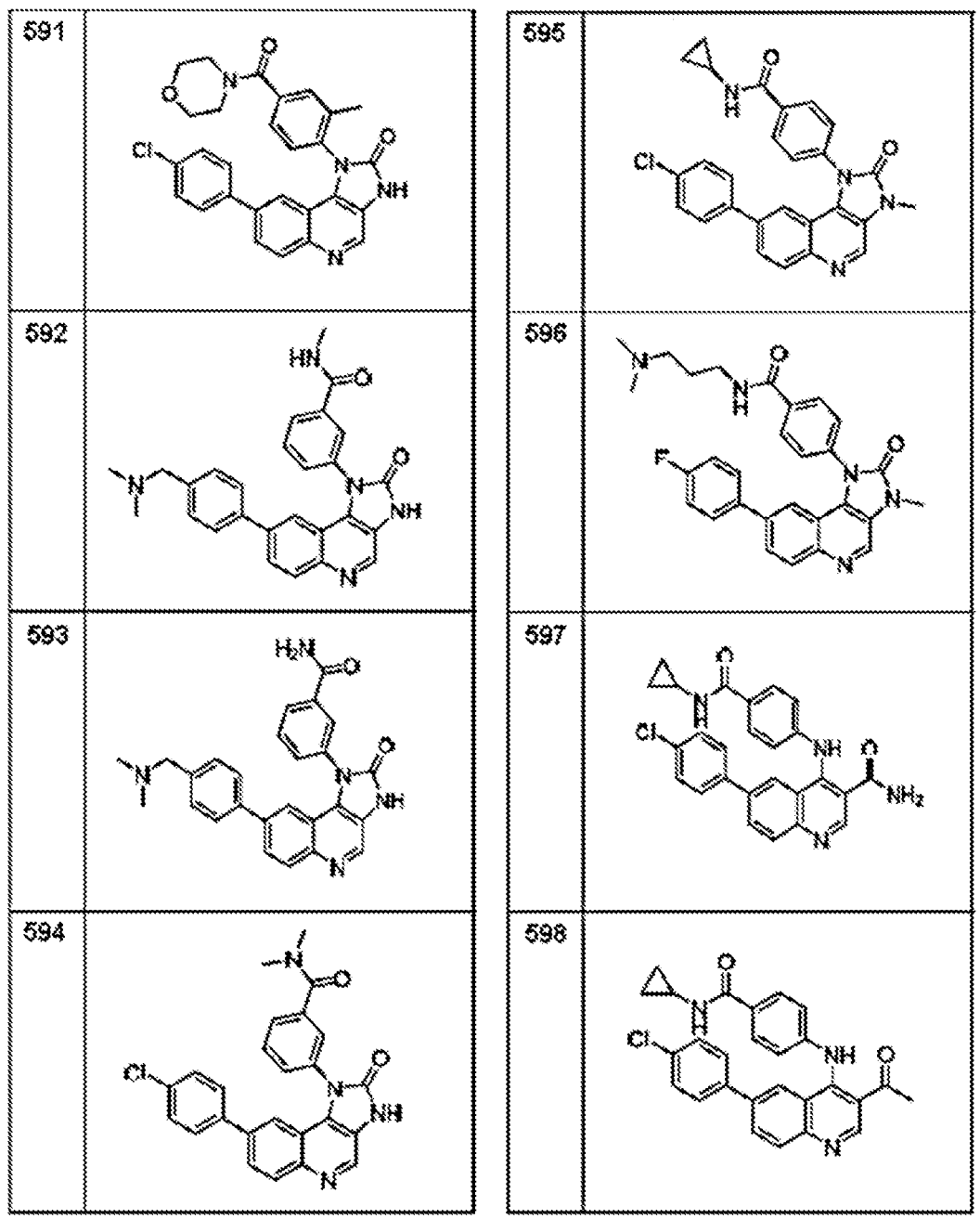
Figure 2C:
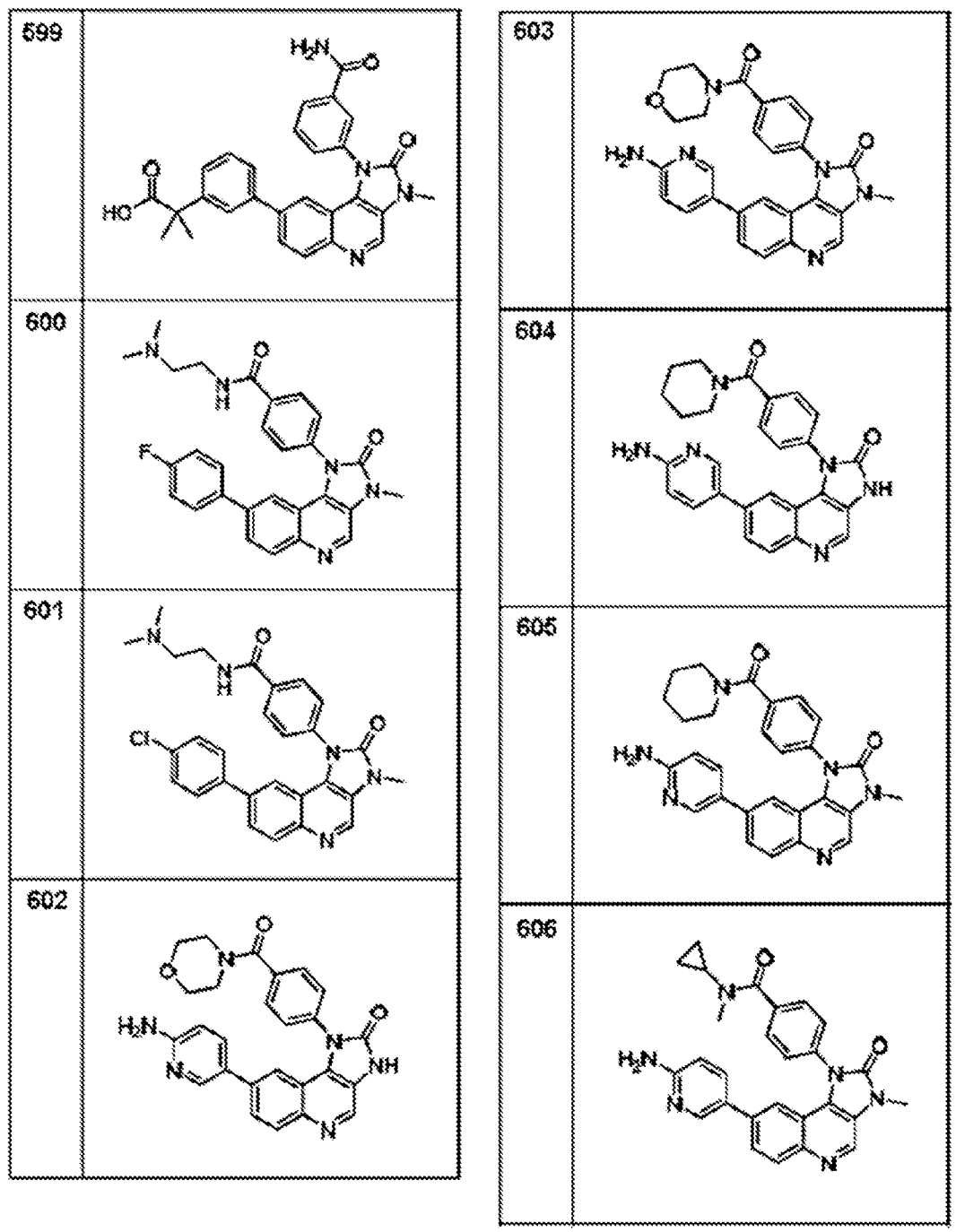
Figure 2D:
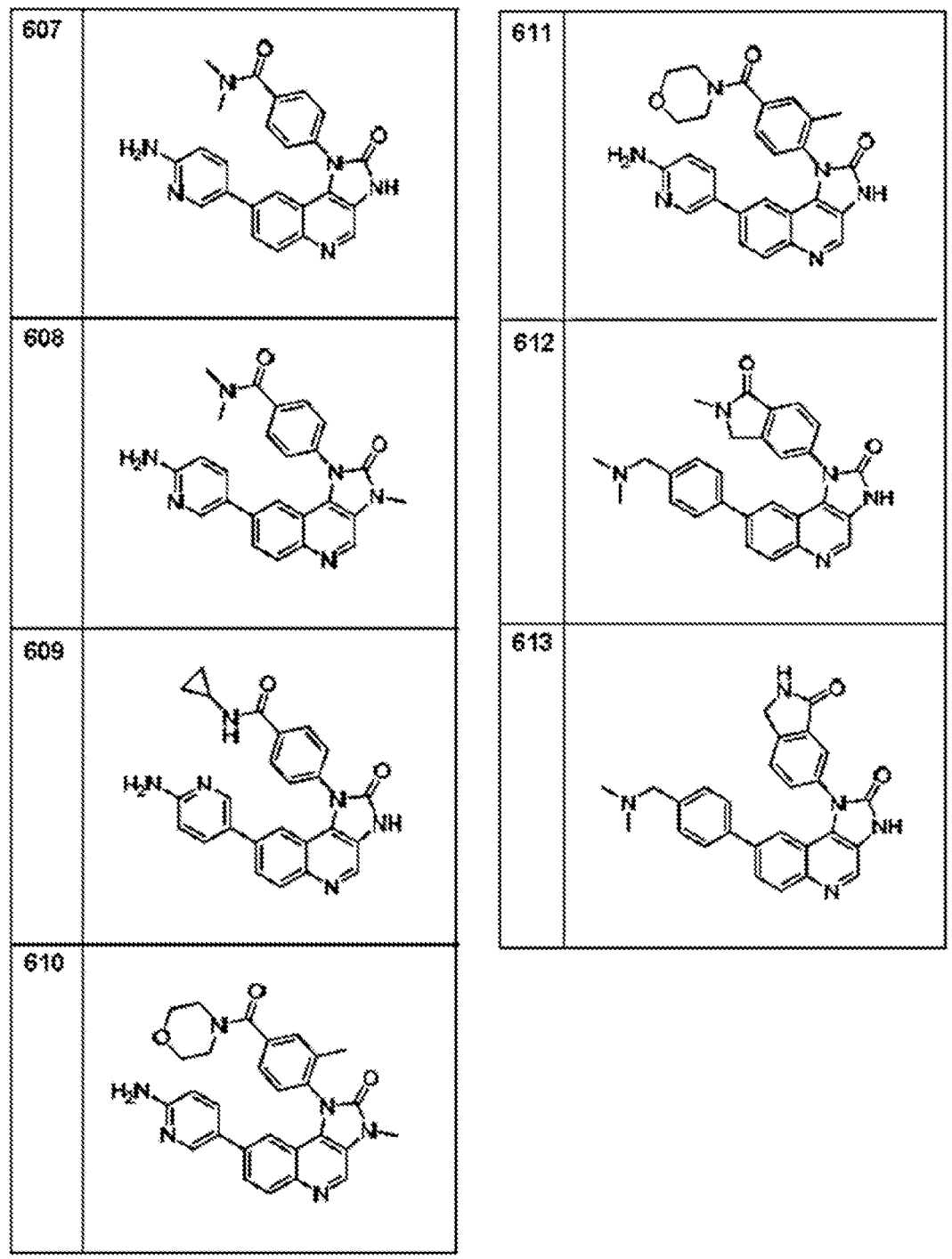
Figure 2D:
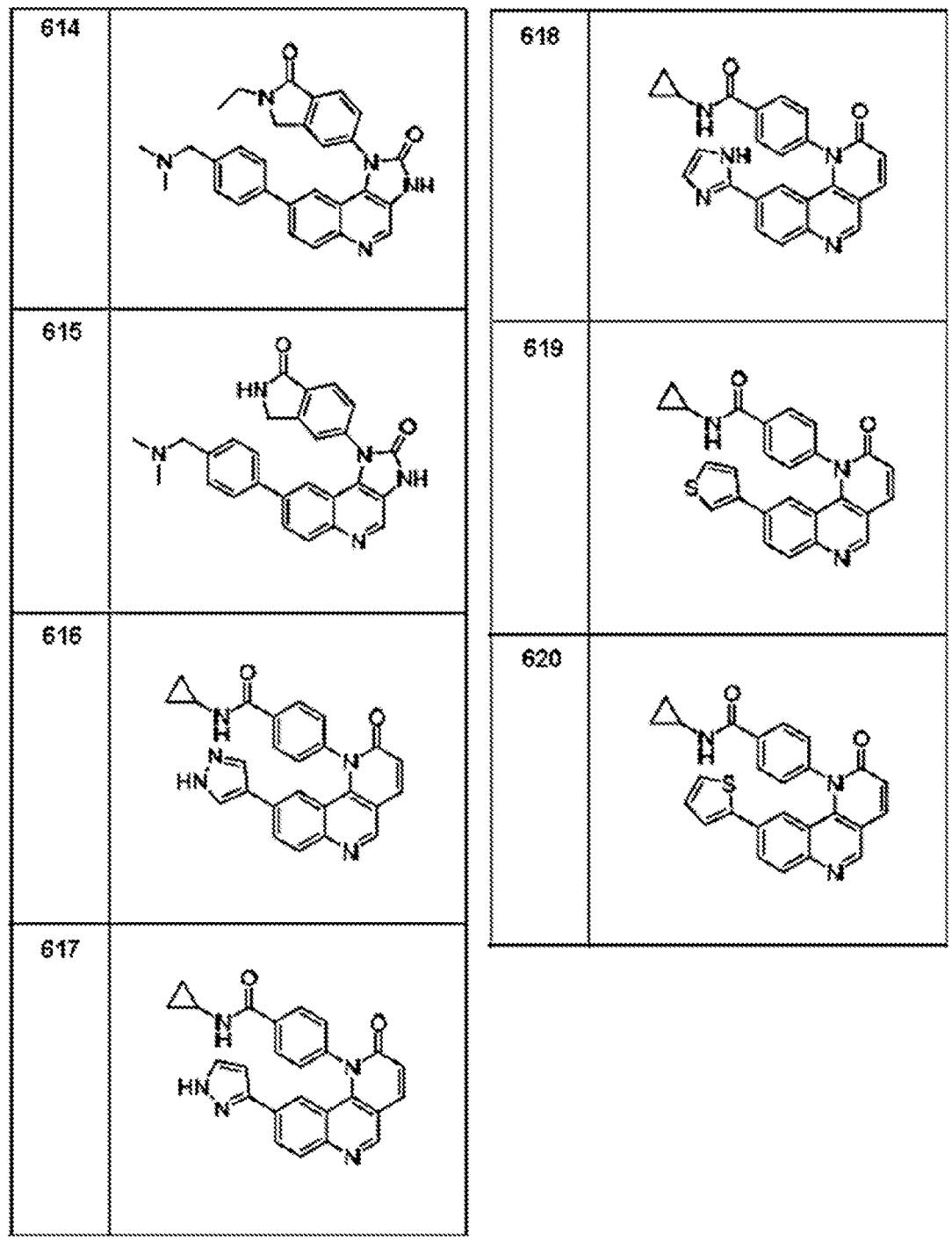
Figure 2D:
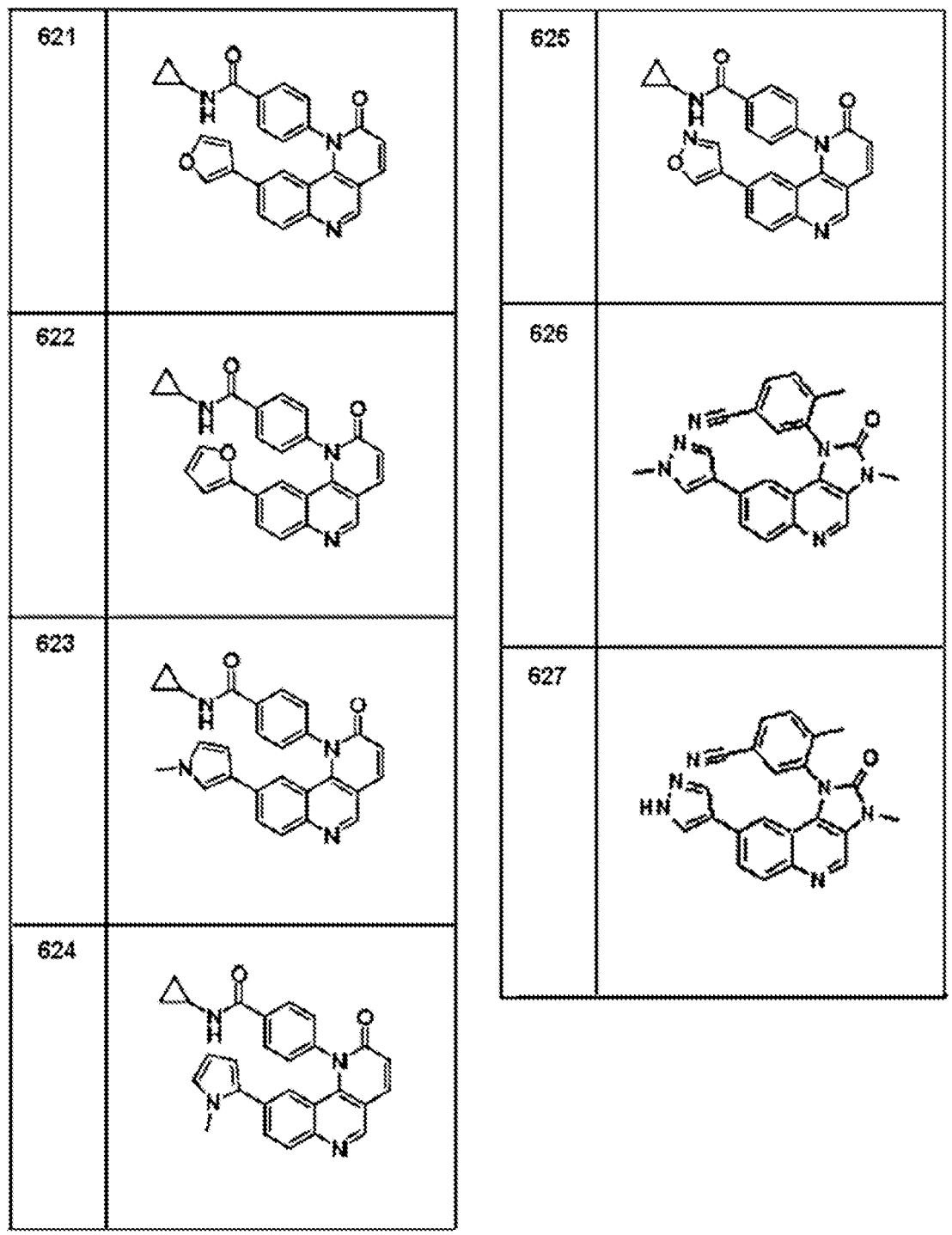
Figure 2D:
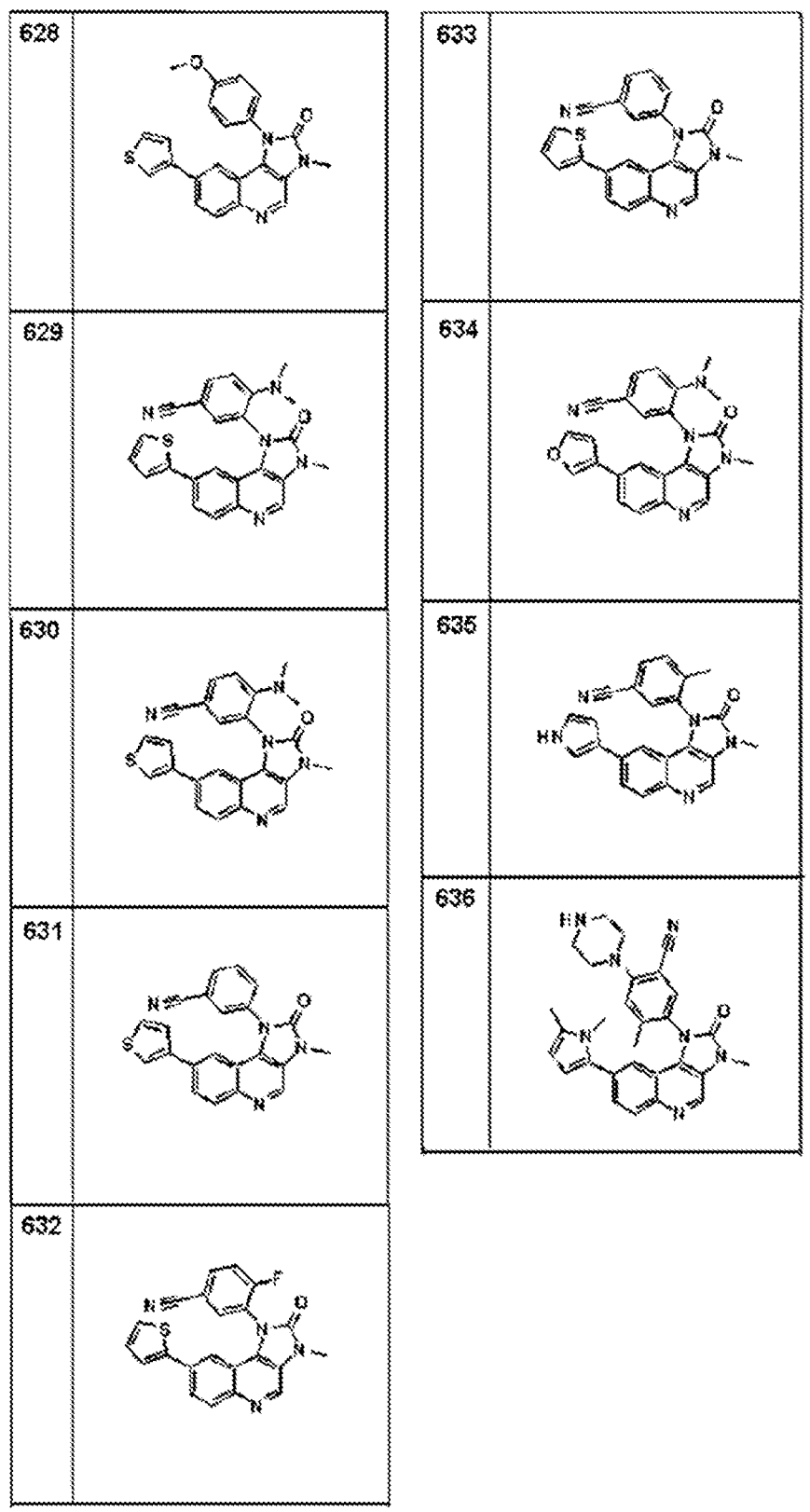
Figure 2D:
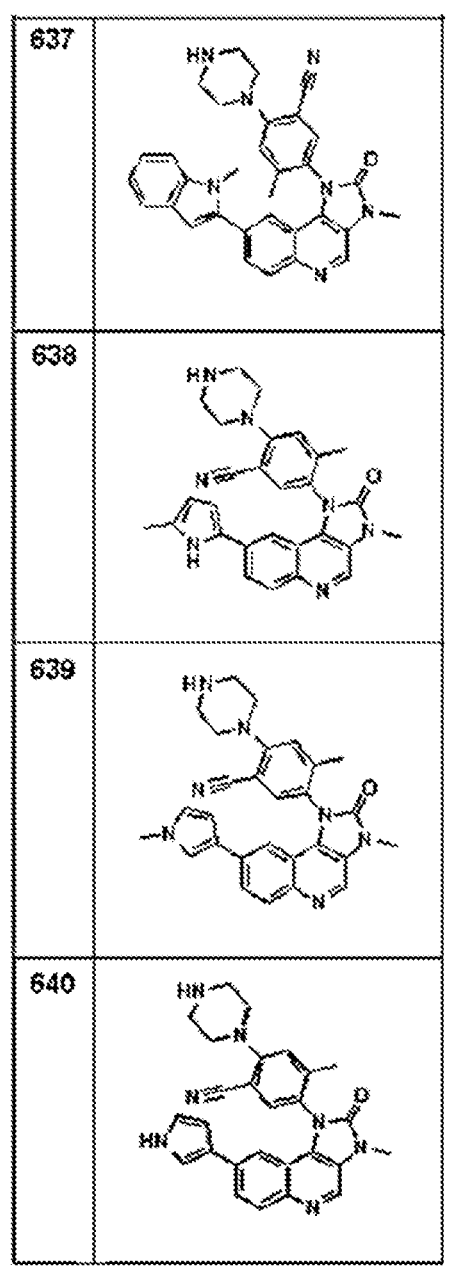

FIG. 2AA-2DE depict the structures of additional compounds in accordance with an embodiment of the invention.

DETAILED DESCRIPTION OF THE INVENTION

In an embodiment, the invention provides a compound of formula (I):

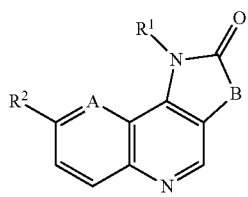

wherein A is $CR^5$ or N,

B is $CR^3$=$CR^4$ or $NR^6$, $R^1$ is $C_{6-10}$ aryl or heteroaryl substituted with at least one substituent selected from —CN, cyanomethyl, —$SO_2R^{13}$, —$SO_2NHR^{15}$, and —$CONR^{11}R^{12}$, optionally further in combination with one or more substituents selected from halo, $C_{1-12}$ alkyl, alkoxy, a heterocyclyl group selected from the group consisting of optionally substituted piperazinyl, morpholinyl, pyrrolinidyl, and diazepinyl, or an aryl bicyclic lactam of the formula:

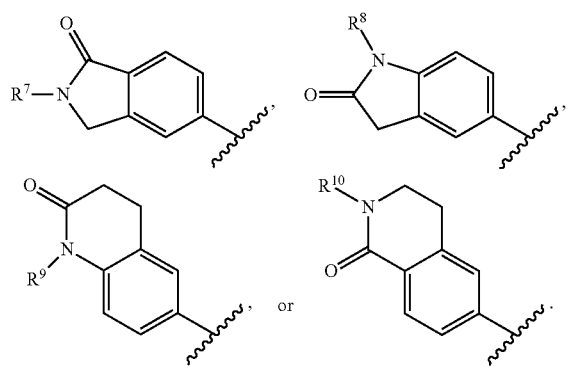

wherein the aryl group of the aryl bicyclic lactam is optionally substituted with at least one substituent selected from —CN, cyanomethyl, —$SO_2R^{13}$, —$SO_2NH_2$, and —$CONR^{11}R^{12}$, optionally further in combination with one or more substituents selected from halo, $C_{1-12}$ alkyl, alkoxy, 2-(dimethylamino)ethyl)amino, dimethylamino, a heterocyclyl group selected from the group consisting of optionally substituted piperazinyl, morpholinyl, pyrrolinidyl, azetidinyl and diazepinyl, $R^2$ is selected from 2-amino-5-pyridinyl, 4-pyridinyl, 2-amino-5-pyrimidinyl, 3-pyridyl, quinolin-3-yl, 5-pyrimidinyl, 2-acetylamino-5-pyridyl, 2-amino-4-methylpyrimidin-5-yl, 1-piperazinyl, indol-5-yl, 1H-imdazol-5-yl, 4-aminophenyl, 1,2,3,6-tetrahydropyridin-4-yl, 1H-pyrazol-4-yl, N-methyl-pyrazol-4-yl, 1H-benzo[d]imidazol-5-yl, 4-sulfonylaminophenyl, 2-dimethylaminopyrimidin-5-yl, 3-trifluoromethylphenyl, bromo, 3-aminophenyl, 4-aminophenyl, vinyl, 4-aminocarbonylphenyl, 3-cyanophenyl, 3-hydroxyphenyl, 3-trifluoromethyl-5-pyridyl, tetrazolyl, 4-chlorophenyl, 4-fluorophenyl, 4-methoxyphenyl, 3-aminocarbonylphenyl, 3-acetylphenyl, 3-cyano-4-chlorophenyl, 3-cyano-5-methylphenyl, 3-hydroxy-4-chlorophenyl, 4-hydroxymethylphenyl, 3-amino-4-chlorophenyl, 2,3-dihydrobenzofuran-6-yl, 1-methyl-1H-indol-5-yl, benzo[d][1,3]dioxo-5-yl, 4-fluorophenyl, 4-hydroxyphenyl, morpholin-1-yl, benzo[b]thiophen-1-yl, 4-methylsulfonylphenyl, benzo[c][1,2,5]oxadiazol-5-yl, 2-(piperidin-1-yl)-3-pyridinyl, 4-carboxyphenyl, 2-methyl-5-pyridyl, 4-methylsulfonylphenyl, 4-dimethylaminocarbonylphenyl, 4-phenylphenyl, 4-methylphenyl, 3-chloro-5-pyridyl, (3-pyrrolidin-1-yl)phenyl, 4-([piperizin-1-yl]carbonyl)phenyl, 4-([morpholin-1-yl]carbonyl)phenyl, 2-hydroxypyrimidin-5-yl, 3-aminosulfonylphenyl, 2-oxo-1,2,3,4,tetrahydroisoquinolin-6-yl, 2-oxo-1,2,3,4,-tetrahydroquinolin-6-yl, 4-(aminomethyl)phenyl, 4-(dimethylaminomethyl)phenyl, 4-(diethylaminomethyl)phenyl, 4-(methylaminocarbonyl)phenyl, 1-oxoindolin-5-yl, 2-oxoindolin-5-yl, 1-oxoisoindolin-5-yl, 2-amino-4-pyridyl, 3-amino-4-chlorophenyl, 4-aminomethylphenyl, 3-methyl-4-chlorophenyl, 3-methoxy-4-chlorophenyl, 4-aminophenyl, 3-methylphenyl, 3-methoxyphenyl, phenyl, 5-indolinone, 5-isoindolinone, 3-aminophenyl, 2-hydroxy-4-chlorophenyl, 4-cyanophenyl, 4-(2-aminoethyl) phenyl, 4-(2-dimethylaminoethyl) phenyl, 4-azetidinylphenyl, 4-ethylphenyl, 3-fluorophenyl, 3-chlorophenyl, 3-dimethylaminomethylphenyl, 3-cyano-4-fluorophenyl, 3-amino-4-fluorophenyl, 4-(1-hydroxy-1-ethylphenyl), 3-methyl-5-pyridyl, 2-acetylamio-5-pyridyl, 2-oxoindolin-5-yl, benzimidazolin-5-yl, 3-dimethylamino-1-propargyl, 2-pyrrolyl, N-methyl-2-pyrrolyl, 2-thiopheneyl, 3-thiopheneyl, 3-furanyl, 3-aminosulfonylphenyl, 4-dimethylaminomethylphenyl, and 4-pyrrolidinomethylphenyl, $R^3$ and $R^4$ are independently selected from hydrogen, hydroxyl, $OR^5$, halogen, optionally substituted $C_{6-10}$ aryl, and optionally substituted $C_{1-6}$ alkyl, $R^5$ is hydrogen, $C_{1-12}$ alkyl, $C_{6-10}$ aryl, halogen, hydroxyl, or $OR^{16}$, $R^6$ is hydrogen, $C_{1-12}$ alkyl, $C_{2-12}$ hydroxyalkyl, $C_{1-6}$ acyl-$C_{1-6}$ alkyl, or $C_{6-10}$ aryl, $R^7$-$R^{10}$ are independently selected from hydrogen, $C_{1-12}$ alkyl, $C_{3-8}$ cycloalkyl, $CH_2COOR^{13}$, and $H_2N(CH_2)_n$— wherein n is an integer of 2-6, $R^{11}$ and $R^{12}$ selected from the group consisting of hydrogen, $C_{1-12}$ alkyl and $C_{3-10}$ cycloalkyl or, taken together with the N to which they are bound, form an optionally substituted 4-7 membered heterocyclyl ring containing O or N atoms, and $R^{13}$ is $C_{1-12}$ alkyl, $R^{15}$ is hydrogen or $C_{1-12}$ alkyl, $R^{16}$ is $C_{1-12}$ alkyl or $C_{6-10}$ aryl or a pharmaceutically acceptable salt thereof, with the provisos that when A is CH, B is $CR^3$=$CR^4$, $R^3$ and $R^4$ are each hydrogen, and $R^2$ is 2-amino-5-pyridyl, $R^1$ is not 3-cyanophenyl or 3-aminosulfonylphenyl.

Referring now to terminology used generically herein, the term "alkyl" means a straight-chain or branched alkyl substituent containing from, for example, 1 to about 6 carbon atoms, preferably from 1 to about 4 carbon atoms, more preferably from 1 to 2 carbon atoms. Examples of such substituents include methyl, ethyl, propyl, isopropyl, n-butyl, sec-butyl, isobutyl, tert-butyl, pentyl, isoamyl, hexyl, and the like.

The term "aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise 4n+2 π electrons, according to Hückel's Rule. The aryl group is optionally substituted with 1, 2, 3, 4, or 5 substituents as recited herein such as with alkyl groups such as methyl groups, ethyl groups, and the like, halo, dihaloalkyl, trihaloalkyl, nitro, hydroxy, alkoxy, aryloxy, amino, alkylamino, dialkylamino, acylamino, acylalkylamino, alkylcarbonyl, alkoxy carbonyl, arylcarbonyl, aryloxy carbonyl, cyanomethyl, alkylsulfonyl, aminosulfonyl, alkylaminosulfonyl, dialkylaminosulfonyl, aminocarbonyl, alkylaminocarbonyl, dialkylaminocarbonyl, thio, alkylthio, arylthio, and the like, wherein the optional substituent can be present at any open position on the aryl group.

The term "heteroaryl" refers to a monocyclic or bicyclic 5 to 10-membered ring system as described herein, wherein the heteroaryl group is unsaturated and satisfies Hückel's rule, and wherein the heteroaryl contains 1-4 heteroatoms independently selected from nitrogen, oxygen and sulfur. Non-limiting examples of suitable heteroaryl groups include furanyl, thiopheneyl, pyrrolyl, pyrazolyl, imidazolyl, 1,2,3-triazolyl, 1,2,4-triazolyl, isoxazolyl, oxazolyl, isothiazolyl, thiazolyl, 1,3,4-oxadiazol-2-yl, 1,2,4-oxadiazol-2-yl, 5-methyl-1,3,4-oxadiazole, 3-methyl-1,2,4-oxadiazole, pyridinyl, pyrimidinyl, pyrazinyl, triazinyl, benzofuranyl, benzothiopheneyl, indolyl, indazolyl, imidazolyl, quinolinyl, isoquinolinyl, benzimidazolyl, benzoxazolinyl, benzothiazolinyl, and quinazolinyl. The term "pyridinyl" is synonymous with the term "pyridyl" and both terms refer to an optionally substituted pyridine group. The heteroaryl groups can be attached at any open position on the heteroaryl groups. The terms "heterocyclic" or "heterocyclyl" refer to a 4 to 12-membered heterocyclic ring system as described herein, wherein the heterocycle contains 1 or 2 heteroatoms independently selected from nitrogen, oxygen, and sulfur, wherein the heterocycle is saturated or monounsaturated. The heterocyclyl or heteroaryl group is optionally substituted with 1, 2, 3, 4, or 5 substituents as recited herein such as with alkyl groups such as methyl groups, ethyl groups, and the like, with hydroxyalkyl groups such as hydroxyl ethyl, or with aryl groups such as phenyl groups, naphthyl groups and the like, wherein the aryl groups can be further substituted with, for example, halo, dihaloalkyl, trihaloalkyl, nitro, hydroxy, alkoxy, aryloxy, amino, alkylamino, dialkylamino, acylamino, acylalkylamino, alkylcarbonyl, alkoxy carbonyl, arylcarbonyl, aryloxy carbonyl, cyanomethyl, alkylsulfonyl, aminosulfonyl, alkylaminosulfonyl, dialkylaminosulfonyl, aminocarbonyl, alkylaminocarbonyl, dialkylaminocarbonyl, thio, alkylthio, arylthio, and the like, wherein the optional substituent can be present at any open position on the heterocyclyl or heteroaryl group.

The term "acyl" refers to an alkylcarbonyl (R—C(=O)—) substituent. The term "aminosulfonyl" refers to a group of the structure: $H_2NSO_2$—. The term "alkylsulfonyl" refers to a group of the structure: alkyl-$SO_2$—. The term "aminocarbonyl" refers to a group of the structure: $R^1R^2NC(=O)$— wherein $R^1$ and $R^2$ are independently hydrogen, alkyl, or aryl.

In any of the above embodiments, A is $CR^5$.
In any of the above embodiments, B is $CR^3$=$CR^4$.

In certain embodiments, $R^1$ is $C_{6-10}$ aryl substituted with —CN.

In certain of these embodiments, $R^2$ is selected from 4-chlorophenyl, 4-dimethylaminomethylphenyl, 4-diethylaminomethylphenyl, 2-amino-4-pyridyl, 2-amino-5-pyridyl, and 4-fluorophenyl.

In certain of these embodiments, $R^1$ is selected from 3-cyanomethylphenyl, 3-cyano-6-methylphenyl, 3-cyano-4-morpholinylphenyl, 3-cyano-2-methylphenyl, 3-cyano-4-piperazinyl-6-methylphenyl, and 3-cyano-4-piperazinylmethylphenyl.

In certain particular embodiments, the compound is selected from:

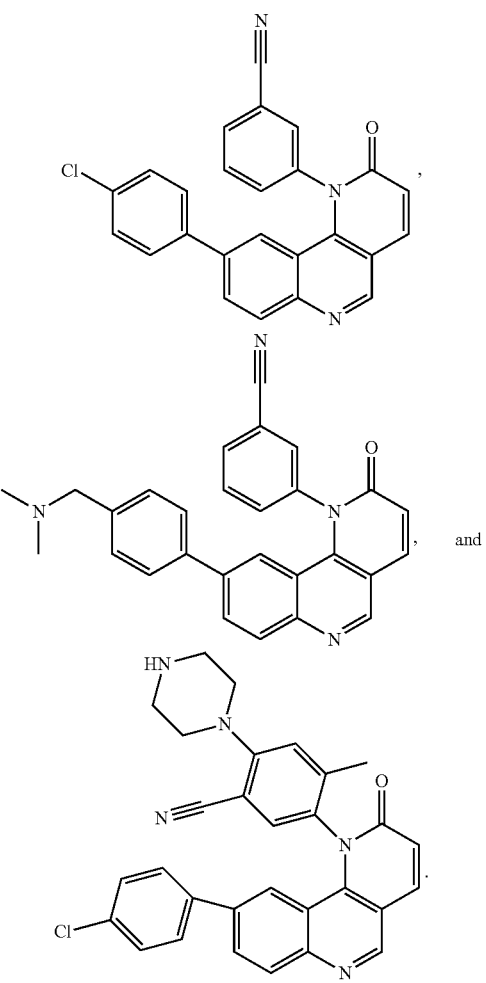

In certain embodiments, $R^1$ is $C_{6-10}$ aryl substituted with —$SO_2R^{13}$.

In certain of these embodiments, $R^2$ is selected from 4-chlorophenyl, 3-hydroxy-4-chlorophenyl, 3-amino-4-chlorophenyl, 4-fluorophenyl, 4-dimethylaminomethylphenyl, 4-aminomethylphenyl, 3-methyl-4-chlorophenyl, 3-methoxy-4-chlorophenyl, 3-cyano-4-chlorophenyl, and 4-pyrrolidinomethylphenyl.

In certain of these embodiments, $R^1$ is selected from 4-methylsulfonylphenyl, 4-ethylsulfonylphenyl, 2-methyl-4-methylsulfonylphenyl, and 3-piperazinylmethyl-4-methylsulfonylphenyl.

In certain particular embodiments, the compound is selected from:

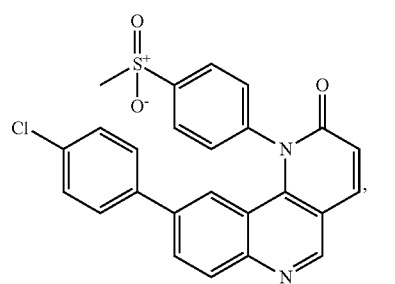
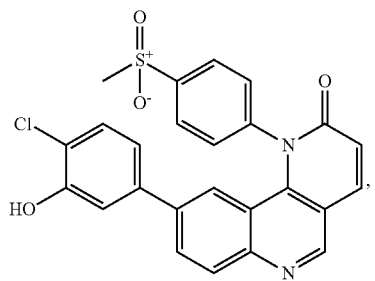
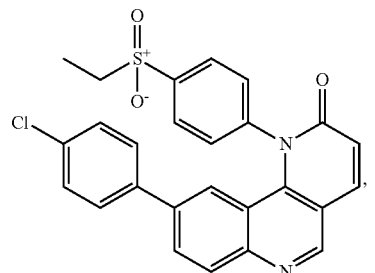
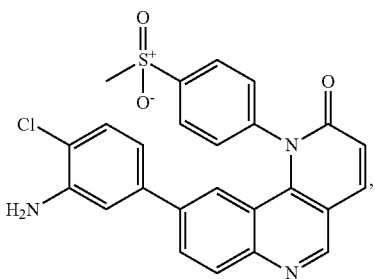
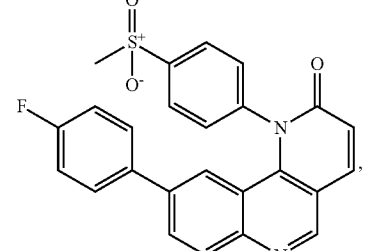
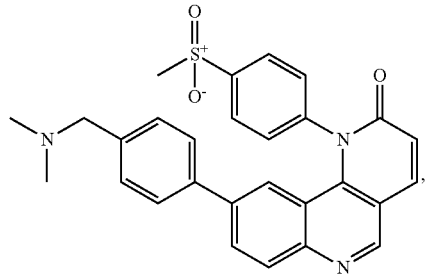
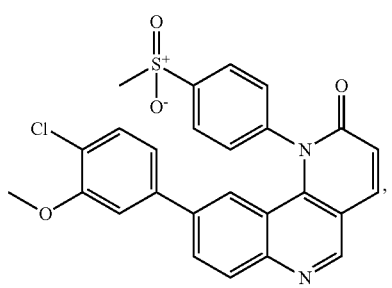
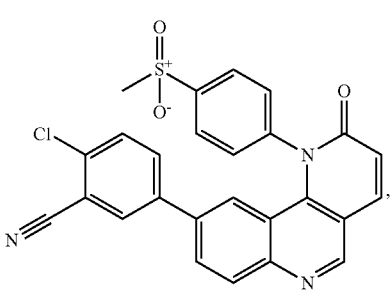
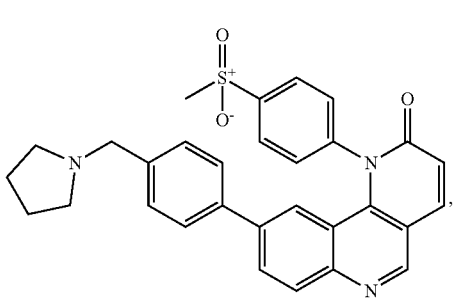
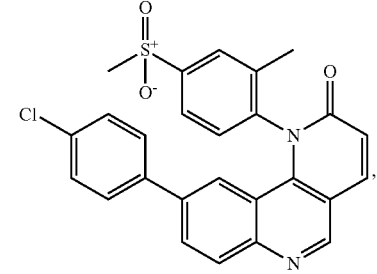
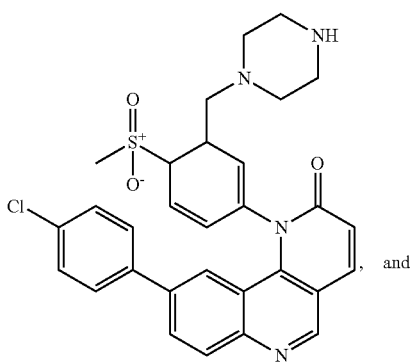

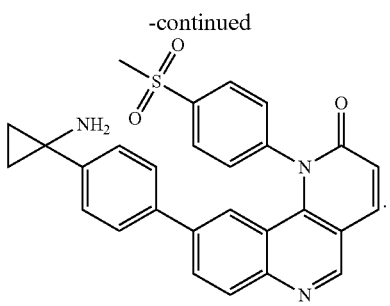

In certain embodiments, $R^1$ is $C_{6-10}$ aryl substituted with —$SO_2NH_2$.

In certain of these embodiments, $R^2$ is 4-chlorophenyl or 2-amino-5-pyridiyl.

In certain of these embodiments, $R^1$ is 4-aminosulfonylphenyl or 3-aminosulfonylphenyl.

In certain embodiments, $R^1$ is $C_{6-10}$ aryl substituted with —$CONR^{11}R^{12}$.

In certain of these embodiments, $R^2$ is selected from 4-chlorophenyl, 4-fluorophenyl, 4-dimethylaminomethylphenyl, 4-aminomethylphenyl, 3-amino-4-chlorophenyl, 3-hydroxy-4-chlorophenyl, 4-aminophenyl, 4-hydroxyphenyl, 4-hydroxymethylphenyl, 3-methylphenyl, 3-methoxyphenyl, 3-cyanophenyl, phenyl, 5-indolinone, 3-hydroxyphenyl, 5-isoindolinone, 3-aminophenyl, 2-hydroxy-4-chlorophenyl, 3-cyano-4-chlorophenyl, 4-cyanophenyl, 4-(2-aminoethyl)phenyl, 4-(2-dimethylaminoethyl)phenyl, 4-azetidinylphenyl, 4-ethylphenyl, 2-amino-5-pyridyl, and 4-(1-aminocycloprop-1-yl)phenyl.

In certain of these embodiments, $R^1$ is selected from 4-methylcarbonylaminophenyl, 4-morpholinocarbonylphenyl, 4-dimethylaminocarbonylphenyl, 4-(3,5-dimethylaminomorphobno)carbonylphenyl, 4-(4-methylpiperazinyl)carbonylphenyl, 4-piperazinylcarbonylphenyl, 4-piperidinylcarbonylphenyl, 4-[N,N-bis(2-hydroxyethyl]carbonylphenyl, 4-cyclopentylaminocarbonylphenyl, 4-azetidinylcarbonylphenyl, 4-(4-hydroxyethylpiperazinyl)carbonylphenyl, 2-methyl-4-methylaminocarbonylphenyl, 3-chloro-4-methylaminocarbonylphenyl, 4-cyclopropylaminocarbonylphenyl, 4-dimethylaminocarbonylphenyl, 4-1-(8-oxa-3-azabicyclo[3.2.1]octan-3-yl)carbonylphenyl, 4-1-(3-hydroxy-8-azabicyclo[3.2.1]octan-8-yl)carbonylphenyl, 1-(5-methyl-2,5-diazabicyclo[2.2.1]heptan-2-yl)carbonylphenyl, 1-(5-methylhexahydropyrrolo[3,4-c]pyrrol-2(1H)-yl)carbonylphenyl, 4-(N-cyclopropyl-N-cyclohexylamino)carbonylphenyl, 4-(N-methyl-N-cyclopropylamino)carbonylphenyl, 4-cyclobutylaminocarbonylphenyl, 2trifluoroethylaminocarbonylphenyl, 4-(2-dimethylaminoethylaminocarbonyl)phenyl, 4-(4-[2-dimethylaminoethyl]piperazin-1-yl-carbonyl)phenyl, 4-cyclopropylaminocarbonylphenyl 4-(1-[2-dimethylaminoethyl]piperidin-4-amino)carbonylphenyl, 4-(N-1-(2-hydroxyethyl)azetidin-3-ylamino)carbonylphenyl, 4-(pyrrolidinyl-3-amino)carbonylphenyl.

In certain particular embodiments, the compound is selected from:

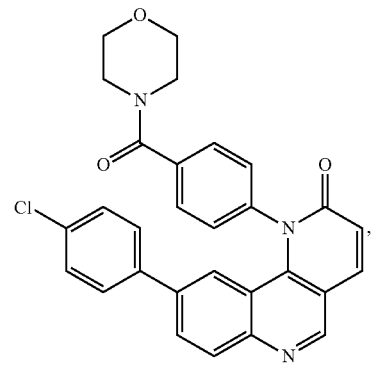

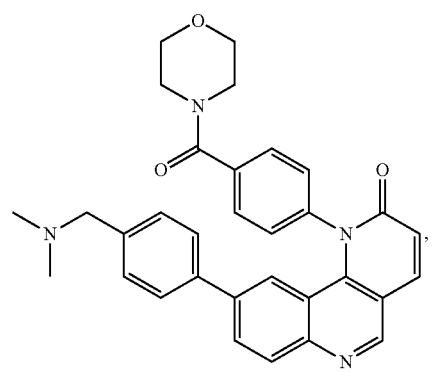

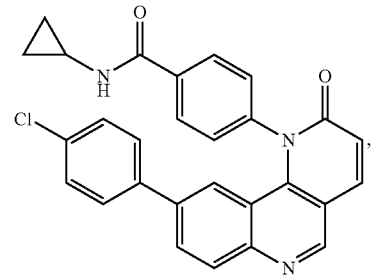

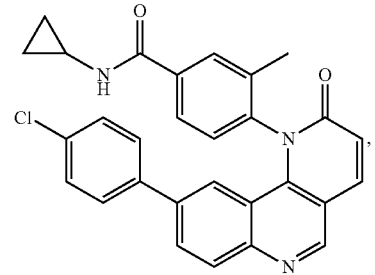

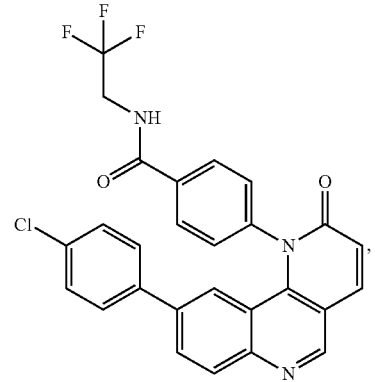

-continued
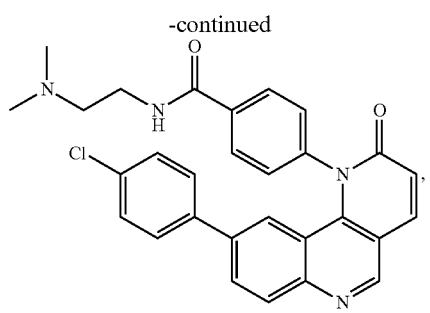
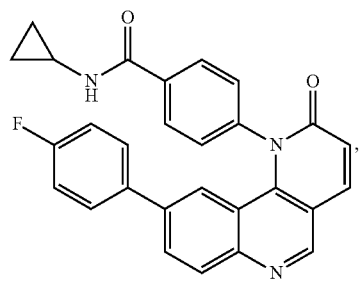
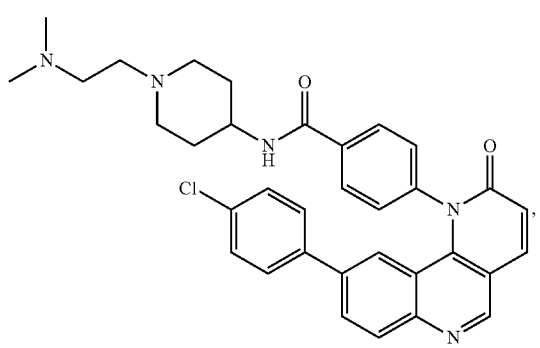
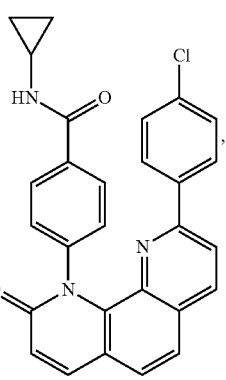
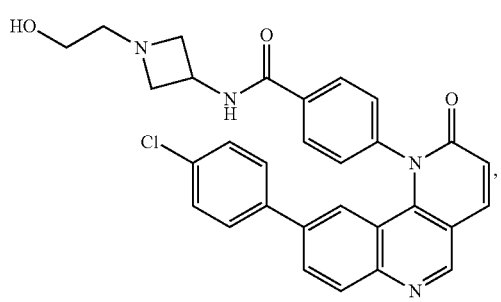
-continued
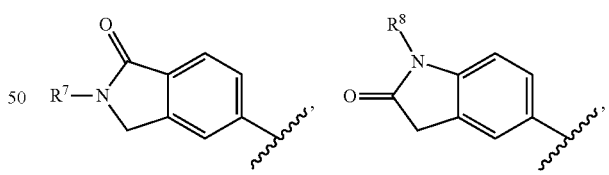
, and
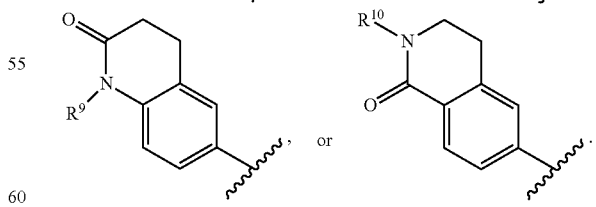
.
In certain embodiments, $R^1$ is a aryl bicyclic lactam of the formula:
or
.
In certain of these embodiments, $R^7$, $R^8$, $R^9$, and $R^{10}$ are hydrogen, $C_{1-12}$ alkyl, or $H_2N(CH_2)_n$— wherein n is an integer of 2-6.
In certain of these embodiments, $R^2$ is selected from 4-chlorophenyl, 4-dimethylaminomethylphenyl, 4-diethylaminomethylphenyl, 4-fluorophenyl, 2-amino-5-pyridyl, and 4-(1-aminocycloprop-1-yl)phenyl.

In certain particular embodiments, the compound is selected from:

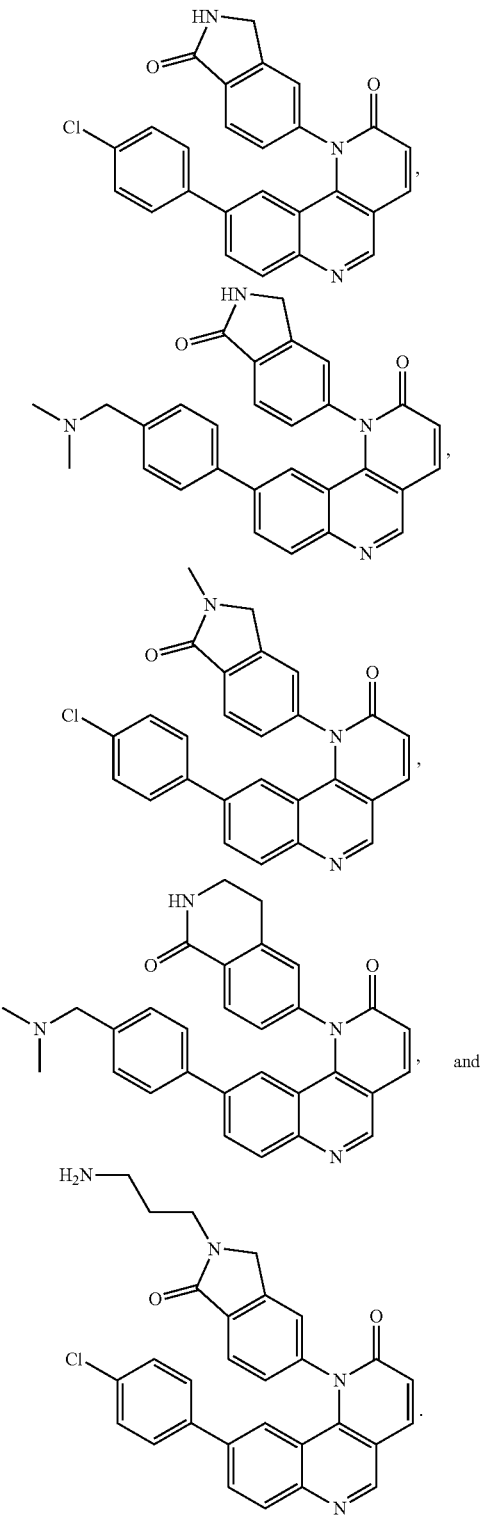

and

In any of the above embodiments, B is NR⁶.
In certain embodiments, $R^1$ is $C_{6-10}$ aryl substituted with —CN.

In certain of these embodiments, $R^6$ is hydrogen or methyl.

In certain of these embodiments, $R^2$ is selected from 4-chlorophenyl, 3-fluorophenyl, 3-chlorophenyl, 3-methoxy-4-chlorophenyl, 3-aminophenyl, 3-methylphenyl, 3-dimethylaminomethylphenyl, 3-cyano-4-fluorophenyl, 3-hydroxy-4-fluorophenyl, 3-methoxy-4-fluorophenyl, 3-cyano-4-chlorophenyl, 3-hydroxy-4-chlorophenyl, 4-fluorophenyl, 3-cyanophenyl, 3-hydroxyphenyl, 3-amino-4-fluorophenyl, 4-dimethylaminophenyl, 3-cyanophenyl, 4-methylphenyl, 4-aminophenyl, 4-(1-hydroxy-1-ethyl)phenyl, 4-(2-aminoethylphenyl, 2-amino-5-pyridyl, 2-amino-5-pyrimidyl, 2-methyl-5-pyridyl, 2-acetylamino-5-pyridyl, 2-oxoindolin-5-yl, benzimidazolin-5-yl, 3-dimethylamino-1-propargyl, 4-(2-dimethylaminoethyl)phenyl, 2-pyrrolyl, N-methyl-2-pyrrolyl, 2-thiopheneyl, 3-thiopheneyl, 3-furanyl, 3-aminosulfonylphenyl, and 4-dimethylaminomethylphenyl.

In certain of these embodiments, $R^1$ is selected from 3-cyano-6-methyl phenyl, 3-cyano-4-piperazinyl-6-methylphenyl, 3-cyanophenyl, 3-cyano-4-piperazinylphenyl, 3-cyano-4-morpholinylphenyl, 4-(4-(2-hydroxyethylpiperazinyl-3-cyanophenyl, 3-cyano-4-(1,4-diazepan-1-yl)phenyl, 3-cyano-4-(4-acetylaminopiperazin-1-yl), 2-methyl-3-cyanophenyl, 3-cyano-4-(3-aminoazetidinyl)-6-methylphenyl, 3-cyano-4-(2-dimethylaminoethyl)-6-methylphenyl, 2-piperazinyl-3-cyano-6-methyl-5-pyridyl, 2-piperazinyl-3-cyano-5-pyridyl, 3-cyano-4-methoxyphenyl, 3-cyano-4-(4-hydroxypiperidinyl)phenyl, 3-cyano-4-(4-aminopiperidinyl)phenyl, and 2-methyl-3-cyanophenyl.

In certain particular embodiments, the compound is selected from:

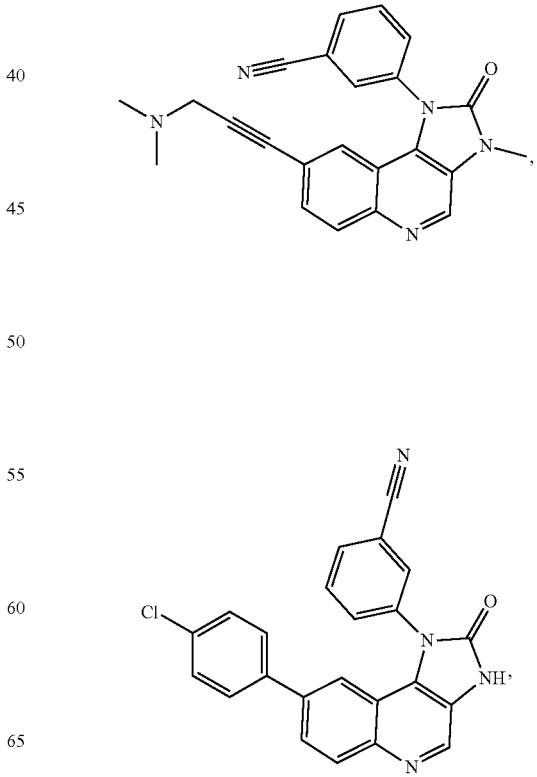

17
-continued
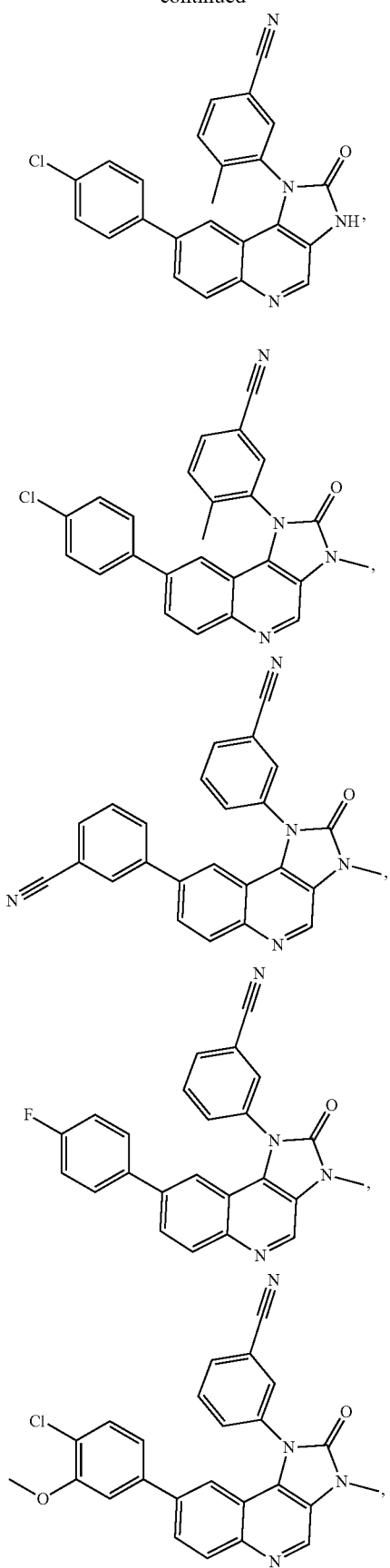
18
-continued
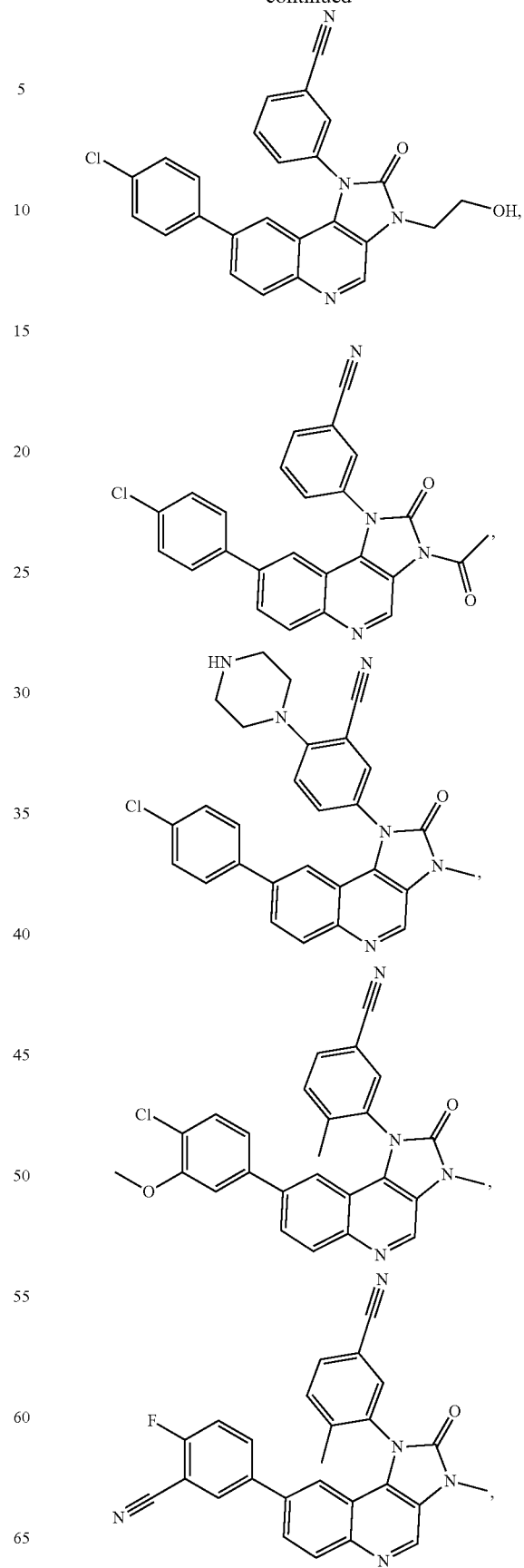

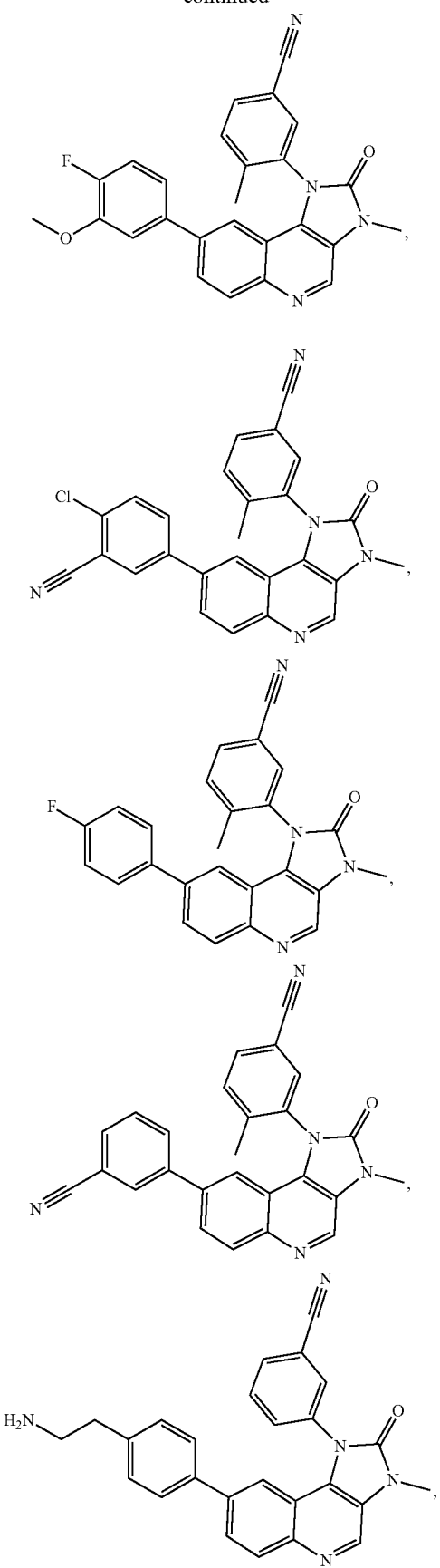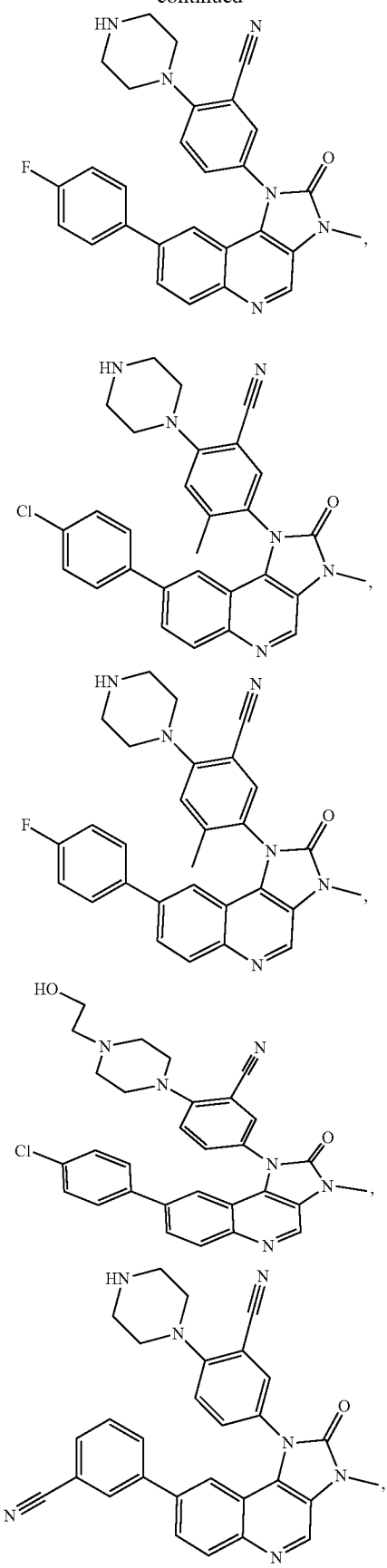

-continued
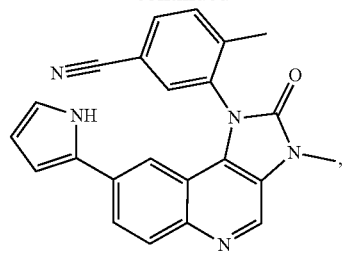
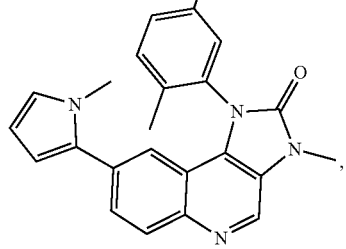
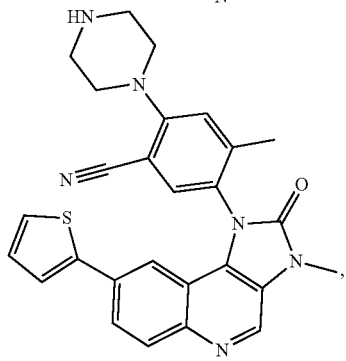
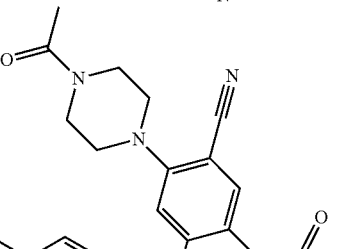
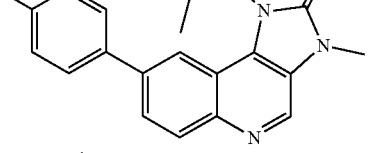
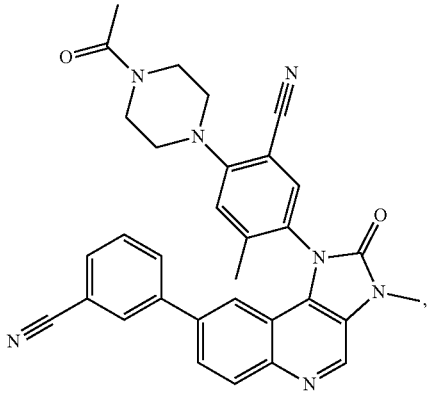
-continued
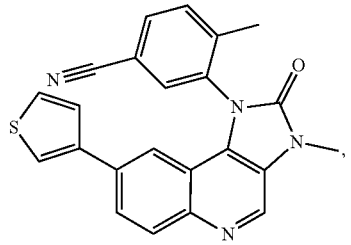
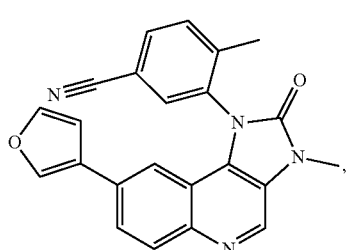
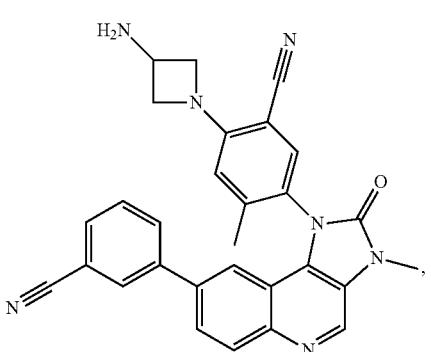
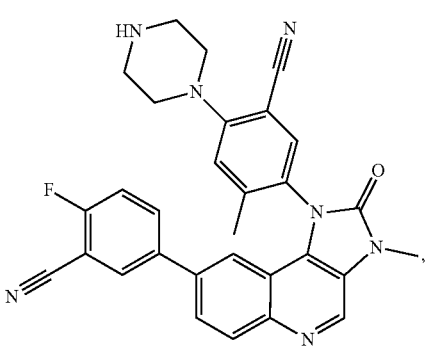
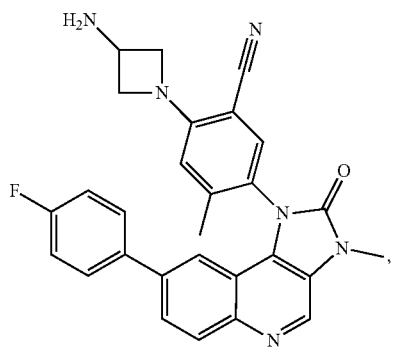

-continued

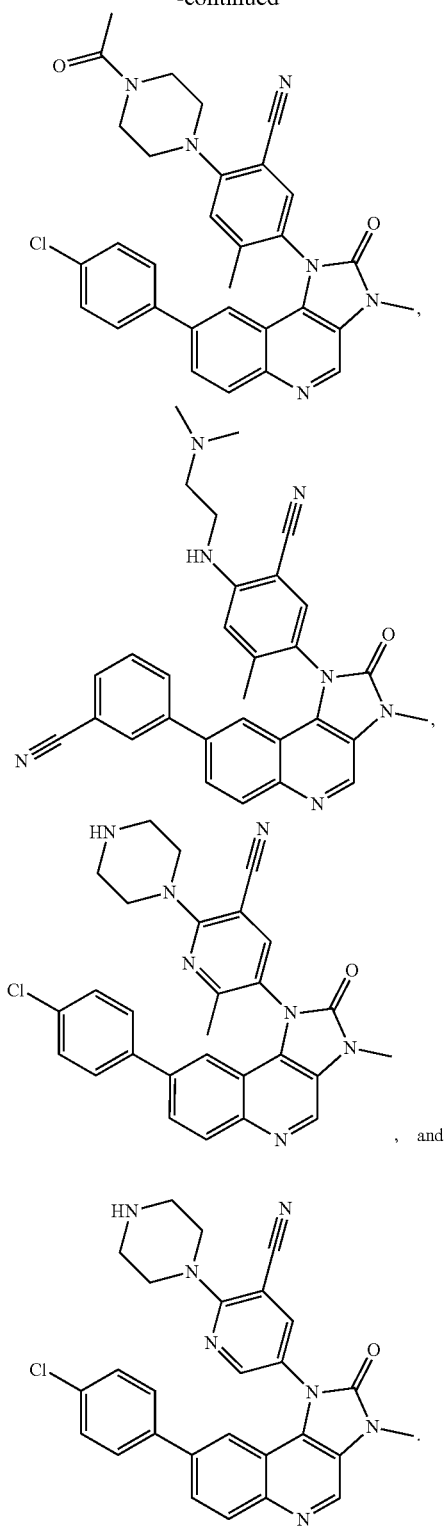

In certain embodiments, R¹ is C$_{6-10}$ aryl substituted with —SO$_2$R$^{13}$.

In certain of these embodiments, R² is 2-amino-5-pyridyl or 4-chlorophenyl.

In certain of these embodiments, R¹ is 4-aminosulfonylphenyl.

In certain particular embodiments, the compound is:

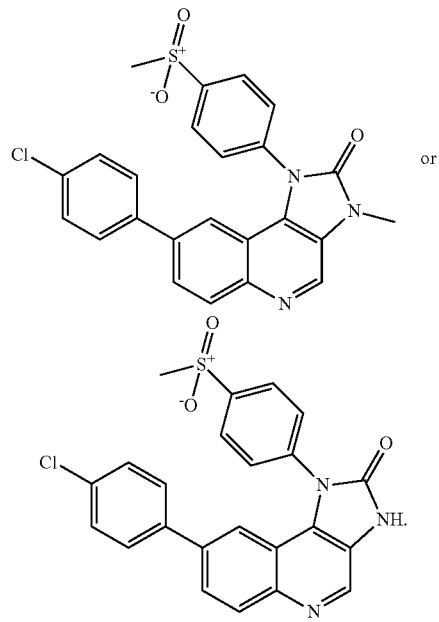

In certain embodiments, R¹ is C$_{6-10}$ aryl substituted with —CONR$^{11}$R$^{12}$.

In certain of these embodiments, R² is selected from 4-chlorophenyl, 2-amino-5-pyridyl, 3-hydroxy-4-chlorophenyl, 4-fluorophenyl, 3-cyanophenyl, 4-dimethylaminomethylphenyl, and 4-methylphenyl.

In certain of these embodiments, R¹ is 4-morpholinocarbonylphenyl, 4-dimethylaminocarbonylphenyl, 4-(N-methyl-N-cyclopropyl)aminocarbonylphenyl, or 4-piperidinocarbonylphenyl.

In certain particular embodiments, the compound is selected from:

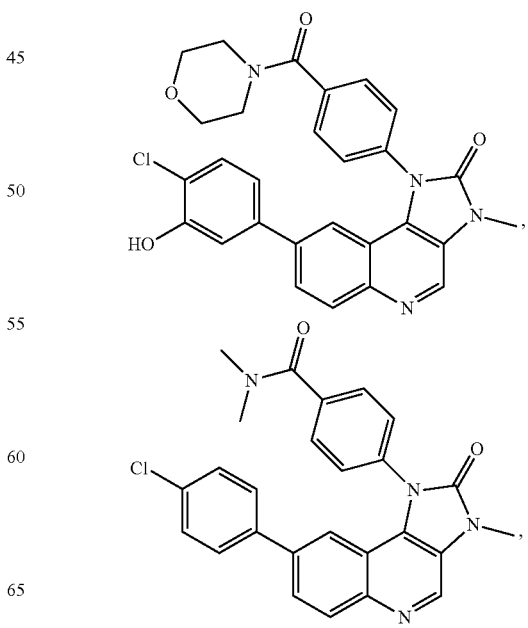

-continued

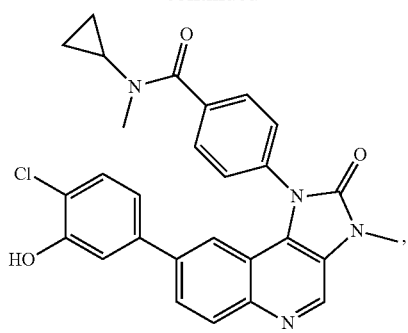

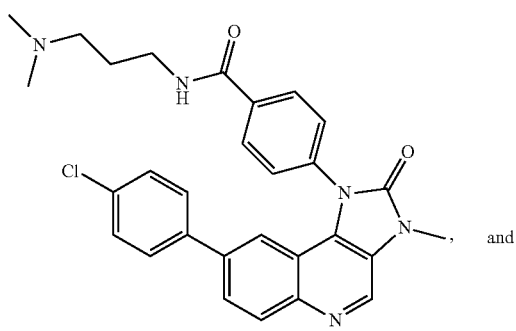

In certain embodiments, R¹ is:

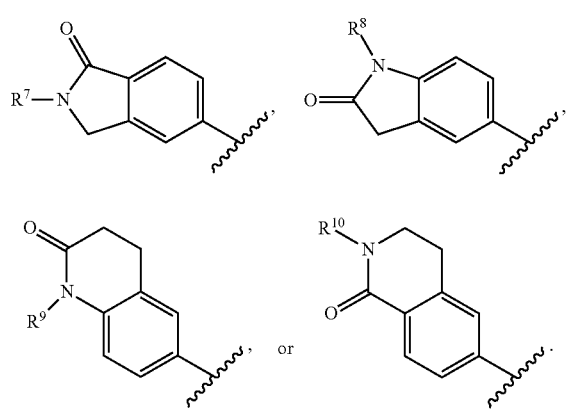

In certain of these embodiments, R² is 4-chlorophenyl or 4-dimethylaminophenyl.

In certain preferred embodiments, R¹ is

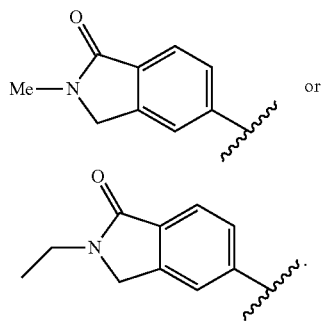

In an embodiment, the invention provides a compound of formula (II):

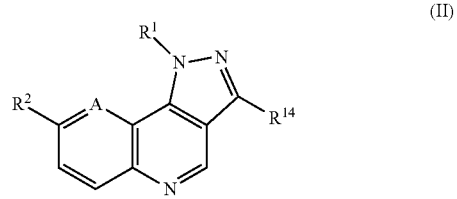

(II)

wherein A is CR⁵ or N,
B is CR³=CR⁴ or NR⁶,
wherein R¹ is $C_{6-10}$ aryl or heteroaryl substituted with one or more substituents selected from the group consisting of $C_{1-12}$ alkyl, $C_{3-10}$ cycloalkyl, alkoxy, —CF₃, heterocyclyl, —CONR¹¹R¹², —SO₂NHR¹⁶, and CN, R² is selected from 2-amino-5-pyridinyl, 4-pyridinyl, 2-amino-5-pyrimidinyl, 3-pyridyl, quinolin-3-yl, 5-pyrimidinyl, 2-amino-5-trifluoromethylpyrimidin-5-yl, 2-acetylamino-5-pyridyl, 2-amino-4-methylpyrimidin-5-yl, 1-piperazinyl, indol-5-yl, 1H-indazol-5-yl, 4-aminophenyl, 1,2,3,6-tetrahydropyridin-4-yl, 1H-pyrazol-4-yl, 1H-benzo[d]imidazol-5-yl, 4-sulfonylaminophenyl, 2-dimethylaminopyrimidin-5-yl, 3-trifluoromethylphenyl, bromo, 3-aminophenyl, vinyl, 4-aminocarbonylphenyl, 3-cyanophenyl, 3-trifluoromethyl-5-pyridyl, tetrazolyl, 4-chlorophenyl, 4-methoxyphenyl, 3-aminocarbonylphenyl, 3-acetylphenyl, 2,3-dihydrobenzofuran-6-yl, 1-methyl-1H-indol-5-yl, benzo[d][1,3]dioxo-5-yl, 4-fluorophenyl, 4-hydroxyphenyl, porpholin-1-yl, benzo[b]thiophen-1-yl, 4-methylsulfonylphenyl, benzo[c][1,2,5]oxadiazol-5-yl, 2-(piperidin-1-yl)-3-pyridinyl, 4-carboxyphenyl, 2-methyl-5-pyridyl, 4-methylsulfonylphenyl, 4-dimethylaminocarbonylphenyl, 4-phenylphenyl, 4-methylphenyl, 3-chloro-5-pyridyl, (3-pyrrolidin-1-yl)phenyl, 4-([piperizin-1-yl]carbonyl)phenyl, 4-([morpholin-1-yl]carbonyl)phenyl, 2-hydroxypyrimidin-5-yl, 3-aminosulfonylphenyl, 2-oxo-1,2,3,4,tetrahydroisoquinolin-6-yl, 2-oxo-1,2,3,4,-tetrahydroquinolin-6-yl, 4-(aminomethyl)phenyl, 4-(dimethylaminomethyl)phenyl, 4-(methylaminocarbonyl)phenyl, 1-oxoindolin-5-yl, 2-oxoindolin-5-yl, and 1-oxoisoindolin-5-yl, R³ and R⁴ are independently selected from hydrogen, hydroxyl, OR⁵, halogen, optionally substituted $C_{6-10}$ aryl, and optionally substituted $C_{1-6}$ alkyl, R⁵ is hydrogen, $C_{1-12}$ alkyl, $C_{6-10}$ aryl, halogen, hydroxyl, or OR⁵, R⁶ is hydrogen, $C_{1-12}$ alkyl or $C_{6-10}$ aryl,

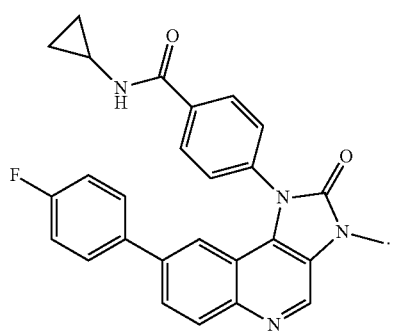

and

R[11] and R[12] selected from the group consisting of hydrogen, $C_{1-12}$ alkyl and $C_{3-10}$ cycloalkyl or, taken together with the N to which they are bound, form an optionally substituted 4-7 membered heterocyclyl ring containing O or N atoms, R[14] is hydrogen or $C_{1-12}$ alkyl, and R[16] is hydrogen or $C_{1-12}$ alkyl, or a pharmaceutically acceptable salt thereof.

In certain preferred embodiments, R[14] is methyl.

In certain of these embodiments, R[2] is 2-amino-5-pyridyl or 4-chlorophenyl.

In certain of these embodiments, R[1] is selected from 3-trifluoromethylphenyl, 4-methylphenyl, 3-cyanophenyl, 3-pyridyl, 4-pyrrolidinylcarbonylphenyl, 4-cyclopropylaminocarbonylphenyl, 4-(3-dimethylaminopropylaminocarbonyl)phenyl, and 3-trifluoromethyl-4-morpholinocarbonylphenyl.

Chemistry

The compounds of the invention can be synthesized using any suitable route. In an embodiment, the compounds of formula (I) wherein A is CH and B is $CR^3=CR^4$ can be synthesized by the route shown in Scheme 1.

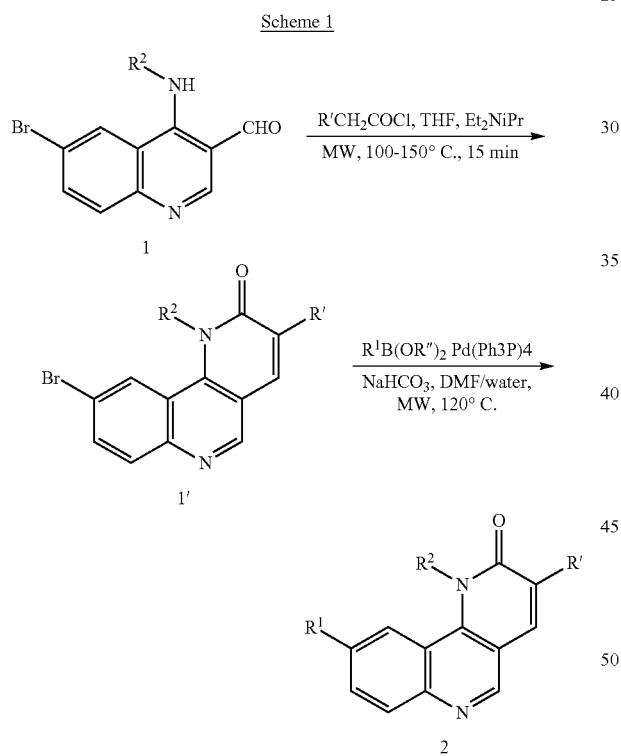

A substituted 4-amino-6-bromoquinoline-3-carbaldehyde 1 can be reacted with an acetyl chloride in the presence of a base such as diethylaminopropylamine in a solvent such as tetrahydrofuran, optionally under microwave irradiation, to give a 9-bromobenzo[h][1,6]naphthyridin-2(1H)-one V. Suzuki coupling of V with an arylboronic acid $R^1B(OR'')_2$ in the presence of a catalyst such as $Pd(Ph_3P)_4$ and a base such as $NaHCO_3$ in a solvent such as DMF/water under microwave irradiation gives the desired compound 2.

In an embodiment, a compound of formula (I) wherein A is CH and B is NR[6] can be synthesized by the route shown in Scheme 2.

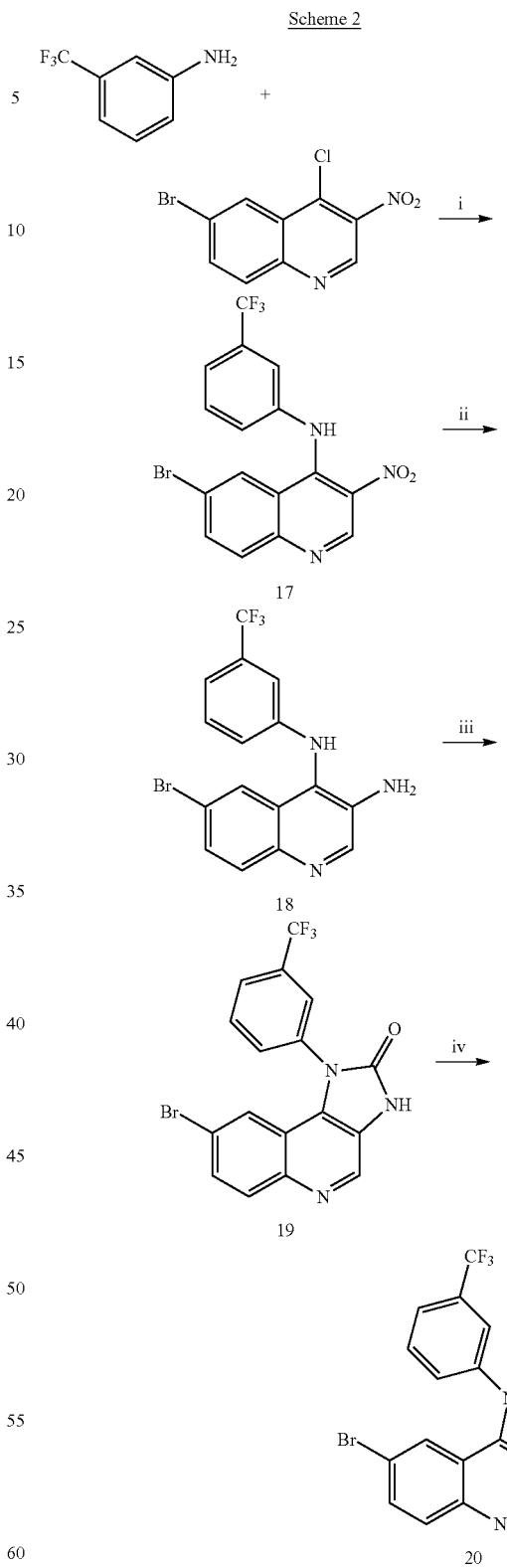

Reagents and conditions, (i) 150° C., 1,4-dioxanes; (ii) $SnCl_2$, 65° C., 3.5 h; (iii) $ClCO_2CCl_3$, $Et_3N$; (iv) MeI, NaH, THF Reaction of a substituted aniline such as, for example, 3-trifluoromethylaniline with 6-bromo-4-chloro-3-nitroquinoline in a solvent such as 1,4-dioxane gives the substituted quinoline 17. Reduction of the nitro group with a reducing agent such as $SnCl_2$ gives the amino compound 18. Cyclization of compound 18 with a carbonylation reagent such as triphogene gives the substituted 8-bromo-1,3-dihydro-2H-imidazo[4,5-c]quinolin-2-one 19. N-alkylation of compound 19 can be performed using an alkylating agent such as methyl iodide in the presence of a base such as NaH in a solvent such as tetrahydrofuran to give the N-alkylated compound 20. Suzuki coupling of compounds 19 and 20 gives 8-functionalized 1,3-dihydro-2H-imidazo[4,5-c]quinolin-2-ones.

The compounds of formula (II) can be prepared by the route shown in Scheme 3.

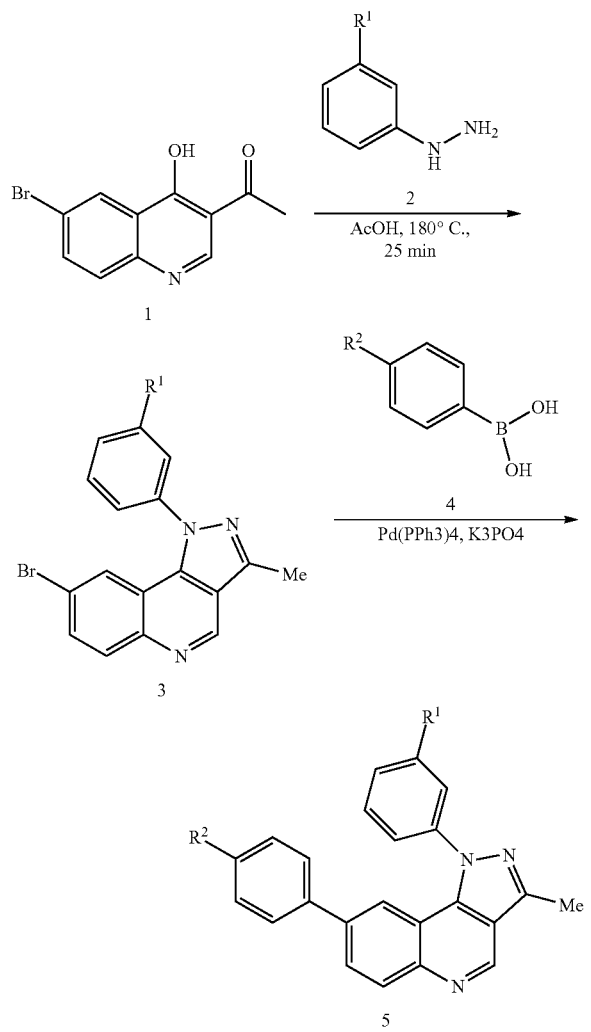

Reaction of 1-(6-bromo-4-hydroxyquinolin-3-yl)ethan-1-one 1 with substituted hydrazine 2 in a solvent such as acetic acid gives substituted 8-bromo-1H-pyrazolo[4,3-c]quinoline 3. Suzuki coupling of 3 with an arylboronic acid 4 in the presence of a catalyst such as $Pd(Ph_3P)_4$ and a base such as $NaHCO_3$ in a solvent such as DMF/water under microwave irradiation gives the desired compound 5.

In an embodiment, the invention provides a method for the preparation of heteroaryl-fused imidazolidin-2-ones. In an embodiment, the method comprises the steps of (a) providing a compound of formula 100:

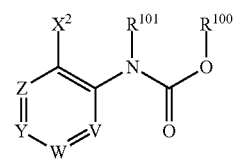

wherein $X^2$ is F, Cl, Br, or I,
V is $CR^{104}$ or N,
W is $CR^{105}$ or N,
Y is $CR^{106}$ or N,
Z is $CR^{107}$ or N, wherein optionally Y and Z,
wherein $R^{104}$-$R^{107}$ are independently hydrogen, optionally substituted alkyl, optionally substituted aryl, or optionally substituted heteroaryl, or when Y is $CR^{106}$ and Z is $CR^{107}$, $R^{106}$ and $R^{106}$, taken together with the carbons to which they are bound, form a fused 5- to 8-membered carbocyclic, aryl, heterocyclyl, or heteroaryl ring, wherein the heterocyclyl contains one or more atoms selected from N, O, and S,
wherein at least one of V, W, Y, and Z is N,
wherein $R^{100}$ is alkyl or aryl,
wherein $R^{101}$ is hydrogen, alkyl, or aryl, and
(b) reacting the compound of formula 100 with an amine of the formula: $R^{102}NH_2$ to give a compound of the formula 101:

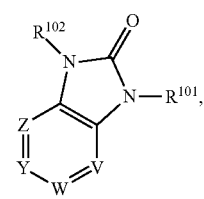

wherein $R^{102}$ is optionally substituted alkyl, optionally substituted cycloalkyl, optionally substituted heterocyclyl, optionally substituted aryl, optionally substituted heteroaryl, optionally substituted arylalkyl, optionally substituted heterocyclylalkyl, optionally substituted cycloalkylalkyl, or optionally substituted heteroarylalkyl.

The method comprises mixing ortho-halo heteroaryl carbamates and a primary amine under conditions such that an imidazolidin-2-one ring is formed. In typical embodiments, an ortho-halo heteroaryl carbamate 100 reacts with a primary amine to give a heteroaryl-fused imidazolidin-2-one 101 as the product (Scheme 4). The reaction usually takes place in preferred acidic conditions under conventional heat or microwave heat. When a polycyclic ortho-halo heteroaryl carbamate 100' is used as the starting material, a polycyclic imidazolidin-2-one product 101' is formed (Scheme 5). The acid used here can be an organic or inorganic acid such as hydrochloric acid (HCl), nitric acid ($HNO_3$), phosphoric acid ($H_3PO_4$), sulphuric acid ($H_2SO_4$), boric acid ($H_3BO_3$), hydrofluoric acid (HF), hydrobromic acid (HBr), perchloric acid ($HClO_4$), formic acid (HCOOH), acetic acid ($CH_3COOH$), propanoic acid ($CH_3CH_2COOH$), and trifluoroacetic acid (TFA). The solvent used here can be a high boiling point solvent such as 2-pentanol, 3-pentanol, cyclohexanol, polyethylene glycol (PEG), 2-methyl-2-butanol, tert-butanol, MeCN, 1,2-dimethoxyethane (DME), 1,2-dichloroethane (DCE), 1,4-dioxane, toluene, N,N-dimethylacetamide (DMA), N,N-dimethylformamide (DMF), 1-methyl-2-pyrrolidinone (NMP), xylenes, dimethylsulfoxide (DMSO), o-dichlorobenezene (o-DCB) and ionic liquid. The reaction temperature is between 25° C. to 250° C.

Scheme 4

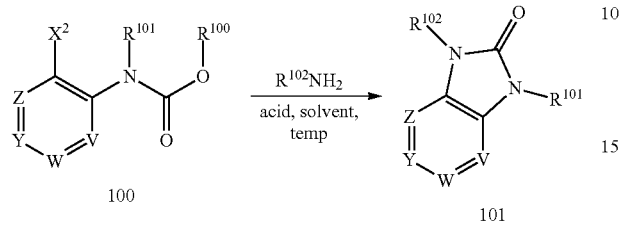

Scheme 5

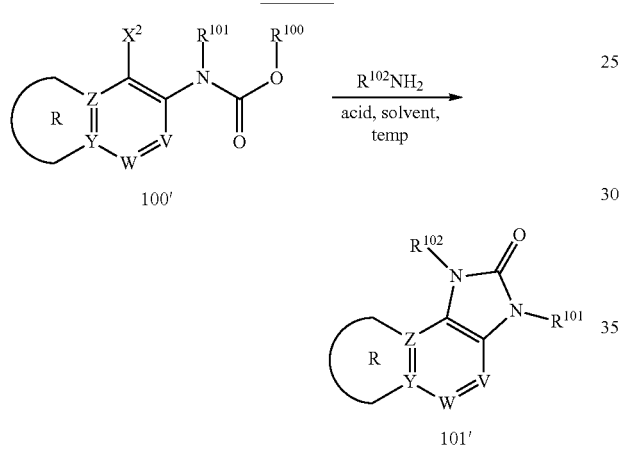

In an embodiment, the method is useful for the synthesis of compounds of formula (I) wherein B is $NR^6$.

The synthesis of carbamate 104 and N-alkyl carbamate 105 can be accomplished as shown in Scheme 6. Reduction of nitro quinoline 102 wherein $X^1$ and $X^2$ are independently halo or $OSO_2R$ wherein R is alkyl, $CF_3$, or optionally substituted aryl with a suitable reducing agent such as $SnCl_2$ or under catalytic hydrogenation conditions provides amino quinoline 103. Reaction of amino quinolone 103 with an alkyl or aryl chloroformate provides carbamate 104. Carbamate 104 can be alkylated, for example, using an alkyl halide or alkyl sulfonate in the presence of a base such as sodium hydride provides N-alkyl carbamate 105.

Scheme 6

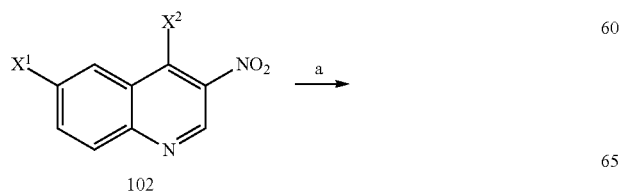

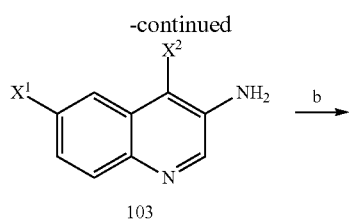

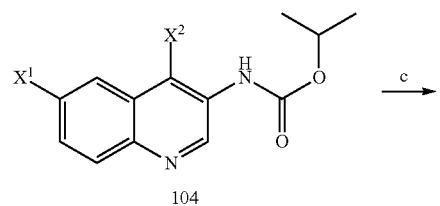

Reagents and conditions:
(a) $SnCl_2 \cdot 2H_2O$, AcOH, EtOH, rfx, 3 h, 64%;
(b) ClCOOiPr, pyr, DCM, rt, 4 h, 66%;
(c) MeI, NaH, THF, rt, 18 h, 93%.

Reaction of N-alkyl carbamate 105 with an optionally substituted arylamine or alkylamine in a solvent such as 3-pentanol under microwave irradiation provides 1,3-dihydro-2H-imidazo[4,5-c]quinolin-2-one 106 as shown in Scheme 7. 1,3-dihydro-2H-imidazo[4,5-c]quinolin-2-one 106 reacts with aryl boronic acids $R^{103}B(OH)_2$ under Suzuki coupling conditions in the presence of a catalyst such as $Pd(PPh_3)_4$ and a base such as $K_3PO_4$ in a solvent or solvent mixture such as $DMF/H_2O/i$-PrOH under microwave irradiation to give 8-arylated 1,3-dihydro-2H-imidazo[4,5-c]quinolin-2-one 107.

Scheme 7

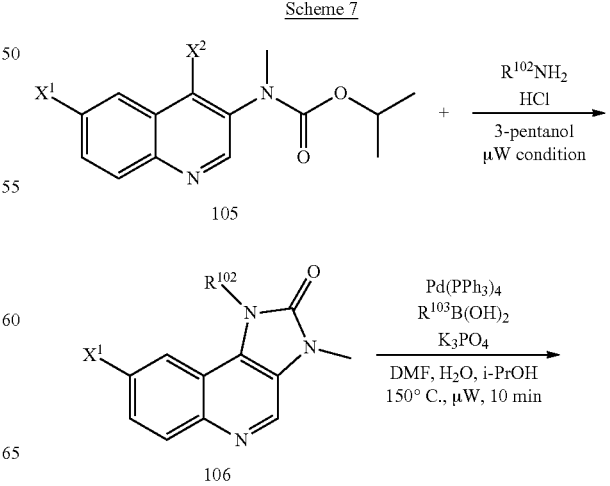

-continued

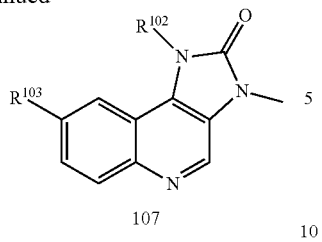
107

Heteroaryl-fused imidazolidin-2-ones are important motifs in the biologically active compounds. For example, the dual PI3K/mTOR inhibitors, NVP-BEZ235 and NVP-BGT226, have both been studied in clinic trials for their potential as future anti-cancer agents. The synthesis of heteroaryl-fused imidazolidin-2-ones usually involves the reaction of phosgene or its derivatives with heteroaryl 1,2-diamines to form the cyclic urea rings. Alternatively, heteroaryl-fused imidazolidin-2-ones were prepared from their corresponding ortho-chloro heteroaryl amines via Pd-catalyzed Buchwald-Hartwig C—N bond formation followed by an intramolecular cyclization. These methods use either toxic phosgene derivatives or expensive transition-metal catalysts. A general, metal-free method using non-toxic reagents is desired for the synthesis of biologically interesting molecules containing polycyclic imidazolidin-2-ones.

NVP-BEZ235 and NVP-BGT226 have both been studied in clinical trials for their potential as future anti-cancer agents. The N-methyl i-Pr carbamate 110 could react satisfactorily with two equivalents of aniline 111 and three equivalents of HCl, subsequent one-pot coupling gave desired 112 (NVP-BEZ235) in 85% yield (Scheme 8). When Boc-protected CF$_3$-substituted aniline 113 was used under optimal condition, the desired product 114 (NVP-BGT226) was obtained as a free base in 42% yield. Additionally, such transformation has been effected on a gram scale under conventional heating. N-methyl i-Pr carbamate 110 reacts with two equivalents of Boc-protected CF$_3$-substituted aniline 113 and ten equivalents of HCl in high boiling point solvent such as N-Methyl-pyrrolidone (NMP), subsequent one-pot coupling furnished desired 114 (NVP-BGT226) in 77% yield (Scheme 8).

Scheme 8

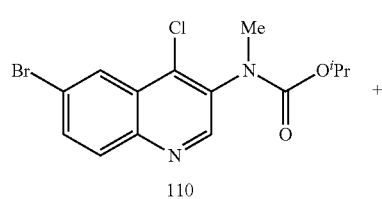
110

-continued

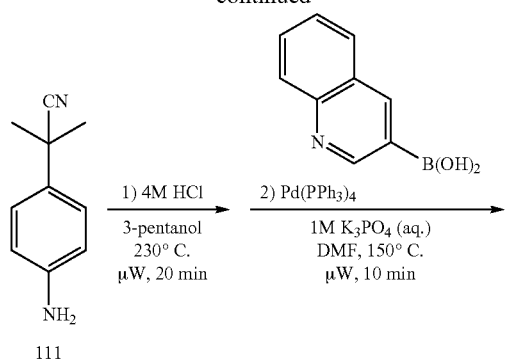

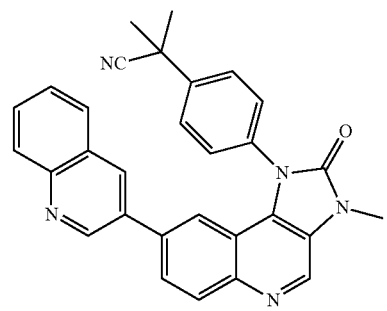
112 (Yield: 85%)

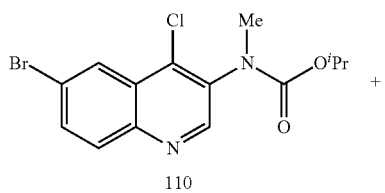
110

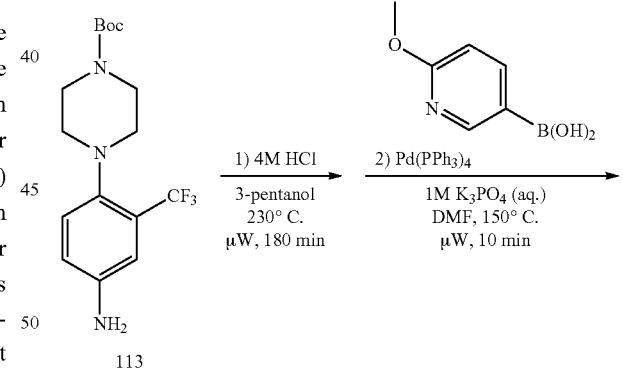

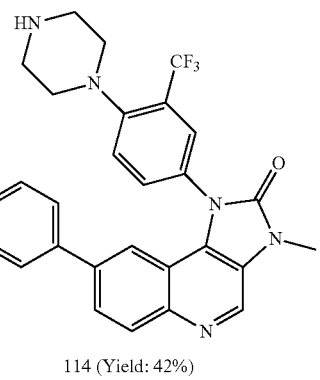
113

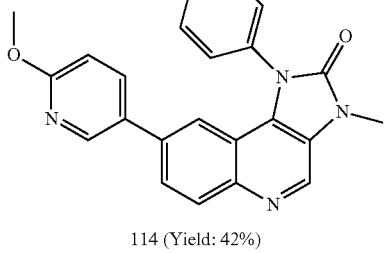
114 (Yield: 42%)

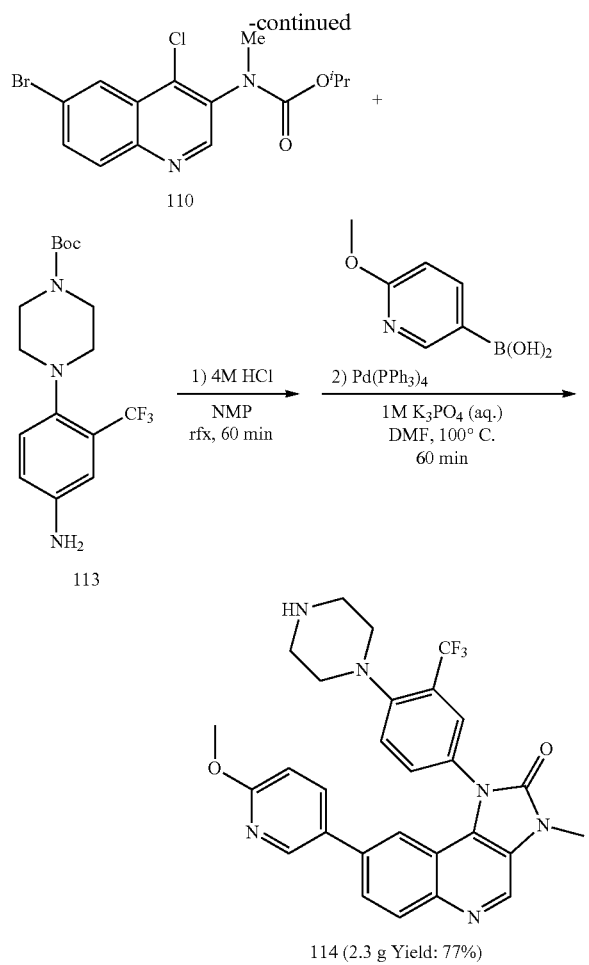

114 (2.3 g Yield: 77%)

The described new method for the synthesis of heteroaryl-fused imidazolidin-2-ones can be applied to the construction of other pharmaceutically active molecules such as I-BET151 (GSK1210151A), a novel small molecule inhibitor of the BET family, which has been investigated substantially in preclinical models for the treatment of mixed lineage leukemia (MLL). Telcagepant, also known as MK0974, is an orally bioavailable calcitonin gene-related peptide (CGRP) receptor antagonist under development for the acute treatment and prevention of migraine (Scheme 9).

Scheme 9

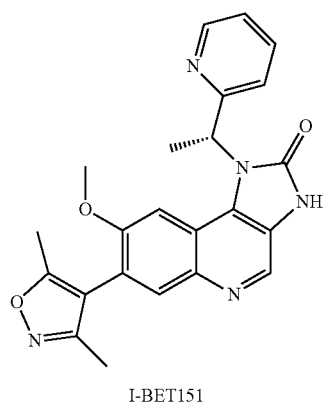

I-BET151

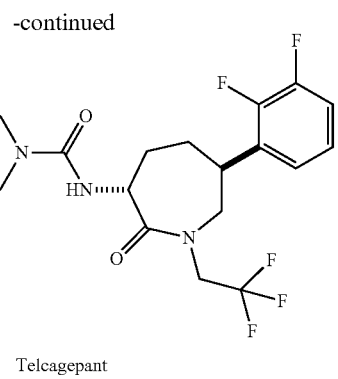

Telcagepant

In accordance with an embodiment of the invention, any of the compounds or salts thereof can be administered in the form of a pharmaceutical composition comprising the compound and a pharmaceutically acceptable carrier.

The pharmaceutically acceptable carriers described herein, for example, vehicles, adjuvants, excipients, or diluents, are well known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, intraperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable carriers and their formulations are further described in A. R. Gennaro, ed., *Remington: The Science and Practice of Pharmacy* (19th ed.), Mack Publishing Company, Easton, Pa. (1995).

The compound of the invention or a composition thereof can be administered as a pharmaceutically acceptable acid-addition, base neutralized or addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, ammonium hydroxide, potassium hydroxide, and organic bases, such as mono-, di-, trialkyl, and aryl amines and substituted ethanolamines. The conversion to a salt is accomplished by treatment of the base compound with at least a stoichiometric amount of an appropriate acid. Typically, the free base is dissolved in an inert organic solvent such as diethyl ether, ethyl acetate, chloroform, ethanol, methanol, and the like, and the acid is added in a similar solvent. The mixture is maintained at a suitable temperature (e.g., between 0° C. and 50° C.). The resulting salt precipitates spontaneously or can be brought out of solution with a less polar solvent.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

It should be recognized that the particular counterion forming a part of any salt of this invention is usually not of a critical nature, so long as the salt as a whole is pharmacologically acceptable and as long as the counterion does not contribute undesired qualities to the salt as a whole.

It is further understood that the above compounds and salts may form solvates, or exist in a substantially uncomplexed form, such as the anhydrous form. As used herein, the term "solvate" refers to a molecular complex wherein the solvent molecule, such as the crystallizing solvent, is incorporated into the crystal lattice. When the solvent incorporated in the solvate is water, the molecular complex is called a hydrate. Pharmaceutically acceptable solvates include hydrates, alcoholates such as methanolates and ethanolates, acetonitrilates and the like. These compounds can also exist in polymorphic forms.

In an embodiment, the invention provides a method of blocking transmission of a *Plasmodium* parasite comprising administering to a mammal in need of such treatment, a therapeutically effective amount of a compound of the invention. In another embodiment, the invention provides a method of treating malaria by killing or arresting the growth of *Plasmodium* organisms in a mammal, wherein the *Plasmodium* organisms are in a gametocyte stage, the method comprising administering to a mammal a therapeutically effective amount of a compound of the invention.

The *Plasmodium* parasite can be any suitable *Plasmodium* parasite. Non-limiting examples of suitable *Plasmodium* parasites include *Plasmodium falciparum, Plasmodium vivax, Plasmodium malariae, Plasmodium ovale*, and *Plasmodium knowlesi*. In a preferred embodiment, the *Plasmodium* parasite is *Plasmodium falciparum*.

In an embodiment, the *Plasmodium* parasite is a *Plasmodium* gametocyte.

In embodiments, the *Plasmodium* gametocyte is a mature stage II-V gametocyte. In a preferred embodiment, the *Plasmodium* gametocyte is a stage III-V gametocyte, e.g., a mature stage III-V gametocyte. In another preferred embodiment, the *Plasmodium* gametocyte is a mature stage V gametocyte.

In certain preferred embodiments, the compound effectively kills *Plasmodium* gametocytes.

In embodiments, the *Plasmodium* parasite is a drug-resistant strain. Examples of drug-resistant strains of *Plasmodium* are described in Kun, J. F. J. et al., Antimicrob Agents Chemother., 1999 September; 43(9): 2205-2208, and references cited therein.

In embodiments, the *Plasmodium* parasite is in an asexual stage. For example, the *Plasmodium* parasite can be a sporozoite, a liver stage parasite, a merozoite, an asexual erythrocyte-stage parasite, a zygote, an ookinete, or an oocyst.

The amount or dose of a compound of the invention or a salt thereof, or a composition thereof should be sufficient to effect a therapeutic or prophylactic response in the mammal. The appropriate dose will depend upon several factors. For instance, the dose also will be determined by the existence, nature and extent of any adverse side effects that might accompany the administration of a particular compound or salt. Ultimately, the attending physician will decide the dosage of the compound of the present invention with which to treat each individual patient, taking into consideration a variety of factors, such as age, body weight, general health, diet, sex, compound or salt to be administered, route of administration, and the severity of the condition being treated. By way of example and not intending to limit the invention, the dose of the compound(s) described herein can be about 0.1 mg to about 1 g daily, for example, about 5 mg to about 500 mg daily. Further examples of doses include but are not limited to: 0.1 mg, 0.15 mg, 0.2 mg, 0.25 mg, 0.5 mg, 0.6 mg, 0.75 mg, 1 mg, 1.5 mg, 2 mg, 3 mg, 4 mg, 5 mg, 6 mg, 7 mg, 8 mg, 9 mg, 10 mg, 12 mg, 15 mg, 17 mg, 20 mg, 25 mg, 30 mg, 35 mg, 40 mg, 45 mg, 50 mg, 55 mg, 60 mg, 70 mg, 75 mg, 80 mg, 85 mg, 90 mg, 95 mg, 100 mg, 125 mg, 140 mg, 150 mg, 175 mg, 200 mg, 225 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1000 mg/kg body weight per day.

In certain embodiments, the method further comprises administering to the mammal at least one additional anti-malarial compound. Any suitable antimalarial compound can be used, many of which are well known in the art. Non-limiting examples of suitable antimalarial compounds include primaquine, bulaquine, artemisinin and derivatives thereof, chloroquine, mefloquine, amodiaquine, piperaquine, pyronaridine, atovaquone, tafenoquine, methylene blue, trioxaquines, endoperoxides such as OZ 439 and OZ 277, decoquinate, 9-anilinoacridines, HIV-protease inhibitors, and natural products such as neem, epoxomicin, harmonine, and riboflavin. In certain preferred embodiments, the compound of the invention is administered in combination with elesclomol, NSC174938, NVP-AUY922, maduramicin, narasin, alvespimycin, omacetaxine, thiram, zinc pyrithione, phanquinone, bortezomib, salinomycin sodium, monensin sodium, dipyrithione, dicyclopentamethylene-thiuram disulfide, YM155, withaferin A, adriamycin, romidepsin, AZD-1152-HQPA, CAY10581, plicamycin, CUDC-101, auranofin, trametinib, GSK-458, afatinib, panobinostat, or any combination thereof.

Illustrative Examples of Embodiments

The invention contains the following embodiments:
1. A compound of formula (I):

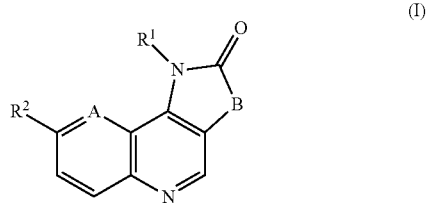

wherein A is $CR^5$ or N,
B is $CR^3$=$CR^4$ or $NR^6$,
$R^1$ is $C_{6-10}$ aryl or heteroaryl substituted with at least one substituent selected from —CN, cyanomethyl, —$SO_2R^{13}$, —$SO_2NHR^{15}$, and —$CONR^{11}R^{12}$, optionally further in combination with one or more substituents selected from halo, $C_{1-12}$ alkyl, alkoxy, a heterocyclyl group selected from the group consisting of optionally substituted piperazinyl, morpholinyl, pyrrolinidyl, and diazepinyl, or an aryl bicyclic lactam of the formula:

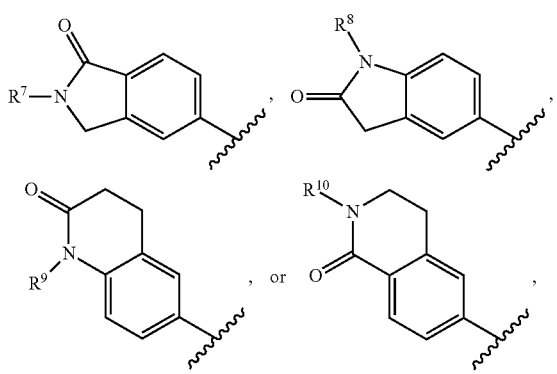

wherein the aryl group of the aryl bicyclic lactam is optionally substituted with at least one substituent selected from —CN, cyanomethyl, —$SO_2R^{13}$, —$SO_2NH_2$, and —$CONR^{11}R^{12}$, optionally further in combination with one or more substituents selected from halo, $C_{1-12}$ alkyl, alkoxy, 2-(dimethylamino)ethyl)amino, dimethylamino, a heterocyclyl group selected from the group consisting of optionally substituted piperazinyl, morpholinyl, pyrrolinidyl, azetidinyl and diazepinyl, $R^2$ is selected from 2-amino-5-pyridinyl, 4-pyridinyl, 2-amino-5-pyrimidinyl, 3-pyridyl, quinolin-3-yl, 5-pyrimidinyl, 2-acetylamino-5-pyridyl, 2-amino-4-methylpyrimidin-5-yl, 1-piperazinyl, indol-5-yl, 1H-imdazol-5-yl, 4-aminophenyl, 1,2,3,6-tetrahydropyridin-4-yl, 1H-pyrazol-4-yl, N-methyl-pyrazol-4-yl, 1H-benzo[d]imidazol-5-yl, 4-sulfonylaminophenyl, 2-dimethylaminopyrimidin-5-yl, 3-trifluoromethylphenyl, bromo, 3-aminophenyl, 4-aminophenyl, vinyl, 4-aminocarbonylphenyl, 3-cyanophenyl, 3-hydroxyphenyl, 3-trifluoromethyl-5-pyridyl, tetrazolyl, 4-chlorophenyl, 4-fluorophenyl, 4-methoxyphenyl, 3-aminocarbonylphenyl, 3-acetylphenyl, 3-cyano-4-chlorophenyl, 3-cyano-5-methylphenyl, 3-hydroxy-4-chlorophenyl, 4-hydroxymethylphenyl, 3-amino-4-chlorophenyl, 2,3-dihydrobenzofuran-6-yl, 1-methyl-1H-indol-5-yl, benzo[d][1,3]dioxo-5-yl, 4-fluorophenyl, 4-hydroxyphenyl, morpholin-1-yl, benzo[b]thiophen-1-yl, 4-methylsulfonylphenyl, benzo[c][1,2,5]oxadiazol-5-yl, 2-(piperidin-1-yl)-3-pyridinyl, 4-carboxyphenyl, 2-methyl-5-pyridyl, 4-methylsulfonylphenyl, 4-dimethylaminocarbonylphenyl, 4-phenylphenyl, 4-methylphenyl, 3-chloro-5-pyridyl, (3-pyrrolidin-1-yl)phenyl, 4-([piperizin-1-yl]carbonyl)phenyl, 4-([morpholin-1-yl]carbonyl)phenyl, 2-hydroxypyrimidin-5-yl, 3-aminosulfonylphenyl, 2-oxo-1,2,3,4,tetrahydroisoquinolin-6-yl, 2-oxo-1,2,3,4,-tetrahydroquinolin-6-yl, 4-(aminomethyl)phenyl, 4-(dimethylaminomethyl)phenyl, 4-(diethylaminomethyl)phenyl, 4-(methylaminocarbonyl)phenyl, 1-oxoindolin-5-yl, 2-oxoindolin-5-yl, 1-oxoisoindolin-5-yl, 2-amino-4-pyridyl, 3-amino-4-chlorophenyl, 4-aminomethylphenyl, 3-methyl-4-chlorophenyl, 3-methoxy-4-chlorophenyl, 4-aminophenyl, 3-methylphenyl, 3-methoxyphenyl, phenyl, 5-indolinone, 5-isoindolinone, 3-aminophenyl, 2-hydroxy-4-chlorophenyl, 4-cyanophenyl, 4-(2-aminoethyl) phenyl, 4-(2-dimethylaminoethyl) phenyl, 4-azetidinylphenyl, 4-ethylphenyl, 3-fluorophenyl, 3-chlorophenyl, 3-dimethylaminomethylphenyl, 3-cyano-4-fluorophenyl, 3-amino-4-fluorophenyl, 4-(1-hydroxy-1-ethyl)phenyl, 3-methyl-5-pyridyl, 2-acetylamio-5-pyridyl, 2-oxoindolin-5-yl, benzimidazolin-5-yl, 3-dimethylamino-1-propargyl, 2-pyrrolyl, N-methyl-2-pyrrolyl, 2-thiopheneyl, 3-thiopheneyl, 3-furanyl, 3-aminosulfonylphenyl, 4-dimethylaminomethylphenyl, and 4-pyrrolidinomethylphenyl, $R^3$ and $R^4$ are independently selected from hydrogen, hydroxyl, $OR^5$, halogen, optionally substituted $C_{6-10}$ aryl, and optionally substituted $C_{1-6}$ alkyl, $R^5$ is hydrogen, $C_{1-12}$ alkyl, $C_{6-10}$ aryl, halogen, hydroxyl, or $OR^{16}$, $R^6$ is hydrogen, $C_{1-12}$ alkyl, $C_{2-12}$ hydroxyalkyl, $C_{1-6}$ acyl-$C_{1-6}$ alkyl, or $C_{6-10}$ aryl, $R^7$-$R^{10}$ are independently selected from hydrogen, $C_{1-12}$ alkyl, $C_{3-8}$ cycloalkyl, $CH_2COOR^{13}$, and $H_2N(CH_2)_n$— wherein n is an integer of 2-6, $R^{11}$ and $R^{12}$ selected from the group consisting of hydrogen, $C_{1-12}$ alkyl and $C_{3-10}$ cycloalkyl or, taken together with the N to which they are bound, form an optionally substituted 4-7 membered heterocyclyl ring containing O or N atoms, and $R^{13}$ is $C_{1-12}$ alkyl, $R^{15}$ is hydrogen or $C_{1-12}$ alkyl, $R^{16}$ is $C_{1-12}$ alkyl, $C_{1-6}$ acyl, or $C_{6-10}$ aryl, or a pharmaceutically acceptable salt thereof, with the provisos that when A is CH, B is $CR^3$=$CR^4$, $R^3$ and $R^4$ are each hydrogen, and $R^2$ is 2-amino-5-pyridyl, $R^1$ is not 3-cyanophenyl or 3-aminosulfonylphenyl.

2. The compound or salt of embodiment 1, wherein A is $CR^5$.

3. The compound or salt of embodiment 2, wherein B is $CR^3$=$CR^4$.

4. The compound or salt of embodiment 3, wherein $R^1$ is $C_{6-10}$ aryl substituted with —CN.

5. The compound or salt of embodiment 4, wherein $R^2$ is selected from 4-chlorophenyl, 4-dimethylaminomethylphenyl, 4-diethylaminomethylphenyl, 2-amino-4-pyridyl, 2-amino-5-pyridyl, and 4-fluorophenyl.

6. The compound or salt of embodiment 4 or 5, wherein $R^1$ is selected from 3-cyanomethylphenyl, 3-cyano-6-methylphenyl, 3-cyano-4-morpholinylphenyl, 3-cyano-2-methylphenyl, 3-cyano-4-piperazinyl-6-methylphenyl, and 3-cyano-4-piperazinylmethylphenyl.

7. The compound or salt of any one of embodiments 3-6, wherein the compound is selected from:

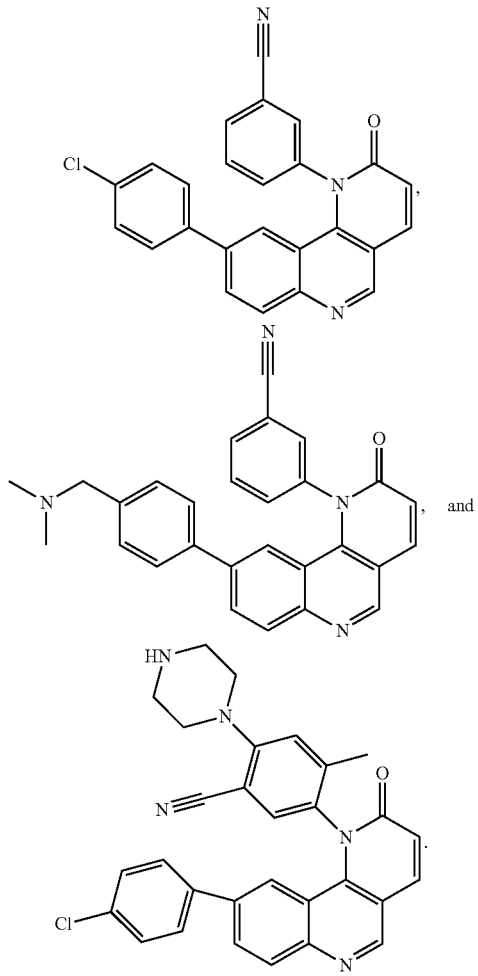

8. The compound or salt of embodiment 3, wherein $R^1$ is $C_{6-10}$ aryl substituted with —$SO_2R^{13}$.

9. The compound or salt of embodiment 8, wherein $R^2$ is selected from 4-chlorophenyl, 3-hydroxy-4-chlorophenyl, 3-amino-4-chlorophenyl, 4-fluorophenyl, 4-dimethylaminomethylphenyl, 4-aminomethylphenyl, 3-methyl-4-chlorophenyl, 3-methoxy-4-chlorophenyl, 3-cyano-4-chlorophenyl, and 4-pyrrolidinomethylphenyl.

10. The compound or salt of embodiment 8 or 9, wherein R¹ is selected from 4-methylsulfonylphenyl, 4-ethylsulfonylphenyl, 2-methyl-4-methylsulfonylphenyl, and 3-piperazinylmethyl-4-methylsulfonylphenyl.

11. The compound or salt of any one of embodiments 8-10, wherein the compound is selected from:

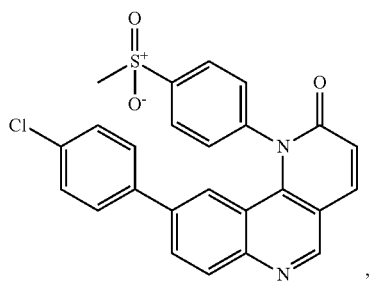

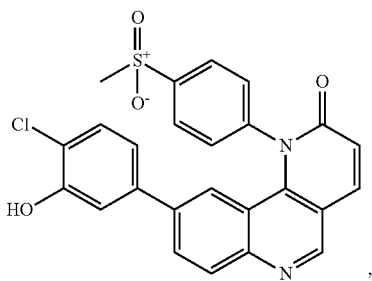

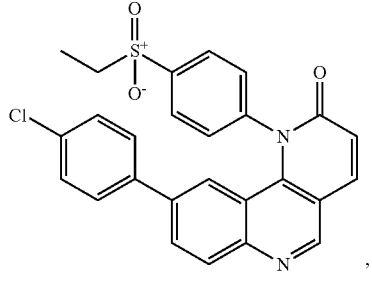

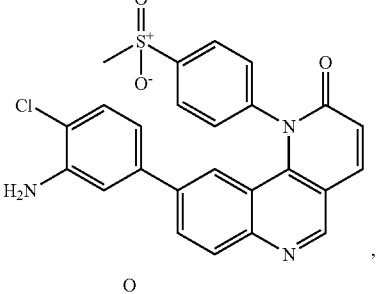

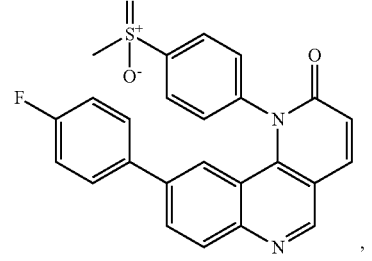

-continued

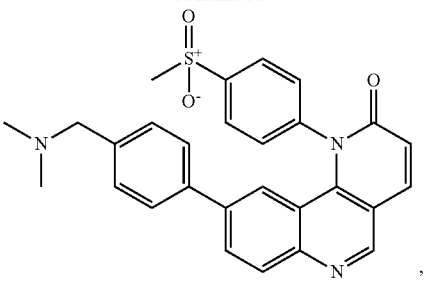

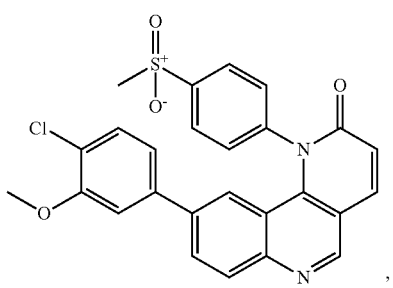

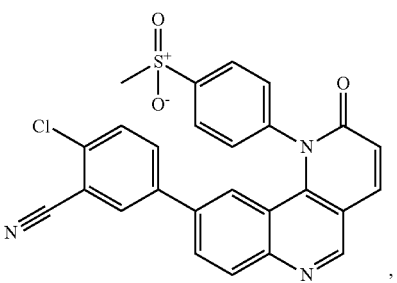

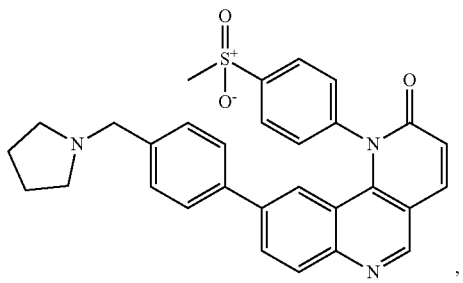

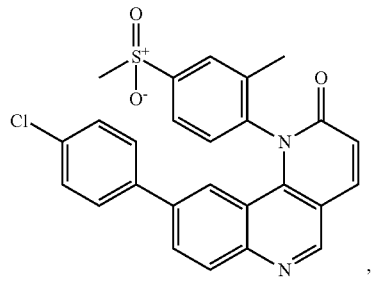

-continued

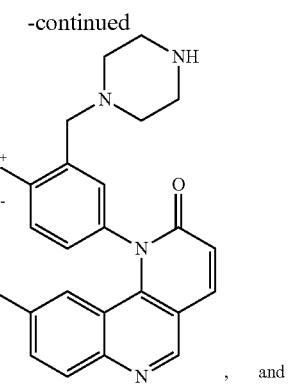

, and

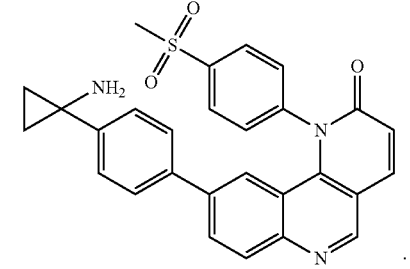

12. The compound or salt of embodiment 3, wherein $R^1$ is $C_{6-10}$ aryl substituted with —SO$_2$NH$_2$.

13. The compound or salt of embodiment 12, wherein $R^2$ is 4-chlorophenyl or 2-amino-5-pyridiyl.

14. The compound or salt of embodiment 12 or 13, wherein $R^1$ is 4-aminosulfonylphenyl or 3-aminosulfonylphenyl.

15. The compound or salt of embodiment 3, wherein $R^1$ is $C_{6-10}$ aryl substituted with —CONR$^{11}$R$^{12}$.

16. The compound or salt of embodiment 15, wherein $R^2$ is selected from 4-chlorophenyl, 4-fluorophenyl, 4-dimethylaminomethylphenyl, 4-aminomethylphenyl, 3-amino-4-chlorophenyl, 3-hydroxy-4-chlorophenyl, 4-aminophenyl, 4-hydroxyphenyl, 4-hydroxymethylphenyl, 3-methylphenyl, 3-methoxyphenyl, 3-cyanophenyl, phenyl, 5-indolinone, 3-hydroxyphenyl, 5-isoindolinone, 3-aminophenyl, 2-hydroxy-4-chlorophenyl, 3-cyano-4-chlorophenyl, 4-cyanophenyl, 4-(2-aminoethyl)phenyl, 4-(2-dimethylaminoethyl)phenyl, 4-azetidinylphenyl, 4-ethylphenyl, 2-amino-5-pyridyl, and 4-(1-aminocycloprop-1-yl)phenyl.

17. The compound or salt of embodiment 15 or 16, wherein $R^1$ is selected from 4-methylcarbonylaminophenyl, 4-morpholinocarbonylphenyl, 4-dimethylaminocarbonylphenyl, 4-(3,5-dimethylaminomorpholino)carbonylphenyl, 4-(4-methylpiperazinyl)carbonylphenyl, 4-piperazinylcarbonylphenyl, 4-piperidinylcarbonylphenyl, 4-[N,N-bis(2-hydroxyethyl]carbonylphenyl, 4-cyclopentylaminocarbonylphenyl, 4-azetidinylcarbonylphenyl, 4-(4-hydroxyethylpiperazinyl)carbonylphenyl, 2-methyl-4-methylaminocarbonylphenyl, 3-chloro-4-methylaminocarbonylphenyl, 4-cyclopropylaminocarbonylphenyl, 4-dimethylaminocarbonylphenyl, 4-1-(8-oxa-3-azabicyclo[3.2.1]octan-3-yl)carbonylphenyl, 4-1-(3-hydroxy-8-azabicyclo[3.2.1]octan-8-yl)carbonylphenyl, 1-(5-methyl-2,5-diazabicyclo[2.2.1]heptan-2-yl)carbonylphenyl, 1-(5-methylhexahydropyrrolo[3,4-c]pyrrol-2(1H)-yl)carbonylphenyl, 4-(N-cyclopropyl-N-cyclohexylamino)carbonylphenyl, 4-(N-methyl-N-cyclopropylamino)carbonylphenyl, 4-cyclobutylaminocarbonylphenyl, 2trifluoroethylaminocarbonylphenyl, 4-(2-dimethylaminoethylaminocarbonyl)phenyl, 4-(4-[2-dimethylaminoethyl]piperazin-1-yl-carbonyl)phenyl, 4-cyclopropylaminocarbonylphenyl 4-(1-[2-dimethylaminoethyl]piperidin-4-amino)carbonylphenyl, 4-(N-(1-(2-hydroxyethyl)azetidin-3-ylamino)carbonylphenyl, 4-(pyrrolidinyl-3-amino)carbonylphenyl.

18. The compound or salt of any one of embodiments 15-17, wherein the compound is selected from:

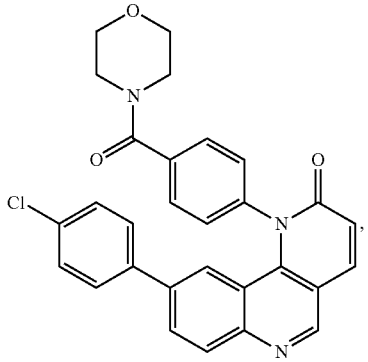

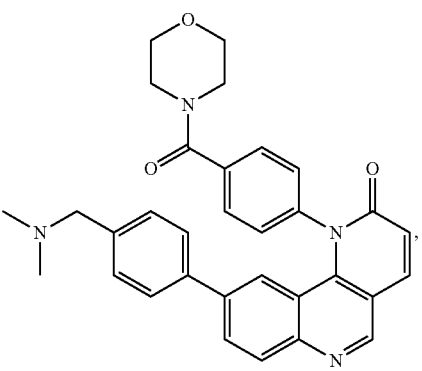

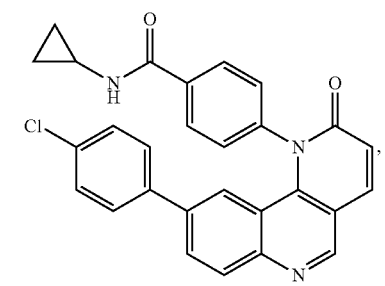

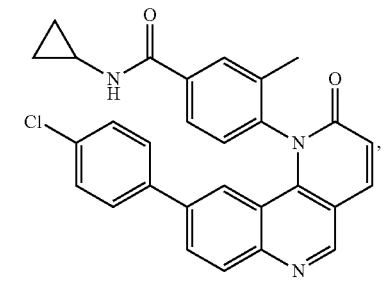

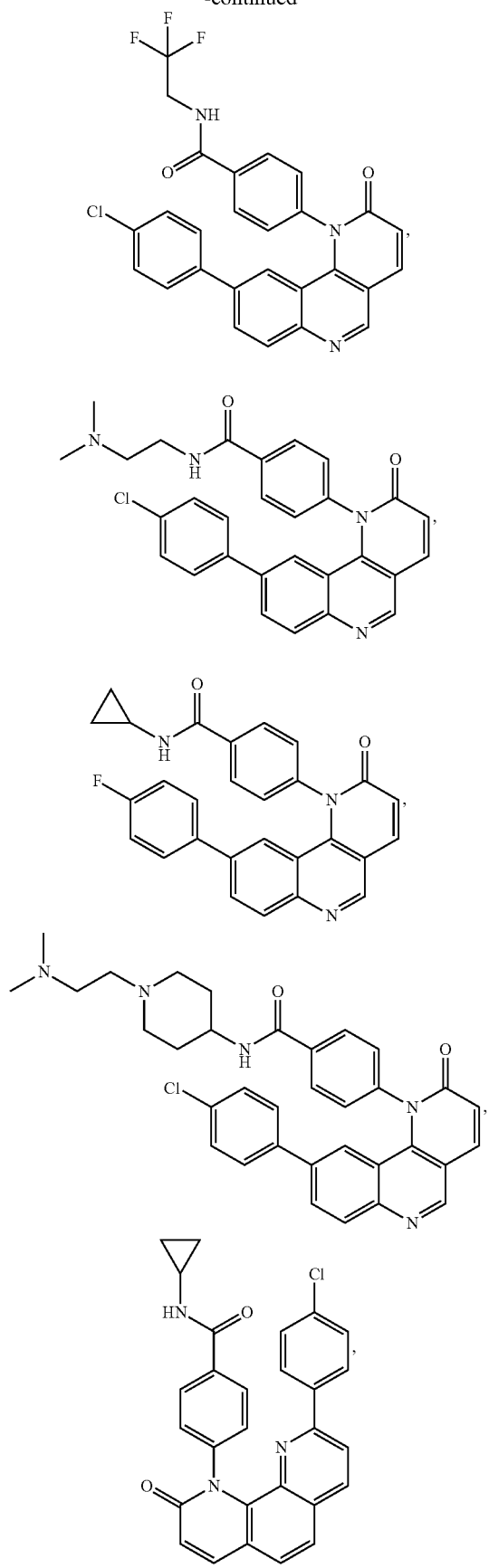
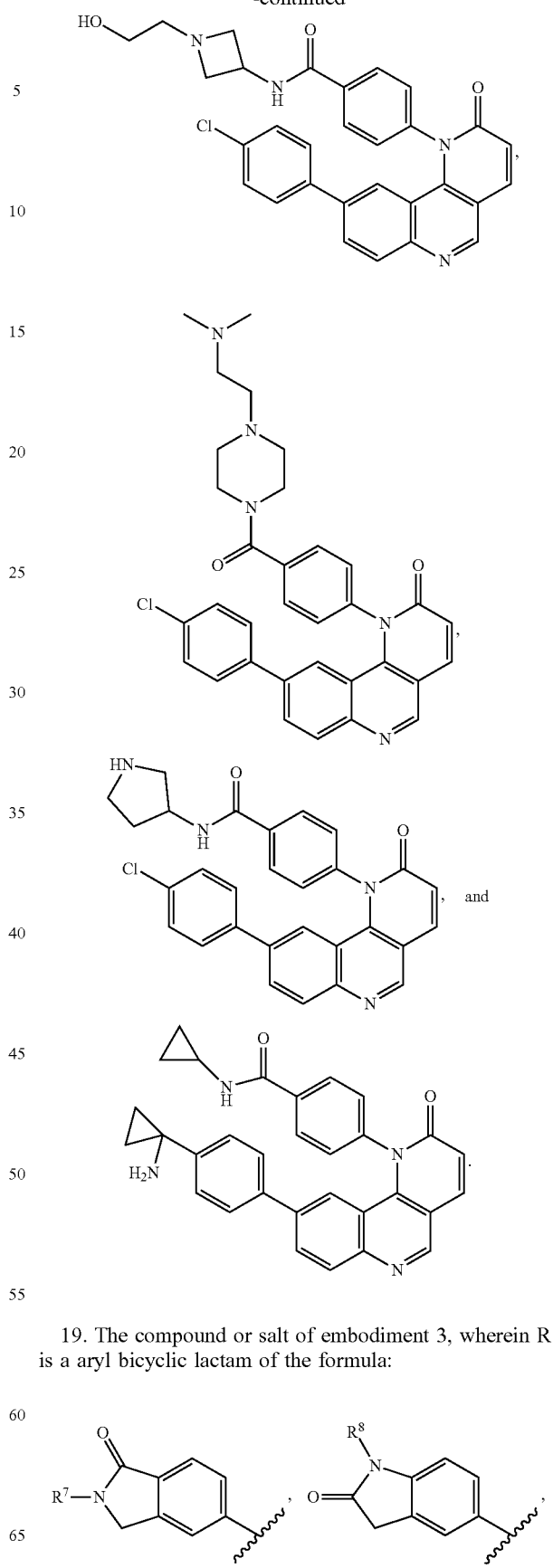
19. The compound or salt of embodiment 3, wherein $R^1$ is a aryl bicyclic lactam of the formula:
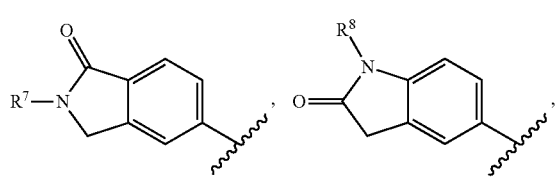

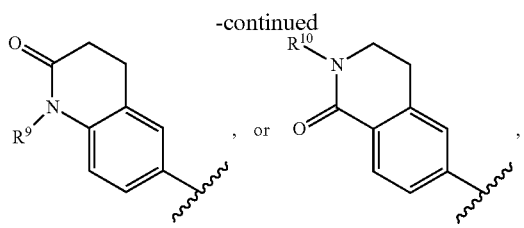

20. The compound or salt of embodiment 19, wherein $R^7$, $R^8$, $R^9$, and $R^{10}$ are hydrogen, $C_{1-12}$ alkyl, or $H_2N(CH_2)_n$— wherein n is an integer of 2-6.

21. The compound or salt of embodiment 19 or 20, wherein $R^2$ is selected from 4-chlorophenyl, 4-dimethylaminomethylphenyl, 4-diethylaminomethylphenyl, 4-fluorophenyl, 2-amino-5-pyridyl, and 4-(1-aminocycloprop-1-yl)phenyl.

22. The compound or salt of any one of embodiments 19-21, wherein the compound is selected from:

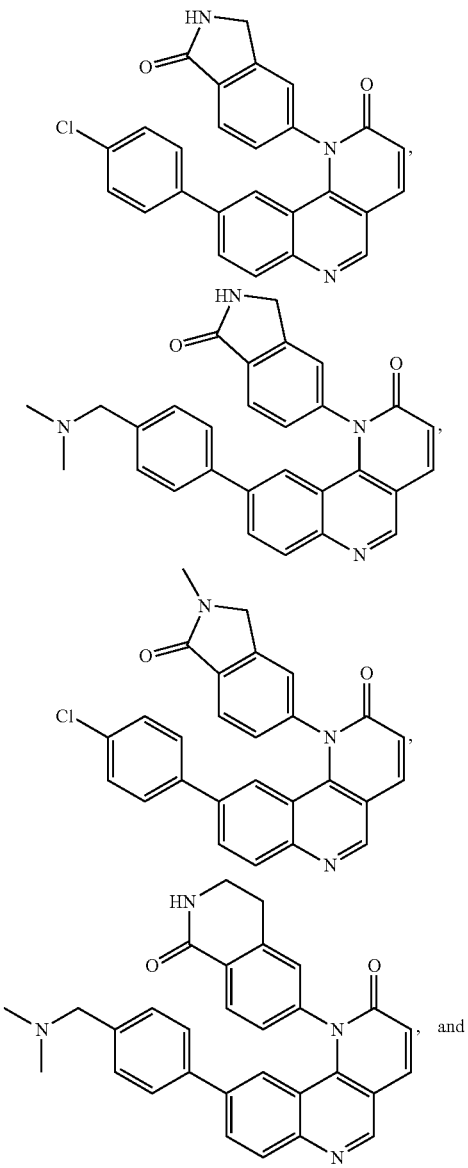

23. The compound or salt of embodiment 3, wherein B is $NR^6$.

24. The compound or salt of embodiment 23, wherein $R^1$ is $C_{6-10}$ aryl substituted with —CN.

25. The compound or salt of embodiment 24, wherein $R^6$ is hydrogen or methyl.

26. The compound or salt of embodiment 24 or 25, wherein $R^2$ is selected from 4-chlorophenyl, 3-fluorophenyl, 3-chlorophenyl, 3-methoxy-4-chlorophenyl, 3-aminophenyl, 3-methylphenyl, 3-dimethylaminomethylphenyl, 3-cyano-4-fluorophenyl, 3-hydroxy-4-fluorophenyl, 3-methoxy-4-fluorophenyl, 3-cyano-4-chlorophenyl, 3-hydroxy-4-chlorophenyl, 4-fluorophenyl, 3-cyanophenyl, 3-hydroxyphenyl, 3-amino-4-fluorophenyl, 4-dimethylaminophenyl, 3-cyanophenyl, 4-methylphenyl, 4-aminophenyl, 4-(1-hydroxy-1-ethyl)phenyl, 4-(2-aminoethyl)phenyl, 2-amino-5-pyridyl, 2-amino-5-pyrimidyl, 2-methyl-5-pyridyl, 2-acetylamino-5-pyridyl, 2-oxoindolin-5-yl, benzimidazolin-5-yl, 3-dimethylamino-1-propargyl, 4-(2-dimethylaminoethyl)phenyl, 2-pyrrolyl, N-methyl-2-pyrrolyl, 2-thiopheneyl, 3-thiopheneyl, 3-furanyl, 3-aminosulfonylphenyl, and 4-dimethylaminomethylphenyl.

27. The compound or salt of any one of embodiments 24-26, wherein $R^1$ is selected from 3-cyano-6-methyl phenyl, 3-cyano-4-piperazinyl-6-methylphenyl, 3-cyanophenyl, 3-cyano-4-piperazinylphenyl, 3-cyano-4-morpholinylphenyl, 4-(4-(2-hydroxyethylpiperazinyl-3-cyanophenyl, 3-cyano-4-(1,4-diazepan-1-yl)phenyl, 3-cyano-4-(4-acetylaminopiperazin-1-yl), 2-methyl-3-cyanophenyl, 3-cyano-4-(3-aminoazetidinyl)-6-methylphenyl, 3-cyano-4-(2-dimethylaminoethyl)-6-methylphenyl, 2-piperazinyl-3-cyano-6-methyl-5-pyridyl, 2-piperazinyl-3-cyano-5-pyridyl, 3-cyano-4-methoxyphenyl, 3-cyano-4-(4-hydroxypiperidinyl)phenyl, 3-cyano-4-(4-aminopiperidinyl)phenyl, and 2-methyl-3-cyanophenyl.

28. The compound or salt of any one of embodiments 24-27, wherein the compound is selected from:

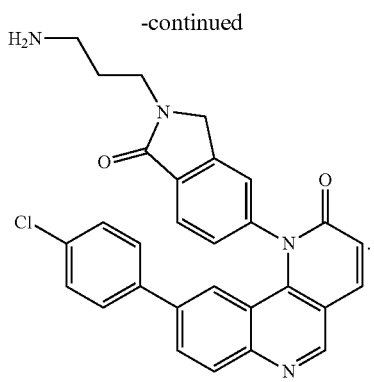

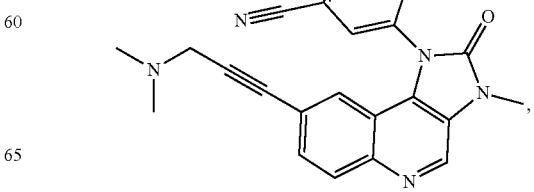

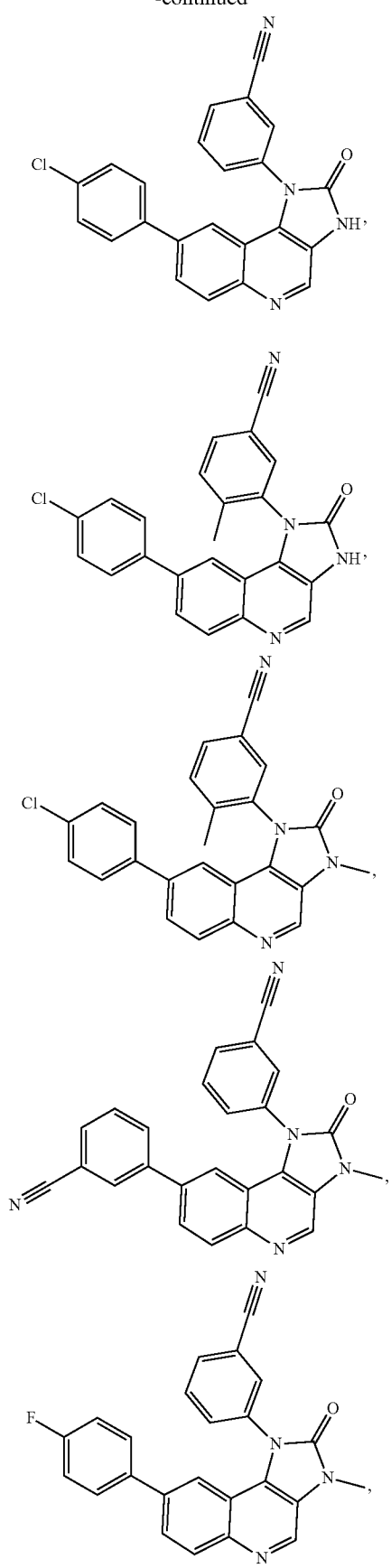
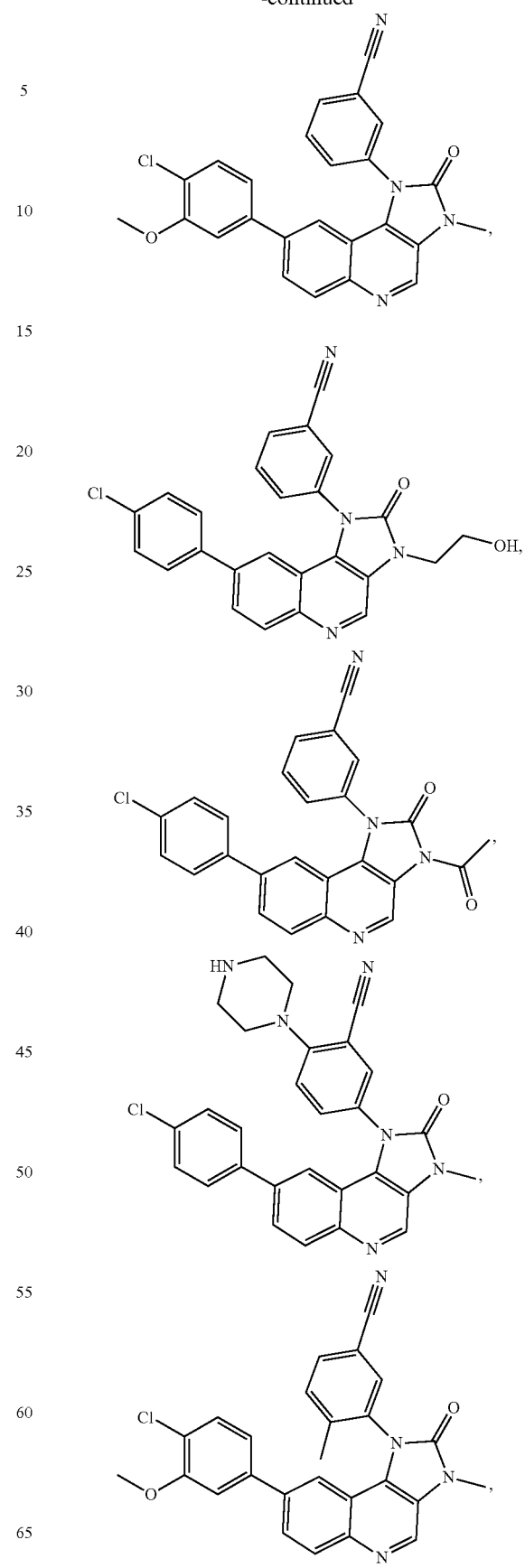

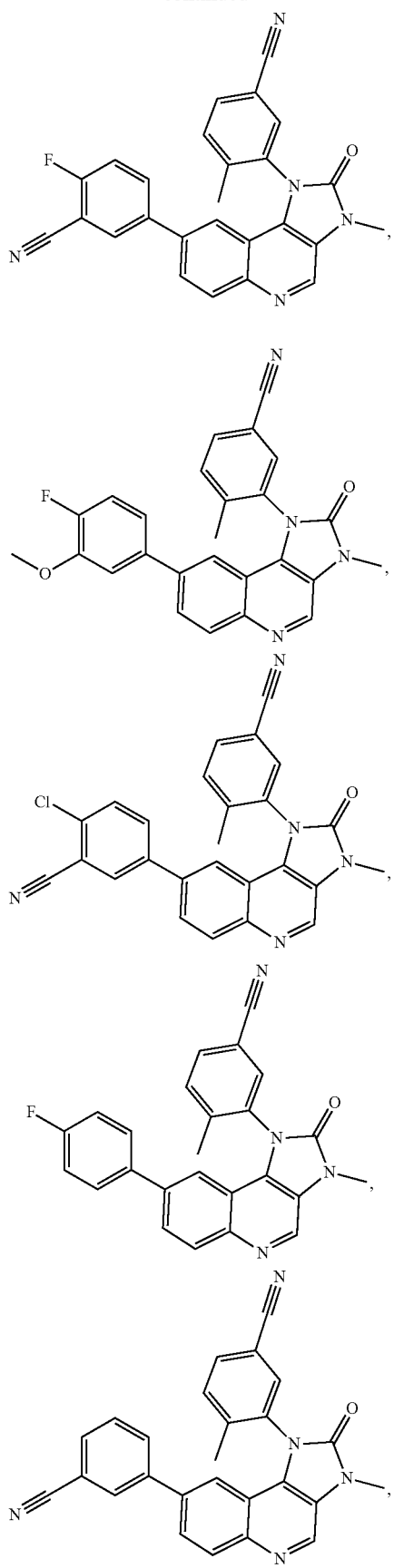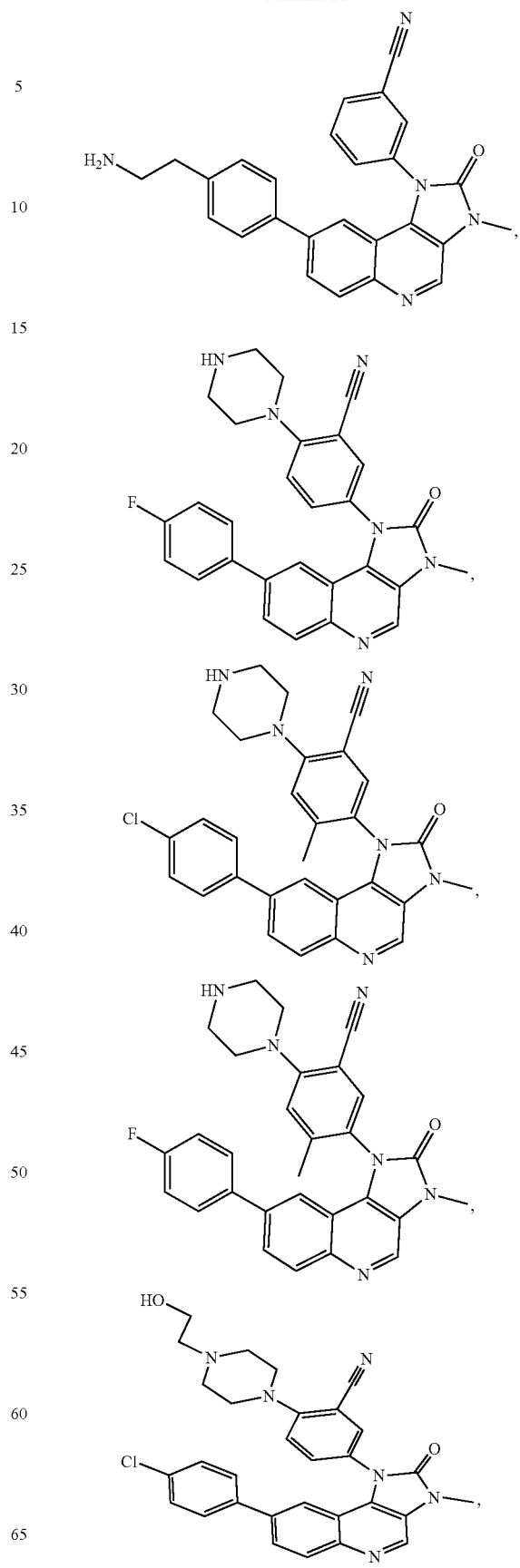

| 55 -continued | 56 -continued |
|---|---|
| 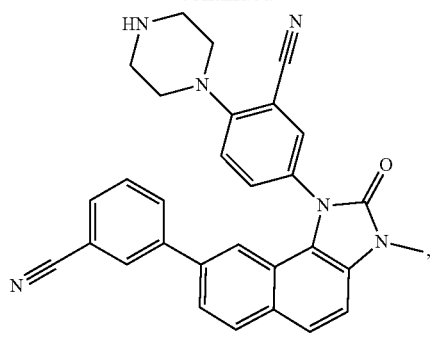 | 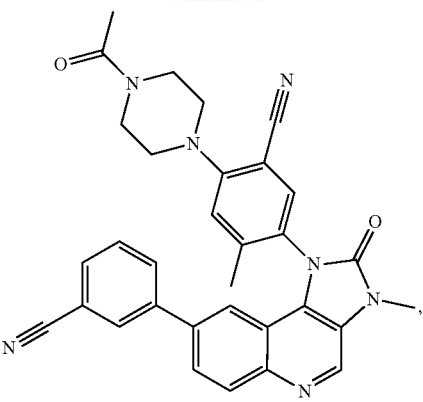 |
| 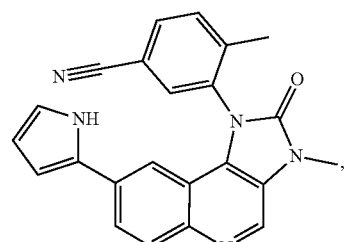 | 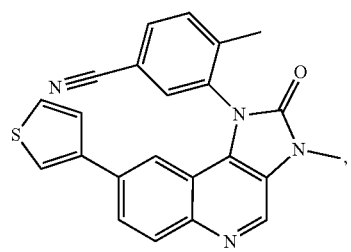 |
| 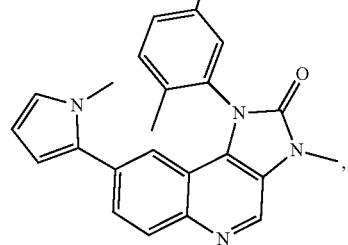 | 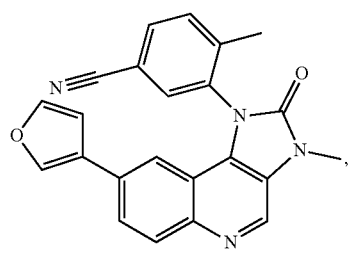 |
| 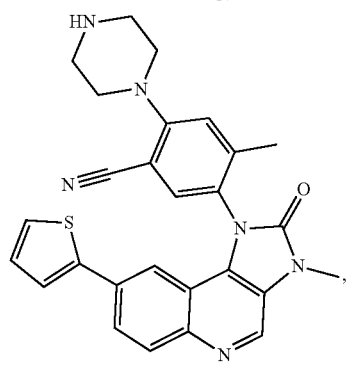 | 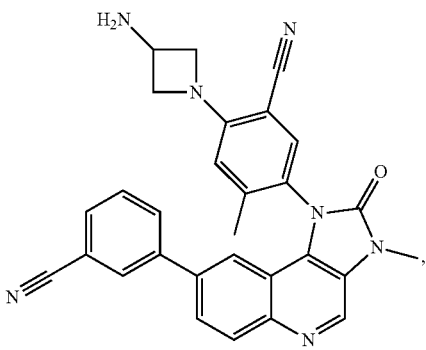 |
| 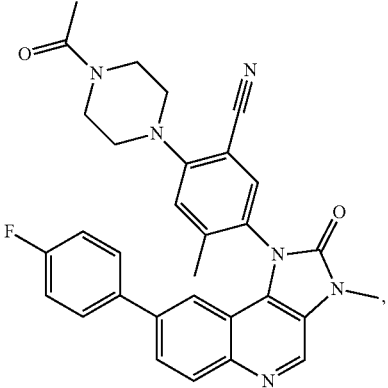 | 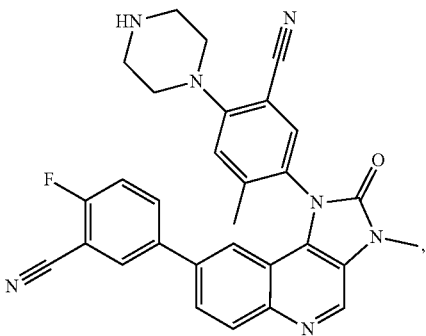 |

57
-continued

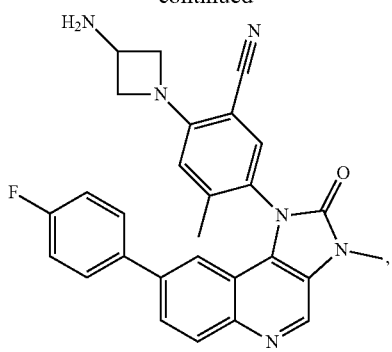

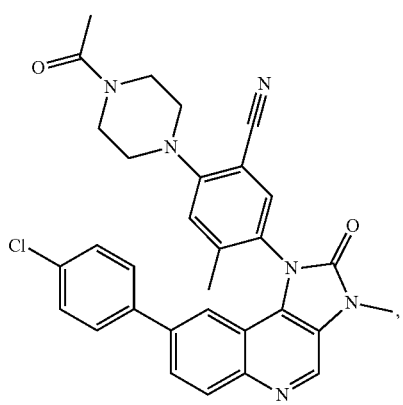

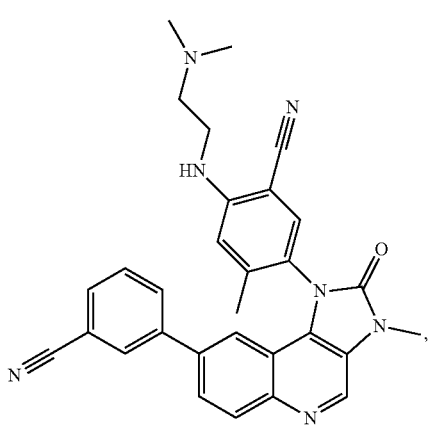

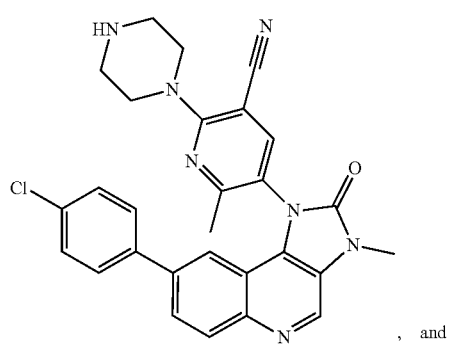
, and

58
-continued

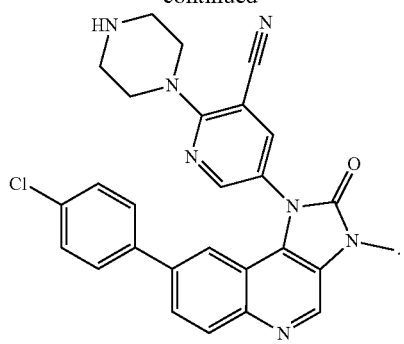

29. The compound or salt of embodiment 23, wherein $R^1$ is $C_{6-10}$ aryl substituted with $-SO_2R^{13}$.

30. The compound or salt of embodiment 29, wherein $R^2$ is 2-amino-5-pyridyl or 4-chlorophenyl.

31. The compound or salt of embodiment 29 or 30 wherein $R^1$ is 4-aminosulfonylphenyl.

32. The compound or salt of any one of embodiments 29-31, wherein the compound is:

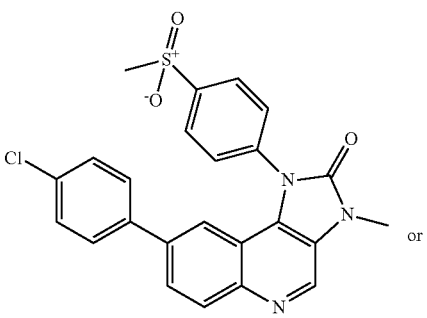
or

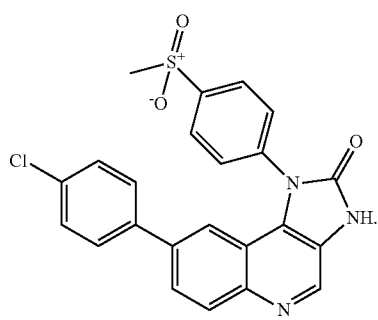

33. The compound or salt of embodiment 23, wherein $R^1$ is $C_{6-10}$ aryl substituted with $-CONR^{11}R^{12}$.

34. The compound or salt of embodiment 33, wherein $R^2$ is selected from 4-chlorophenyl, 2-amino-5-pyridyl, 3-hydroxy-4-chlorophenyl, 4-fluorophenyl, 3-cyanophenyl, 4-dimethylaminomethylphenyl, and 4-methylphenyl.

35. The compound or salt of embodiment 33 or 34, wherein $R^1$ is 4-morpholinocarbonylphenyl, 4-dimethylaminocarbonylphenyl, 4-(N-methyl-N-cyclopropyl)aminocarbonylphenyl, or 4-piperidinocarbonylphenyl.

36. The compound or salt of any one of embodiments 33-35, wherein the compound is selected from:

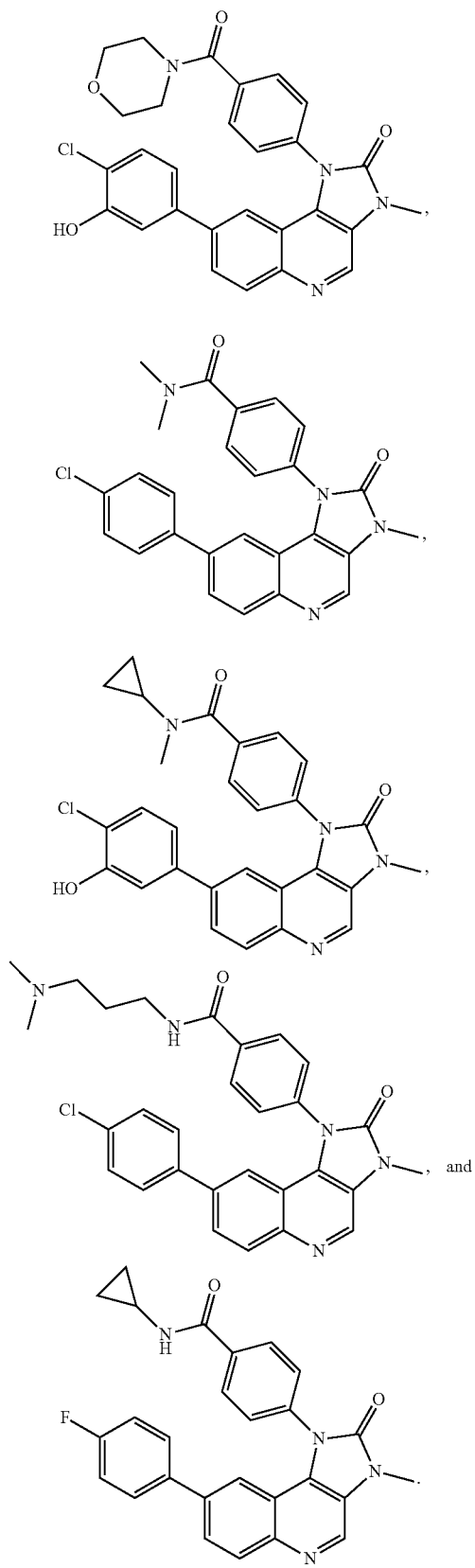

37. The compound or salt of embodiment 23, wherein $R^1$ is:

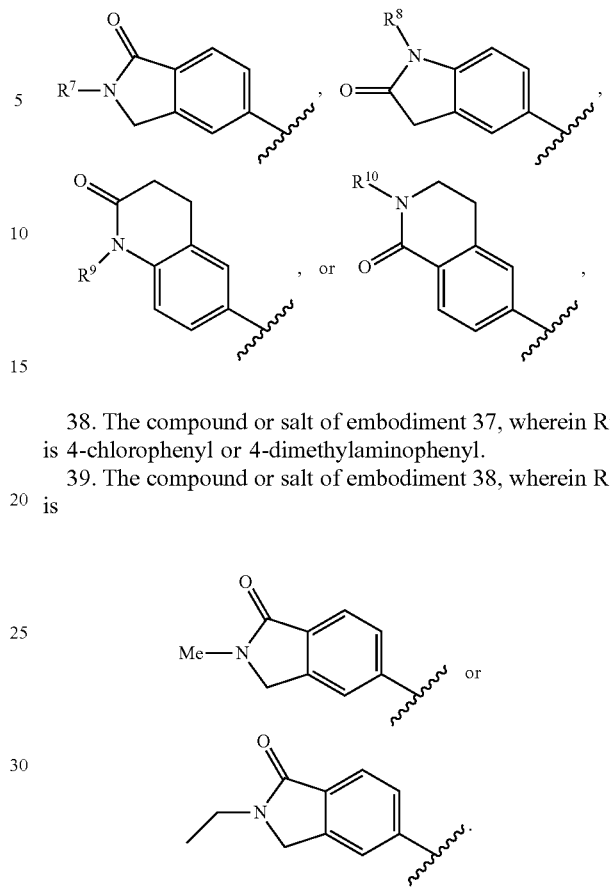

38. The compound or salt of embodiment 37, wherein $R^2$ is 4-chlorophenyl or 4-dimethylaminophenyl.

39. The compound or salt of embodiment 38, wherein $R^1$ is

40. A pharmaceutical composition comprising a compound or salt of any one of embodiments 1-39 and a pharmaceutically acceptable carrier.

41. A method of blocking transmission of a *Plasmodium* parasite comprising administering to a mammal in need of such treatment, a therapeutically effective amount of a first compound of any one of embodiments 1-39, optionally in combination with an antimalarial compound selected from elesclomol, NSC174938, NVP-AUY922, maduramicin, narasin, alvespimycin, omacetaxine, thiram, zinc pyrithione, phanquinone, bortezomib, salinomycin sodium, monensin sodium, dipyrithione, dicyclopentamethylene-thiuram disulfide, YM155, withaferin A, adriamycin, romidepsin, AZD-1152-HQPA, CAY10581, plicamycin, CUDC-101, auranofin, trametinib, GSK-458, afatinib, and panobinostat.

42. A method of treating malaria by killing or arresting the growth of *Plasmodium* organisms in a mammal, wherein the *Plasmodium* organisms are in a gametocyte stage, the method comprising administering to a mammal a therapeutically effective amount of a first compound of any one of embodiments 1-39, optionally in combination with an antimalarial compound selected from elesclomol, NSC174938, NVP-AUY922, maduramicin, narasin, alvespimycin, omacetaxine, thiram, zinc pyrithione, phanquinone, bortezomib, salinomycin sodium, monensin sodium, dipyrithione, dicyclopentamethylene-thiuram disulfide, YM155, withaferin A, adriamycin, romidepsin, AZD-1152-HQPA, CAY10581, plicamycin, CUDC-101, auranofin, trametinib, GSK-458, afatinib, and panobinostat.

43. A compound of any one of embodiments 1-39 for use in blocking transmission of a *Plasmodium* parasite in a mammal in need of therefore, optionally for use in combination with an antimalarial compound selected from elesclomol, NSC174938, NVP-AUY922, maduramicin, narasin, alvespimycin, omacetaxine, thiram, zinc pyrithione, phanquinone, bortezomib, salinomycin sodium, monensin sodium, dipyrithione, dicyclopentamethylene-thiuram disulfide, YM155, withaferin A, adriamycin, romidepsin, AZD-1152-HQPA, CAY10581, plicamycin, CUDC-101, auranofin, trametinib, GSK-458, afatinib, and panobinostat.

44. A compound of any one of embodiments 1-39 for use in killing or arresting the growth of *Plasmodium* organisms in a mammal, wherein the *Plasmodium* organisms are in a gametocyte stage, optionally for use in combination with an antimalarial compound selected from elesclomol, NSC174938, NVP-AUY922, maduramicin, narasin, alvespimycin, omacetaxine, thiram, zinc pyrithione, phanquinone, bortezomib, salinomycin sodium, monensin sodium, dipyrithione, dicyclopentamethylene-thiuram disulfide, YM155, withaferin A, adriamycin, romidepsin, AZD-1152-HQPA, CAY10581, plicamycin, CUDC-101, auranofin, trametinib, GSK-458, afatinib, and panobinostat.

45. A compound of formula (II):

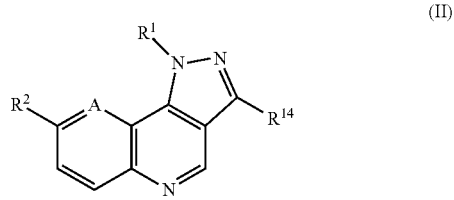

wherein A is CR or N,
wherein $R^1$ is $C_{6-10}$ aryl or heteroaryl substituted with one or more substituents selected from the group consisting of $C_{1-12}$ alkyl, $C_{3-10}$ cycloalkyl, alkoxy, —$CF_3$, heterocyclyl, —$CONR^{11}R^{12}$, —$SO_2NHR^{16}$, and CN, $R^2$ is selected from 2-amino-5-pyridinyl, 4-pyridinyl, 2-amino-5-pyrimidinyl, 3-pyridyl, quinolin-3-yl, 5-pyrimidinyl, 2-acetylamino-5-pyridyl, 2-amino-4-methylpyrimidin-5-yl, 1-piperazinyl, indol-5-yl, 1H-indazol-5-yl, 4-aminophenyl, 1,2,3,6-tetrahydropyridin-4-yl, 1H-pyrazol-4-yl, 1H-benzo[d]imidazol-5-yl, 4-sulfonylaminophenyl, 2-dimethylaminopyrimidin-5-yl, 3-trifluoromethylphenyl, bromo, 3-aminophenyl, vinyl, 4-aminocarbonylphenyl, 3-cyanophenyl, 3-trifluoromethyl-5-pyridyl, tetrazolyl, 4-chlorophenyl, 4-methoxyphenyl, 3-aminocarbonylphenyl, 3-acetylphenyl, 2,3-dihydrobenzofuran-6-yl, 1-methyl-1H-indol-5-yl, benzo[d][1,3]dioxo-5-yl, 4-fluorophenyl, 4-hydroxyphenyl, morpholin-1-yl, benzo[b]thiophen-1-yl, 4-methylsulfonylphenyl, benzo[c][1,2,5]oxadiazol-5-yl, 2-(piperidin-1-yl)-3-pyridinyl, 4-carboxyphenyl, 2-methyl-5-pyridyl, 4-methylsulfonylphenyl, 4-dimethylaminocarbonylphenyl, 4-phenylphenyl, 4-methylphenyl, 3-chloro-5-pyridyl, (3-pyrrolidin-1-yl)phenyl, 4-([piperizin-1-yl]carbonyl)phenyl, 4-([morpholin-1-yl]carbonyl)phenyl, 2-hydroxypyrimidin-5-yl, 3-aminosulfonylphenyl, 2-oxo-1,2,3,4,tetrahydroisoquinolin-6-yl, 2-oxo-1,2,3,4,-tetrahydroquinolin-6-yl, 4-(aminomethyl)phenyl, 4-(dimethylaminomethyl)phenyl, 4-(methylaminocarbonyl)phenyl, 1-oxoindolin-5-yl, 2-oxoindolin-5-yl, and 1-oxoisoindolin-5-yl, $R^{11}$ and $R^{12}$ selected from the group consisting of hydrogen, $C_{1-12}$ alkyl and $C_{3-10}$ cycloalkyl or, taken together with the N to which they are bound, form an optionally substituted 4-7 membered heterocyclyl ring containing O or N atoms, $R^{14}$ is hydrogen or $C_{1-12}$ alkyl, and
$R^{16}$ is hydrogen or $C_{1-12}$ alkyl,
or a pharmaceutically acceptable salt thereof.

46. The compound or salt of embodiment 45, wherein $R^{14}$ is methyl.

47. The compound or salt of embodiment 45 or 46, wherein $R^2$ is 2-amino-5-pyridyl or 4-chlorophenyl.

48. The compound or salt of any one of embodiments 45-47, wherein $R^1$ is selected from 3-trifluoromethylphenyl, 4-methylphenyl, 3-cyanophenyl, 3-pyridyl, 4-pyrrolidinylcarbonylphenyl, 4-cyclopropylaminocarbonylphenyl, 4-(3-dimethylaminopropylaminocarbonyl)phenyl, and 3-trifluoromethyl-4-morpholinocarbonylphenyl.

49. A pharmaceutical composition comprising a compound or salt of any one of embodiments 45-48 and a pharmaceutically acceptable carrier.

50. A method of blocking transmission of a *Plasmodium* parasite comprising administering to a mammal in need of such treatment, a therapeutically effective amount of a first compound of any one of embodiments 45-48, optionally in combination with an antimalarial compound selected from elesclomol, NSC174938, NVP-AUY922, maduramicin, narasin, alvespimycin, omacetaxine, thiram, zinc pyrithione, phanquinone, bortezomib, salinomycin sodium, monensin sodium, dipyrithione, dicyclopentamethylene-thiuram disulfide, YM155, withaferin A, adriamycin, romidepsin, AZD-1152-HQPA, CAY10581, plicamycin, CUDC-101, auranofin, trametinib, GSK-458, afatinib, and panobinostat.

51. A method of treating malaria by killing or arresting the growth of *Plasmodium* organisms in a mammal, wherein the *Plasmodium* organisms are in a gametocyte stage, the method comprising administering to a mammal a therapeutically effective amount of a first compound of any one of embodiments 45-48 and/or a second compound selected from elesclomol, NSC174938, NVP-AUY922, maduramicin, narasin, alvespimycin, omacetaxine, thiram, zinc pyrithione, phanquinone, bortezomib, salinomycin sodium, monensin sodium, dipyrithione, dicyclopentamethylene-thiuram disulfide, YM155, withaferin A, adriamycin, romidepsin, AZD-1152-HQPA, CAY10581, plicamycin, CUDC-101, auranofin, trametinib, GSK-458, afatinib, and panobinostat.

52. A compound of any one of embodiments 45-48 for use in blocking transmission of a *Plasmodium* parasite in a mammal in need of therefore, optionally for use in combination with an antimalarial compound selected from elesclomol, NSC174938, NVP-AUY922, maduramicin, narasin, alvespimycin, omacetaxine, thiram, zinc pyrithione, phanquinone, bortezomib, salinomycin sodium, monensin sodium, dipyrithione, dicyclopentamethylene-thiuram disulfide, YM155, withaferin A, adriamycin, romidepsin, AZD-1152-HQPA, CAY10581, plicamycin, CUDC-101, auranofin, trametinib, GSK-458, afatinib, and panobinostat.

53. A compound of any one of embodiments 45-48 for use in killing or arresting the growth of *Plasmodium* organisms in a mammal, wherein the *Plasmodium* organisms are in a gametocyte stage, optionally for use in combination with an antimalarial compound selected from elesclomol, NSC174938, NVP-AUY922, maduramicin, narasin, alvespimycin, omacetaxine, thiram, zinc pyrithione, phanquinone, bortezomib, salinomycin sodium, monensin sodium, dipyrithione, dicyclopentamethylene-thiuram disulfide, YM155, withaferin A, adriamycin, romidepsin, AZD-1152-

HQPA, CAY10581, plicamycin, CUDC-101, auranofin, trametinib, GSK-458, afatinib, and panobinostat.

54. A method of synthesizing a compound of formula 101, comprising the steps of:
(a) providing a compound of formula 100:

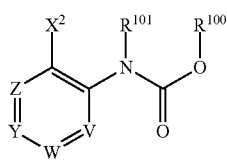

100 wherein $X^2$ is F, Cl, Br, or I,
V is $CR^{104}$ or N,
W is $CR^{105}$ or N,
Y is $CR^{106}$ or N,
Z is $CR^{107}$ or N, wherein optionally Y and Z,
wherein $R^{104}$-$R^{107}$ are independently hydrogen, optionally substituted alkyl, optionally substituted aryl, or optionally substituted heteroaryl, or when Y is $CR^{106}$ and Z is $CR^{107}$, $R^{106}$ and $R^{106}$, taken together with the carbons to which they are bound, form an optionally substituted fused 5- to 8-membered carbocyclic, aryl, heterocyclyl, or heteroaryl ring, wherein the heterocyclyl contains one or more atoms selected from N, O, and S,
wherein at least one of V, W, Y, and Z is N,
wherein $R^{100}$ is alkyl or aryl, and
wherein $R^{101}$ is hydrogen, alkyl, or aryl,
(b) reacting the compound of formula 100 with an amine of the formula: $R^{102}NH_2$ to give a compound of the formula 101:

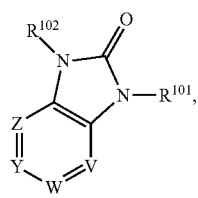

101 wherein $R^{102}$ is optionally substituted alkyl, optionally substituted cycloalkyl, optionally substituted heterocyclyl, optionally substituted aryl, optionally substituted heteroaryl, optionally substituted arylalkyl, optionally substituted heterocyclylalkyl, optionally substituted cycloalkylalkyl, or optionally substituted heteroarylalkyl.

55. The method of embodiment 54, wherein the reacting step (b) is conducted in the presence of an acid.

56. The method of embodiment 55, wherein the acid is selected from hydrochloric acid, nitric acid, phosphoric acid, sulfuric acid, boric acid, hydrofluoric acid, hydrobromic acid, perchloric acid, formic acid, acetic acid, propanoic acid, and trifluoroacetic acid.

57. The method of any one of embodiments 54-56, wherein the reacting is conducted in an aliphatic alcohol solvent.

The following examples further illustrate the invention but, of course, should not be construed as in any way limiting its scope.

Materials and Methods

Cell culture. Asexual parasites of *P. falciparum* strain 3D7 were cultured as described previously [Trager W, et al., *Journal of Parasitology* 2005, 91: 484-486], Stage III-V gametocytes were selected and enriched with 3-day treatment with 50 mM N-acetylglucosamine (NAG) and the following Percoll density gradient centrifugation after gametocyte production [Tanaka T Q, et al., *Molecular and Biochemical Parasitology*, 2011, 111: 160-163], Gametocytes of HB3 and Dd2 strains were produced and then set up for assay in a similar process. HepG2 cells (ATCC, cat. no. 77400) were cultured in 175-$cm^2$ tissue culture flasks with 30 ml growth medium at 37° C. in a 5% $CO_2$ humidified atmosphere. Growth medium was made with Dulbecco's Modified Eagle Medium with 10% fetal bovine serum (FBS). Growth medium was replaced every other day and cells were passed at 75% confluence.

Compound library and gametocyte assay screen. The approved drug library was collected with 4,265 compounds from traditional chemical suppliers, specialty collections, pharmacies and custom synthesis [Huang R et al., *Science Translational Medicine*, 2011, 3: 80ps16] that included 49% drugs approved for human or animal use by the US Food and Drug Administration (FDA), 23% approved in Canada/UK/EU/Japan, and the remaining 28% either in clinical trials or research tool compounds. The Malaria Box contained 400 drugs or tool compounds with the confirmed activities on blood-staged *P. falciparum* and assessed cytotoxicity against mammalian cells [Gamo F J et al., *Nature*, 2010 465: 305-U356; Guiguemde W A et al., *Nature*, 2010, 465: 311-315], The MIPE library was an internal collection of 550 kinase inhibitors, which contain approved drugs and drug candidates in preclinical and clinical stages [Mathews L A et al., *Journal of Biomolecular Screening*, 2012, 17: 1231-1242], Compounds from all libraries were obtained as powder samples and dissolved in DMSO as 10 mM stock solutions, except several hundreds from the approved drug library that were prepared as 4.47 mM stock solutions due to solubility limitations.

Compound screening experiments were performed as previously described [Tanaka T Q et al., *Molecular and Biochemical Parasitology*, 2013, 3188: 20-25], Briefly, 2.5 µl/well incomplete medium was dispensed into each well of 1,536-well plates using the Multidrop Combi followed by 23 nl compound transferring using the NX-TR Pintool (WAKO Scientific Solutions, San Diego, Calif.). 2.5 µl/well of gametocytes was dispensed with a seeding density of 20,000 cells/well using the Multidrop Combi. The assay plates were incubated for 72 h at 37° C. with 5% $CO_2$. After addition of 5 µl/well of 2× AlamarBlue dye (Life Technologies, cat. no. DALI 100), the plates were incubated for 24 h at 37° C. with 5% $CO_2$ and were read in a fluorescence detection mode (Ex=525 nm, Em=598 nm) on a ViewLux plate reader (PerkinElmer).

Small molecule pull-down. Affinity matrix: To make ahead-connected affinity probe of Torin 2, a tetraethylene glycol linker was attached to 1-(piperazin-1-yl)propan-1-one of HWW030 and then coupled to Affi-Gel 10 resin (Bio-Rad Laboratories, cat. no. 153-6046) under mild basic conditions to afford Torin 2 matrix (T2M). See detailed version in Example 7. Torin 1 was similarly immobilized to resin and used as a negative control (TIM). The resultant affinities probes were incubated with gametocyte lysates, the bound proteins were eluted from resin by boiling in SDS-PAGE sample loading buffer. The eluted fractions were separated by SDS-PAGE and visualized by silver staining. RBC infected with gametocytes (3D7 strain: Stage III-V) were washed 3 times with PBS and then lysed by 0.05% saponin treatment in PBS for 5 min at room temperature. The prepared gametocytes were washed 3 times with PBS and frozen at −80° C. The affinity precipitation experiment was processed as previously described [Zhang Q et al., *Proceedings of the National Academy of Sciences of the United States of America*, 2007, 104: 7444-7448; Arastu-Kapur S et al., *Nature Chemical Biology*, 2008, 4: 203-213], The frozen samples were lysed with homogenization buffer (60 mM glycerophosphate, 15 mM p-nitrophenyl phosphate, 25 mM MOPS (pH 7.2), 15 mM EGTA, 15 mM MgCl2, 1 mM DTT, protease inhibitors (Roche Diagnostics, cat. no.

11836170001), and 0.5% Nonidet P-40). Cell lysates were centrifuged at 16,000×g for 20 min at 4° C., and the supernatant was collected. Protein concentration in the supernatant was determined by using a BCA protein assay kit (Pierce Chemical, cat. no. 23225). The lysate (0.5 mg) was then added to the packed affinity matrix, and bead buffer (50 mM Tris HCl (pH 7.4), 5 mM NaF, 250 mM NaCl, 5 mM EDTA, 5 mM EGTA, protease inhibitors, and 0.1% Nonidet P-40) was added to a final volume of 1 ml. After rotating at 4° C. for 2 h, the mixture was centrifuged at 16,000×g for 2 min at 4° C., and the supernatant was removed. The affinity matrix was then washed (six times) with cold bead buffer and eluted by boiling with SDS-PAGE sample loading buffer at 95° C. for 5 min. Supernatants were separated on a 10% Bis-Tris gel (Life Technologies, cat. no. NP0315BOX) and visualized by silver staining using a Pierce Silver Stain Kit for Mass Spectrometry (Pierce Chemical, cat. no. 24600).

DARTS (drug affinity responsive target stability). The 3D7 gametocytes were lysed with M-PER supplemented with protease and phosphatase inhibitors as previously described [Lomenick B et al., *Proceedings of the National Academy of Sciences of the United States of America*, 2009, 106: 21984-21989]. After centrifugation at 16,000×g for 20 min, protein concentration in the supernatant was quantified and 2 μg/μl proteins were treated with 600 nM of Torin 2 or 600 nM of Torin 1 for 2 h at room temperature. The samples were treated with 46 μg/ml pronase (Sigma-Aldrich, cat. no. P6911) for 30 min at room temperature. The digestion was stopped by adding the SDS-PAGE sample loading buffer and boiled at 70° C. for 10 min. The samples were separated on a 10% Bis-Tris gel and visualized by silver staining.

Malaria Mouse Model. *Plasmodium berghei* ANKA (Pb) parasites were maintained by serial passage by intraperitoneal (i.p.) injection in outbred mice. Two days before feeding, female mice were infected i.p. with 200-400 μl whole blood from a Pb-infected mouse with >10% parasitemia. On the day of feeding, the mice were checked for exflagellation and injected intravenously (i.v.) with drug vehicle alone (10% N-methylpyrrolidnone, 40% PEG 400 in water), or (a) 2-4 mg/kg Torin 2 (one or two doses), (b) 8 mg/kg NVP-AUY922 (two doses), or (c) 8 mg/kg Alvespimycin (two doses). Two hours post treatment, mice were anesthetized and *Anopheles Stephensi* mosquitoes were allowed to feed on infected mice for 15 minutes. Parasitemia, gametocytemia, and presence of exflagellation were examined as described previously [Blagborough A M et al., *Nature Communications*, 2013, 4: 1812]. Mosquitoes were maintained on 5% (w/v) glucose at 19° C. and 80% relative humidity. At day 10 post feeding, mosquito midguts were dissected and transmission was measured by staining mosquito midguts with 0.2% mercurochrome and counting the numbers of oocysts per midgut.

Data analysis. The primary screen data was analyzed using customized software developed internally [Wang Y et al., *Current Chemical Genomics* 2010, 4: 57-66], $IC_{50}$ values were calculated using the Prism software (Graphpad Software, Inc. San Diego, Calif.). Data were presented as means±SEM with n=3 independent experiments.

General materials and methods for chemical synthesis. All commercially available reagents, compounds, and solvents were purchased and used without further purification. 9-Bromo-1-(3-(trifluoromethyl)phenyl)benzo[h][1,6]naphthyridin-2(1H)-one was prepared according to the method described by Liu and coworkers (Liu, Q. et. al., *J. Med. Chem.*, 2011, 1473-1480). Column chromatography on silica gel was performed on Biotage KPSil pre-packed cartridges using the Biotage SP-1 automated chromatography system. Reverse phase column chromatography was performed on RediSep preparative C-18 column using the Teledyne ISCO combiflash Rf system. $^1$H spectra were recorded using an Inova 400 MHz spectrometer (Varian). Samples were analyzed on an Agilent 1200 series LC/MS. Method A used an Enomenex Kinetex 1.7 micron column and a flow rate of 1.1 mL/min. The mobile phase was a mixture of acetonitrile and $H_2O$ each containing 0.05% trifluoroacetic acid. A gradient of 4% to 100% acetonitrile over 4 minutes was used during analytical analysis. Method B used a Zorbax™ Eclipse XDB-C18 reverse phase (5 micron, 4.6×150 mm) column and a flow rate of 1.1 mL/min. The mobile phase was a mixture of acetonitrile and $H_2O$ each containing 0.05% trifluoroacetic acid. A gradient of 5% to 100% acetonitrile over 8 minutes was used during analytical analysis.

Example 1

This example demonstrates an In vitro drug activity on gametocytes.

Stage III-V gametocytes (blood stage *P. falciparum* parasites) were enriched with treatment with 50 mM N-acetylglucosamine (NAG) and Percoll density gradient centrifugation as described previously[1]. Briefly, 2.5 μl/well incomplete medium was dispensed into each well of 1,536-well plates using the Multidrop Combi followed by 23 nl compound transfer using the NX-TR Pintool (WAKO Scientific Solutions, San Diego, Calif.). Then, 2.5 μl/well of gametocytes was dispensed with a seeding density of 20,000 cells/well using the Multidrop Combi. The assay plates were incubated for 72 h at 37° C. with 5% $CO_2$. After addition of 5 μl/well of 2× AlamarBlue dye (Life Technologies, cat. no. DALI 100), the plates were incubated for 24 h at 37° C. with 5% $CO_2$ and then were read in a fluorescence detection mode (Ex=525 nm, Em=598 nm) on a ViewLux plate reader (PerkinElmer).

Example 2

This example demonstrates In vitro drug activity on asexual parasites in accordance with an embodiment of the invention.

Asexual parasites of *P. falciparum* strain 3D7 were cultured as described previously (Trager, W. et al., *J. Parasitol.* 2005, 91(3): 484-486). Drug activity on asexual stage parasites was tested using a SYBR Green assay as described previously (Eastman, R. T. et al., *Antimicrob. Agents Chemother.* 2013, 57(1): 425-435; Smilkstein, M. et al., *Antimicrob. Agents Chemother.* 2004, 48(5): 1803-1806). Briefly, parasites were diluted to 0.5% parasitemia in complete culture medium with 2% hematocrit and drugs diluted in DMSO (≤0.5%) and were loaded into a 96-well plate (200 μl/well). No drug and RBC alone wells were included as positive and background controls, respectively, and each testing condition was examined in duplicated. After 72 h incubation under the standard culture condition and a freeze-thaw lysis step at −80° C. and room temperature, 100 μl/well of lysis buffer containing SYBR Green I was added to the parasite culture and incubated for 30 min at room temperature. The fluorescence of each well was measured at 520 nm following excitation at 490 nm using a FLUOstar Optima™ microplate reader (BMG Labtech).

Example 3

This example demonstrates a synthesis of compounds, in accordance with an embodiment of the invention.

A general procedure for the synthesis of compound 2 is shown in Scheme 1.

Aldehydes 1 were prepared using a reported procedure (*J. Med. Chem.* 2011, 54(5): 1473-1480). A solution of 1 (300 μmole) in 3 mL of THF were added 300 μL of $Et_2N/Pr$ and R'CH$_2$COCl (3000 μmole). The mixture was heated in a microwave between 100 to 150° C. for 15 min. The crude product was purified by column chromatography on silica gel using dichloromethane in methanol (0-20%) as eluent to give 1'. A mixture of 1' (1.0 equiv), boronic acid or boronic acid pinacol ester (3.0 equiv), tetrakis(triphenylphosphine) palladium (0.05 equiv), DMF (1.5 mL) and saturated NaHCO$_3$ aqueous solution (0.5 mL) was charged in a microwave vial. Nitrogen was bubbled through the mixture for 3 min. The vial was capped and heated in a microwave at 120-150° C. for 15 min. The reaction mixture was filtered through a plug of Celite and the filtrate was purified by reverse phase column chromatography using acetonitrile (containing 0.1% TFA)/water (containing 0.1% TFA) as an eluent to give 2.

9-(4-chlorophenyl)-1-(4-(morpholine-4-carbonyl)phenyl)benzo[h][1,6]naphthyridin-2(1H)-one

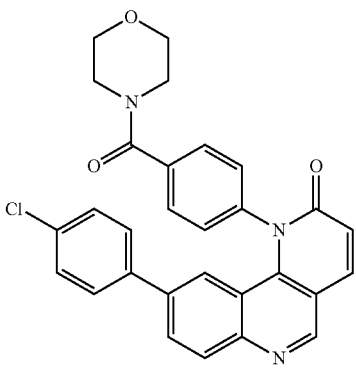 [SMILES: O=C(c1ccc(-n2c(=O)ccc3cnc4ccc(-c5ccc(Cl)cc5)cc4c32)cc1)N1CCOCC1]

LC/MS (Method B): (electrospray+ve), m/z 496.1 (MH)$^+$, $t_R$=4.712, UV$_{254}$=100%

9-(4-((dimethylamino)methyl)phenyl)-1-(4-(morpholine-4-carbonyl)phenyl)benzo[h][1,6]naphthyridin-2(1H)-one

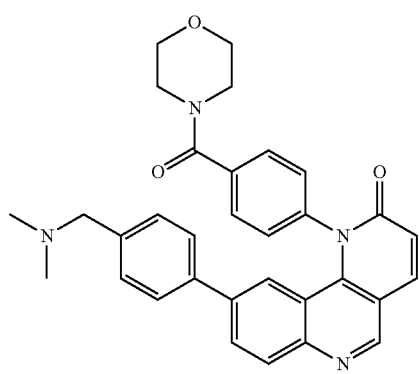 [SMILES: CN(C)Cc1ccc(-c2ccc3ncc4ccc(=O)n(-c5ccc(C(=O)N6CCOCC6)cc5)c4c3c2)cc1]

LC/MS (Method B): (electrospray+ve), m/z 519.2 (MH)$^+$, $t_R$=3.462, UV$_{254}$=100%

4-(9-(4-chlorophenyl)-2-oxobenzo[h][1,6]naphthyridin-1(2H)-yl)-N-cyclopropylbenzamide

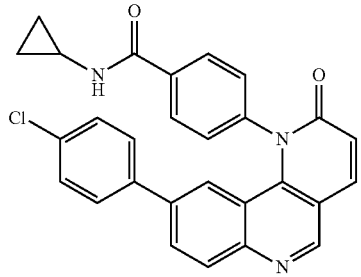 [SMILES: O=C(NC1CC1)c1ccc(-n2c(=O)ccc3cnc4ccc(-c5ccc(Cl)cc5)cc4c32)cc1]

LC/MS (Method B): (electrospray+ve), m/z 466.1 (MH)$^+$, $t_R$=4.659, UV$_{254}$=100%

4-(9-(4-chlorophenyl)-2-oxobenzo[h][1,6]naphthyridin-1(2H)-yl)-N-cyclopropyl-3-methylbenzamide

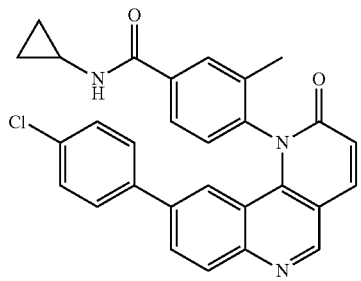 [SMILES: Cc1cc(C(=O)NC2CC2)ccc1-n1c(=O)ccc2cnc3ccc(-c4ccc(Cl)cc4)cc3c21]

LC/MS (Method B): (electrospray+ve), m/z 480.1 (MH)$^+$, $t_R$=4.765, UV$_{254}$=100%

4-(9-(4-chlorophenyl)-2-oxobenzo[h][1,6]naphthyridin-1(2H)-yl)-N-(2,2,2-trifluoroethyl)benzamide

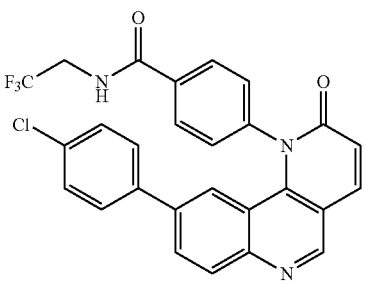 [SMILES: O=C(NCC(F)(F)F)c1ccc(-n2c(=O)ccc3cnc4ccc(-c5ccc(Cl)cc5)cc4c32)cc1]

White solid, isolated yield: 18.3%. $^1$H NMR (400 MHz, DMSO-d$_6$) δ 9.42 (t, J=6.2 Hz, 1H), 9.17 (s, 1H), 8.35 (d, J=9.5 Hz, 1H), 8.23-8.17 (m, 2H), 8.12 (dd, J=8.6, 0.5 Hz, 1H), 8.01 (dd, J=8.7, 2.0 Hz, 1H), 7.73-7.67 (m, 2H), 7.35-7.28 (m, 2H), 7.09-7.05 (m, 3H), 6.95 (d, J=9.4 Hz, 1H), 4.30-4.16 (m, 2H); LC/MS (Method B): (electrospray+ve), m/z 508.0 (MH)$^+$, $t_R$=4.992, UV$_{254}$=100%

69

4-(9-(4-chlorophenyl)-2-oxobenzo[h][1,6]naphthyridin-1(2H)-yl)-N-(2-(dimethylamino)ethyl)benzamide

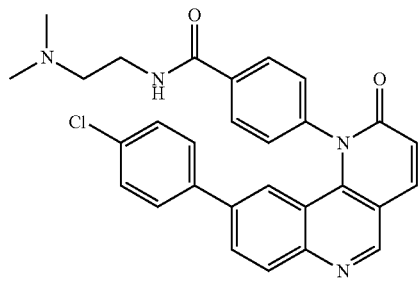 [SMILES: CN(C)CCNC(=O)c1ccc(-n2c(=O)ccc3cnc4ccc(-c5ccc(Cl)cc5)cc4c32)cc1]

Off-white solid, isolated yield: 28.4%. $^1$H NMR (400 MHz, DMSO-d$_6$) δ 9.19 (s, 1H), 8.95 (t, J=5.7 Hz, 1H), 8.36 (d, J=9.5 Hz, 1H), 8.19-8.10 (m, 3H), 8.02 (dd, J=8.7, 1.9 Hz, 1H), 7.73-7.67 (m, 2H), 7.38-7.31 (m, 2H), 7.14-7.08 (m, 2H), 7.06 (dd, J=1.9, 0.5 Hz, 1H), 6.96 (d, J=9.4 Hz, 1H), 3.73 (q, J=6.0 Hz, 2H), 3.34 (q, J=6.0 Hz, 2H), 2.90 (d, J=4.8 Hz, 7H); LC/MS (Method B): (electrospray+ve), m/z 497.3 (MH)$^+$, t$_R$=3.667, UV$_{254}$=100%

N-cyclopropyl-4-(9-(4-fluorophenyl)-2-oxobenzo[h][1,6]naphthyridin-1(2H)-yl)benzamide

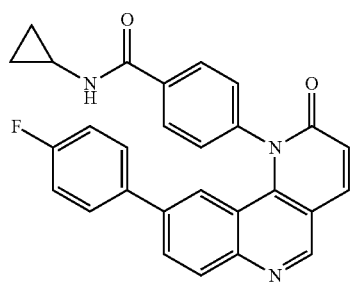 [SMILES: O=C(NC1CC1)c1ccc(-n2c(=O)ccc3cnc4ccc(-c5ccc(F)cc5)cc4c32)cc1]

Off-white solid, isolated yield: 19.25%. $^1$H NMR (400 MHz, DMSO-d$_6$) δ 9.16 (s, 1H), 8.70 (d, J=4.4 Hz, 1H), 8.34 (d, J=9.5 Hz, 1H), 8.11 (dd, J=8.5, 6.3 Hz, 3H), 7.99 (dd, J=8.7, 2.0 Hz, 1H), 7.65-7.60 (m, 2H), 7.16-7.08 (m, 4H), 6.97 (d, J=2.3 Hz, 1H), 6.95 (d, J=9.4 Hz, 1H), 3.02-2.94 (m, 1H), 0.79 (td, J=7.0, 4.6 Hz, 2H), 0.69-0.59 (m, 2H); LC/MS (Method B): (electrospray+ve), m/z 450.1 (MH)$^+$, t$_R$=4.372, UV$_{254}$=100%

70

4-(9-(4-chlorophenyl)-2-oxobenzo[h][1,6]naphthyridin-1(2H)-yl)-N-(1-(2-(dimethylamino)ethyl)piperidin-4-yl)benzamide

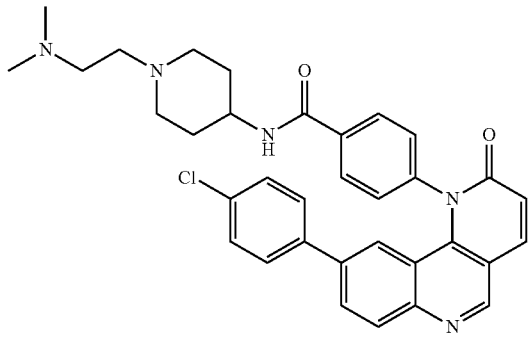 [SMILES: CN(C)CCN1CCC(NC(=O)c2ccc(-n3c(=O)ccc4cnc5ccc(-c6ccc(Cl)cc6)cc5c43)cc2)CC1]

4-(9-(4-chlorophenyl)-2-oxobenzo[h][1,6]naphthyridin-1(2H)-yl)-N-(1-(2-hydroxyethyl)azetidin-3-yl)benzamide

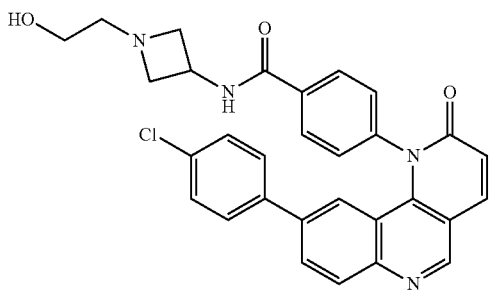 [SMILES: O=C(NC1CN(CCO)C1)c1ccc(-n2c(=O)ccc3cnc4ccc(-c5ccc(Cl)cc5)cc4c32)cc1]

LC/MS (Method B): (electrospray+ve), m/z 525.2 (MH)+, t$_R$=2.666, UV$_{254}$=100%

9-(4-chlorophenyl)-1-(4-(4-(2-(dimethylamino)ethyl)piperazine-1-carbonyl)phenyl)benzo[h][1,6]naphthyridin-2(1H)-one

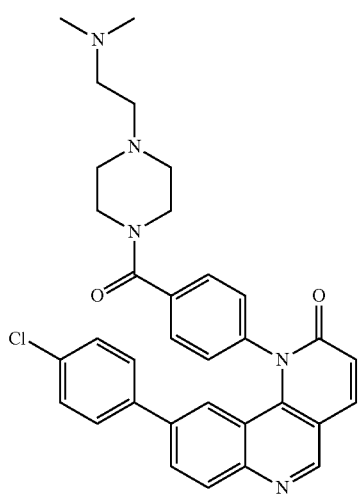 [SMILES: CN(C)CCN1CCN(C(=O)c2ccc(-n3c(=O)ccc4cnc5ccc(-c6ccc(Cl)cc6)cc5c43)cc2)CC1]

LC/MS (Method B): (electrospray+ve), m/z 566.3 (MH)+, $t_R$=2.731, UV$_{254}$=100%

4-(9-(4-chlorophenyl)-2-oxobenzo[h][1,6]naphthyridin-1(2H)-yl)-N-(pyrrolidin-3-yl)benzamide

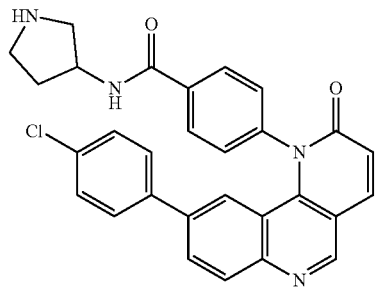 [SMILES: O=C(NC1CCNC1)c1ccc(-n2c(=O)ccc3cnc4ccc(-c5ccc(Cl)cc5)cc4c32)cc1]

LC/MS (Method B): (electrospray+ve), m/z 495.2 (MH)$^+$, $t_R$=2.713, UV$_{254}$=100%

4-(9-(4-(1-aminocyclopropyl)phenyl)-2-oxobenzo[h][1,6]naphthyridin-1(2H)-yl)-N-cyclopropylbenzamide

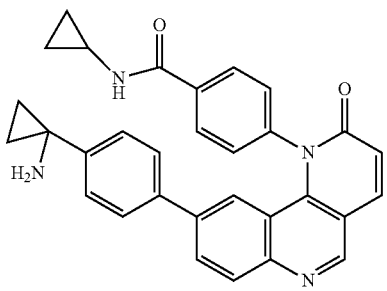 [SMILES: NC1(c2ccc(-c3ccc4ncc5ccc(=O)n(-c6ccc(C(=O)NC7CC7)cc6)c5c4c3)cc2)CC1]

LC/MS (Method B): (electrospray+ve), m/z 487.3 (MH)$^+$, $t_R$=2.264, UV$_{254}$=100%

9-(4-chlorophenyl)-1-(1-oxoisoindolin-5-yl)benzo[h][1,6]naphthyridin-2(1H)-one

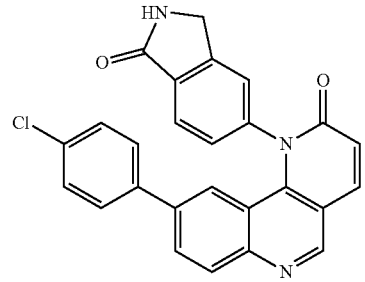 [SMILES: O=C1NCc2cc(-n3c(=O)ccc4cnc5ccc(-c6ccc(Cl)cc6)cc5c43)ccc21]

LC/MS (Method B): (electrospray+ve), m/z 438.1 (MH)$^+$, $t_R$=4.145, UV$_{254}$=100%

9-(4-((dimethylamino)methyl)phenyl)-1-(1-oxoisoindolin-5-yl)benzo[h][1,6]naphthyridin-2(1H)-one

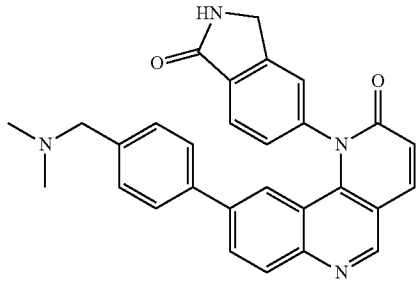 [SMILES: CN(C)Cc1ccc(-c2ccc3ncc4ccc(=O)n(-c5ccc6c(c5)CNC6=O)c4c3c2)cc1]

LC/MS (Method B): (electrospray+ve), m/z 461.2 (MH)$^+$, $t_R$=3.149, UV$_{254}$=100%

9-(4-chlorophenyl)-1-(2-methyl-1-oxoisoindolin-5-yl)benzo[h][1,6]naphthyridin-2(1H)-one

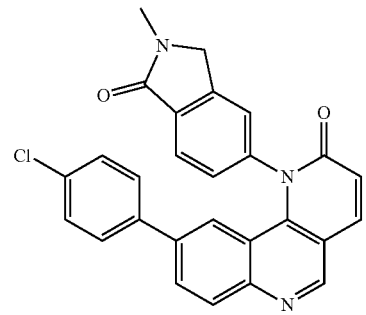 [SMILES: CN1Cc2cc(-n3c(=O)ccc4cnc5ccc(-c6ccc(Cl)cc6)cc5c43)ccc2C1=O]

LC/MS (Method B): (electrospray+ve), m/z 452.1 (MH)$^+$, $t_R$=4.309, UV$_{254}$=100%

9-(4-((dimethylamino)methyl)phenyl)-1-(1-oxo-1,2,3,4-tetrahydroisoquinolin-6-yl)benzo[h][1,6]naphthyridin-2(1H)-one

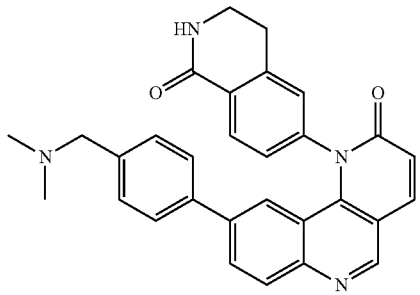 [SMILES: CN(C)Cc1ccc(-c2ccc3ncc4ccc(=O)n(-c5ccc6c(c5)CCNC6=O)c4c3c2)cc1]

Isolated yield: 30.1%. LC/MS (Method B): (electrospray+ve), m/z 475.1 (MH)$^+$, $t_R$=3.257, UV$_{254}$=100%

1-(2-(3-aminopropyl)-1-oxoisoindolin-5-yl)-9-(4-chlorophenyl)benzo[h][1,6]naphthyridin-2(1H)-one

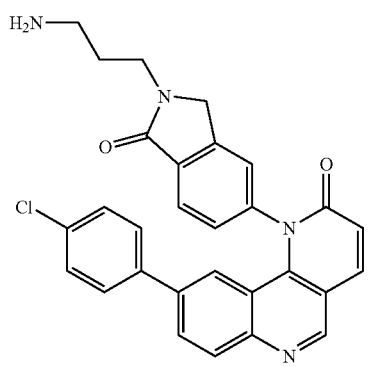 [SMILES: NCCCN1Cc2cc(-n3c(=O)ccc4cnc5ccc(-c6ccc(Cl)cc6)cc5c43)ccc2C1=O]

Off-white solid, isolated yield: 24.83% 4H NMR (400 MHz, DMSO-d$_6$) δ 9.19 (s, 1H), 8.36 (d, J=9.5 Hz, 1H), 8.12 (dd, J=8.7, 0.5 Hz, 1H), 8.00 (dd, J=8.7, 2.0 Hz, 1H), 7.96 (dd, J=8.0, 0.6 Hz, 1H), 7.89 (dd, J=1.8, 0.7 Hz, 1H), 7.74 (s, 4H), 7.64 (dd, J=8.0, 1.8 Hz, 1H), 7.30-7.24 (m, 2H), 7.05-7.00 (m, 2H), 6.97 (d, J=9.5 Hz, 1H), 6.91 (dd, J=2.0, 0.6 Hz, 1H), 4.75-4.55 (m, 2H), 3.83 (dt, J=14.3, 7.3 Hz, 1H), 3.63 (dt, J=13.6, 6.5 Hz, 1H), 2.89 (s, 2H), 2.02-1.91 (m, 2H); LC/MS (Method B): (electrospray+ve), m/z 495.0 (MH)$^+$, t$_R$=3.783, UV$_{254}$=100%

9-(4-chlorophenyl)-1-(4-(methylsulfonyl)phenyl)benzo[h][1,6]naphthyridin-2(1H)-one

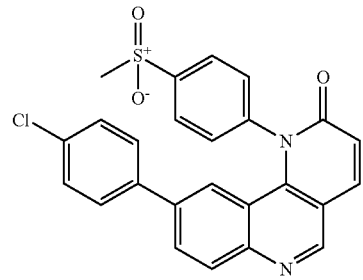

LC/MS (Method B): (electrospray+ve), m/z 461.1 (MH)$^+$, t$_R$=4.389, UV$_{254}$=100%

9-(4-chloro-3-hydroxyphenyl)-1-(4-(methylsulfonyl)phenyl)benzo[h][1,6]naphthyridin-2(1H)-one

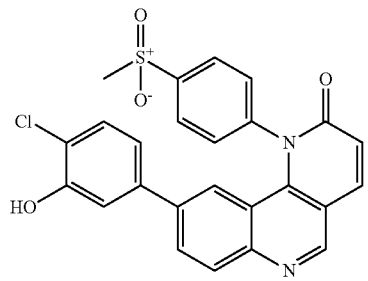 [SMILES: C[S+](=O)([O-])c1ccc(-n2c(=O)ccc3cnc4ccc(-c5ccc(Cl)c(O)c5)cc4c32)cc1]

LC/MS (Method B): (electrospray+ve), m/z 477.1 (MH)$^+$, t$_R$=4.178, UV$_{254}$=100%

9-(4-chlorophenyl)-1-(4-(ethylsulfonyl)phenyl)benzo[h][1,6]naphthyridin-2(1H)-one

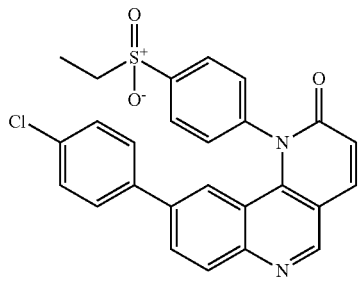 [SMILES: CC[S+](=O)([O-])c1ccc(-n2c(=O)ccc3cnc4ccc(-c5ccc(Cl)cc5)cc4c32)cc1]

LC/MS (Method B): (electrospray+ve), m/z 475.1 (MH)$^+$, t$_R$=4.982, UV$_{254}$=100%

9-(3-amino-4-chlorophenyl)-1-(4-(methylsulfonyl)phenyl)benzo[h][1,6]naphthyridin-2(1H)-one

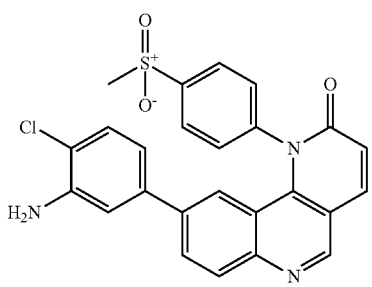 [SMILES: C[S+](=O)([O-])c1ccc(-n2c(=O)ccc3cnc4ccc(-c5ccc(Cl)c(N)c5)cc4c32)cc1]

LC/MS (Method B): (electrospray+ve), m/z 476.1 (MH)$^+$, t$_R$=4.331, UV$_{254}$=100%

9-(4-fluorophenyl)-1-(4-(methylsulfonyl)phenyl)benzo[h][1,6]naphthyridin-2(1H)-one

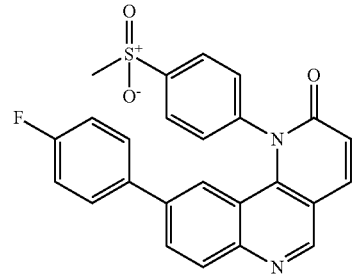 [SMILES: C[S+](=O)([O-])c1ccc(-n2c(=O)ccc3cnc4ccc(-c5ccc(F)cc5)cc4c32)cc1]

LC/MS (Method B): (electrospray+ve), m/z 445.1 (MH)$^+$, t$_R$=4.478, UV$_{254}$=100%

75

9-(4-((dimethylamino)methyl)phenyl)-1-(4-(methyl-sulfonyl)phenyl)benzo[h][1,6]naphthyridin-2(1H)-one

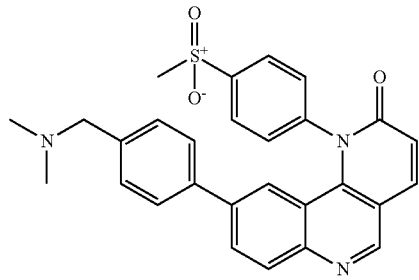 [SMILES: CN(C)Cc1ccc(-c2ccc3ncc4ccc(=O)n(-c5ccc([S+](C)(=O)[O-])cc5)c4c3c2)cc1]

LC/MS (Method B): (electrospray+ve), m/z 484.2 (MH)$^+$, t$_R$=3.264, UV$_{254}$=100%

9-(4-chloro-3-methoxyphenyl)-1-(4-(methylsulfonyl)phenyl)benzo[h][1,6]naphthyridin-2(1H)-one

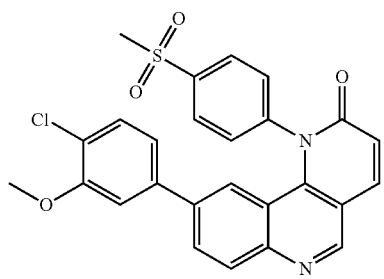 [SMILES: COc1cc(-c2ccc3ncc4ccc(=O)n(-c5ccc(S(C)(=O)=O)cc5)c4c3c2)ccc1Cl]

Off-white solid, isolated yield: 38.6%. LC/MS (Method B): (electrospray+ve), m/z 491.1 (MH)$^+$, t$_R$=4.866, UV$_{254}$=100%

2-chloro-5-(1-(4-(methylsulfonyl)phenyl)-2-oxo-1,2-dihydrobenzo[h][1,6]naphthyridin-9-yl)benzonitrile

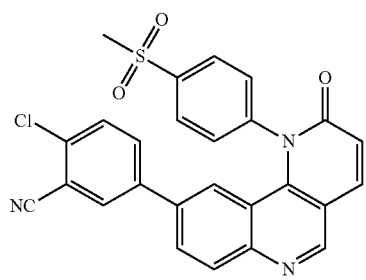 [SMILES: CS(=O)(=O)c1ccc(-n2c(=O)ccc3cnc4ccc(-c5ccc(Cl)c(C#N)c5)cc4c32)cc1]

Yellow solid, isolated yield: 9.67%. $^1$H NMR (400 MHz, DMSO-d$_6$) δ 9.22 (s, 1H), 8.37 (d, J=9.5 Hz, 1H), 8.23 (dt, 2H), 8.18-8.14 (m, 2H), 8.10 (dd, J=8.7, 1.9 Hz, 1H), 7.86 (dt, 2H), 7.67 (d, J=8.5 Hz, 1H), 7.00 (d, J=1.9 Hz, 1H), 6.98 (d, J=9.4 Hz, 1H), 6.92 (dd, J=8.6, 2.3 Hz, 1H), 3.36 (s, 3H); LC/MS (Method B): (electrospray+ve), m/z 486.1 (MH)$^+$, t$_R$=4.634, UV$_{254}$=100%

76

1-(4-(methylsulfonyl)phenyl)-9-(4-(pyrrolidin-1-ylmethyl)phenyl)benzo[h][1,6]naphthyridin-2(1H)-one

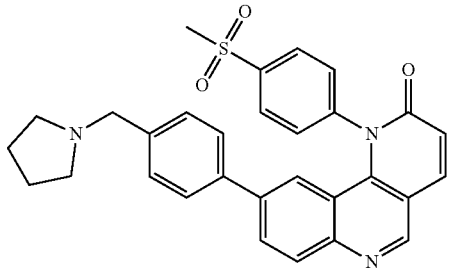 [SMILES: CS(=O)(=O)c1ccc(-n2c(=O)ccc3cnc4ccc(-c5ccc(CN6CCCC6)cc5)cc4c32)cc1]

Off-white solid, isolated yield: 2.405% $^1$H NMR (400 MHz, DMSO-d$_6$) δ 9.17 (s, 1H), 8.35 (d, J=9.5 Hz, 1H), 8.28-8.22 (m, 2H), 8.12 (d, J=8.6 Hz, 1H), 8.01 (dd, J=8.7, 1.9 Hz, 1H), 7.88-7.83 (m, 2H), 7.34 (d, J=7.7 Hz, 2H), 7.12-7.09 (m, 1H), 7.02 (d, J=7.8 Hz, 2H), 6.96 (d, J=9.4 Hz, 1H), 2.44 (s, 5H), 1.72 (s, 5H); LC/MS (Method B): (electrospray+ve), m/z 510.4 (MH)$^+$, t$_R$=3.302, UV$_{254}$=100%

9-(4-chlorophenyl)-1-(2-methyl-4-(methylsulfonyl)phenyl)benzo[h][1,6]naphthyridin-2(1H)-one

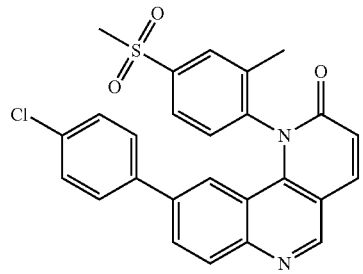 [SMILES: Cc1cc(S(C)(=O)=O)ccc1-n1c(=O)ccc2cnc3ccc(-c4ccc(Cl)cc4)cc3c21]

Yellow solid, isolated yield: 2.89%. $^1$H NMR (400 MHz, DMSO-d$_6$) δ 9.21 (s, 1H), 8.40 (d, J=9.5 Hz, 1H), 8.23 (dd, J=1.9, 0.7 Hz, 1H), 8.15 (dd, J=8.6, 0.5 Hz, 1H), 8.11-8.03 (m, 2H), 7.77-7.73 (m, 1H), 7.49-7.44 (m, 2H), 7.13-7.06 (m, 2H), 7.05-7.03 (m, 1H), 7.00 (d, J=9.5 Hz, 1H), 3.36 (s, 3H), 2.12 (s, 3H); LC/MS (Method B): (electrospray+ve), m/z 475.1 (MH)$^+$, t$_R$=4.966, UV$_{254}$=100%

9-(4-chlorophenyl)-1-(4-(methylsulfonyl)-3-(piper-azin-1-ylmethyl)phenyl)benzo[h][1,6]naphthyridin-2(1H)-one

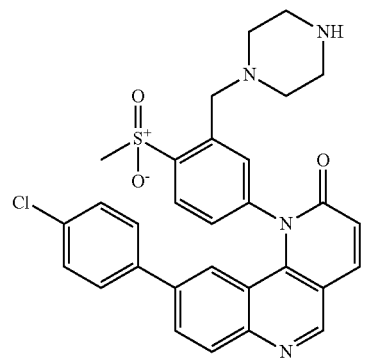 [SMILES: C[S+](=O)([O-])c1ccc(-n2c(=O)ccc3cnc4ccc(-c5ccc(Cl)cc5)cc4c32)cc1CN1CCNCC1]

LC/MS (Method B): (electrospray+ve), m/z 559.1 (MH)$^+$, $t_R$=4.318, UV$_{254}$=100%

9-(4-(1-aminocyclopropyl)phenyl)-1-(4-(methyl-sulfonyl)phenyl)benzo[h][1,6]naphthyridin-2(1H)-one

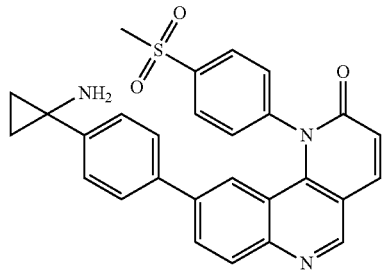 [SMILES: CS(=O)(=O)c1ccc(-n2c(=O)ccc3cnc4ccc(-c5ccc(C6(N)CC6)cc5)cc4c32)cc1]

Off-white solid, isolated yield: 3.24%. $^1$H NMR (400 MHz, DMSO-d$_6$) δ 9.19 (s, 1H), 8.36 (d, J=9.5 Hz, 1H), 8.26-8.20 (m, 2H), 8.14 (dd, J=8.6, 0.5 Hz, 1H), 8.03 (dd, J=8.7, 1.9 Hz, 1H), 7.89-7.84 (m, 2H), 7.46-7.41 (m, 2H), 7.15-7.09 (m, 2H), 7.05 (dd, J=2.0, 0.6 Hz, 1H), 6.97 (d, J=9.4 Hz, 1H), 3.34 (s, 4H), 1.38-1.32 (m, 2H), 1.22-1.16 (m, 2H); LC/MS (Method B): (electrospray+ve), m/z 482.1 (MH)$^+$, $t_R$=3.459, UV$_{254}$=100%

Example 4

This example demonstrates a synthesis of compounds, in accordance with an embodiment of the invention.

A reaction scheme for the synthesis of compounds 13 and 14 is shown in Scheme 2.

8-(4-chloro-3-hydroxyphenyl)-3-methyl-1-(4-(mor-pholine-4-carbonyl)phenyl)-1H-imidazo[4,5-c]qui-nolin-2(3H)-one

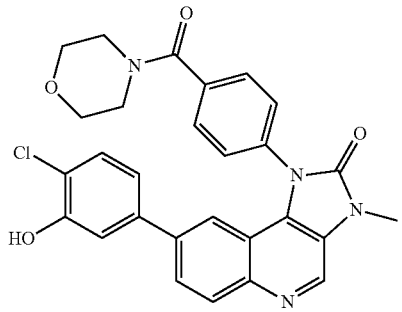 [SMILES: Cn1c(=O)n(-c2ccc(C(=O)N3CCOCC3)cc2)c2c3cc(-c4ccc(Cl)c(O)c4)ccc3ncc21]

Off-white solid, isolated yield: 24%. LC/MS (Method B): (electrospray+ve), m/z 515.2 (MH)$^+$, $t_R$=3.995, UV$_{254}$=100%

4-(8-(4-chlorophenyl)-3-methyl-2-oxo-2,3-dihydro-1H-imidazo[4,5-c]quinolin-1-yl)-N,N-dimethylbenz-amide

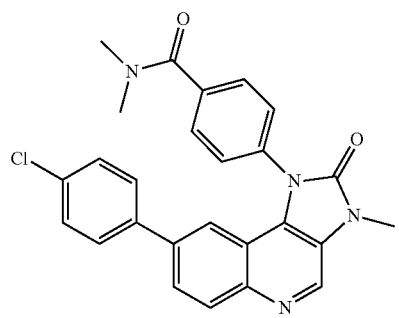 [SMILES: CN(C)C(=O)c1ccc(-n2c(=O)n(C)c3cnc4ccc(-c5ccc(Cl)cc5)cc4c32)cc1]

Off-white solid, isolated yield: 18%. $^1$H NMR (400 MHz, DMSO-d$_6$) δ 9.16 (s, 1H), 8.17 (d, J=8.9 Hz, 1H), 8.01 (d, J=8.9 Hz, 1H), 7.78-7.72 (m, 4H), 7.46 (d, 0.7=8.5 Hz, 2H), 7.38 (d, J=8.6 Hz, 2H), 7.23 (s, 1H), 3.64 (s, 3H), 3.08 (s, 3H), 2.98 (s, 3H); LC/MS (Method B): (electrospray+ve), m/z 457.1 (MH)$^+$, $t_R$=4.153, UV$_{254}$=100%

4-(8-(4-chloro-3-hydroxyphenyl)-3-methyl-2-oxo-2,3-dihydro-1H-imidazo[4,5-c]quinolin-1-yl)-N-cyclo-propyl-N-methylbenzamide

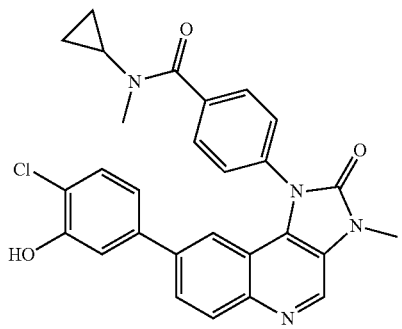 [SMILES: CN(C(=O)c1ccc(-n2c(=O)n(C)c3cnc4ccc(-c5ccc(Cl)c(O)c5)cc4c32)cc1)C1CC1]

Off-white solid, isolated yield: 18%. $^1$H NMR (400 MHz, DMSO-$d_6$) δ 10.28 (s, 1H), 9.12 (s, 1H), 8.15 (d, J=8.9 Hz, 1H), 7.82 (d, J=8.6 Hz, 1H), 7.79 (d, J=8.3 Hz, 2H), 7.73 (d, J=8.3 Hz, 2H), 7.36 (s, 1H), 7.31 (d, J=8.2 Hz, 1H), 7.29 (s, 1H), 6.95 (s, 1H), 6.76 (d, J=8.1 Hz, 1H), 3.63 (s, 3H), 3.02 (s, 3H), 2.93-2.87 (m, 1H), 0.33 (d, J=70.3 Hz, 3H); LC/MS (Method B): (electrospray+ve), m/z 499.2 (MH)$^+$, $t_R$=4.162, UV$_{254}$=100%

4-(8-(4-chlorophenyl)-3-methyl-2-oxo-2,3-dihydro-1H-imidazo[4,5-c]quinolin-1-yl)-N-(3-(dimethylamino)propyl)benzamide

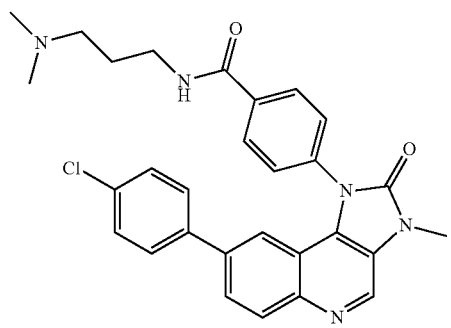

LC/MS (Method B): (electrospray+ve), m/z 514.1 (MH)$^+$, $t_R$=3.492, UV$_{254}$=100%

N-cyclopropyl-4-(8-(4-fluorophenyl)-3-methyl-2-oxo-2,3-dihydro-1H-imidazo[4,5-c]quinolin-1-yl)benzamide

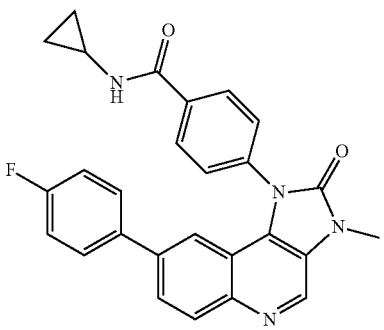 [SMILES: Cn1c(=O)n(-c2ccc(C(=O)NC3CC3)cc2)c2c3cc(-c4ccc(F)cc4)ccc3ncc21]

LC/MS (Method B): (electrospray+ve), m/z 453.2 (MH)$^+$, $t_R$=3.894, UV$_{254}$=100%

3-(8-(3-(dimethylamino)prop-1-yn-1-yl)-3-methyl-2-oxo-2,3-dihydro-1H-imidazo[4,5-c]quinolin-1-yl)benzonitrile

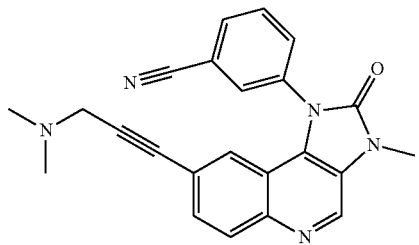

LC/MS (Method B): (electrospray+ve), m/z 382.1 (MH)$^+$, $t_R$=2.916, UV$_{254}$=100%

3-(8-(4-chlorophenyl)-2-oxo-2,3-dihydro-1H-imidazo[4,5-c]quinolin-1-yl)benzonitrile

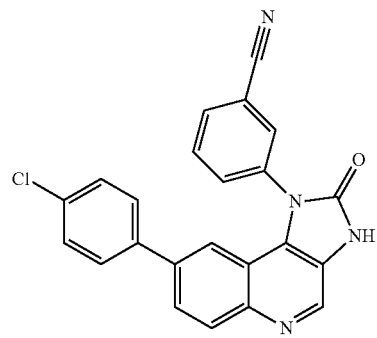 [SMILES: N#Cc1cccc(-n2c(=O)[nH]c3cnc4ccc(-c5ccc(Cl)cc5)cc4c32)c1]

LC/MS (Method B): (electrospray+ve), m/z 397.1 (MH)$^+$, $t_R$=4.452, UV$_{254}$=100%

3-(8-(4-chlorophenyl)-3-methyl-2-oxo-2,3-dihydro-1H-imidazo[4,5-c]quinolin-1-yl)benzonitrile

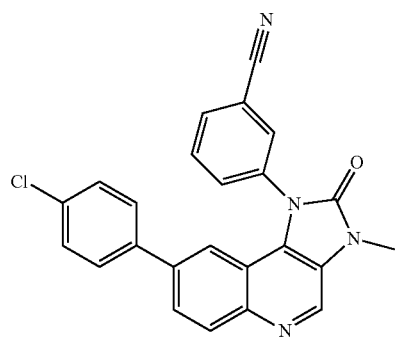 [SMILES: Cn1c(=O)n(-c2cccc(C#N)c2)c2c3cc(-c4ccc(Cl)cc4)ccc3ncc21]

LC/MS (Method B): (electrospray+ve), m/z 411.1 (MH)$^+$, $t_R$=4.626, UV$_{254}$=100%

81

3-(8-(4-chlorophenyl)-2-oxo-2,3-dihydro-1H-imidazo[4,5-c]quinolin-1-yl)-4-methylbenzonitrile

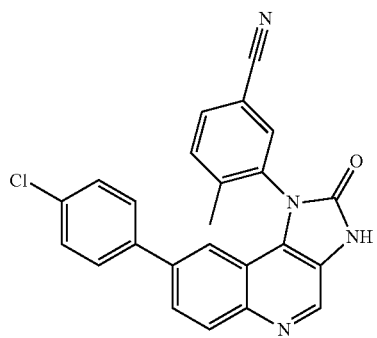 [SMILES: Cc1ccc(C#N)cc1-n1c(=O)[nH]c2cnc3ccc(-c4ccc(Cl)cc4)cc3c21]

Off-white solid, isolated yield: 22%. ¹H NMR (400 MHz, DMSO-d₆) δ 12.16 (s, 1H), 8.94 (s, 1H), 8.28 (d, J=1.8 Hz, 1H), 8.16 (d, J=8.9 Hz, 1H), 8.12 (dd, J=8.0, 1.8 Hz, 1H), 7.99 (dd, J=9.0, 2.1 Hz, 1H), 7.84 (d, J=8.1 Hz, 1H), 7.52-7.47 (m, 2H), 7.37-7.33 (m, 2H), 6.98 (d, J=2.0 Hz, 1H), 2.21 (s, 3H); LC/MS (Method B): (electrospray+ve), m/z 411.1 (MH)⁺, $t_R$=4.666, UV₂₅₄=100%

3-(8-(4-chlorophenyl)-3-methyl-2-oxo-2,3-dihydro-1H-imidazo[4,5-c]quinolin-1-yl)-4-methylbenzonitrile

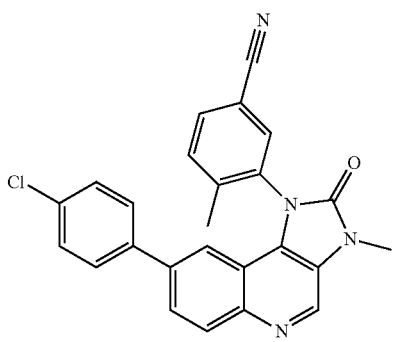 [SMILES: Cc1ccc(C#N)cc1-n1c(=O)n(C)c2cnc3ccc(-c4ccc(Cl)cc4)cc3c21]

Off-white solid, isolated yield: 9%. ¹H NMR (400 MHz, DMSO-d₆) δ 9.16 (s, 1H), 8.26 (d, J=1.8 Hz, 1H), 8.17 (d, J=8.9 Hz, 1H), 8.13 (dd, 0.7=8.0, 1.7 Hz, 1H), 7.98 (dd, J=8.9, 2.0 Hz, 1H), 7.85 (d, J=8.0 Hz, 1H), 7.52-7.48 (m, 2H), 7.37-7.33 (m, 2H), 6.98 (d, J=2.0 Hz, 1H), 3.65 (s, 3H), 2.20 (s, 3H); LC/MS (Method B): (electrospray+ve), m/z 425.1 (MH+), $t_R$=4.847, UV₂₅₄=100%

82

3,3'-(3-methyl-2-oxo-2,3-dihydro-1H-imidazo[4,5-c]quinoline-1,8-diyl)dibenzonitrile

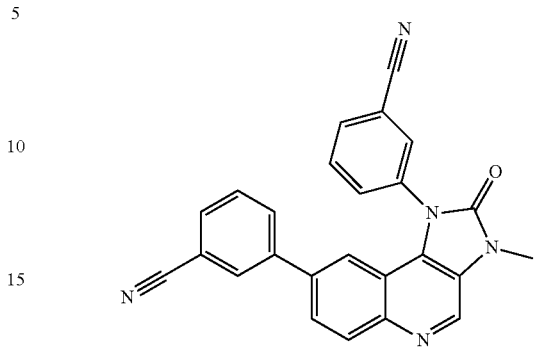

Off-white solid, isolated yield: 37%. LC/MS (Method B): (electrospray+ve), m/z 402.1 (MH)⁺, $t_R$=4.011, UV₂₅₄=100%

3-(8-(4-fluorophenyl)-3-methyl-2-oxo-2,3-dihydro-1H-imidazo[4,5-c]quinolin-1-yl)benzonitrile

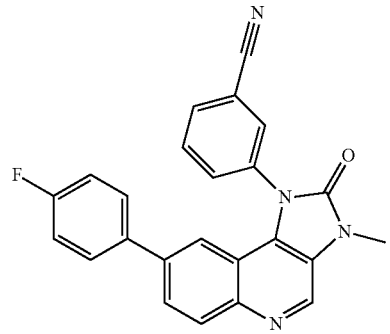 [SMILES: Cn1c(=O)n(-c2cccc(C#N)c2)c2c3cc(-c4ccc(F)cc4)ccc3ncc21]

Off-white solid, isolated yield: 20%. ¹H NMR (400 MHz, DMSO-d₆) δ 9.07 (s, 1H), 8.33 (s, 1H), 8.18-8.12 (m, 2H), 8.09 (d, J=8.2 Hz, 1H), 7.93 (t, 0.7=8.0 Hz, 2H), 7.42 (dd, J=8.7, 5.4 Hz, 2H), 7.27 (t, J=8.7 Hz, 2H), 7.16 (s, 1H), 3.62 (s, 3H); LC/MS (Method B): (electrospray+ve), m/z 395.1 (MH)⁺, $t_R$=4.262, UV₂₅₄=100%

3-(8-(4-chloro-3-methoxyphenyl)-3-methyl-2-oxo-2,3-dihydro-1H-imidazo[4,5-c]quinolin-1-yl)benzonitrile

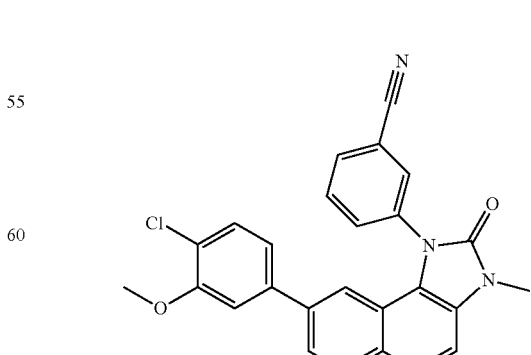

Off-white solid, isolated yield: 7%. ¹H NMR (400 MHz, DMSO-d₆) δ 9.03 (s, 1H), 8.30 (d, J=2.0 Hz, 1H), 8.16 (d, J=7.8 Hz, 1H), 8.12 (d, J=8.9 Hz, 1H), 8.07 (dd, J=7.6, 1.9 Hz, 1H), 7.93 (dd, 1H), 7.90 (t, J=8.0 Hz, 1H), 7.45 (d, J=8.2 Hz, 1H), 7.17 (d, J=2.0 Hz, 1H), 7.01 (dd, J=8.2, 2.0 Hz, 1H), 6.96 (d, J=2.0 Hz, 1H), 3.85 (s, 3H), 3.60 (s, 3H); LC/MS (Method B): (electrospray+ve), m/z 441.1 (MH)⁺, $t_R$=4.583, $UV_{254}$=100%

3-(8-(4-chlorophenyl)-3-(2-hydroxy ethyl)-2-oxo-2,3-dihydro-1H-imidazo[4,5-c]quinolin-1-yl)benzonitrile

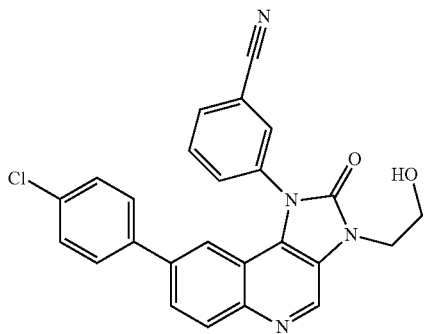 [SMILES: N#Cc1cccc(-n2c(=O)n(CCO)c3cnc4ccc(-c5ccc(Cl)cc5)cc4c32)c1]

Off-white solid, isolated yield: 12%. ¹H NMR (400 MHz, DMSO-d₆) δ 9.15 (s, 1H), 8.33 (d, J=2.0 Hz, 1H), 8.17 (t, J=8.1 Hz, 2H), 8.10 (dd, J=7.7, 1.8 Hz, 1H), 7.99-7.91 (m, 2H), 7.52-7.48 (m, 2H), 7.42-7.39 (m, 2H), 7.21 (d, J=2.0 Hz, 1H), 4.19 (t, J=5.3 Hz, 2H), 3.81 (d, J=5.4 Hz, 2H), 3.48 (s, 1H); LC/MS (Method B): (electrospray+ve), m/z 441.1 (MH)⁺, $t_R$=4.389, $UV_{254}$=100%

3-(3-acetyl-8-(4-chlorophenyl)-2-oxo-2,3-dihydro-1H-imidazo[4,5-c]quinolin-1-yl)benzonitrile

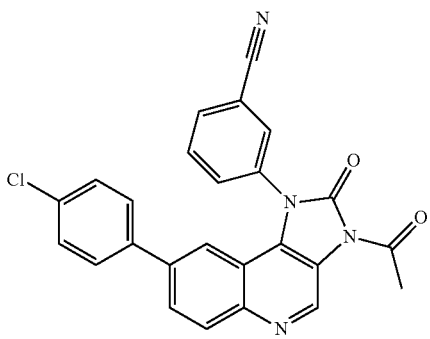 [SMILES: CC(=O)n1c(=O)n(-c2cccc(C#N)c2)c2c3cc(-c4ccc(Cl)cc4)ccc3ncc21]

Off-white solid, isolated yield: 8%. LC/MS (Method B): (electrospray+ve), m/z 439.1 (MH)⁺, $t_R$=5.215, $UV_{254}$=100%

5-(8-(4-chlorophenyl)-3-methyl-2-oxo-2,3-dihydro-1H-imidazo[4,5-c]quinolin-1-yl)-2-(piperazin-1-yl)benzonitrile

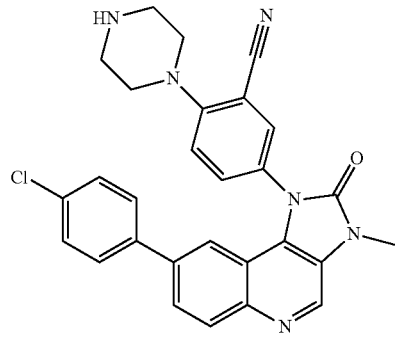 [SMILES: Cn1c(=O)n(-c2ccc(N3CCNCC3)c(C#N)c2)c2c3cc(-c4ccc(Cl)cc4)ccc3ncc21]

LC/MS (Method B): (electrospray+ve), m/z 495.2 (MH)⁺, $t_R$=3.337, $UV_{254}$=100

3-(8-(4-chloro-3-methoxyphenyl)-3-methyl-2-oxo-2,3-dihydro-1H-imidazo[4,5-c]quinolin-1-yl)-4-methylbenzonitrile

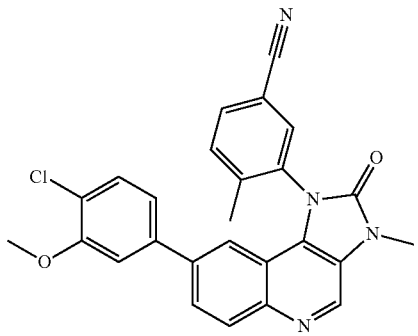

Off-white solid, isolated yield: 17%. ¹H NMR (400 MHz, DMSO-d₆) δ 9.12 (s, 1H), 8.26 (d, J=1.8 Hz, 1H), 8.16 (d, J=8.9 Hz, 1H), 8.12 (dd, J=8.0, 1.8 Hz, 1H), 7.99 (dd, J=8.9, 2.1 Hz, 1H), 7.83 (d, J=8.0 Hz, 1H), 7.48 (d, J=8.2 Hz, 1H), 7.02 (d, J=2.0 Hz, 1H), 7.02-6.99 (m, 1H), 6.93 (d, J=2.1 Hz, 1H), 3.88 (s, 3H), 3.65 (s, 3H), 2.19 (s, 3H); LC/MS (Method B): (electrospray+ve), m/z 455.1 (MH)⁺, $t_R$=4.581, $UV_{254}$=100%

5-(1-(5-cyano-2-methylphenyl)-3-methyl-2-oxo-2,3-dihydro-1H-imidazo[4,5-c]quinolin-8-yl)-2-fluorobenzonitrile

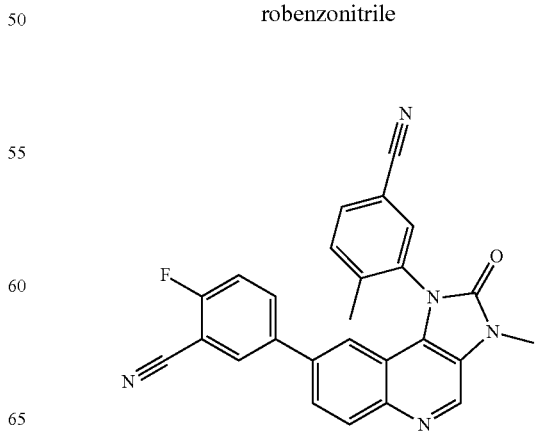

85

Off-white solid, isolated yield: 19%. $^1$H NMR (400 MHz, DMSO-d$_6$) δ 9.10 (s, 1H), 8.24 (d, J=1.7 Hz, 1H), 8.16 (d, J=8.9 Hz, 1H), 8.08 (dd, J=8.0, 1.8 Hz, 1H), 7.97 (dd, J=8.9, 2.1 Hz, 1H), 7.88 (dd, J=6.1, 2.3 Hz, 1H), 7.84 (d, J=8.1 Hz, 1H), 7.61 (d, J=9.0 Hz, 1H), 7.21-6.95 (m, 1H), 6.94 (s, 1H), 3.65 (s, 3H), 2.19 (s, 3H); LC/MS (Method B): (electrospray+ve), m/z 434.2 (MH)$^+$, t$_R$=4.248, UV$_{254}$=100%

3-(8-(4-fluoro-3-methoxyphenyl)-3-methyl-2-oxo-2,3-dihydro-1H-imidazo[4,5-c]quinolin-1-yl)-4-methylbenzonitrile

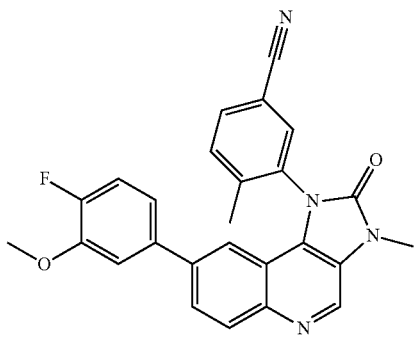

Off-white solid, isolated yield: 19%. $^1$H NMR (400 MHz, DMSO-d$_6$) δ 9.13 (s, 1H), 8.26 (d, J=1.8 Hz, 1H), 8.16 (d, J=8.9 Hz, 1H), 8.12 (dd, J=8.0, 1.8 Hz, 1H), 7.99 (dd, J=9.0, 2.0 Hz, 1H), 7.84 (d, J=8.1 Hz, 1H), 7.27 (dd, J=11.3, 8.4 Hz, 1H), 7.00-6.93 (m, 3H), 3.86 (s, 3H), 3.65 (s, 3H), 2.20 (s, 3H); LC/MS (Method B): (electrospray+ve), m/z 439.1 (MH)$^+$, t$_R$=4.290, UV$_{254}$=100%

2-chloro-5-(1-(5-cyano-2-methylphenyl)-3-methyl-2-oxo-2,3-dihydro-1H-imidazo[4,5-c]quinolin-8-yl)benzonitrile

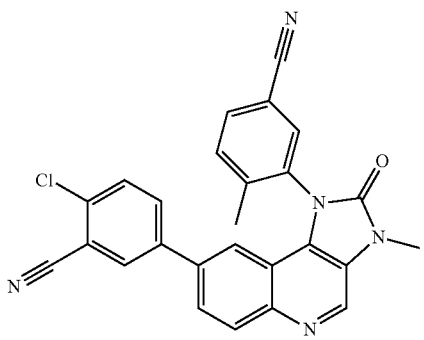 [SMILES: Cc1ccc(C#N)cc1-n1c(=O)n(C)c2cnc3ccc(-c4ccc(F)c(C#N)c4)cc3c21]

Off-white solid, Isolated yield: 15%. LC/MS (Method B): (electrospray+ve), m/z 450.1 (MH)$^+$, t$_R$=4.462, UV$_{254}$=100%

86

3-(8-(4-fluorophenyl)-3-methyl-2-oxo-2,3-dihydro-1H-imidazo[4,5-c]quinolin-1-yl)-4-methylbenzonitrile

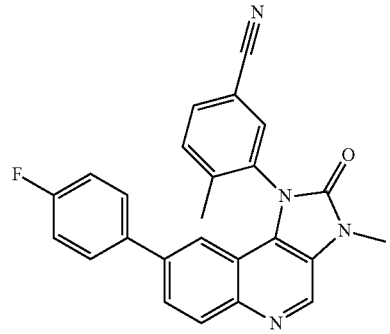 [SMILES: Cc1ccc(C#N)cc1-n1c(=O)n(C)c2cnc3ccc(-c4ccc(F)cc4)cc3c21]

Off-white solid, isolated yield: 23%. $^1$H NMR (400 MHz, DMSO-d$_6$) δ 9.15 (s, 1H), 8.26 (d, J=1.8 Hz, 1H), 8.16 (d, J=8.9 Hz, 1H), 8.12 (dd, J=8.0, 1.8 Hz, 1H), 7.98 (d, J=2.1 Hz, 1H), 7.85 (d, J=8.0 Hz, 1H), 7.39-7.35 (m, 2H), 7.27 (t, J=8.8 Hz, 2H), 6.97 (d, J=2.1 Hz, 1H), 3.65 (s, 3H), 2.21 (s, 3H); LC/MS (Method B): (electrospray+ve), m/z 409.1 (MH)$^+$, t$_R$=4.279, UV$_{254}$=100%

3-(8-(3-cyanophenyl)-3-methyl-2-oxo-2,3-dihydro-1H-imidazo[4,5-c]quinolin-1-yl)-4-methylbenzonitrile

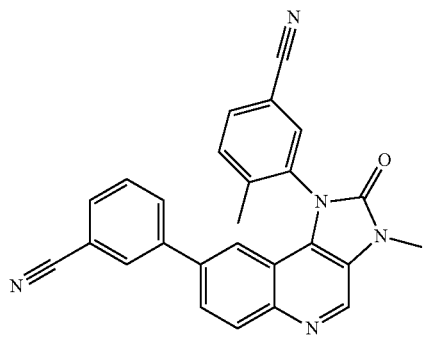 [SMILES: Cc1ccc(C#N)cc1-n1c(=O)n(C)c2cnc3ccc(-c4cccc(C#N)c4)cc3c21]

Off-white solid, isolated yield: 16%. $^1$H NMR (400 MHz, DMSO-d$_6$) δ 9.09 (s, 1H), 8.26 (d, J=1.8 Hz, 1H), 8.16 (d, J=8.8 Hz, 1H), 8.09 (dd, J=8.0, 1.8 Hz, 1H), 7.99 (dd, J=8.9, 2.1 Hz, 1H), 7.85 (d, J=8.2 Hz, 2H), 7.77 (d, J=1.4 Hz, 1H), 7.63 (dd, 2H), 6.99 (d, J=2.1 Hz, 1H), 3.65 (s, 3H), 2.20 (s, 3H); LC/MS (Method B): (electrospray+ve), m/z 416.1 (MH)$^+$, t$_R$=4.052, UV$_{254}$=100%

87

3-(8-(4-(2-aminoethyl)phenyl)-3-methyl-2-oxo-2,3-dihydro-1H-imidazo[4,5-c]quinolin-1-yl)benzonitrile

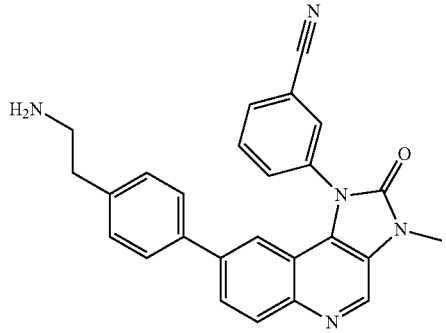 [SMILES: Cn1c(=O)n(-c2cccc(C#N)c2)c2c3cc(-c4ccc(CCN)cc4)ccc3ncc21]

Off-white solid, isolated yield: 28%. LC/MS (Method B): (electrospray+ve), m/z 420.1 (MH)$^+$, $t_R$=3.131, UV$_{254}$=100%

5-(8-(4-fluorophenyl)-3-methyl-2-oxo-2,3-dihydro-1H-imidazo[4,5-c]quinolin-1-yl)-2-(piperazin-1-yl)benzonitrile

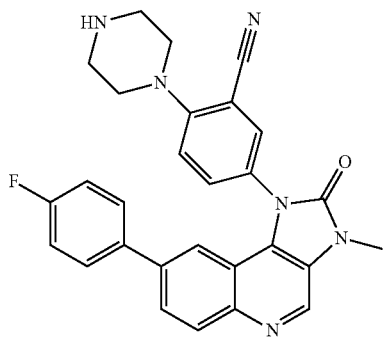 [SMILES: Cn1c(=O)n(-c2ccc(N3CCNCC3)c(C#N)c2)c2c3cc(-c4ccc(F)cc4)ccc3ncc21]

LC/MS (Method B): (electrospray+ve), m/z 479.2 (MH)$^+$, $t_R$=3.135, UV$_{254}$=100%

5-(8-(4-chlorophenyl)-3-methyl-2-oxo-2,3-dihydro-1H-imidazo[4,5-c]quinolin-1-yl)-4-methyl-2-(piperazin-1-yl)benzonitrile

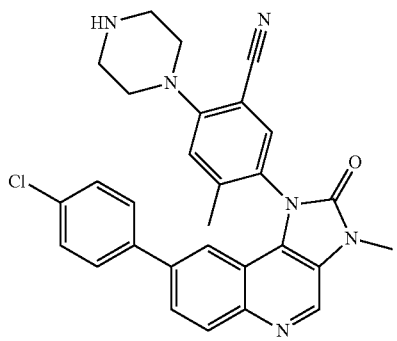 [SMILES: Cc1cc(N2CCNCC2)c(C#N)cc1-n1c(=O)n(C)c2cnc3ccc(-c4ccc(Cl)cc4)cc3c21]

LC/MS (Method B): (electrospray+ve), m/z 509.2 (MH)$^+$, $t_R$=3.378, UV$_{254}$=100%

88

5-(8-(4-fluorophenyl)-3-methyl-2-oxo-2,3-dihydro-1H-imidazo[4,5-c]quinolin-1-yl)-4-methyl-2-(piperazin-1-yl)benzonitrile

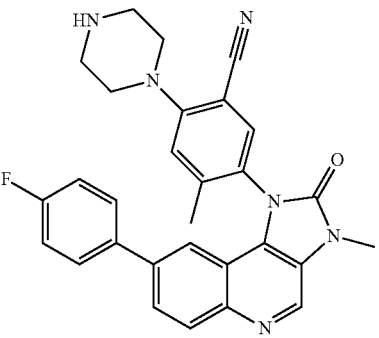 [SMILES: Cc1cc(N2CCNCC2)c(C#N)cc1-n1c(=O)n(C)c2cnc3ccc(-c4ccc(F)cc4)cc3c21]

LC/MS (Method B): (electrospray+ve), m/z 493.3 (MH)$^+$, $t_R$=3.195, UV$_{254}$=100%

5-(8-(4-chlorophenyl)-3-methyl-2-oxo-2,3-dihydro-1H-imidazo[4,5-c]quinolin-1-yl)-2-(4-(2-hydroxyethyl)piperazin-1-yl)benzonitrile

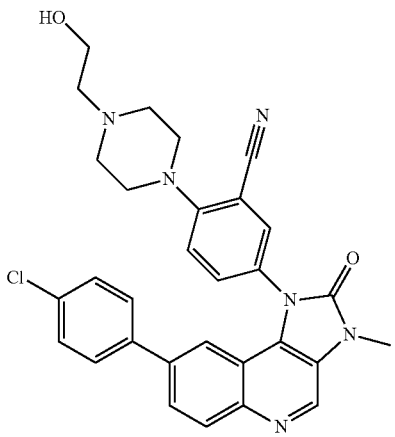 [SMILES: Cn1c(=O)n(-c2ccc(N3CCN(CCO)CC3)c(C#N)c2)c2c3cc(-c4ccc(Cl)cc4)ccc3ncc21]

LC/MS (Method B): (electrospray+ve), m/z 539.3 (MH)$^+$, $t_R$=3.401, UV$_{254}$=100%

5-(8-(3-cyanophenyl)-3-methyl-2-oxo-2,3-dihydro-1H-imidazo[4,5-c]quinolin-1-yl)-2-(piperazin-1-yl)benzonitrile

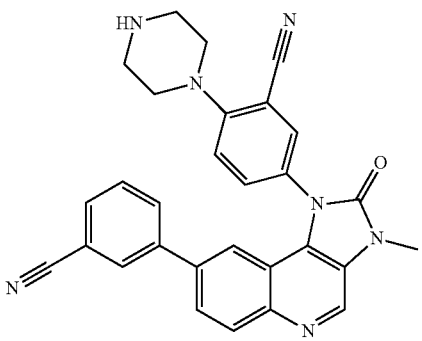 [SMILES: Cn1c(=O)n(-c2ccc(N3CCNCC3)c(C#N)c2)c2c3cc(-c4cccc(C#N)c4)ccc3ncc21]

LC/MS (Method B): (electrospray+ve), m/z 486.1 (MH)+, $t_R$=3.282, UV$_{254}$=100%

4-methyl-3-(3-methyl-2-oxo-8-(1H-pyrrol-2-yl)-2,3-dihydro-1H-imidazo[4,5-c]quinolin-1-yl)benzonitrile

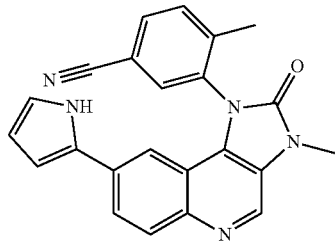 [SMILES: Cc1ccc(C#N)cc1-n1c(=O)n(C)c2cnc3ccc(-c4ccc[nH]4)cc3c21]

LC/MS (Method B): (electrospray+ve), m/z 380.1 (MH)+, $t_R$=3.645, UV$_{254}$=100%

4-methyl-3-(3-methyl-8-(1-methyl-1H-pyrrol-2-yl)-2-oxo-2,3-dihydro-1H-imidazo[4,5-c]quinolin-1-yl)benzonitrile

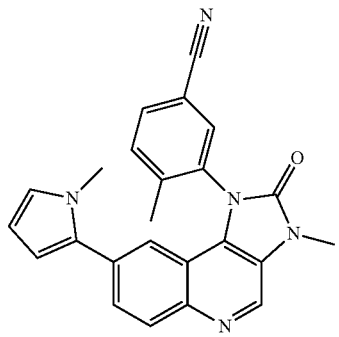 [SMILES: Cc1ccc(C#N)cc1-n1c(=O)n(C)c2cnc3ccc(-c4cccn4C)cc3c21]

LC/MS (Method B): (electrospray+ve), m/z 394.1 (MH)+, $t_R$=4.004, UV$_{254}$=100%

4-methyl-5-(3-methyl-2-oxo-8-(thiophen-2-yl)-2,3-dihydro-1H-imidazo[4,5-c]quinolin-1-yl)-2-(piperazin-1-yl)benzonitrile

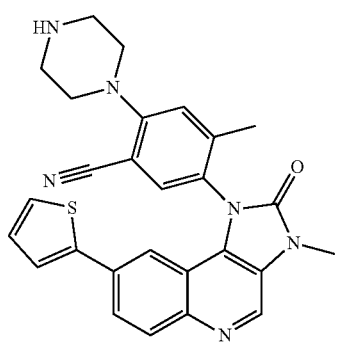 [SMILES: Cc1cc(N2CCNCC2)c(C#N)cc1-n1c(=O)n(C)c2cnc3ccc(-c4cccs4)cc3c21]

LC/MS (Method B): (electrospray+ve), m/z 481.1 (MH)+, $t_R$=2.962, UV$_{254}$=100%

2-(4-acetylpiperazin-1-yl)-5-(8-(4-fluorophenyl)-3-methyl-2-oxo-2,3-dihydro-1H-imidazo[4,5-c]quinolin-1-yl)-4-methylbenzonitrile

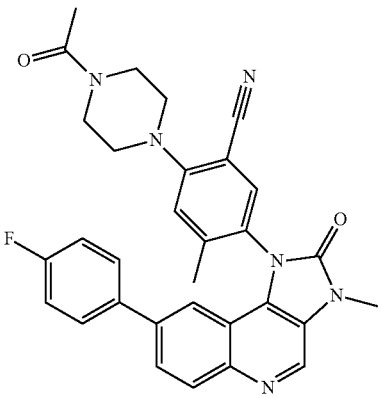 [SMILES: CC(=O)N1CCN(c2cc(C)c(-n3c(=O)n(C)c4cnc5ccc(-c6ccc(F)cc6)cc5c43)cc2C#N)CC1]

LC/MS (Method B): (electrospray+ve), m/z 535.1 (MH)+, $t_R$=4.093, UV$_{254}$=100%

2-(4-acetylpiperazin-1-yl)-5-(8-(3-cyanophenyl)-3-methyl-2-oxo-2,3-dihydro-1H-imidazo[4,5-c]quinolin-1-yl)-4-methylbenzonitrile

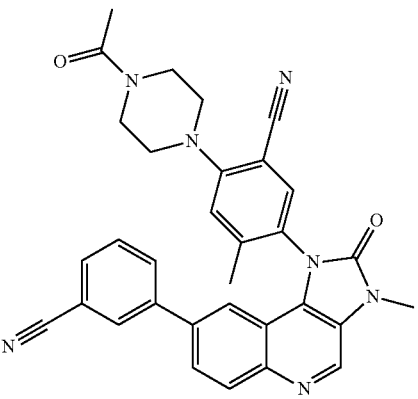 [SMILES: CC(=O)N1CCN(c2cc(C)c(-n3c(=O)n(C)c4cnc5ccc(-c6cccc(C#N)c6)cc5c43)cc2C#N)CC1]

LC/MS (Method B): (electrospray+ve), m/z 542.1 (MH)+, $t_R$=3.954, UV$_{254}$=100%

4-methyl-3-(3-methyl-2-oxo-8-(thiophen-3-yl)-2,3-dihydro-1H-imidazo[4,5-c]quinolin-1-yl)benzonitrile

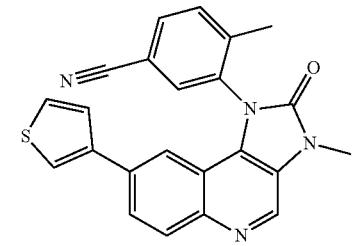 [SMILES: Cc1ccc(C#N)cc1-n1c(=O)n(C)c2cnc3ccc(-c4ccsc4)cc3c21]

91

LC/MS (Method B): (electrospray+ve), m/z 397.1 (MH)$^+$, $t_R$=3.920, UV$_{254}$=100%

3-(8-(furan-3-yl)-3-methyl-2-oxo-2,3-dihydro-1H-imidazo[4,5-c]quinolin-1-yl)-4-methylbenzonitrile

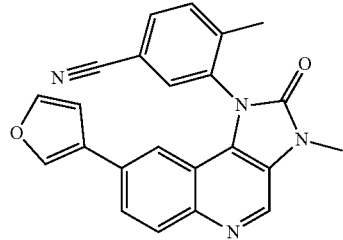 [SMILES: Cc1ccc(C#N)cc1-n1c(=O)n(C)c2cnc3ccc(-c4ccoc4)cc3c21]

LC/MS (Method B): (electrospray+ve), m/z 381.1 (MH)$^+$, $t_R$=3.845, UV$_{254}$=100%

2-(3-aminoazetidin-1-yl)-5-(8-(3-cyanophenyl)-3-methyl-2-oxo-2,3-dihydro-1H-imidazo[4,5-c]quinolin-1-yl)-4-methylbenzonitrile

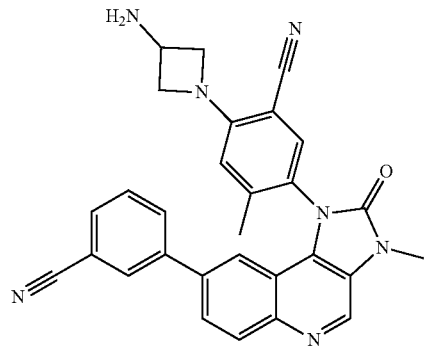 [SMILES: Cc1cc(N2CC(N)C2)c(C#N)cc1-n1c(=O)n(C)c2cnc3ccc(-c4cccc(C#N)c4)cc3c21]

LC/MS (Method B): (electrospray+ve), m/z 486.1 (MH)$^+$, $t_R$=3.290, UV$_{254}$=100%

5-(8-(3-cyano-4-fluorophenyl)-3-methyl-2-oxo-2,3-dihydro-1H-imidazo[4,5-c]quinolin-1-yl)-4-methyl-2-(piperazin-1-yl)benzonitrile

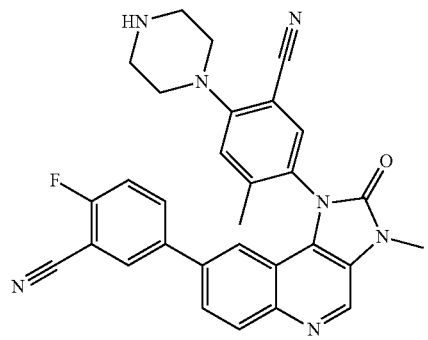 [SMILES: Cc1cc(N2CCNCC2)c(C#N)cc1-n1c(=O)n(C)c2cnc3ccc(-c4ccc(F)c(C#N)c4)cc3c21]

LC/MS (Method B): (electrospray+ve), m/z 518.1 (MH)$^+$, $t_R$=3.455, UV$_{254}$=100%

92

2-(3-aminoazetidin-1-yl)-5-(8-(4-fluorophenyl)-3-methyl-2-oxo-2,3-dihydro-1H-imidazo[4,5-c]quinolin-1-yl)-4-methylbenzonitrile

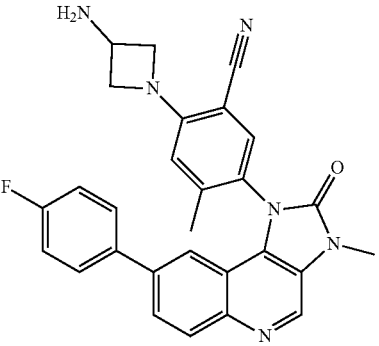 [SMILES: Cc1cc(N2CC(N)C2)c(C#N)cc1-n1c(=O)n(C)c2cnc3ccc(-c4ccc(F)cc4)cc3c21]

LC/MS (Method B): (electrospray+ve), m/z 479.1 (MH)$^+$, $t_R$=3.380, UV$_{254}$=100%

2-(4-acetylpiperazin-1-yl)-5-(8-(4-chlorophenyl)-3-methyl-2-oxo-2,3-dihydro-1H-imidazo[4,5-c]quinolin-1-yl)-4-methylbenzonitrile

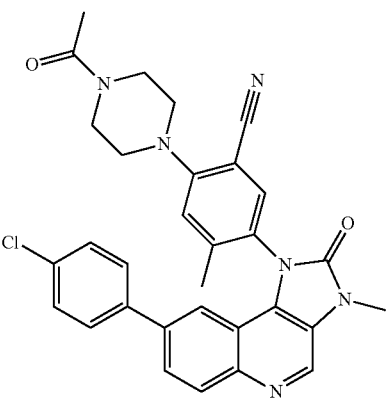 [SMILES: CC(=O)N1CCN(c2cc(C)c(-n3c(=O)n(C)c4cnc5ccc(-c6ccc(Cl)cc6)cc5c43)cc2C#N)CC1]

LC/MS (Method B): (electrospray+ve), m/z 551.1 (MH)$^+$, $t_R$=4.309, UV$_{254}$=100%

5-(8-(3-cyanophenyl)-3-methyl-2-oxo-2,3-dihydro-1H-imidazo[4,5-c]quinolin-1-yl)-2-((2-(dimethylamino)ethyl)amino)-4-methylbenzonitrile

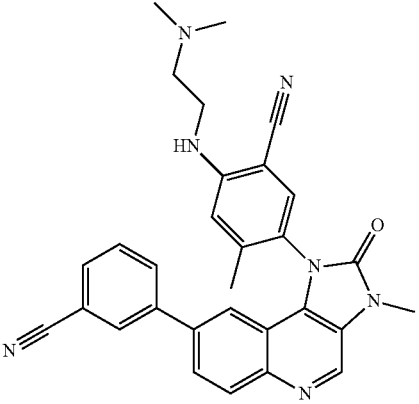 [SMILES: Cc1cc(NCCN(C)C)c(C#N)cc1-n1c(=O)n(C)c2cnc3ccc(-c4cccc(C#N)c4)cc3c21]

LC/MS (Method B): (electrospray+ve), m/z 502.1 (MH)+, $t_R$=3.348, UV$_{254}$=100%

8-(4-chlorophenyl)-3-methyl-1-(4-(methylsulfonyl)phenyl)-1H-imidazo[4,5-c]quinolin-2(3H)-one

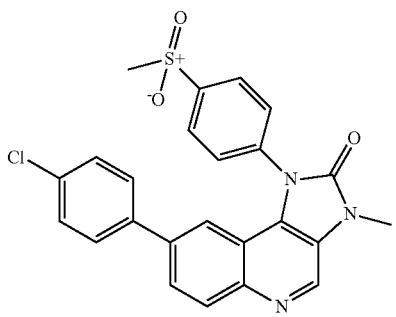

Off-white solid, isolated yield: 12%. $^1$H NMR (400 MHz, DMSO-d$_6$) δ 9.05 (s, 1H), 8.28 (d, J=8.4 Hz, 2H), 8.13 (d, J=8.9 Hz, 1H), 8.00 (d, J=8.4 Hz, 2H), 7.92 (dd, J=8.9, 2.1 Hz, 1H), 7.43-7.36 (m, 4H), 7.11 (d, J=2.0 Hz, 1H), 3.62 (s, 3H), 3.41 (s, 3H); LC/MS (Method B): (electrospray+ve), m/z 464.1 (MH)+, $t_R$=4.238, UV$_{254}$=100%

8-(4-chlorophenyl)-1-(4-(methylsulfonyl)phenyl)-1,3-dihydro-2H-imidazo[4,5-c]quinolin-2-one

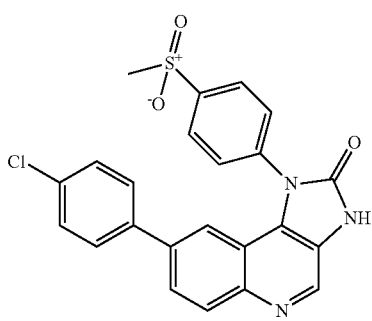

LC/MS (Method B): (electrospray+ve), m/z 450.1 (MH)+, $t_R$=4.119, UV$_{254}$=100%

Example 5

This example demonstrates a synthesis of compounds, in accordance with an embodiment of the invention.

A representative synthesis is shown in Scheme 3. To a 10 mL microwave tube charged with bromide 1 (2.25 mmol) in acetic acid (5 mL) were added hydrazine 2 (4.5 mmol, 2.0 equiv). The reaction was heated under MW at 180° C. for 25 min, and was monitored by LC-MS. Then the reaction mixture was concentrated in vacuo, and the product was triturated with water to afford the product 3 in 75% yield.

To a 10 mL microwave tube charged with bromide 3 (0.3 mmol in DMF (1.5 mL) were added i-PrOH (0.75 mL) and 0.75 mL aqueous K3PO4 solution (0.8 M, 2 equiv). The mixture was stirred for 5 min. Nitrogen gas was bubbled through the reaction solution for 1-2 min, then Pd(PP3)4 (0.05 equiv) and boronic acid/ester 4 (2 equiv) were added. The mixture was heated in a MW at 150° C. for 10 min. The mixture was filtered through Celite and the filtrate was concentrated under vacuum. The crude was treated with 50% TFA in CH$_2$Cl$_2$ at room temperature for 2 h, then the solvent was removed under vacuum, and the crude was purified by silica gel chromatograph with DCM/10% NH$_4$OH in MeOH.

(4-(8-(4-chlorophenyl)-3-methyl-1H-pyrazolo[4,3-c]quinolin-1-yl)phenyl)(pyrrolidin-1-yl)methanone

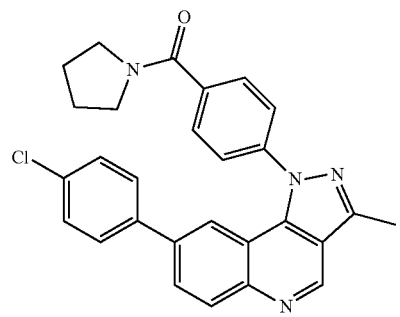 [SMILES: Cc1nn(-c2ccc(C(=O)N3CCCC3)cc2)c2c1cnc1ccc(-c3ccc(Cl)cc3)cc12]

LC/MS (Method B): (electrospray+ve), m/z 467.2 (MH)+, $t_R$=4.705, UV$_{254}$=100%

4-(8-(4-chlorophenyl)-3-methyl-1H-pyrazolo[4,3-c]quinolin-1-yl)-N-cyclopropylbenzamide

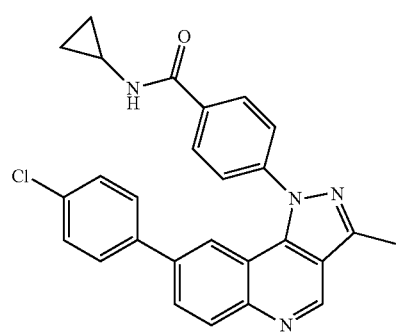 [SMILES: Cc1nn(-c2ccc(C(=O)NC3CC3)cc2)c2c1cnc1ccc(-c3ccc(Cl)cc3)cc12]

LC/MS (Method B): (electrospray+ve), m/z 453.1 (MH)+, $t_R$=4.536, UV$_{254}$=100%

4-(8-(4-chlorophenyl)-3-methyl-1H-pyrazolo[4,3-c]quinolin-1-yl)-N-(3-(dimethylamino)propyl)benzamide

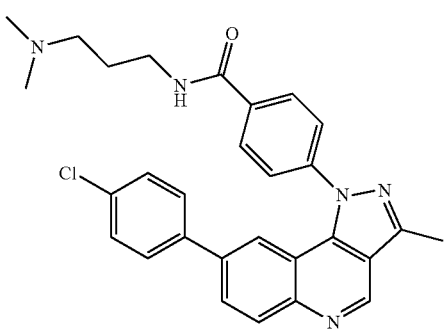

LC/MS (Method B): (electrospray+ve), m/z 498.2 (MH)+, $t_R$=3.795, UV$_{254}$=100%.

95

(4-(8-(4-chlorophenyl)-3-methyl-1H-pyrazolo[4,3-c]quinolin-1-yl)phenyl)(morpholino)methanone

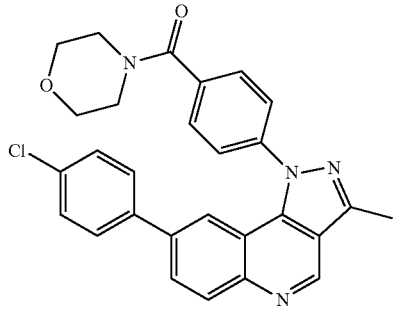 [SMILES: Cc1nn(-c2ccc(C(=O)N3CCOCC3)cc2)c2c1cnc1ccc(-c3ccc(Cl)cc3)cc12]

LC/MS (Method B): (electrospray+ve), m/z 483.1 (MH)$^+$, $t_R$=4.350, UV$_{254}$=100%.

(4-(8-(4-chlorophenyl)-3-methyl-1H-pyrazolo[4,3-c]quinolin-1-yl)-2-(trifluoromethyl)phenyl)(morpholino)methanone

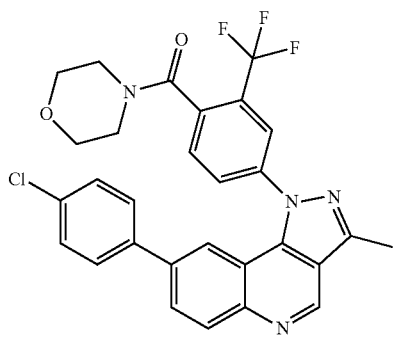 [SMILES: Cc1nn(-c2ccc(C(=O)N3CCOCC3)c(C(F)(F)F)c2)c2c1cnc1ccc(-c3ccc(Cl)cc3)cc12]

LC/MS (Method B): (electrospray+ve), m/z 551.1 (MH)$^+$, $t_R$=4.830, UV$_{254}$=100%

N-cyclopropyl-3-(8-(4-((dimethylamino)methyl)phenyl)-3-methyl-1H-pyrazolo[4,3-c]quinolin-1-yl)benzamide

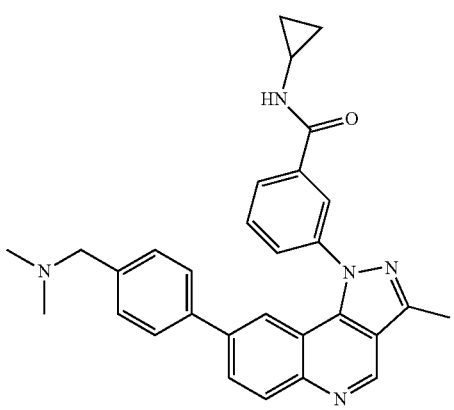

LC/MS (Method B): (electrospray+ve), m/z 476.2 (MH)$^+$, $t_R$=3.265, UV$_{254}$=100%.

96

(3-(8-(4-((dimethylamino)methyl)phenyl)-3-methyl-1H-pyrazolo[4,3-c]quinolin-1-yl)phenyl)(morpholino)methanone

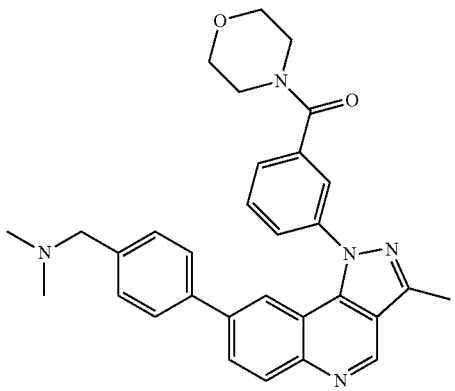

LC/MS (Method B): (electrospray+ve), m/z 506.2 (MH)$^+$, $t_R$=3.193, UV$_{254}$=100%.

3-(8-(4-chlorophenyl)-3-methyl-1H-pyrazolo[4,3-c]quinolin-1-yl)-N-cyclopropylbenzamide

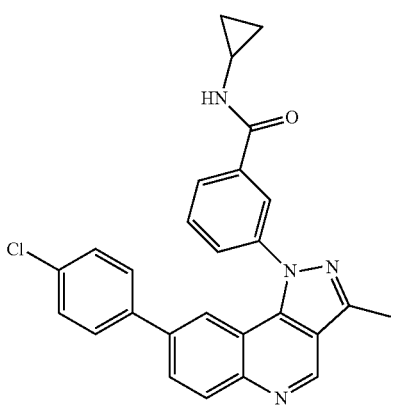 [SMILES: Cc1nn(-c2cccc(C(=O)NC3CC3)c2)c2c1cnc1ccc(-c3ccc(Cl)cc3)cc12]

LC/MS (Method B): (electrospray+ve), m/z 453.2 (MH)$^+$, $t_R$=4.659, UV$_{254}$=100%.

97

(3-(8-(4-chlorophenyl)-3-methyl-1H-pyrazolo[4,3-c]quinolin-1-yl)phenyl)(morpholino)methanone

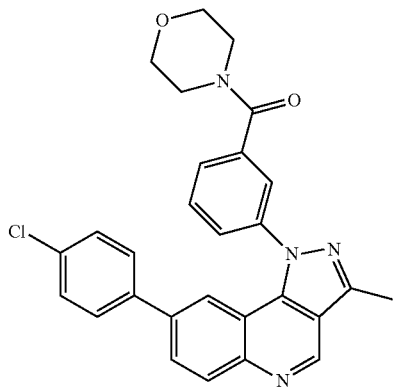 [SMILES: Cc1nn(-c2cccc(C(=O)N3CCOCC3)c2)c2c1cnc1ccc(-c3ccc(Cl)cc3)cc12]

LC/MS (Method B): (electrospray+ve), m/z 483.2 (MH)⁺, $t_R$=4.503, UV$_{254}$=100%.

4-(8-(4-chlorophenyl)-1H-pyrrolo[3,2-c]quinolin-1-yl)-N-cyclopropylbenzamide

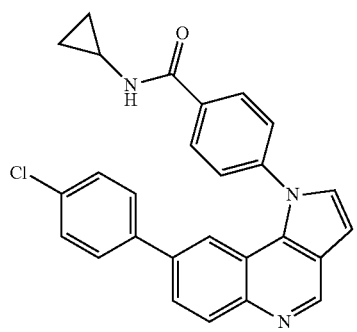 [SMILES: O=C(NC1CC1)c1ccc(-n2ccc3cnc4ccc(-c5ccc(Cl)cc5)cc4c32)cc1]

LC/MS (Method B): (electrospray+ve), m/z 438.2 (MH)⁺, $t_R$=5.765, UV$_{254}$=100%.

3-(8-(6-aminopyridin-3-yl)-3-methyl-1H-pyrazolo[4,3-c]quinolin-1-yl)-N-cyclopropylbenzamide

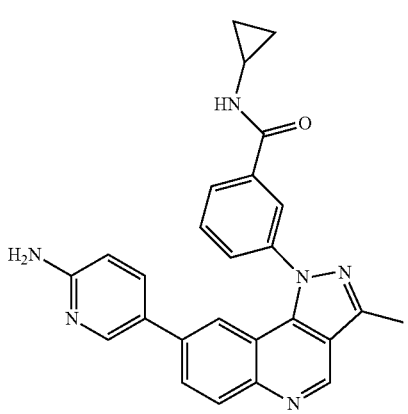 [SMILES: Cc1nn(-c2cccc(C(=O)NC3CC3)c2)c2c1cnc1ccc(-c3ccc(N)nc3)cc12]

98

LC/MS (Method B): (electrospray+ve), m/z 435.2 (MH)⁺, $t_R$=3.107, UV$_{254}$=100%.

(3-(8-(6-aminopyridin-3-yl)-3-methyl-1H-pyrazolo[4,3-c]quinolin-1-yl)phenyl)(morpholino)methanone

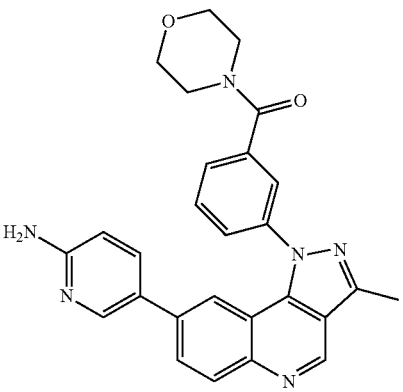 [SMILES: Cc1nn(-c2cccc(C(=O)N3CCOCC3)c2)c2c1cnc1ccc(-c3ccc(N)nc3)cc12]

LC/MS (Method B): (electrospray+ve), m/z 465.2 (MH)⁺, $t_R$=3.061, UV$_{254}$=100%.

3-(8-(4-chlorophenyl)-3-methyl-1H-pyrazolo[4,3-c]quinolin-1-yl)benzonitrile

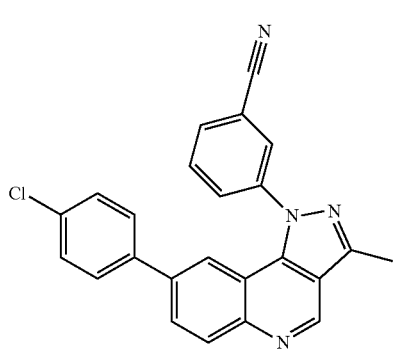 [SMILES: Cc1nn(-c2cccc(C#N)c2)c2c1cnc1ccc(-c3ccc(Cl)cc3)cc12]

LC/MS (Method B): (electrospray+ve), m/z 395.1 (MH)⁺, $t_R$=5.027, UV$_{254}$=100%.

3-(8-(3-(1-aminocyclopropyl)phenyl)-3-methyl-1H-pyrazolo[4,3-c]quinolin-1-yl)benzonitrile

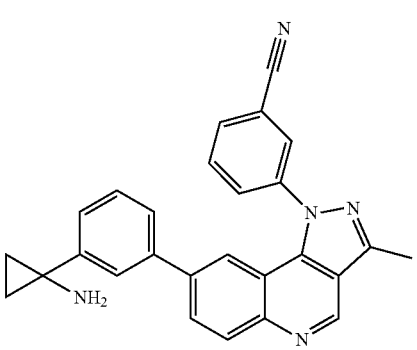 [SMILES: Cc1nn(-c2cccc(C#N)c2)c2c1cnc1ccc(-c3cccc(C4(N)CC4)c3)cc12]

101

3-(8-(4-((dimethylamino)methyl)phenyl)-3-methyl-1H-pyrazolo[4,3-c]quinolin-1-yl)benzonitrile

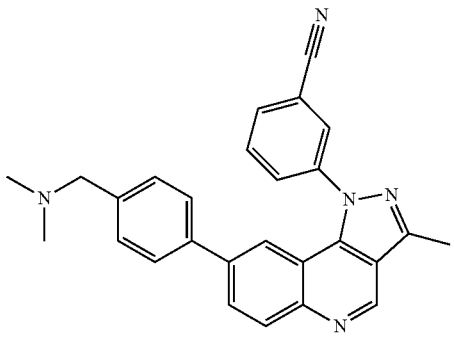

LC/MS (Method B): (electrospray+ve), m/z 418.2 (MH)$^+$, t$_R$=3.387, UV$_{254}$=100%.

3-(8-(6-aminopyridin-3-yl)-3-methyl-1H-pyrazolo[4,3-c]quinolin-1-yl)benzonitrile

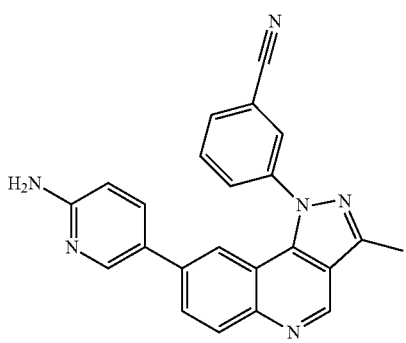 [SMILES: Cc1nn(-c2cccc(C#N)c2)c2c1cnc1ccc(-c3ccc(N)nc3)cc12]

LC/MS (Method B): (electrospray+ve), m/z 377.1 (MH)$^+$, t$_R$=3.219, UV$_{254}$=100%.

4-methyl-3-(3-methyl-8-(1-methyl-1H-pyrazol-4-yl)-2-oxo-2,3-dihydro-1H-imidazo[4,5-c]quinolin-1-yl)benzonitrile

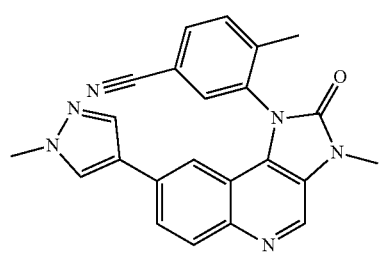

LC/MS (Method B): (electrospray+ve), m/z 395.2 (MH)$^+$, t$_R$=3.376, UV$_{254}$=100%.

102

4-methyl-3-(3-methyl-2-oxo-8-(1H-pyrazol-4-yl)-2,3-dihydro-1H-imidazo[4,5-c]quinolin-1-yl)benzonitrile

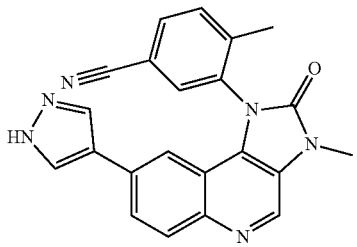

LC/MS (Method B): (electrospray+ve), m/z 381.1 (MH)$^+$, t$_R$=3.100, UV$_{254}$=100%.

1-(4-methoxyphenyl)-3-methyl-8-(thiophen-3-yl)-1,3-dihydro-2H-imidazo[4,5-c]quinolin-2-one

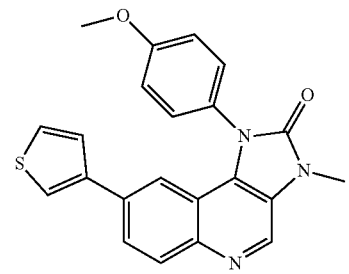 [SMILES: COc1ccc(-n2c(=O)n(C)c3cnc4ccc(-c5ccsc5)cc4c32)cc1]

LC/MS (Method B): (electrospray+ve), m/z 388.1 (MH)$^+$, t$_R$=4.054, UV$_{254}$=100%.

4-(dimethylamino)-3-(3-methyl-2-oxo-8-(thiophen-2-yl)-2,3-dihydro-1H-imidazo[4,5-c]quinolin-1-yl)benzonitrile

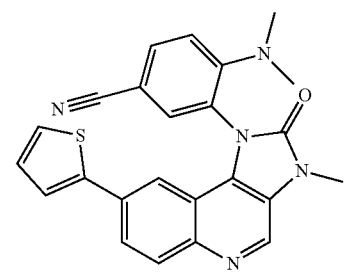 [SMILES: CN(C)c1ccc(C#N)cc1-n1c(=O)n(C)c2cnc3ccc(-c4cccs4)cc3c21]

LC/MS (Method B): (electrospray+ve), m/z 426.1 (MH)$^+$, t$_R$=4.021, UV$_{254}$=100%.

103

4-(dimethylamino)-3-(3-methyl-2-oxo-8-(thiophen-3-yl)-2,3-dihydro-1H-imidazo[4,5-c]quinolin-1-yl)benzonitrile

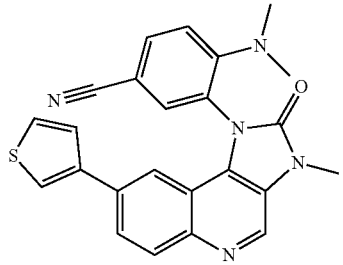 [SMILES: CN(C)c1ccc(C#N)cc1-n1c(=O)n(C)c2cnc3ccc(-c4ccsc4)cc3c21]

LC/MS (Method B): (electrospray+ve), m/z 426.1 (MH)+, $t_R$ 4.082. UV$_{254}$=100%.

3-(3-methyl-2-oxo-8-(thiophen-3-yl)-2,3-dihydro-1H-imidazo[4,5-c]quinolin-1-yl)benzonitrile

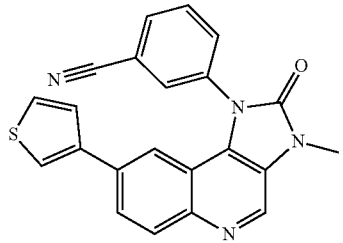 [SMILES: Cn1c(=O)n(-c2cccc(C#N)c2)c2c3cc(-c4ccsc4)ccc3ncc21]

LC/MS (Method B): (electrospray+ve), m/z 383.1 (MH)+, $t_R$=3.893, UV$_{254}$=100%.

4-fluoro-3-(3-methyl-2-oxo-8-(thiophen-2-yl)-2,3-dihydro-1H-imidazo[4,5-c]quinolin-1-yl)benzonitrile

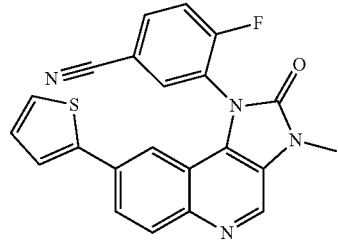 [SMILES: Cn1c(=O)n(-c2cc(C#N)ccc2F)c2c3cc(-c4cccs4)ccc3ncc21]

LC/MS (Method B): (electrospray+ve), m/z 401.1 (MH)+, $t_R$=4.139, UV$_{254}$=100%.

104

3-(3-methyl-2-oxo-8-(thiophen-2-yl)-2,3-dihydro-1H-imidazo[4,5-c]quinolin-1-yl)benzonitrile

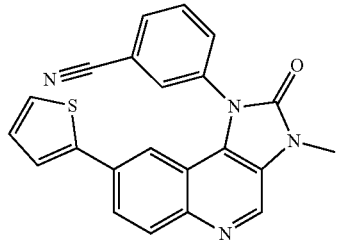 [SMILES: Cn1c(=O)n(-c2cccc(C#N)c2)c2c3cc(-c4cccs4)ccc3ncc21]

LC/MS (Method B): (electrospray+ve), m/z 383.1 (MH)+, $t_R$=4.019, UV$_{254}$=100%.

4-(dimethylamino)-3-(8-(furan-3-yl)-3-methyl-2-oxo-2,3-dihydro-1H-imidazo[4,5-c]quinolin-1-yl)benzonitrile

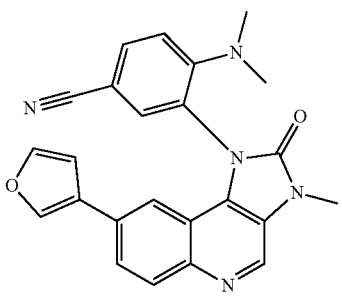 [SMILES: CN(C)c1ccc(C#N)cc1-n1c(=O)n(C)c2cnc3ccc(-c4ccoc4)cc3c21]

LC/MS (Method B): (electrospray+ve), m/z 410.1 (MH)+, $t_R$=3.867, UV$_{254}$=100%.

4-methyl-3-(3-methyl-2-oxo-8-(1H-pyrrol-3-yl)-2,3-dihydro-1H-imidazo[4,5-c]quinolin-1-yl)benzonitrile

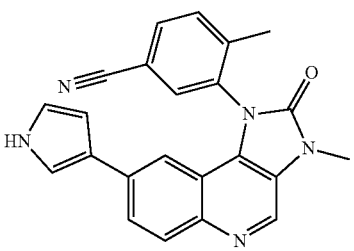 [SMILES: Cc1ccc(C#N)cc1-n1c(=O)n(C)c2cnc3ccc(-c4cc[nH]c4)cc3c21]

LC/MS (Method B): (electrospray+ve), m/z 380.2 (MH)+, $t_R$=3.486, UV$_{254}$=100%.

Example 6

This example demonstrates the gametocytocidal activity and activity against asexual parasites in accordance with an embodiment of the invention.

Compounds were screened against gametocytes and asexual parasites as described in Examples 1 and 2. The results are set forth in Tables 1-8.

TABLE 1

| # | Gametocyte EC50 (nM) | Asexual EC50 (nM) | mTOR (nM) | Microsomal Stability (rat) $T_{1/2}$ (min) | Sol @ pH 7.4 (ug/mL) | PAMPA Permeability ($\times 10^6$ cm/s) |
|---|---|---|---|---|---|---|
| 1 | 88.85 | 27.95 | 643.6 | — | — | — |
| 2 | 427.5 | 291 | 4316 | >30.0 | >64.0 | 1040.6 |
| 3 | 264.3 | 111.4 | 12820 | 12.1 | <0.1 | 621.2 |
| 4 | 54.99 | 14.92 | 12820 | 9.6 | <1 | 21 |
| 5 | 507.5 | N/A | 3557 | — | 7.03 | 725.27 |
| 6 | 101.7 | N/A | 100000 | — | 0.02 | ND |
| 7 | 25.07 | 13.05 | 1433 | — | >66.00 | — |
| 8 | 139.3 | 60.32 | 1305 | 14.5 | <1 | <1 |
| 9 | 2570 | 667.7 | 50000 | 10.9 | 58.6 | 1492.3 |
| 10 | 469.2 | 72.19 | 2077 | 18 | >66 | 0 |
| 11 | 54.99 | 14.92 | 12820 | 9.6 | <1 | 21 |
| 12 | 125.5 | 55.82 | 50000 | — | — | — |
| 13 | 135.1 | 80.36 | 50000 | 0 | 0 | 0 |
| 14 | 425 | 113 | 114300 | — | — | — |
| 15 | 521.2 | 730.4 | 50000 | — | — | — |
| 16 | 69.39 | 23.74 | 6175 | — | — | — |
| 17 | — | — | — | — | — | — |
| 18 | — | — | — | — | — | — |
| 19 | — | — | — | — | — | — |
| 20 | 22.59 | 11.65 | 42.71 | >30.0 | <1.0 | 505.6 |
| 21 | 17.02 | 13.79 | 232.5 | 12.7 | 1.1 | 606 |
| 22 | 114.7 | 34.56 | 101.7 | >30.0 | <1.0 | ND |
| 23 | 40.35 | 22.47 | 182.9 | 3.5 | 1.48 | 58.15 |
| 24 | 23.35 | 5.876 | 75.31 | 19 | 5.7 | 547.9 |

TABLE 2

| # | Gametocyte EC50 (nM) | Asexual EC50 (nM) | mTOR (nM) | Microsomal Stability (rat) $T_{1/2}$ (min) | Sol @ pH 7.4 (ug/mL) | PAMPA Permeability ($\times 10^6$ cm/s) |
|---|---|---|---|---|---|---|
| 25 | 117 | 14.72 | 6251 | >30.0 | <1.0 | <1.5 |
| 26 | 177.6 | 37.83 | 27290 | >30.0 | 1.2 | ND |
| 27 | 107.8 | 0 | 178.9 | >30.0 | <1.0 | <1.0 |
| 28 | 95.31 | 16.17 | 57.76 | >30.0 | <1.0 | 33.9 |
| 29 | 88.48 | 19.75 | 119.2 | >30.0 | <1.0 | — |
| 30 | 336.3 | 117.9 | 2902 | >30.0 | 30.4 | 677.9 |
| 31 | 222 | 33.47 | 458 | >30.0 | <1.0 | 40.7 |
| 32 | 92.76 | 85.53 | 50000 | >30.0 | <1.0 | 39.6 |
| 33 | — | 288.4 | 6606 | >30 | 61 | 439.2 |
| 34 | — | 59.4 | 4268 | 17.1 | <1 | <1 |
| 35 | — | 75.77 | 0 | >30 | 4.3 | 35 |
| 36 | — | 187.7 | 1083 | >30 | 5.9 | 6.5 |
| 37 | — | — | — | — | — | — |
| 38 | 187.1 | 219.7 | 1116 | 12.7 | <1.0 | 32.5 |
| 39 | 426 | 413.7 | 469.2 | 1.7 | <1.0 | — |
| 40 | 51.73 | 14.6 | 174.3 | >30.0 | <1.0 | <1.0 |
| 41 | 89.41 | 23.12 | 189.5 | 6.3 | <1.0 | ND |
| 42 | 118.5 | 37.36 | 254.7 | 4.9 | <1.0 | 97.4 |
| 43 | Inactive | 43850 | 1642 | >30.0 | >74.0 | <1.0 |
| 44 | 135.4 | 31.17 | 86.36 | 4.6 | <1.0 | 34.8 |
| 45 | 208.8 | 77.83 | 32.8 | 8.9 | <1.0 | 144.4 |
| 46 | 259.7 | 62.51 | 1275 | 8.3 | <1.0 | ND |
| 47 | 377.3 | 66.37 | 399.4 | >30.0 | 2.1 | <2.9 |
| 48 | 560.9 | 200.2 | 1315 | >30.0 | <1.0 | <1.0 |
| 49 | 1994 | 3192 | 448.2 | 4.3 | <1.0 | 235.8 |
| 50 | 1826 | 932.4 | 2698 | 3 | 2.7 | 164.4 |
| 51 | 291.3 | 202.9 | 1658 | >30.0 | 4.3 | 43.1 |
| 52 | 35210 | 14730 | 25790 | <1.0 | 57.2 | 200.8 |
| 53 | 6850 | 3791 | 11060 | 2.8 | 9.6 | 115.9 |
| 54 | 393.1 | 145.9 | 1678 | 51.7 | >69.00 | — |
| 55 | 5335 | N/A | 3537 | 9.45 | >71.00 | 788.14 |
| 56 | 1548 | N/A | 440.7 | >30.00 | 0.01 | 716.98 |
| 57 | 839.9 | 380.6 | 3371 | >30.0 | 7.9 | 527.8 |
| 58 | 890.4 | N/A | 10570 | 13.5 | <0.10 | 1527.98 |
| 59 | 25.36 | 9.069 | 345.5 | 12.8 | <0.10 | <1.00 |
| 60 | 1951 | N/A | 18480 | >30.00 | 21.28 | 1646.44 |
| 61 | | 8.486 | 211.6 | >30 | 2.3 | <1 |
| 62 | 1325 | 558.5 | 11610 | >30.00 | >84.00 | — |
| 63 | 342.1 | 147.3 | 4738 | — | — | — |
| 64 | 1046 | 488.7 | 350 | >30 | 1.4 | <12.3 |
| 65 | 461 | 43.08 | 756.2 | 2.9 | <1 | 5.4 |
| 66 | 350.4 | — | 1308 | 1.4 | <1 | 135 |
| 67 | 1338 | — | 6117 | 1.7 | <1 | 1449.1 |
| 68 | — | 131.4 | 8033 | >30 | 15.7 | 148.7 |
| 69 | — | 1940 | 100000 | >30 | >73 | 828.3 |
| 70 | — | 20.1 | 373.9 | 31.3 | 1.2 | 148.4 |
| 71 | — | 56.65 | 2106 | >30 | 2 | 133.5 |
| 72 | — | — | — | — | — | — |
| 73 | — | — | — | — | — | — |
| 74 | — | — | — | — | — | — |
| 75 | — | — | — | — | — | — |

TABLE 2-continued

| # | Gametocyte EC50 (nM) | Asexual EC50 (nM) | mTOR (nM) | Microsomal Stability (rat) $T_{1/2}$ (min) | Sol @ pH 7.4 (ug/mL) | PAMPA Permeability ($\times 10^6$ cm/s) |
|---|---|---|---|---|---|---|
| 76 | — | — | — | — | — | — |
| 77 | 294.6 | 81.67 | 17.03 | >30.0 | 33.6 | <1.0 |
| 78 | 11.57 | 6.116 | 10.15 | >30.0 | <1.0 | ND |
| 79 | 22.81 | 4.756 | 32.37 | >30.0 | <1.0 | <11.8 |
| 80 | 213.6 | N/A | 33.29 | 7.1 | 49.68 | 50.85 |
| 81 | 33.86 | N/A | 81.93 | — | 10 | 5.1 |
| 82 | 166.7 | 150.4 | 231.4 | — | — | — |
| 83 | 74.74 | N/A | 173.6 | >30.00 | 5.62 | 58.31 |
| 84 | — | — | — | — | — | — |

TABLE 3

| # | Gametocyte EC50 (nM) | Asexual EC50 (nM) | mTOR (nM) | Microsomal Stability (rat) $T_{1/2}$ (min) | Sol @ pH 7.4 (ug/mL) | PAMPA Permeability ($\times 10^6$ cm/s) |
|---|---|---|---|---|---|---|
| 85 | 77.58 | 6.895 | — | 9 | <1.0 | 793.8 |
| 86 | 211.5 | 177.2 | 3776 | >30.0 | 61.6 | 459 |
| 87 | 139.2 | 24.36 | 241.1 | >30.0 | 2.6 | 33.1 |
| 88 | 141.3 | 56.7 | 1841 | — | 0.51 | 117.49 |
| 89 | — | 52.14 | 2689 | >30 | <1 | <1 |
| 90 | — | 74.11 | 19840 | >30 | 13.6 | 802 |
| 91 | — | 33.02 | 4415 | >30 | <1 | 54.2 |
| 92 | — | 27.2 | 613.8 | >30 | 13.3 | 3.9 |
| 93 | — | 27.9 | 450.7 | >30 | <1 | 76.3 |
| 94 | — | 24.92 | 4188 | >30 | 13.6 | 1.9 |
| 95 | — | 15.67 | 1731 | >30 | 54.7 | 674 |
| 96 | — | 37.29 | 1291 | >30 | 11.4 | 7.8 |
| 97 | — | 100.6 | 1400 | >30 | 7.1 | 35.8 |
| 98 | — | 19.34 | 994 | >30 | 0 | 0 |
| 99 | 130 | 46.68 | — | 16.9 | <1.0 | 1054.5 |
| 100 | 45.51 | 14.78 | 1531 | 3.8 | <1.0 | 314.6 |
| 101 | 305.4 | 107 | 1780 | 4.5 | <1.0 | — |
| 102 | 116.5 | 185.8 | 5191 | 5 | 7.5 | 1083.4 |
| 103 | 71.34 | 74.26 | 2997 | 10.5 | 6.3 | 76.1 |
| 104 | 193.7 | 214.7 | 2680 | 1.4 | <1.0 | 388.8 |
| 105 | 94.33 | 47.9 | 779.9 | 5.9 | 14.8 | 284.6 |
| 106 | 125.6 | 63.99 | 1735 | 2.1 | <1.0 | 621 |
| 107 | 65.9 | 32.29 | 541.4 | 6.9 | <1.0 | 10.1 |
| 108 | 59.06 | 61.43 | 1165 | <1.0 | <1.0 | 119.3 |
| 109 | 17.97 | 60.7 | 3260 | 12.3 | 4.2 | 226.8 |
| 110 | 138.9 | 40.75 | 9459 | 2.2 | 1.1 | — |
| 111 | 284.8 | 240.8 | 1135 | >30.0 | 19.8 | — |
| 112 | 178.9 | 76.78 | 3581 | 5 | 5 | — |
| 113 | 75.94 | 29.93 | 1370 | 13.6 | <1.0 | — |
| 114 | 13.57 | 6.953 | 431.3 | 23.3 | <1.0 | — |
| 115 | 6.213 | 8.144 | 229.4 | 9 | <1.0 | <1.0 |
| 116 | 65.02 | 22.02 | 454.6 | <1.0 | <1.0 | 383.1 |
| 117 | Inactive | 14410 | 4734 | >30.0 | >80.0 | — |
| 118 | 29.61 | 6.603 | 269.1 | >30.0 | <1.0 | — |
| 119 | 32.39 | 7.547 | 75.39 | 18.4 | <1.0 | — |
| 120 | 35.85 | 7.498 | 224.6 | >30.0 | <1.0 | — |
| 121 | 443.1 | 221 | 522.6 | 5.4 | — | 242.7 |
| 122 | 370.9 | 261.2 | 1303 | 5.4 | — | 822.3 |
| 123 | 442.4 | 145.2 | 857 | 7.3 | — | — |
| 124 | 349 | 144.2 | 1357 | 19.7 | — | 20.4 |
| 125 | 39.76 | 8.083 | 506.1 | — | — | — |
| 126 | 118.2 | 24.04 | 372.4 | 1.7 | <1.0 | 1238.7 |
| 127 | 169.1 | 105.3 | 338.7 | 12.2 | 7.3 | 9.1 |
| 128 | 31.45 | 6.054 | 310.6 | 12.7 | 1.5 | 735.4 |
| 129 | 680 | 1445 | 856.7 | >30.0 | 20.3 | 5.4 |
| 130 | 72.2 | 20.17 | 202.1 | >30.0 | 9.2 | 467.2 |
| 131 | 17360 | 17480 | 1557 | >30.0 | >75.0 | 1.9 |
| 132 | 344.1 | 63.1 | 736.2 | <1.0 | <1.0 | 2316 |
| 133 | 10120 | 3997 | inactive | >30.0 | <1.0 | <5.4 |
| 134 | 255.7 | 72.67 | 2007 | 10.5 | <1.0 | 142.1 |
| 135 | 100000 | 77800 | inactive | >30.0 | >80.0 | 3 |
| 136 | 732.7 | 94.52 | 3591 | 7.8 | 8.6 | 1292.9 |
| 137 | 1004 | 187.9 | 1518 | 1.6 | <1.0 | — |
| 138 | 276.8 | 173.2 | 1278 | 4.8 | <1.0 | 890.6 |
| 139 | 152.9 | 20.63 | 405.1 | 4.3 | <1.0 | 238.4 |
| 140 | 272.2 | 59.24 | 6373 | 9.6 | >77.0 | 1393.8 |
| 141 | 260.1 | 47.47 | 8043 | 4.2 | 66.5 | 1500.6 |

TABLE 3-continued

| # | Gametocyte EC50 (nM) | Asexual EC50 (nM) | mTOR (nM) | Microsomal Stability (rat) $T_{1/2}$ (min) | Sol @ pH 7.4 (ug/mL) | PAMPA Permeability ($\times 10^6$ cm/s) |
|---|---|---|---|---|---|---|
| 142 | 50000 | 13770 | 46170 | 1.4 | <1.0 | ND |
| 143 | 242.1 | 63.12 | 671.6 | 1.6 | <1.0 | 1421.5 |
| 144 | 1761 | 367.7 | 2083 | 4.1 | <1.0 | 1470.8 |
| 145 | 266.3 | 60.65 | 1214 | 4.9 | <1.0 | 362.8 |
| 146 | 1814 | 535.8 | 5732 | 9.6 | 63 | 98.3 |
| 147 | 18300 | 4809 | 21220 | 3.1 | >90.0 | 108.6 |
| 148 | 4575 | 601.1 | 18170 | >30.0 | 21.8 | — |
| 149 | 839.5 | 408.6 | 6235 | >30.0 | 8.8 | — |
| 150 | 6229 | 3824 | 7873 | 2.4 | 3.9 | — |
| 151 | 52.67 | 19.05 | 3720 | 3.5 | <1.0 | — |
| 152 | 4038 | 2205 | 796.2 | 3.3 | <1.0 | — |
| 153 | 52.91 | 126.8 | 18360 | 9.4 | <1.0 | 57.9 |
| 154 | 101.7 | 159.9 | 765.7 | 8 | <1.0 | <1.0 |
| 155 | 3113 | 1235 | 27970 | 10.7 | <1.0 | <1.0 |
| 156 | 1576 | 686.7 | 67630 | 5.6 | <1.0 | <1.0 |
| 157 | 7430 | 3350 | 50000 | 6.8 | <1.0 | <1.0 |
| 158 | 3556 | 1555 | 7899 | 18.8 | <1.0 | <2.4 |
| 159 | 320.5 | 91.59 | 3523 | — | — | — |
| 160 | 270.1 | 96.06 | 9278 | >30.0 | >79.0 | <1.0 |
| 161 | 1536 | 512.5 | 47050 | >30.0 | >82.0 | 5.4 |
| 162 | 894.7 | 368 | 32080 | >30.0 | >83.0 | <1.0 |
| 163 | 246.5 | 93.88 | 6497 | >30.0 | >72.0 | 231.9 |
| 164 | 809 | 594.4 | 40420 | >30.0 | >79.0 | 238.3 |
| 165 | 4091 | 933.7 | 50000 | >30.0 | >80.0 | 1.8 |
| 166 | 179.4 | 72.73 | 8762 | >30.0 | >70.0 | 426.6 |
| 167 | 469 | 223.2 | 22690 | >30.0 | >76.0 | 1.5 |
| 168 | 224.3 | 85.97 | 1194 | >30.0 | 17.3 | 1.4 |
| 169 | 629.7 | 301 | 631.5 | — | 2.8 | 204.2 |
| 170 | 168.1 | 122.2 | 3773 | 13.3 | 2.7 | 591 |
| 171 | 240.4 | 47.51 | 154.3 | 2.8 | >72.0 | 31.3 |
| 172 | 202.8 | 121 | 967.8 | >30.0 | 2.3 | 12.3 |
| 173 | 2526 | — | 100000 | — | >77.00 | 365.72 |
| 174 | 265 | 132.7 | 7636 | >30.00 | >68.00 | 49.89 |
| 175 | 1618 | 731 | 11780 | >30.00 | 66.62 | — |
| 176 | 282.7 | 90.23 | 556.2 | — | <0.10 | ND |
| 177 | 902.1 | — | 9038 | — | >74.00 | — |
| 178 | 918 | 444.9 | 5312 | — | — | — |
| 179 | 1696 | 451.1 | 100000 | 19.4 | <1 | <1 |
| 180 | 1821 | 931.4 | 2454 | >30 | 43.7 | 3.8 |
| 181 | 1923 | 1584 | 830.4 | >30 | 17.3 | 36.3 |
| 182 | 1479 | 459 | 1439 | 10.8 | 1.1 | 0 |
| 183 | 131.1 | 49.84 | 794.5 | >30 | 28.4 | <1 |
| 184 | 820.6 | 171.3 | 18050 | >30 | 56.1 | 292.5 |
| 185 | 1144 | 352.5 | 50000 | 15.1 | 3.4 | 35.5 |
| 186 | 572.8 | 207.2 | 12440 | — | — | — |
| 187 | 4588 | 1605 | 724.6 | 0 | 0 | 0 |
| 188 | 601.5 | — | 7201 | 21.5 | <1 | 1247 |
| 189 | 357.9 | — | 6514 | >30 | >78 | 212.5 |
| 190 | 248.5 | — | 10680 | >30 | >77 | 0 |
| 191 | 172.3 | — | 4337 | 26.7 | 2.4 | 606.4 |
| 192 | | 174.4 | 11990 | 24.7 | <1 | 0 |
| 193 | 813.6 | — | 8290 | >30 | >81 | 161.6 |
| 194 | 701.5 | — | 100000 | 6.9 | <1 | 1078.4 |
| 195 | 275.8 | — | 781.4 | 8.8 | <1 | 148 |
| 196 | 100000 | — | 100000 | 18 | <1 | 85.9 |
| 197 | 65140 | — | 2384 | >30 | >77 | 3.5 |
| 198 | | 263.6 | 13840 | >30 | >75 | 6.1 |
| 199 | | 108.8 | 16510 | 5.6 | 1.4 | 1442.8 |
| 200 | | 60.03 | 15370 | 0 | 7.2 | 1070.1 |
| 201 | | 1619 | 17280 | 12.6 | <1 | 13.8 |
| 202 | | 120.4 | 3267 | >30 | 57.8 | 415.1 |
| 203 | | 17.23 | 512.8 | 29.3 | 1.2 | 749.5 |
| 204 | | 14.26 | 257.1 | >30 | <1 | <1 |
| 205 | | 177.2 | 1061 | 0 | 2.2 | 455.6 |
| 206 | | 48.9 | 19640 | 7.1 | 44.1 | 427.6 |
| 207 | | 145.4 | 168.8 | >30 | 58.1 | <1 |
| 208 | | 65.92 | 21750 | 13.2 | 35.5 | 247.9 |
| 209 | | 537.7 | 2492 | 4 | <1 | <1 |
| 210 | | 14470 | 100000 | 2.7 | <1 | 0 |
| 211 | | 3878 | 43090 | >30 | >83 | 227 |
| 212 | | 3888 | 15800 | >30 | >79 | 188.7 |
| 213 | | 130.2 | 1299 | 18.9 | <1 | <1 |
| 214 | | 18.82 | 339.4 | 21.2 | <1 | 333.1 |
| 215 | | 177.5 | 763.8 | 6.3 | <1 | 492.1 |
| 216 | | 42.23 | 832.1 | 6.7 | <1 | 1.1 |
| 217 | | 531.3 | 17830 | >30 | >83 | 130 |

TABLE 3-continued

| # | Gametocyte EC50 (nM) | Asexual EC50 (nM) | mTOR (nM) | Microsomal Stability (rat) $T_{1/2}$ (min) | Sol @ pH 7.4 (ug/mL) | PAMPA Permeability ($\times 10^6$ cm/s) |
|---|---|---|---|---|---|---|
| 218 | | 1684 | 16250 | >30 | >69 | 100.4 |
| 219 | | 370.7 | 3288 | >30 | 6.3 | 3.3 |
| 220 | | 156.1 | 4247 | 12.6 | 9.4 | 127.4 |
| 221 | | 45.47 | 1504 | 22.2 | <1 | 133.1 |
| 222 | | 22.83 | 820.6 | 27.2 | 7.1 | 757.6 |
| 223 | | 58.02 | 7119 | — | 3.4 | 1178.5 |
| 224 | | 46000 | 100000 | 0 | >74 | <1 |
| 225 | | 19.75 | 916.9 | 23.3 | <1 | 735.2 |
| 226 | | 208.1 | 8446 | — | — | — |
| 227 | | 66.45 | 16000 | — | — | — |
| 228 | | 194.9 | 11220 | — | — | — |
| 229 | | 232.4 | 19250 | — | — | — |
| 230 | | 98.17 | 50000 | — | — | — |
| 231 | | 22.74 | 850.5 | 18 | <1 | 364.4 |
| 232 | | 53.43 | 1065 | >30 | 9.2 | 7.6 |
| 233 | | 162.4 | 6306 | >30 | >76 | 155.1 |
| 234 | | 2219 | 18920 | 1.4 | <1 | 874.2 |
| 235 | | 24450 | 100000 | 3.4 | <1 | 563.9 |
| 236 | | 1198 | 50000 | >30 | >78 | <1 |
| 237 | | 39510 | 100000 | >30 | >65 | 3.3 |
| 238 | | 56.84 | 214.8 | >30 | <1 | 438.9 |
| 239 | | 17.47 | 242.2 | >30 | <1 | 79.9 |
| 240 | | 52.88 | 443.6 | >30 | 31.6 | <1 |
| 241 | | 334.7 | 6061 | >30 | >74 | 18.6 |
| 242 | | 488.7 | 373 | >30 | >74 | <1 |
| 243 | | 676.9 | 14600 | >30 | >76 | 382.2 |
| 244 | | 1635 | 7873 | >30 | >76 | 216.2 |
| 245 | | 3817 | 10410 | >30 | >61 | 11.7 |
| 246 | | 1257 | 645.9 | >30 | >72 | 1.5 |
| 247 | | 81.83 | 1903 | 16.7 | <1 | 846 |
| 248 | | 329.2 | 23380 | 10.6 | 51.2 | ND |
| 249 | | 575.5 | 14760 | 7.9 | >82 | 1066.3 |
| 250 | | 549 | 2911 | >30 | 9.5 | 14.3 |
| 251 | | 2374 | 100000 | 1.3 | <1 | <1 |
| 252 | | 100000 | 100000 | — | — | — |
| 253 | | 257.8 | 8463 | >30 | >80 | 352.9 |
| 254 | | 206.2 | 3012 | >30 | 53.1 | 5.7 |
| 255 | | 181.9 | 12950 | 2.3 | >88 | 1044.2 |
| 256 | | 500.7 | 8776 | 3.5 | <1 | 663.6 |
| 257 | | 60.78 | 2719 | >30 | >84 | 1.5 |
| 258 | | 34.3 | 2541 | 24.4 | 0 | 0 |
| 259 | | 24.18 | 655.9 | 2.6 | 0 | 0 |
| 260 | | 62.41 | 5024 | 2.1 | 0 | 0 |
| 261 | | 60.03 | 1871 | 1.7 | 0 | 0 |
| 262 | | 213.8 | 5399 | 4.3 | 0 | 0 |
| 263 | | 58.82 | 1512 | >30 | 0 | 0 |
| 264 | | 56.56 | 1321 | 4.5 | 0 | 0 |
| 265 | | 132 | 2064 | 1.9 | 0 | 0 |
| 266 | | 58.28 | 3013 | 2.8 | 0 | 0 |
| 267 | | 58.15 | 3878 | 8 | 0 | 0 |
| 268 | | 211.1 | 4985 | 2 | 0 | 0 |
| 269 | | 389.9 | 3874 | >30 | 0 | 0 |
| 270 | | 348.4 | 3254 | >30 | 0 | 0 |
| 271 | | 612.6 | 16140 | 14 | 0 | 0 |
| 272 | | 52.07 | 5227 | 21.9 | 11.8 | 625.8 |
| 273 | | 18.9 | 4164 | >30 | <1 | 0 |
| 274 | | 40.61 | 4900 | 21.4 | 63.8 | 1007.1 |
| 275 | | 44.22 | 4039 | 19.9 | 65.6 | 426.8 |
| 276 | | 222.2 | 21760 | 5.8 | 34.8 | 973.2 |
| 277 | | 82.48 | 3631 | 3.8 | 19.9 | 354 |
| 278 | | 110.2 | 8000 | 2.6 | >83 | 1383.7 |
| 279 | | 50.5 | 1317 | 15.8 | >84 | 49.1 |
| 280 | | 152.4 | 1609 | >30 | 73.6 | 49.1 |
| 281 | | 27.38 | 2180 | 3 | >86 | 33.4 |
| 282 | | 71.4 | 4536 | 4.1 | >86 | 598.2 |
| 283 | | 69.1 | 15090 | 2.7 | 70.7 | 1184.7 |
| 284 | | 182.9 | 9354 | 7.5 | 36.6 | 280.6 |
| 285 | | 59.71 | 1506 | >30 | 41.6 | 159.4 |
| 286 | | 53.68 | 11770 | 2.4 | 35.6 | 863.4 |
| 287 | | 58.44 | 2083 | 4.3 | <1 | 21.7 |
| 288 | | 283.9 | 1258 | 1.2 | <1 | 18.8 |
| 289 | | 86.73 | 9216 | 1.7 | <1 | 141.1 |
| 290 | | 64.38 | 4806 | 3 | 63.1 | 310.7 |
| 291 | | 210.9 | 4975 | 3.1 | 0 | 772.9 |
| 292 | | 1137 | 15560 | 1.7 | 0 | 3.4 |
| 293 | | 146.3 | 6103 | 22.9 | 0 | 241.2 |

TABLE 3-continued

| # | Gametocyte EC50 (nM) | Asexual EC50 (nM) | mTOR (nM) | Microsomal Stability (rat) $T_{1/2}$ (min) | Sol @ pH 7.4 (ug/mL) | PAMPA Permeability ($\times 10^6$ cm/s) |
|---|---|---|---|---|---|---|
| 294 | | 2046 | 4586 | 8.4 | 0 | 0 |
| 295 | | 162.2 | 23740 | 10.6 | 0 | 638.9 |
| 296 | | 477.2 | 18600 | 7.1 | 0 | 509.8 |
| 297 | | 150.1 | 11020 | 1.6 | 0 | 936.2 |
| 298 | | 949.5 | 50000 | 1.5 | 0 | 148.2 |
| 299 | | 55.34 | 5830 | — | — | — |
| 300 | | 32.74 | 3792 | — | — | — |
| 301 | | 205.5 | 50000 | >30 | <1 | 0 |
| 302 | | 16.37 | 1595 | 12 | <1 | 0 |
| 303 | | 6.446 | 237.6 | >30 | 0.7 | 0 |
| 304 | | 19.2 | 853.5 | — | — | — |
| 305 | | 483.3 | 4727 | — | — | — |
| 306 | | 100.2 | 8864 | — | — | — |
| 307 | | 190.9 | 39900 | — | — | — |
| 308 | | 23.56 | 2099 | — | — | — |
| 309 | | 553.9 | 3824 | — | — | — |
| 310 | | 413.7 | 3373 | — | — | — |
| 311 | | 53.26 | 198.2 | — | — | — |
| 312 | | 1853 | 500000 | — | — | — |
| 313 | | 39.03 | 1429 | — | — | — |
| 314 | | 429.4 | 780 | — | — | — |
| 315 | | 137 | 100000 | — | — | — |
| 316 | | 412.1 | 8154 | — | — | — |
| 317 | | 201.7 | 8572 | — | — | — |
| 318 | — | — | — | — | — | — |
| 319 | — | — | — | — | — | — |
| 320 | — | — | — | — | — | — |
| 321 | — | — | — | — | — | — |
| 322 | — | — | — | — | — | — |
| 323 | — | — | — | — | — | — |
| 324 | — | — | — | — | — | — |
| 325 | — | — | — | — | — | — |
| 326 | — | — | — | — | — | — |
| 327 | — | — | — | — | — | — |
| 328 | — | — | — | — | — | — |
| 329 | — | — | — | — | — | — |
| 330 | — | — | — | — | — | — |
| 331 | — | — | — | — | — | — |
| 332 | 1519 | 859 | 494.9 | >30.0 | >64.0 | 31.9 |
| 333 | 411.2 | 238.7 | 213.5 | — | — | — |
| 334 | 19.73 | 8.213 | 88.72 | >30.0 | 30 | 14.9 |
| 335 | 17.74 | 14.44 | 28.21 | >30.0 | 2.8 | <2.2 |
| 336 | 40.99 | 10.17 | 19.71 | >30.0 | <1.0 | <3.6 |
| 337 | 6232 | 1574 | 3229 | >30.0 | >68.0 | — |
| 338 | 65.86 | N/A | 150.5 | — | 0.32 | 140.79 |

TABLE 4

| # | Gametocyte EC50 (nM) | Asexual EC50 (nM) | mTOR (nM) | Microsomal Stability (rat) $T_{1/2}$ (min) | Sol @ pH 7.4 (ug/mL) | PAMPA Permeability ($\times 10^6$ cm/s) |
|---|---|---|---|---|---|---|
| 339 | 9.19 | 0 | 299.9 | >30.0 | <1.0 | <1.0 |
| 340 | 616.5 | 266.1 | 15200 | >30.0 | >68.0 | 5.2 |
| 341 | 82.95 | 69.08 | 620.5 | 12.4 | <1.0 | ND |
| 342 | 349.8 | 129.9 | 6710 | >30.00 | 31.01 | 12.72 |
| 343 | — | 20.85 | 447.6 | >30 | 13.4 | <2.5 |
| 344 | 1505 | 0 | 3539 | 19.2 | <1.0 | 238.8 |
| 345 | 3832 | 2.342 | 7622 | <1.0 | — | — |
| 346 | 48.38 | 18.57 | 574.1 | — | — | — |
| 347 | 1719 | 667.7 | 14370 | >30.0 | >70.0 | 317.6 |
| 348 | 2446 | 1458 | 23930 | >30.0 | >72.0 | 289.4 |
| 349 | 26780 | 14220 | 16230 | >30.0 | >68.0 | 2.5 |
| 350 | 1003 | 546.2 | 10110 | — | >68.0 | — |
| 351 | 2162 | 155.9 | 433 | — | — | — |
| 352 | 100000 | 18750 | 11480 | — | >72.0 | 343.6 |
| 353 | 2514 | 588.7 | 50000 | >30.0 | 0 | NOT_DETERMINED |
| 354 | 1907 | 687.4 | 15790 | >30.0 | >74.0 | 292.3 |
| 355 | 28750 | 2022 | 2516 | >30.0 | >77.0 | — |
| 356 | 65.49 | 24.98 | 1044 | >30.00 | <0.10 | NOT_DETERMINED |
| 357 | 2197 | 862.9 | 8193 | >30.00 | >70.00 | 40.53 |
| 358 | 2184 | 878.5 | 6888 | — | >72.00 | 1209.2 |
| 359 | 129.7 | 23.44 | 1328 | 14.9 | 0.06 | — |

TABLE 4-continued

| # | Gametocyte EC50 (nM) | Asexual EC50 (nM) | mTOR (nM) | Microsomal Stability (rat) $T_{1/2}$ (min) | Sol @ pH 7.4 (ug/mL) | PAMPA Permeability ($\times 10^6$ cm/s) |
|---|---|---|---|---|---|---|
| 360 | 736 | 170.2 | 1696 | 19.2 | 0.73 | 635.05 |
| 361 | 6441 | 1575 | 100000 | >30.00 | <0.10 | 199.84 |
| 362 | 81.71 | 8.86 | 1278 | 7.4 | 0.6 | 98.56 |
| 363 | 860.2 | 449.6 | 4610 | — | 57.74 | 8.76 |
| 364 | 100000 | 4582 | 50000 | >30 | 2.7 | 75.9 |
| 365 | 30610 | 481.5 | 126.9 | 0 | 55.9 | <1.8 |
| 366 | 3759 | 1235 | 12120 | 0 | 14.8 | 47.8 |
| 367 | 104.7 | 29 | 326.5 | 12.8 | 0 | ND |
| 368 | 2195 | 1283 | 3401 | >30 | 6.5 | 2.9 |
| 369 | 2942 | 1228 | 17820 | 26 | 15.7 | 55 |
| 370 | 4115 | 296.2 | 1456 | >30 | 27.3 | <1 |
| 371 | 2473 | 471.6 | 31140 | >30 | 45.3 | 1.2 |
| 372 | 1049 | 540.2 | 50000 | >30 | <1 | <1 |
| 373 | 45.72 | 349.6 | 1735 | >30 | 3.3 | <6.3 |
| 374 | 12930 | 4183 | 50000 | >30 | 52.5 | <1.6 |
| 375 | 714.8 | 389.1 | 50000 | >30 | 13.1 | <1.1 |
| 376 | 198.6 | 115 | 460.1 | 0 | 0 | 0 |
| 377 | 384.1 | 3.841 | 1177 | 0 | 0 | 0 |
| 378 | 1546 | — | 17200 | >30 | >70 | 2.3 |
| 379 | — | 2956 | 7400 | 23 | <1 | 31 |
| 380 | — | 310.5 | 1365 | >30 | 2.6 | <10.7 |
| 381 | — | 263.8 | 652.7 | >30 | 44.9 | 4 |
| 381 | — | 8.438 | 2938 | — | — | — |
| 383 | — | 62.31 | 1837 | — | — | — |
| 384 | — | 1322 | 100000 | — | — | — |
| 385 | — | — | — | — | — | — |
| 386 | — | — | — | — | — | — |
| 387 | 1838 | 315.8 | 262.6 | >30.0 | 1.4 | <4.1 |
| 388 | 88.15 | 28.19 | 120 | — | 11.8 | 2 |
| 389 | 65.27 | 21.83 | 90.23 | — | <1.0 | <9.7 |
| 390 | 115.8 | 75.16 | 60.97 | >30.0 | 4.2 | 25 |
| 391 | 56.28 | 12.26 | 126.8 | >30.00 | 10 | ND |
| 392 | 46.08 | 22.04 | 122.6 | >30.00 | 33.81 | 133.39 |
| 393 | 30.71 | 9.305 | 19.62 | — | 6.26 | <1.10 |
| 394 | 438.5 | 129.8 | 107.5 | >30 | <1 | <1 |
| 395 | 46000 | — | 53.39 | >30 | 11.3 | 3.9 |

TABLE 5

| # | Gametocyte EC50 (nM) | Asexual EC50 (nM) | mTOR (nM) | Microsomal Stability (rat) $T_{1/2}$ (min) | Sol @ pH 7.4 (ug/mL) | PAMPA Permeability ($\times 10^6$ cm/s) |
|---|---|---|---|---|---|---|
| 396 | — | 144.1 | 15140 | >30 | 46.4 | 207.8 |
| 397 | 232.3 | 267.8 | Inactive | >30.0 | <1.0 | — |
| 398 | 194.1 | 104.9 | 2471 | >30.0 | <1.0 | — |
| 399 | 522.2 | 219.3 | 100000 | >30.0 | <1.0 | ND |
| 400 | 294 | 165.2 | 100000 | >30.0 | <1.0 | 1464.6 |
| 401 | 190.2 | 86.7 | 1271 | >30.0 | <1.0 | 296.7 |
| 402 | 343.1 | 139.9 | 53210 | >30.0 | 1.9 | 222.8 |
| 403 | 262.2 | 125.3 | 100000 | >30.0 | 3.1 | ND |
| 404 | 1644 | 681.4 | 50000 | >30.0 | 0.9 | 19.5 |
| 405 | 665.7 | 298.4 | 100000 | 2.4 | <0.1 | ND |
| 406 | 13.07 | 8.463 | 216.5 | 19.4 | <1 | ND |
| 407 | 104.2 | 52.41 | 50000 | >30 | <1 | 0 |
| 408 | 304.7 | 10.04 | 100000 | 0 | 0 | 0 |
| 409 | 105.7 | 52.89 | 50000 | 0 | 0 | 0 |
| 410 | 36.3 | 2.488 | 100000 | 0 | 0 | 0 |
| 411 | 108.7 | 61.4 | 100000 | 0 | 0 | 0 |
| 412 | 39.88 | 6.574 | 100000 | 0 | 0 | 0 |
| 413 | 53.99 | 29.35 | 2730 | 0 | 0 | 0 |
| 414 | 38.71 | 14.21 | 584.2 | — | — | — |
| 415 | 18.63 | 21.43 | 15870 | — | — | — |
| 416 | 21.64 | 39.63 | 930.6 | — | — | — |
| 417 | 36.45 | — | 319 | 0 | <1 | <1 |
| 418 | — | 7.934 | 700.2 | — | — | — |
| 419 | — | 82.94 | 30380 | — | — | — |
| 420 | — | 144.2 | 30220 | — | — | — |
| 421 | — | 18.91 | 18940 | — | — | — |
| 422 | — | 5.866 | 1870 | — | — | — |
| 423 | — | 50.42 | 15400 | — | — | — |
| 424 | — | 22.99 | 12510 | — | — | — |
| 425 | — | 48.43 | 5000 | — | — | — |

TABLE 5-continued

| # | Gametocyte EC50 (nM) | Asexual EC50 (nM) | mTOR (nM) | Microsomal Stability (rat) T$_{1/2}$ (min) | Sol @ pH 7.4 (ug/mL) | PAMPA Permeability (×10$^6$ cm/s) |
|---|---|---|---|---|---|---|
| 426 | — | 29.43 | 6418 | — | — | — |
| 427 | — | 75.16 | 30600 | — | — | — |
| 428 | — | 27.77 | 11000 | — | — | — |
| 429 | — | 10.52 | 12570 | — | — | — |
| 430 | — | 58.45 | 4622 | — | — | — |
| 431 | — | — | — | — | — | — |
| 432 | — | — | — | — | — | — |
| 433 | — | 17.07 | 6100 | — | — | — |
| 434 | Inactive | 45000 | >46000 uM | 11.3 | <1.0 | ND |
| 435 | | 3657 | 364.6 | >30 | 30.8 | 11 |
| 436 | 1966 | 891.9 | 12450 | >30.0 | 52.9 | 767.2 |
| 437 | 44.34 | 14.4 | 529.3 | >30.0 | <1.0 | 3.1 |
| 438 | 169.3 | 174.1 | 100000 | 27.2 | <1.0 | <1.0 |
| 439 | 843.9 | 37.93 | 714.1 | >30.0 | 1.4 | 18.4 |
| 440 | 2179 | 786.6 | 100000 | >30.0 | <1.0 | ND |
| 441 | 685.5 | 319.1 | 516.2 | >30.0 | <1.0 | <1.0 |
| 442 | 1992 | 449.1 | 100000 | — | — | — |
| 443 | 68.27 | 44.55 | 302.4 | >30.0 | 3.3 | 644.7 |
| 444 | 279.7 | 106.1 | 427.8 | 12.8 | <1.0 | 406.6 |
| 445 | 734.7 | 269.4 | 630.3 | — | — | — |
| 446 | — | 1669 | 6805 | >30 | 1 | <16.2 |
| 447 | — | 139.3 | 16340 | 26.7 | 7.4 | 1377.3 |
| 448 | 50000 | 20020 | 100000 | >30.0 | 0.4 | ND |
| 449 | 100000 | 6346 | 100000 | 2.9 | 0.2 | ND |
| 450 | 312.8 | 88.3 | 1108 | 17.9 | <0.10 | — |
| 451 | 50000 | 8408 | 100000 | — | <0.10 | ND |
| 452 | 2917 | 1186 | 100000 | >30 | <0.1 | ND |
| 453 | 100000 | 3996 | 479.6 | 14.9 | 29.3 | <0.5 |
| 454 | 1627 | 301.2 | 100000 | 0 | <0.1 | ND |
| 455 | 2060 | 1013 | 6581 | — | — | — |
| 456 | 3156 | 931.4 | 1313 | 397.4 | 3.9 | <0.9 |
| 457 | 2543 | 667.9 | 50000 | >30 | <1 | <13.5 |
| 458 | 456.7 | 22.05 | 42820 | — | — | — |
| 459 | 443 | 88.47 | 100000 | — | — | — |
| 460 | 100000 | 147.7 | 50000 | 9.8 | <1 | 927.1 |
| 461 | — | 1766 | 100000 | 9.9 | 43.8 | ND |
| 462 | — | 569.1 | 100000 | 8.2 | <1 | 2112.3 |
| 463 | — | 3417 | 100000 | 17.1 | <1 | 306.8 |
| 464 | 137.2 | 45.3 | 10680 | 18.5 | <1 | 1021.6 |
| 465 | 525.5 | 113.4 | 50000 | >30 | <1 | 953.8 |
| 466 | 18.31 | 3.626 | 7762 | >30 | 6.6 | 174.1 |
| 467 | 23.69 | 15.04 | 1776 | 17.6 | <1 | 792 |
| 468 | 114 | 60.19 | 7448 | 0 | 0 | 0 |
| 469 | 125.5 | 52.96 | 100000 | 18.6 | 42.7 | 814.3 |
| 470 | 217.2 | 163.6 | 20420 | 0 | 0 | 0 |
| 471 | 156.3 | 60.34 | 6030 | 0 | 0 | 0 |
| 472 | 71.56 | 20.6 | 4764 | 0 | 0 | 0 |
| 473 | 39.3 | 16.87 | 3115 | 0 | 0 | 0 |
| 474 | 24.99 | 17.6 | 3382 | 0 | 0 | 0 |
| 475 | 24.5 | 11.1 | 459.7 | 0 | 0 | 0 |
| 476 | 473.8 | 231.3 | 19430 | — | — | — |
| 477 | 2371 | 1615 | 4288 | 0 | 0 | 0 |
| 478 | 292.5 | — | 49380 | >30 | >66 | 0 |
| 479 | 141.1 | — | 1250 | 11.2 | <1 | <13.3 |
| 480 | 8715 | — | 3258 | 11.9 | <1 | 0 |
| 481 | 851.2 | — | 3462 | 10 | 35.9 | <1 |
| 482 | 2749 | — | 6901 | 0 | 39.7 | 35.8 |
| 484 | 306 | — | 1312 | 0 | <1 | 81.6 |
| 485 | 81.01 | — | 562.6 | 0 | <1 | 13 |
| 486 | 77.87 | — | 299.5 | 0 | <1 | <4.6 |
| 487 | — | 469.4 | 100000 | 30.5 | 37.9 | 804.3 |
| 488 | — | 4845 | 100000 | >30 | <1 | ND |
| 489 | — | 55.86 | 100000 | >30 | <1 | 0 |
| 490 | — | 2984 | 100000 | >30 | <1 | ND |
| 491 | — | 51.4 | 22990 | 4.7 | 53 | 1585.7 |
| 492 | — | 944.1 | 2384 | >30 | <1 | <1 |
| 493 | — | 805.4 | 100000 | >30 | <1 | ND |
| 494 | — | 433.3 | 100000 | >30 | <1 | ND |
| 495 | — | 2972 | 100000 | >30 | <1 | 192.2 |
| 496 | — | 130.1 | 2358 | >30 | <1 | <5.3 |
| 497 | — | 132.1 | 6485 | 12.9 | <1 | 0 |
| 498 | — | 3736 | 100000 | 30.4 | 57.5 | 1434.3 |
| 500 | — | 1499 | 100000 | — | 48.1 | 1393.2 |
| 501 | — | 259.7 | 100000 | 7.4 | 53.6 | 993.7 |
| 502 | — | 18.53 | 682.2 | 7.2 | <1 | ND |
| 503 | — | 542.7 | 47880 | 23.3 | <1 | ND |

TABLE 5-continued

| # | Gametocyte EC50 (nM) | Asexual EC50 (nM) | mTOR (nM) | Microsomal Stability (rat) T$_{1/2}$ (min) | Sol @ pH 7.4 (ug/mL) | PAMPA Permeability (×10$^6$ cm/s) |
|---|---|---|---|---|---|---|
| 504 | — | 187.8 | 500000 | >30 | 27.4 | 960.1 |
| 505 | — | 16.78 | 12320 | >30 | <1 | 0 |
| 506 | — | 27.17 | 4579 | >30 | 1.1 | <1 |
| 507 | — | 221.8 | 8798 | >30 | 56.7 | 720.1 |
| 508 | — | 75.14 | 3176 | >30 | 58.4 | 1010.7 |
| 509 | — | 100.3 | 43950 | >30 | >68 | 1289 |
| 510 | — | 25.33 | 100000 | 8.5 | <1 | 1361 |
| 511 | — | 8.5 | 100000 | — | — | — |
| 512 | — | 19.75 | 18500 | — | — | — |
| 513 | — | 26.5 | 39070 | 22.5 | <1 | 0 |
| 514 | — | 147.4 | 100000 | 5.2 | <1 | ND |
| 515 | — | 7.082 | 50000 | 12.1 | 0 | 1471.9 |
| 516 | — | 465.9 | 100000 | 7 | 0 | 1285.5 |
| 517 | — | 12.33 | 100000 | — | — | — |
| 518 | — | 2819 | 1876 | — | — | — |
| 519 | — | 5.728 | 722 | — | — | — |
| 520 | — | 38.03 | 21200 | — | — | — |
| 521 | — | 117.8 | 4237 | — | — | — |
| 522 | — | 260.1 | 100000 | — | — | — |
| 523 | — | 1033 | 9590 | — | — | — |
| 524 | — | 40.01 | 6470 | — | — | — |
| 525 | — | 191.5 | 29140 | — | — | — |
| 526 | — | — | — | — | — | — |
| 527 | — | — | — | — | — | — |
| 528 | — | — | — | — | — | — |
| 529 | — | — | — | — | — | — |
| 530 | — | — | — | — | — | — |
| 531 | — | — | — | — | — | — |
| 532 | — | — | — | — | — | — |
| 533 | — | — | — | — | — | — |
| 534 | — | — | — | — | — | — |
| 535 | — | — | — | — | — | — |
| 536 | — | — | — | — | — | — |
| 537 | — | — | — | — | — | — |
| 538 | — | — | — | — | — | — |
| 539 | — | — | — | — | — | — |
| 540 | — | — | — | — | — | — |
| 541 | — | — | — | — | — | — |
| 542 | — | — | — | — | — | — |
| 543 | — | — | — | — | — | — |
| 544 | 482.5 | 385.6 | 174.1 | >30.0 | <1.0 | <17.5 |
| 545 | 118.1 | 98.4 | 499.1 | >30.0 | <1.0 | 20 |
| 546 | 63.1 | 37.07 | 28.44 | — | <1.0 | <6.2 |
| 547 | 4.101 | 2.69 | 46.71 | >30.0 | <1.0 | — |
| 548 | 27.94 | 6.836 | 490.2 | >30.0 | 43.5 | 3.3 |
| 549 | 7.232 | 3.995 | 541.4 | >30.0 | 43.8 | 199.1 |
| 550 | 310.3 | 140.9 | 5548 | ND | 2.5 | 145.9 |
| 551 | 31.9 | 21.51 | 111 | >30.0 | 1.6 | 12.7 |
| 552 | 1111 | 97.77 | 2908 | >30.0 | 2.3 | 4.6 |
| 553 | 92.85 | 77.96 | 553.9 | >30.0 | 1.3 | <1.0 |
| 554 | 707.9 | 298.8 | 12330 | >30.0 | 8.6 | 543.6 |
| 555 | 706.7 | 301 | 50000 | — | — | — |
| 556 | 21400 | 6332 | 50000 | — | 20.7 | 100.7 |
| 557 | 58.16 | 13.61 | 420.4 | 25.9 | 1.4 | 529.2 |
| 558 | 372.3 | 101.7 | 1264 | 20.8 | 3.4 | 0 |
| 559 | 655 | 386.8 | 289.6 | 5.3 | 5.3 | 275 |
| 560 | 1837 | 377.1 | 84.97 | >30 | 11.5 | 0 |
| 561 | 22.07 | 9.823 | 44.49 | >30.00 | 1.51 | 377.44 |
| 562 | 50000 | 1285 | 100000 | >30.00 | <0.10 | <30.20 |
| 563 | 3562 | 897.2 | 50000 | 0 | 11.3 | 0 |
| 564 | 18.29 | 5.258 | 985.5 | 0 | 0 | 0 |
| 626 | — | 23.33 | 26260 | >30 | 47.9 | 78.6 |
| 627 | — | 17.14 | 3535 | >30 | 29.9 | 80.3 |
| 628 | — | 97.97 | 557.9 | 14 | <1 | 876.8 |
| 629 | — | 163.6 | 22780 | >30 | <1 | 983.9 |
| 630 | — | 57.2 | 28400 | >30 | <1 | 810.6 |
| 631 | — | 45.16 | 100000 | 9.1 | <1 | 2.5 |
| 632 | — | 12.96 | 9384 | 7.6 | <1 | 1241.2 |
| 633 | — | 48.49 | 50000 | 12.1 | <1 | 382 |
| 634 | — | 1221 | 220000 | 2.8 | 11 | 339.4 |
| 635 | — | 19.16 | 26730 | — | — | — |

TABLE 6

| # | Gametocyte EC50 (nM) | Asexual EC50 (nM) | mTOR (nM) | Microsomal Stability (rat) $T_{1/2}$ (min) | Sol @ pH 7.4 (ug/mL) | PAMPA Permeability ($\times 10^6$ cm/s) |
|---|---|---|---|---|---|---|
| 565 | 1332 | 445.7 | 19430 | >30.0 | <1.0 | ND |
| 566 | 816.3 | 526 | 15670 | >30.0 | <1.0 | ND |
| 567 | 3737 | 7805 | 2906 | >30 | 56.7 | 0 |
| 568 | 14570 | 4370 | 50000 | — | — | — |
| 569 | 100000 | 14680 | 6560 | — | — | — |
| 570 | 28740 | — | 2694 | >30 | 3.7 | 1.7 |
| 571 | 228.3 | 68.11 | 170.8 | >30.0 | 4 | 27.8 |
| 572 | 557.8 | 67.75 | 25.37 | — | — | — |

TABLE 7

| # | Gametocyte EC50 (nM) | Asexual EC50 (nM) | mTOR (nM) | Microsomal Stability (rat) $T_{1/2}$ (min) | Sol @ pH 7.4 (ug/mL) | PAMPA Permeability ($\times 10^6$ cm/s) |
|---|---|---|---|---|---|---|
| 573 | 237.2 | 54.66 | 794.5 | >30.0 | <1.0 | >1625.0 |
| 574 | 536.5 | 115.5 | 1477 | 25.8 | <1.0 | 222.9 |
| 575 | 337.5 | 218.1 | 1059 | 22.7 | 3.3 | 3 |
| 576 | — | 153.7 | 8427 | — | — | — |
| 577 | — | 197.2 | 100000 | — | — | — |
| 578 | 2769 | 2174 | 18080 | 18.5 | <1.0 | <4.8 |
| 579 | 719.3 | 418.2 | 28100 | — | — | — |
| 580 | 1118 | 1231 | 4304 | — | 5.4 | 654.6 |
| 581 | 1060 | 632.2 | 1824 | — | 5.2 | ND |
| 582 | 1850 | 992 | 10020 | 5.5 | <1.0 | ND |
| 583 | 37450 | Inactive | 3575000 | 12.2 | <1.0 | ND |
| 584 | 2619 | 494.9 | 1452 | 17.8 | <1.0 | 31.6 |
| 585 | 7647 | 1092 | 171.4 | 19 | <1.0 | 79.3 |
| 586 | 8025 | 4802 | 10510 | >30.0 | >77.0 | 220.3 |
| 587 | 688.6 | 245 | 6702 | 18.2 | <1.0 | ND |
| 588 | 5312 | 1424 | 100000 | 18.5 | <1.0 | 83.1 |
| 589 | 100000 | 913.8 | 100000 | — | — | — |
| 590 | 1083 | 217.8 | 4761 | 5.3 | 2 | 1345.4 |
| 591 | 1909 | 1066 | 2095 | 6.2 | <1.0 | 1336.2 |
| 592 | 50140 | — | 37960 | >30 | 12.7 | <1 |
| 593 | 100000 | — | 100000 | — | — | — |
| 594 | — | 4275 | 100000 | 19.6 | <1 | 144.8 |
| 595 | — | 683.3 | 100000 | — | — | — |
| 596 | — | 349.9 | 26820 | — | — | — |
| 597 | — | 490.1 | 100000 | — | — | — |
| 598 | — | 5124 | 100000 | — | — | — |
| 599 | — | 43840 | 6384 | — | — | — |
| 600 | — | 251.4 | 14470 | — | — | — |
| 601 | — | 431.3 | 7223 | — | — | — |
| 602 | 3348 | 302.4 | 127.4 | >30.0 | <1.0 | <3.1 |
| 603 | 107.5 | 82.18 | 195.4 | >30.0 | 1.1 | <6.4 |
| 604 | 374 | 107.4 | 33.56 | 6.5 | <1.0 | <12.3 |
| 605 | 159.4 | 60.87 | 111.3 | 15.6 | <1.0 | 231.6 |
| 606 | 120 | 50.73 | 79.18 | >30.0 | 1.9 | 70.9 |
| 607 | 5635 | 113.9 | 116.2 | >30.0 | 4.9 | <1.9 |
| 608 | 106 | 34.84 | 210 | >30.0 | 7 | 12.2 |
| 609 | 28990 | 351.9 | 335 | >30.0 | 4.5 | ND |
| 610 | 150.4 | 50.9 | 257 | >30 | 3.9 | 0 |
| 611 | 2232 | 225.6 | 234 | >30.0 | 1.6 | <3.6 |

TABLE 8

| # | Gametocyte EC50 (nM) | Asexual EC50 (nM) | mTOR (nM) | Microsomal Stability (rat) $T_{1/2}$ (min) | Sol @ pH 7.4 (ug/mL) | PAMPA Permeability ($\times 10^6$ cm/s) |
|---|---|---|---|---|---|---|
| 612 | 16870 | 5660 | 11410 | 2.2 | 54.4 | — |
| 613 | 100000 | 14080 | 13650 | >30.0 | 37.7 | 2.9 |
| 614 | 11290 | 3534 | 12050 | >30.0 | 58.6 | — |
| 615 | 100000 | 3800 | 29840 | >30.0 | 40 | 3.1 |

Example 7

This example demonstrates a synthesis of compounds, in accordance with an embodiment of the invention.

N-methyl isopropyl carbamate 4 of 6-bromo-4-chloroquinolin-3-amines 2, one example of the key intermediate, can be synthesized from commercially available 6-bromo-4-chloroquinolin-3-amine 1 in three steps: stannous chloride mediated reduction of 1 followed by carbamate synthesis through isopropyl chloroformate gave 3, subsequent methylation provided 4, as shown in Scheme 6.

Scheme 6

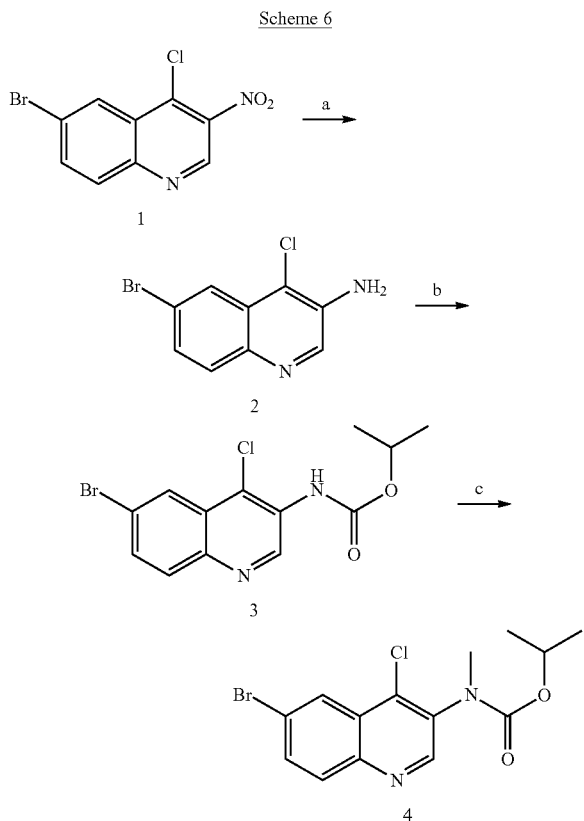

Reagents and conditions:
(a) SnCl$_2$*2H$_2$O, AcOH, EtOH, rfx, 3 h, 64%;
(b) ClCOOiPr, pyr, DCM, rt, 4 h, 66%;
(c) MeI, NaH, THF, rt, 18 h, 93%.

One aspect of the invention provides a process of making a compound of structure 6 in a high boiling point organic reaction medium under microwave irradiation, further coupling the compound of structure 6 with the boronic species to obtain the compound of structure 7, as shown in Scheme 7. with the boronic species to obtain the compound of structure 7, as shown in Scheme 7.

Scheme 7

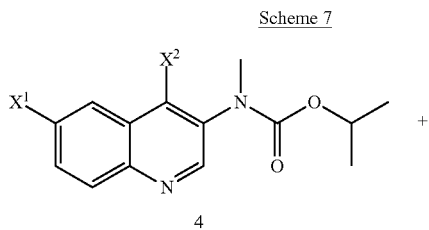

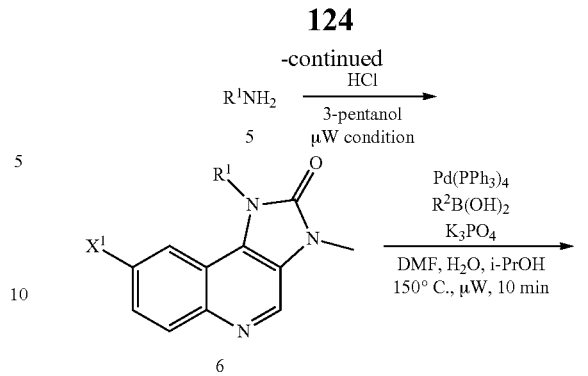

Preparation of 6-bromo-4-chloroquinolin-3-amine 2

To a mixture of 25 g (85 mmol) of 6-bromo-4-chloro-3-nitroquinoline 1 with 500 mL of EtOH and 75 mL of AcOH was added 98 g (435 mmol) SnCl$_2$ dihydrate as one portion. The reaction mixture was then refluxed for 3 hours. The reaction mixture was cooled to 0° C. and the pH was adjusted to basic with saturated NaHCO$_3$. The mixture was extracted with 1 L of EtOAc three times. The EtOAc layers were combined, dried over MgSO4 and concentrated. The resulting solid was triturated with Et$_2$O to provide 14.3 g of 2 as a pale-yellow solid.

Preparation of isopropyl (6-bromo-4-chloroquinolin-3-yl)carbamate 3

Under an inert atmosphere, to a stirred solution of 2 (7.98 g, 31 mmol) in anhydrous DCM (140 mL) at 0° C. was added pyridine (37.2 mmol), followed by 34.1 mL isopropyl chloroformate (34.1 mmol, as 1M solution in PhMe) dropwise. The solution was stirred at 0° C. for a further 15 min before the ice bath was removed and stirring continued at rt for 4 hours. Then 200 mL DCM was added at 0° C., followed by an equal volume of saturated NaHCO$_3$ and several drops of MeOH. The mixture was extracted with 200 mL of DCM three times. The organic layers were combined, dried (MgSO$_4$) and concentrated. The resulting orange red mixture was triturated with Et$_2$O (100 mL×3), providing 7.0 g pure product 3 as a pale-orange solid.

Preparation of isopropyl (6-bromo-4-chloroquinolin-3-yl)(methyl)carbamate 4

Under an inert atmosphere, to a stirred solution of 3 (7 g, 20.3 mmol) in anhydrous THF (100 mL) at 0° C., was added portion-wise NaH (1.63 g, 40.7 mmol, 60% dispersion in mineral oil). After 15 min, iodomethane (3.8 mL, 61.1 mmol) was added dropwise and the resulting mixture was stirred at 0° C. for 60 min and then at rt for 18 hours. At 0° C., 200 mL saturated NH$_4$Cl was added. The mixture was extracted with 200 mL of EtOAc three times. The EtOAc layers were combined, dried (MgSO$_4$) and concentrated.

The residual mixture was then passed through a silica gel column, and the product eluted with DCM and MeOH. The resulting pale orange oil was left under vacuum, providing 6.7 g product 4 as pale-yellow solid.

Preparation of Compound 7 Through One-Pot Two Step Synthesis

In a 0.5 mL-2.0 mL conical shaped microwave reaction vial, isopropyl (6-bromo-4-chloroquinolin-3-yl)(methyl) carbamate 4 (36 mg, 0.1 mmol) and 1.0 mL of 3-pentanol were mixed, followed by aniline 5 (0.2 mmol) and 75 uL HCl (0.3 mmol, 4.0 M in dioxane). The mixture was microwave irradiated at 230° C. for several minutes. 0.5 mL DMF and 0.5 mL 1M $K_3PO_4$ (106 mg $K_3PO_4$ in 0.5 mL FLO)$^a$ were added. With stirring, the air was displaced with nitrogen. Boronic acid/ester (0.2 mmol) and $Pd(PPh_3)_4$ (0.003 mmol) were introduced. The mixture was microwave heated at 150° C. for 10 minutes. The reaction mixture was cooled and 5 mL of saturated $NaHCO_3$ was introduced. The reaction mixture was extracted with three 7 mL portions of DCM. The organic extract was dried ($MgSO_4$), filtered and concentrated. To obtain a pure product, the residual mixture was passed through a silica gel column, and the product 7 was eluted with DCM and MeOH.

$^a$ Note: For difficult examples, molar ratio (4:5:HCl)=1:4:5, volume of 1M $K_3PO_4$=0.7 mL.

Preparation of Compound 6 Through Conventional Reflux

In a round bottomed flask, N-methyl carbamate 4 (3 mmol) and 10 mL cyclohexanol were mixed, followed by aniline 5 (9 mmol) and HCl (12 mmol, 4.0 M in dioxane). The mixture was refluxed for 4 hours (or until reaction was complete). Then at 0° C., 30 mL of saturated $NaHCO_3$ was introduced. The mixture was then extracted with three 30 mL portions of DCM. The organic extract was dried ($MgSO_4$), filtered and concentrated. The resulting mixture was passed through a silica gel column, and product 6 was eluted with DCM and MeOH.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:
1. A compound of formula (I):

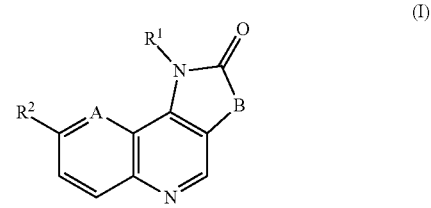

wherein A is $CR^5$ or N,
B is $CR^3$=$CR^4$,
$R^1$ is $C_{6-10}$ aryl or heteroaryl substituted with at least one substituent selected from —CN, cyanomethyl, —$SO_2R^{13}$, —$SO_2NHR^{15}$, and —$CONR^{11}R^{12}$, optionally further in combination with one or more substituents selected from halo, $C_{1-12}$ alkyl, alkoxy, a heterocyclyl group selected from the group consisting of optionally substituted piperazinyl, morpholinyl, pyrrolinidyl, and diazepinyl, or an aryl bicyclic lactam of the formula:

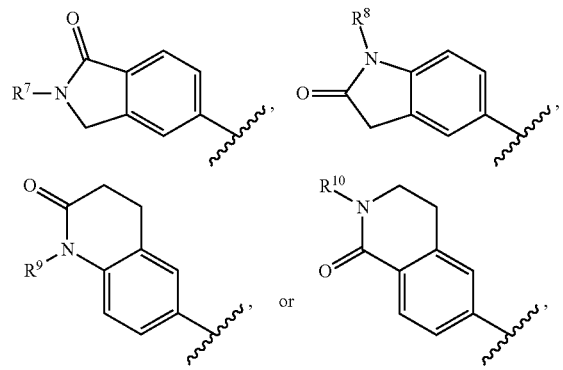

wherein the aryl group of the aryl bicyclic lactam is optionally substituted with at least one substituent selected from —CN, cyanomethyl, —$SO_2R^{13}$, —SO$_2$NH$_2$, and —CONR$^{11}$R$^{12}$, optionally further in combination with one or more substituents selected from halo, C$_{1-12}$ alkyl, alkoxy, 2-(dimethylamino) ethyl)amino, dimethylamino, a heterocyclyl group selected from the group consisting of optionally substituted piperazinyl, morpholinyl, pyrrolinidyl, azetidinyl, and diazepinyl, R$^2$ is selected from 4-pyridinyl, 2-amino-5-pyrimidinyl, 3-pyridyl, quinolin-3-yl, 5-pyrimidinyl, 2-acetylamino-5-pyridyl, 2-amino-4-methylpyrimidin-5-yl, 1-piperazinyl, indol-5-yl, 1H-imidazol-5-yl, 4-aminophenyl, 1,2,3,6-tetrahydropyridin yl, 1H-pyrazol-4-yl, N-methyl-pyrazol-4-yl, 1H-benzo[d]imidazol-5-yl, 4-sulfonylaminophenyl, 2-dimethylaminopyrimidin-5-yl, 3-trifluoromethylphenyl, bromo, 3-aminophenyl, vinyl, 4-aminocarbonylphenyl, 3-cyanophenyl, 3-hydroxyphenyl, 3-trifluoromethyl-5-pyridyl, tetrazolyl, 4-chlorophenyl, 4-fluorophenyl, 4-methoxyphenyl, 3-aminocarbonylphenyl, 3-acetylphenyl, 3-cyano-4-chlorophenyl, 3-cyano-5-methylphenyl, 3-hydroxy-4-chlorophenyl, 4-hydroxymethylphenyl, 3-amino-4-chlorophenyl, 2,3-dihydrobenzofuran-6-yl, 1-methyl-1H-indol-5-yl, benzo[d][1,3]dioxo-5-yl, 4-fluorophenyl, 4-hydroxyphenyl, morpholin-1-yl, benzo[b]thiophen-1-yl, 4-methyl sulfonylphenyl, benzo[c][1,2,5]oxadiazol-5-yl, 2-(piperidin-1-yl)-3-pyridinyl, 4-carboxyphenyl, 2-methyl-5-pyridyl, 4-methyl sulfonylphenyl, 4-dimethylaminocarbonylphenyl, 4-phenylphenyl, 4-methylphenyl, 3-chloro-5-pyridyl, (3-pyrrolidin-1-yl)phenyl, 4-([piperizin-1-yl]carbonyl)phenyl, 4-([morpholin-1-yl]carbonyl)phenyl, 2-hydroxypyrimidin-5-yl, 3-aminosulfonylphenyl, 2-oxo-1,2,3,4,tetrahydroisoquinolin-6-yl, 2-oxo-1,2,3,4,-tetrahydroquinolin-6-yl, 4-(methylaminocarbonyl)phenyl, 1-oxoindolin-5-yl, 2-oxoindolin-5-yl, 1-oxoisoindolin-5-yl, 2-amino-4-pyridyl, 4-aminomethylphenyl, 3-methoxy-4-chlorophenyl, 3-methylphenyl, 3-methoxyphenyl, phenyl, 5-indolinone, 5-isoindolinone, 2-hydroxy-4-chlorophenyl, 4-cyanophenyl, 4-azetidinylphenyl, 4-ethylphenyl, 3-fluorophenyl, 3-chlorophenyl, 3-dimethylaminomethylphenyl, 3-cyano-4-fluorophenyl, 3-amino-4-fluorophenyl, 4-(1-hydroxy-1-ethylphenyl, 3-methyl-5-pyridyl, 2-acetylamio-5-pyridyl, 2-oxoindolin-5-yl, benzimidazolin-5-yl, 3-dimethylamino-1-propargyl, 2-pyrrolyl, N-methyl-2-pyrrolyl, 2-thiopheneyl, 3-thiopheneyl, 3-furanyl, and 3-aminosulfonylphenyl, R$^3$ and R$^4$ are independently selected from hydrogen, hydroxyl, OR$^5$, halogen, optionally substituted C$_{6-10}$ aryl, and optionally substituted C$_{1-6}$ alkyl, R$^5$ is hydrogen, C$_{1-12}$ alkyl, C$_{6-10}$ aryl, halogen, hydroxyl, or OR$^{16}$ R$^7$-R$^{10}$ are independently selected from hydrogen, C$_{1-12}$ alkyl, C$_{3-8}$ cycloalkyl, CH$_2$COOR$^{13}$, and H$_2$N(CH$_2$)$_n$— wherein n is an integer of 2-6, R$^{11}$ and R$^{12}$ selected from the group consisting of hydrogen, C$_{1-12}$ alkyl and C$_{3-10}$ cycloalkyl or, taken together with the N to which they are bound, form an optionally substituted 4-7 membered heterocyclyl ring containing O or N atoms, and R$^{13}$ is C$_{1-12}$ alkyl, R$^{15}$ is hydrogen or C$_{1-12}$ alkyl, and R$^{16}$ is C$_{1-12}$ alkyl, C$_{1-6}$ acyl, or C$_{6-10}$ aryl, or a pharmaceutically acceptable salt thereof.

2. The compound or salt of claim 1, wherein A is CH, B is CR$^3$=CR$^4$, R$^2$ is selected from 4-chlorophenyl, 3-hydroxy-4-chlorophenyl, 3-amino-4-chlorophenyl, 4-fluorophenyl, 4-dimethylaminomethylphenyl, 4-aminomethylphenyl, 3-methyl-4-chlorophenyl, 3-methoxy-4-chlorophenyl, 3-cyano-4-chlorophenyl, and 4-pyrrolidinomethylphenyl, and R$^1$ is selected from 4-methyl sulfonylphenyl, 4-ethyl sulfonylphenyl, 2-methyl-4-methyl sulfonylphenyl, and 3-piperazinylmethyl-4-methylsulfonylphenyl.

3. The compound or salt of claim 1, wherein A is CH, B is CR$^3$=CR$^4$, R$^2$ is 4-chlorophenyl and R$^1$ is 4-aminosulfonylphenyl or 3-aminosulfonylphenyl.

4. The compound or salt of claim 1, wherein A is CH, B is CR$^3$=CR$^4$, R$^1$ is C$_{6-10}$ aryl substituted with —CONR$^{11}$R$^{12}$, R$^2$ is selected from 4-chlorophenyl, 4-fluorophenyl, 4-dimethylaminomethylphenyl, 4-aminomethylphenyl, 3-amino-4-chlorophenyl, 3-hydroxy-4-chlorophenyl, 4-aminophenyl, 4-hydroxyphenyl, 4-hydroxymethylphenyl, 3-methylphenyl, 3-methoxyphenyl, 3-cyanophenyl, phenyl, 5-indolinone, 3-hydroxyphenyl, 5-isoindolinone, 3-aminophenyl, 2-hydroxy-4-chlorophenyl, 3-cyano-4-chlorophenyl, 4-cyanophenyl, 4-(2-aminoethyl)phenyl, 4-(2-dimethylaminoethyl)phenyl, 4-azetidinylphenyl, 4-ethylphenyl, 2-amino-5-pyridyl, and 4-(1-aminocycloprop-1-yl)phenyl, and R$^1$ is selected from 4-methylcarbonylaminophenyl, 4-morpholinocarbonylphenyl, 4-dimethylaminocarbonylphenyl, 4-(3,5-dimethylaminomorpholino)carbonylphenyl, 4-(4-methylpiperazinyl)carbonylphenyl, 4-piperazinylcarbonylphenyl, 4-piperidinylcarbonylphenyl, 4-[N,N-bis(2-hydroxyethyl]carbonylphenyl, 4-cyclopentylaminocarbonylphenyl, 4-azetidinylcarbonylphenyl, 4-(4-hydroxyethylpiperazinyl)carbonylphenyl, 2-methyl-4-methylaminocarbonylphenyl, 3-chloro-4-methylaminocarbonylphenyl, 4-cyclopropylaminocarbonylphenyl, 4-dimethylaminocarbonylphenyl, 4-1-(8-oxa azabicyclo[3.2.1]octan-3-yl)carbonylphenyl, 4-1-(3-hydroxy-8-azabicyclo[3.2.1]octan yl)carbonylphenyl, 1-(5-methyl-2,5-diazabicyclo[2.2.1]heptan-2-yl)carbonylphenyl, 1-(5-methylhexahydropyrrolo[3,4-c]pyrrol-2(1H)-yl)carbonylphenyl, 4-(N-cyclopropyl-N-cyclohexylamino)carbonylphenyl, 4-(N-methyl-N-cyclopropylamino)carbonylphenyl, 4-cyclobutylaminocarbonylphenyl, 2-trifluoroethylaminocarbonylphenyl, 4-(2-dimethylaminoethylaminocarbonyl)phenyl, 4-(4-[2-dimethylaminoethyl]piperazin-1-yl-carbonyl)phenyl, 4-cyclopropylaminocarbonylphenyl 4-(1-[2-dimethylaminoethyl]piperidin-4-amino)carbonylphenyl, 4-(N-(1-(2-hydroxyethyl)azetidin-3-ylamino)carbonylphenyl, and 4-(pyrrolidinyl-3-amino)carbonylphenyl.

5. The compound or salt of claim 1, wherein A is CH, B is CR$^3$=CR$^4$, and R$^1$ is an aryl bicyclic lactam of the formula:

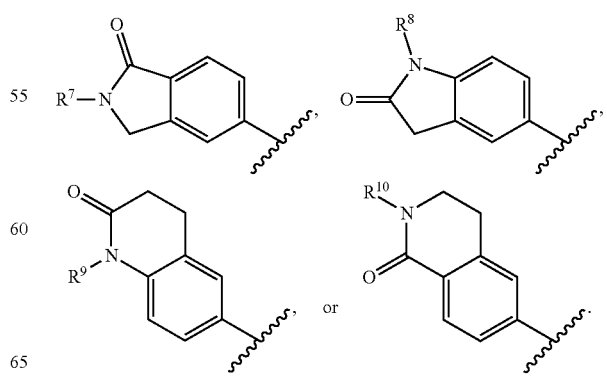

6. The compound or salt of claim 5, wherein the compound is selected from:

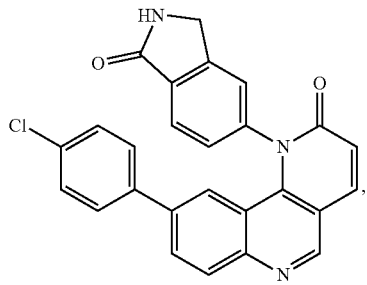

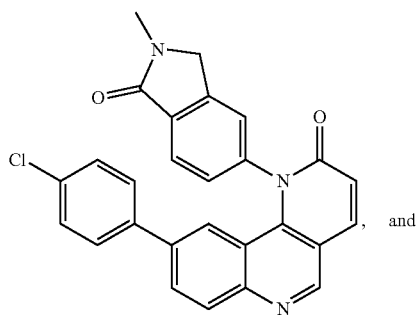
, and

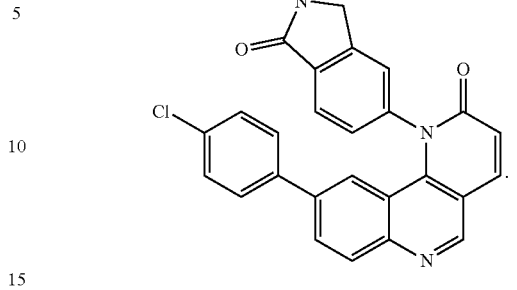
.

7. A pharmaceutical composition comprising a compound or salt of claim 1 and a pharmaceutically acceptable carrier.

8. A method of blocking transmission of a *Plasmodium* parasite or treating malaria by killing or arresting the growth of *Plasmodium* organisms in a mammal, wherein the *Plasmodium* organisms are in a gametocyte stage comprising administering to a mammal in need of such treatment, a therapeutically effective amount of a compound or salt of claim 1, optionally in combination with an antimalarial compound selected from elesclomol, NSC174938, NVP-AUY922, maduramicin, narasin, alvespimycin, omacetaxine, thiram, zinc pyrithione, phanquinone, bortezomib, salinomycin sodium, monensin sodium, dipyrithione, dicyclopentamethylene-thiuram disulfide, YM4155, withaferin A, adriamycin, romidepsin, AZD-1152-HQPA, CAY10581, plicamycin, CUDC-101, auranofin, trametinib, GSK-458, afatinib, and panobinostat, and any combination thereof.

* * * * *